(12) United States Patent
Clauss et al.

(10) Patent No.: US 8,242,126 B2
(45) Date of Patent: Aug. 14, 2012

(54) QUINAZOLINEDIONE DERIVATIVES, PREPARATION THEREOF AND THERAPEUTIC USES THEREOF

(75) Inventors: Annie Clauss, Paris (FR); Christophe Glaess, Paris (FR); Gilbert Marciniak, Paris (FR); Nicolas Muzet, Paris (FR); Jean-Francois Nave, Paris (FR); André Seyer, Paris (FR); Bertrand Vivet, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/754,163

(22) Filed: Apr. 5, 2010

(65) Prior Publication Data

US 2010/0298298 A1    Nov. 25, 2010

Related U.S. Application Data

(63) Continuation of application No. PCT/FR2008/001384, filed on Oct. 3, 2008.

(30) Foreign Application Priority Data

Oct. 3, 2007 (FR) ...................................... 07 06931

(51) Int. Cl.
*A61K 31/517* (2006.01)
(52) U.S. Cl. ............... 514/266.22; 514/266.3; 544/284; 544/285
(58) Field of Classification Search .................. 544/284, 544/285
See application file for complete search history.

(56) References Cited

FOREIGN PATENT DOCUMENTS

| WO | WO 93/19068 | 9/1993 |
|---|---|---|
| WO | WO 2006/092691 | 9/2006 |
| WO | WO 2006/092692 | 9/2006 |
| WO | WO 2007/067946 | 6/2007 |

OTHER PUBLICATIONS

West, Anthony R., Solid State Chemistry and its Applications, Wiley, New York, 1988, pp. 358 and 365.*
Morissette et al. "High-throughput crystallization: polymorphs, salts, co-crystals and solvates of pharmaceutical solids." 2004, Advanced Drug Delivery Reviews, 56, 275-300.*
Wang, P., et. al., Cloning, Characterization, and Tissue Distribution of Mouse Phosphodiesterase 7A1, Biochemical and Biophysicai Research Communications, vol. 276, pp. 1271-1277, (2000).
Bender, A. T., et. al., Cyclic Nucleotide Phosphodiesterases: Molecular Regulation to Clinical Use, Pharmacological Reviews, vol. 58, No. 3, pp. 488-520, (2006).
Bloom, T. J., et. al., Identification and Tissue-Specific Expression of PDE7 Phosphodiesterase Splice Variants PNAS, vol. 93, pp. 14188-14192, (1996).

Diehn, M., et. al., Genomic Expression Programs and The Integration of the CD28 Costimulatory Signal in T Cell Activation, PNAS, vol. 99, No. 18, (2002), pp. 11796-11801.
Gardner, C., et. al., Cloning and Characterization of the Human and Mouse PDE7B, a Novel CAMP-Specific Cyclic Nucleotide Phosphodiesterase, Biochemical and Biophysical Research Communications, vol. 272, pp. 186-192, (2000).
Giembycz, M. A., et. al., Phosphodiesterase 7 (PDE7) as a Therapeutic Target, Drugs of the Future, (2006), vol. 31, No. 3, pp. 207-229.
Glavas, N. A., et. al., T Cell Activation Up-Regulates Cyclic Nucleotide Phosphodiesterases 8A1 and 7A3, PNAS, (2001), vol. 98, No. 11, pp. 6319-6324.
Han, P., et. al., Alternative Splicing of the High Affinity CAMP-Specific Phosphodiesterase (PDE7) MRNA in Human Skeletal Muscle and Heart, The Journal of Biological Chemistry, vol. 272, No. 26, (1997), pp. 16152-16157.
Kinoshita, T., et. al., Phosphodiesterase Inhibitors, Pentoxifylline and Rolipram, Increase Bone Mass Mainly by Promoting Bone Formation in Normal Mice, Bone, vol. 27, No. 6. pp. 811-817, (2000).
Lee, R., et. al., PDE7A is Expressed in Human B-Lymphocytes and is Up-Regulated by Elevation of Intracellular CAMP, Cellular Signalling, vol. 14, (2002), pp. 277-284.
Li, L., et al., CD3- and CD28-Dependent Induction of PDE7 Required for T Cell Activation, Science, vol. 283, pp. 848-851, (1999).
Lowe, J. A., et. al., Structure-Activity Relationship of Quinazolinedione Inhibitors of Calcium-Independent Phosphodiesterase, J. Med. Chem., (1991), vol. 34, pp. 624-628.
Lugnier, C., et. al., Cyclic Nucleotide Phosphodiesterase (PDE) Superfamily: A New Target for The Development of Specific Therapeutic Agents, Pharmacology & Therapeutics, vol. 109, (2006), pp. 366-398.
Michael, T., et. al., Isolation and Characteriztion of a Previously Undetected Human CAMP Phosphodiesterase by Complementation of CAMP Phosphodiesterase-Deficient *Saccharomyces cerevisiae*, The Journal of Biological Chemistry, vol. 268, No. 17, (1993), pp. 12925-12932.

(Continued)

*Primary Examiner* — James O Wilson
*Assistant Examiner* — Brian McDowell
(74) *Attorney, Agent, or Firm* — Jiang Lin; Serena Farquharson-Torres

(57) ABSTRACT

The invention relates to quinazolinedione derivatives of the general formula (I):

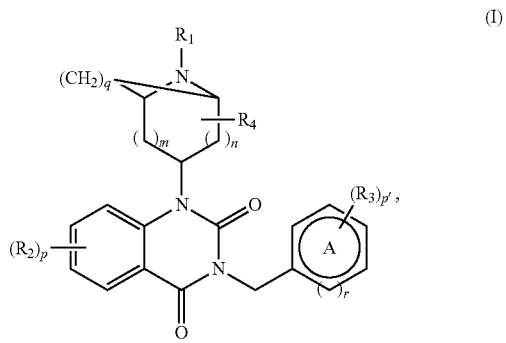

wherein A, $R_1$, $R_2$, $R_3$, $R_4$, m, n, p, p', and r are as defined herein, processes for the preparation thereof and their therapeutic applications.

12 Claims, No Drawings

OTHER PUBLICATIONS

Miro, X., et. al., Differential Distribution of CAMP-Specific Phosphodiesterase 7A MRNA in Rat Brain and Peripheral Organs, Synapse, vol. 40, pp. 201-214, (2001).

Miyamoto, K., et. al., , Reduction of Bone Loss by Denbufylline, an Inhibitor of Phosphodiesterase 4, Biochemical Pharmacology, vol. 54, pp. 613-617, (1997).

Nakata, A., et. al., Potential Role of Phosphodiesterase 7 In Human T Cell Function: Comparative Effects of Two Phosphodiesterase Inhibitors, Clin. Exp. Immunol., (2002), vol. 128, pp. 460-466.

Perry, M. J., et. al., Chemotherapeutic Potential of Phosphodiesterase Inhibitors, Current Opinion in Chemical Biology, vol. 2, No. 4, (1998), pp. 472-481.

Pitts, W. J., et. al., Identification of Purine Inhibitors of Phosphodiesterase 7 (PDE7), Bioorganic & Medicinal Chemistry Letters, vol. 14, (2004), pp. 2955-2958.

Reyes-Irisarri, E., et. al., Neuronal Expression of CAMP-Specific Phosphodiesterase 7B MRNA In The Rat Brain, Neuroscience, vol. 132, (2005), pp. 1173-1185.

Saldou, N., et. al., Comparision of Recombinant Human PDE4 Isoforms: Interaction With Substrate and inhibitors, Cell. Signal., vol. 10, No. 6, pp. 427-440, (1998).

Sasaki, T., et. al., Identification of Human PDE7B, a CAMP-Specific Phosphodiesterase, Biochemical and Biophysical Research Communications, vol. 271, (2000), pp. 576-583.

Smith, S. J., et. al., Discovery of BRL 50481 [3-(N,N-Dimethylsulfonamido)-4-Methyl-Nitrobenzene], a Selective Inhibitor of Phosphodiesterase 7: In Vitro Studies in Human Monocytes, Lung Macrophages, and CD8 T-Lymphocytes, Molecular Pharmacology, vol. 66, No. 6, pp. 1679-1689, (2004).

Smith, S. J., et. al., , Ubiquitous Expression of Phosphodiesterase 7A in Human Proinflammatory and Immune Cells, Am. J. Physiol. Lung, Cell, Mol Physiol, vol. 284, pp. 279-289, (2003).

* cited by examiner

QUINAZOLINEDIONE DERIVATIVES, PREPARATION THEREOF AND THERAPEUTIC USES THEREOF

A subject-matter of the invention is quinazolinedione derivatives, the processes whereby they are obtained and their therapeutic applications.

The invention relates to quinazolinedione derivatives which are inhibitors of phosphodiesterase 7 (PDE7). Some of these derivatives also inhibit phosphodiesterase 8 (PDE8).

Phosphodiesterases (PDEs) are intracellular enzymes responsible for the hydrolysis of cAMP (cyclic adenosine 3',5'-monophosphate) and cGMP (cyclic guanosine 3',5'-monophosphate) secondary messengers to give inactive 5'-monophosphate nucleotides. cAMP and cGMP play an essential role in cell signalling pathways and are involved in numerous physiological processes.

The inhibition of phosphodiesterases is reflected by an increase in intracellular concentrations of cAMP and cGMP, resulting in the specific activation of phosphorylation pathways involved in varied functional responses. The increase in the intracellular concentrations of cAMP or of cGMP using selective inhibitors of phosphodiesterases appears to be a promising approach in the treatment of various diseases (Bender and Beavo, Pharmacol. Rev., (2006) 58, 488-520). The inhibitors of phosphodiesterases are thus of interest as therapeutic agents and as pharmacological tools.

To date, eleven families of phosphodiesterases have been identified. They are distinguished by their primary structure, their substrate specificity and their sensitivity with regard to various effectors and inhibitors specific for PDEs. Each family is composed of one or more genes which are expressed in various tissues in the form of splicing variants (Bender and Beavo, Pharmacol. Rev., (2006) 58, 488-520; Lugnier, Pharmacol. Therapeut., (2006) 109, 366-398).

PDE4, PDE7 and PDE8 specifically hydrolyse cAMP and PDE5, PDE6 and PDE9 specifically hydrolyse cGMP.

The family PDE7 is represented by the isoforms PDE7A and PDE7B originating from two distinct genes.

Human PDE7A (Michaeli et al., J. Biol. Chem., (1993) 268, 12925-12932; Han et al., J. Biol. Chem., (1997) 272, 16152-16157; Wang et al., Biochem. Biophys. Res. Commun., (2000) 276, 1271-1277) and human PDE7B (Sasaki et al., Biochem. Biophys. Res. Commun., (2000), 271, 575-583; Gardner et al., Biochem. Biophys. Res. Commun., (2000) 272, 186-192) selectively hydrolyse cAMP with Michaelis constants (Km) of 0.1 to 0.2 µM and 0.13 to 0.2 µM respectively. The catalytic part of PDE7B exhibits approximately 67% homology with that of PDE7A.

Three splicing variants are known for PDE7A. PDE7A1 and PDE7A3 are expressed mainly in the cells of the immune system and of the lungs, while PDE7A2 is above all expressed in the muscles of the skeleton, the heart and the kidneys. For PDE7B, three variants have also recently been identified (Giembycz and Smith, Drugs Future, (2006) 31, 207-229).

The tissue distribution profiles for PDE7A and PDE7B are very different, suggesting that these two isoforms have distinct functions from the physiological viewpoint. While PDE7A is copiously expressed in haematopoietic cells, the lungs, the placenta, Leydig cells, the spleen, the collecting tubes of the kidneys, and the adrenal glands, strong expression of PDE7B is detected in the pancreas, the heart, the thyroid and the muscles of the skeleton (Giembycz and Smith, Drugs Future, (2006) 31, 207-229). However, coexpression of the messenger RNAs (mRNAs) of PDE7A and PDE7B is observed in some tissues. This is the case in the osteoblasts (Ahlstrom et al., Cell Mol. Biol. Lett., (2005) 10, 305-319) and in some regions of the brain: several areas of the cortex, the dentate gyrus, the majority of the components of the olfactory system, the striatum, numerous nuclei of the thalamus and the pyramidal cells of the hippocampus (Miro et al., Synapse, (2001) 40, 201-214; Reyes-Irisarri et al., Neuroscience, (2005) 132, 1173-1185). In contrast, in some areas of the brain, only one of the two isoforms is expressed. Thus, only the mRNAs of PDE7A are present in many nuclei of the brain stem. Likewise, the mRNAs of PDE7B are present at high concentrations in the nucleus accombens and the dorsal motor nucleus of the vagus nerve, while the mRNAs of PDE7A are not detected there (Miro et al., Synapse, (2001) 40, 201-214; Reyes-Irisarri et al., Neuroscience, (2005) 132, 1173-1185).

The protein PDE7A1 is well expressed in blood T lymphocytes, bronchial epithelial cell lines, lung fibroblasts and eosinophils (Smith et al., Am. J. Physiol. Lung Cell Mol. Physiol., (2003) 284: L279-L289). Several reports suggest that PDE7A might play a role in the activation of T lymphocytes (Li et al., Science, (1999) 283, 848-851; Glavas et al., PNAS, (2001) 98, 6319-6324; Nakata et al., Clin. Exp. Immunol., (2002), 128, 460-466; Smith et al., Mol. Pharmacol., (2004) 66, 1679-1689). The protein PDE7A1 is also expressed in cells which play a central role in the pathogenesis of asthma and chronic obstructive pulmonary disease (COPD), such as T lymphocytes (CD4+ and CD8+), monocytes, neutrophils, alveolar macrophages, or cells of the smooth muscles of the airways and pulmonary vessels (Smith et al., Am. J. Physiol. Lung Cell Mol. Physiol., (2003) 284: L279-L289). The localization of PDE7A in proinflammatory cells and cells of the immune system and its potential role in the activation of T lymphocytes suggest that selective inhibitors of PDE7 might have applications in the field of diseases related to T lymphocytes and in that of diseases of the pulmonary tract.

The protein PDE7A is also present in B lymphocytes and in the WSU-CLL B lymphocyte cell line originating from a patient suffering from chronic lymphocytic leukaemia. Treatment of the WSU-CLL cells with IC242, a specific inhibitor of PDE7, increases the expression of PDE7A (Lee et al., Cell Signal, (2002) 14, 277-284). Furthermore, it has been shown that the expression of the protein PDE7B is approximately 5 to 90 times higher in peripheral blood mononuclear cells (PBMCs) of patients suffering from chronic lymphocytic leukaemia (CLL-PBMC) than in the PBMCs isolated from the blood of normal subjects (WO 2007/067946). BRL-50481, a selective inhibitor of PDE7, induces in a dose-dependent way the apoptosis of CLL-PBMCs but it is without effect on PBMCs of normal subjects. These observations suggest that selective inhibitors of PDE7 might be effective in the treatment of this type of leukaemia.

Selective inhibitors of PDE4 increase bone mineral density in the rat and the mouse and their effects appear to be related to a reduction in the activity of the osteoclasts and to an increase in that of the osteoblasts (Miyamoto et al., Biochem. Pharmacol., (1997) 54, 613-617; Waki et al., Jpn. J. Pharmacol., (1999) 79, 477-483; Kinoshita et al., Bone, (2000) 27, 811-817). A PDE7 activity has been detected in osteoblasts (Ahlström et al., Cell Mol. Biol. Lett., (2005) 10, 305-319). By increasing the intracellular concentration of cAMP, the inhibitors of PDE7, like the inhibitors of PDE4, might prove to be effective in the treatment of osteopenia and osteoporosis.

Furthermore, recent studies (WO2006/092691, WO2006/092692) report the pharmacological activities of various inhibitors of PDE7 in models of neuropathic pain in the rat, suggesting applications in the treatment of various types of pain and more particularly in that of neuropathic pain.

A subject-matter of the present invention is in particular quinazolinedione derivatives, which are powerful inhibitors of PDE7, or inhibitors of PDE7 and of PDE8 according to the derivatives, their preparation and their therapeutic applications.

The subject-matter of the invention is compounds of following general formula (I):

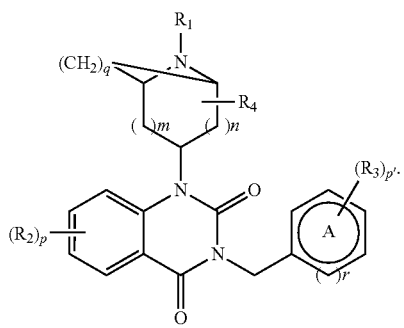

in which
A represents an aryl group or a heteroaryl group;
$R_1$ represents:
a hydrogen atom,
—C(O)R in which R is a hydrogen atom, a ($C_1$-$C_6$) alkoxy group, an aryl group, a ($C_3$-$C_6$) cycloalkyl group or a ($C_1$-$C_6$) alkyl group, the said alkyl optionally being substituted by:
 one or more hydroxyl group(s),
 a benzyloxy group,
 a ($C_1$-$C_6$) alkoxy group, optionally substituted by an aryl, or
 a ($C_3$-$C_6$) cycloalkyl group,
an optionally substituted ($C_1$-$C_6$) alkyl group;
$R_2$ represents:
a hydrogen atom,
a halogen atom,
a cyano group,
a nitro group,
a ($C_1$-$C_6$) alkyl group optionally substituted by an —$NH_2$ or else by an —NHC(O)Rb group,
an —ORa group in which Ra represents:
 a hydrogen atom,
 a ($C_1$-$C_6$) alkyl group optionally substituted by one or more halogen atom(s), by one or more hydroxyl group(s), by an aryl group and/or by one or more cyano group(s),
 a ($C_2$-$C_6$) alkynyl group,
 an aryl group;
$R_3$ represents:
a hydrogen atom,
a halogen atom,
a hydroxyl group,
a cyano group,
an —$SCF_3$ group,
a nitro group,
an oxo group,
an —$S(O)_{0-2}$-alkyl group, an —$S(O)_{0-2}$-heterocycloalkyl group, an —O—$SO_2$-aryl group optionally substituted by one or more halogen atom(s);
an -alkylaminoalkyl or -cycloalkylaminoalkyl group, each optionally substituted on the end alkyl,
an optionally substituted sulphonamide group,
an aryl group or a heteroaryl group, the said group being monocyclic or polycyclic and in addition optionally being substituted by a ($C_1$-$C_6$) alkyl group, by one or more halogen atom(s) or by a ($C_1$-$C_6$) alkoxy group,
a heterocycloalkyl group optionally substituted by a ($C_1$-$C_6$) alkyl group,
a ($C_1$-$C_6$) alkyl group optionally substituted by:
 one or more halogen atom(s),
 an aryl group which can be substituted by one or more halogen atom(s) or by one or more hydroxyl group(s),
 a heteroaryl group,
 one or more hydroxyl group(s) which can be substituted by an aryl group itself optionally substituted by one or more halogen atom(s), or
 a heterocycloalkyl group optionally substituted by a CO(O)Ra group or by a ($C_1$-$C_6$) alkyl group,
a —C(O)NRbRc group,
a —C(O)ORc group or an —O—C(O)ORc group,
a ($C_1$-$C_6$) alkoxy group, optionally substituted by
 an aminoalkyl group,
 an aminocycloalkyl group,
 a cycloalkyl group,
 a heterocycloalkyl group,
 a monocyclic or polycyclic heteroaryl group,
 one or more hydroxyl group(s),
 one or more halogen atom(s),
 a ($C_1$-$C_6$) alkoxy group,
 a —C(O)ORc group,
 a —C(O)NRbRc group,
 an oxo group, and/or
 an aryl group, itself optionally substituted by one or more halogen atom(s), a cyano group, a ($C_1$-$C_6$) alkoxy group, an —O-haloalkyl group and/or a haloalkyl group,
an —O-cycloalkyl group, an —O-aryl group or an —O-heterocycloalkyl group, each optionally substituted by
 an aryl group, itself optionally substituted by one or more halogen atom(s) or by a ($C_1$-$C_6$) alkyl group,
 an oxo group,
 one or more halogen atom(s), and/or
 a ($C_1$-$C_6$) alkyl group, which can itself be substituted by an aryl group and/or an oxo group,
an —NH—CO—NH-aryl group, an —NH—CO—NH-heteroaryl group or an —NH—CO—NH—($C_1$-$C_6$) alkyl group, each optionally being substituted by one or more halogen atom(s), by a cyano group, by a nitro group, by one or more hydroxyl group(s) or by a ($C_1$-$C_6$) alkoxy group,
an —N—($C_1$-$C_6$) alkyl group, it being possible for the ($C_1$-$C_6$) alkyl group to be substituted by
 one or more oxo group(s), and/or
 one or more aryl group(s) optionally substituted by one or more halogen atom(s) and/or by an $SO_2$ group,
an —NH—CO-aryl group or an —NH—CO-heteroaryl group, each optionally being substituted by one or more halogen atom(s);
or else $R_3$ forms, with A, a polycyclic heteroaryl group optionally substituted by a ($C_1$-$C_6$) alkoxy group or a ($C_1$-$C_6$) alkyl group optionally substituted by an, aryl group which can itself be substituted by one or more halogen atom(s);
$R_4$ represents a hydrogen atom, an oxo group or a ($C_1$-$C_6$) alkyl group;
Rb represents:
a hydrogen atom,
a ($C_1$-$C_6$) alkyl group optionally substituted by one or more halogen atom(s), by one or more hydroxyl, cyano, amino, heterocycloalkyl or ($C_1$-$C_6$) alkoxy group(s) or by an aryl group optionally substituted by one or more halogen atom(s), a ($C_3$-$C_6$) cycloalkyl group, a ($C_2$-$C_6$) alkynyl group, a ($C_1$-$C_6$) alkoxy group, an aryl group optionally substituted by one or more halogen atom(s);

Rc represents a hydrogen atom or a ($C_1$-$C_6$) alkyl group optionally substituted by one or more halogen atom(s); or then Rb and Rc form, together with the nitrogen atom to which they are attached, a polycyclic heteroaryl group or a heterocycloalkyl group;

m and n represent, independently of one another, the value 0, 1 or 2, it being understood that m+n≦3;

p and p' represent, independently of one another, the value 1, 2 or 3, it being understood that, when p is greater than or equal to 2, then the $R_2$ groups are on separate carbon atoms and can be different from one another and, when p' is greater than or equal to 2, then the $R_3$ groups are on separate carbon atoms and can be different from one another;

q represents the value 0 or 2, it being understood that, when q=0, then the nitrogenous heterocyclic group attached to the nitrogen situated in the 1 position of the 2,4-dioxo-1,2,3,4-tetrahydroquinazoline ring system is no longer bridged and is of the type:

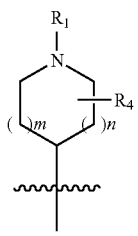

r represents the value 0 or 1.

The compounds of general formula (I) can comprise one or more asymmetric carbons. They can thus exist in the form of enantiomers or of diastereoisomers. These enantiomers or diastereoisomers, and their mixtures, including racemic mixtures, come within the invention.

Due to their structure, the compounds of general formula (I) can also exist in the form of isomers of rotamer or atropisomer type.

The compounds of formula (I) can also exist in the form of bases or addition salts with acids. Such addition salts come within the invention.

These salts are advantageously prepared with pharmaceutically acceptable acids but the salts of other acids, for example of use in the purification or separation of the compounds of general formula (I) also come within the invention.

The compounds of general formula (I) can also occur in the crystalline, amorphous or oily form, these forms coming within the invention.

The compounds of general formula (I) can in addition occur in the form of hydrates or of solvates, namely in the form of combinations or of associations with one or more molecules of water or with a solvent. Such hydrates and solvates also come within the invention.

According to the present invention, the N-oxides of the compounds comprising an amine also come within the invention.

The compounds of formula (I) according to the present invention also comprise those in which one or more hydrogen, carbon or halogen, in particular chlorine or fluorine, atoms have been replaced by their radioactive isotopes, for example tritium, in order to replace hydrogen, or carbon-14, in order to replace carbon-12. Such labelled compounds are of use in research, metabolism or pharmacokinetic studies or in biological and pharmacological assays as tools.

In the context of the invention, the following definitions apply:

in ($C_1$-$C_6$), the numerical indices determine the possible number of carbon atoms present in a chain or a ring. Thus, by way of example, $C_1$-$C_6$ represents a carbon chain which can have from 1 to 6 carbon atoms. Likewise, by way of example, ($C_1$-$C_5$) represents a carbon chain which can have from 1 to 5 carbon atoms or also ($C_3$-$C_6$) can represent a saturated carbon ring which can have from 3 to 6 carbon atoms;

alkoxy: an —O-alkyl group comprising a saturated, linear or branched, aliphatic chain;

alkynyl: a mono- or polyunsaturated, linear or branched, aliphatic group comprising, for example, one or two acetylenic unsaturations. For example, a ($C_2$-$C_6$) alkynyl group can represent an ethynyl, propynyl, and the like;

alkyl: a saturated, linear or branched, aliphatic group; for example, a ($C_1$-$C_6$) alkyl group represents a linear or branched carbon chain of 1 to 6 carbon atoms, in particular a methyl, ethyl, propyl, isopropyl, butyl, isobutyl, sec-butyl, tert-butyl or pentyl;

aminoalkyl: an —NH($C_1$-$C_6$) alkyl or also —N(($C_1$-$C_6$) alkyl)$_2$ group;

aryl: an optionally substituted monocyclic aromatic system comprising from 5 to 14 members per ring, preferably from 5 to 10 members per ring. Mention may be made, as examples of monocyclic aryl groups, of phenyl or naphthyl; the aryl group can be substituted by a group which can be one or more halogen atom(s), a hydroxyl group, a cyano group, a trifluoromethylthio group, a nitro group, an alkyl group, an alkoxy group, an alkylthio group, a methylsulphonyl group, an alkylaminoalkyl group or alkylaminocycloalkyl group which is optionally substituted, an alkylaminoalkoxy or cycloalkylaminoalkoxy group or a sulphonamide group, for example:

polycyclic aryl: an optionally substituted polycyclic aromatic system comprising from 5 to 14 members per ring, preferably from 5 to 10 members per ring, and comprising from 2 to 10 rings, at least one of the rings of which is aromatic. Mention may be made, as examples of polycyclic aryl groups, of aceanthrylene, anthracene, azulene, coronene, rubicene or naphthalene; the polycyclic aryl group can be substituted by a group which can be one or more halogen atom(s), a hydroxyl group, a cyano group, a trifluoromethylthio group, a nitro group, an alkyl group, an alkoxy group, an alkylthio group, a methylsulphonyl group, an alkylaminoalkyl or alkylaminocycloalkyl group which is optionally substituted, an alkylaminoalkoxy or cycloalkylaminoalkoxy group or a sulphonamide group, for example;

a bridged ring: a bicyclic structure comprising, according to the invention, a nitrogen atom, in which at least two carbon atoms are connected via a single bond or a carbon chain which can comprise 2 carbon atoms. By way of example, the abovementioned ring is of the type:

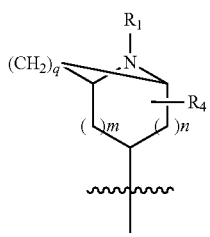

with q=1 or 2.

- cycloalkyl: a saturated cyclic aliphatic group comprising from 3 to 8 carbon atoms. Mention may be made, by way of example, of a cyclopropyl, methylcyclopropyl, cyclobutyl, cyclopentyl or cyclohexyl group;
- halogen: a fluorine, a chlorine, a bromine or an iodine;
- haloalkyl: $(C_1-C_6)$ alkyl substituted by one to three halogen atom(s);
- heteroaryl: a monocyclic aromatic system comprising from 5 to 14 ring members, preferably from 5 to 10 ring members, and comprising one to several heteroatoms, such as nitrogen, oxygen or sulphur atoms. The nitrogen atoms can be in the form of N-oxides. For example, a monocyclic heterocycle can be a pyran, a pyrazine, a pyrazole, a pyridazine, a pyridine, a pyrimidine, a pyrrole, an isothiazole, an isoxazole, a furan, an imidazole, a morpholine, a thiophene, a piperazine, a diazetidine, a dihydropyrrolidine, a piperidine, an azepine, and the like; a bicyclic heterocycle can be an isoquinoline, a pteridine, a chroman, and the like; a tricyclic heterocycle can be a phenanthroline, a xanthene, and the like;
- polycyclic heteroaryl: an optionally substituted polycyclic aromatic system comprising from 5 to 14 members per ring, preferably from 5 to 10 members per ring, and comprising from 2 to 10 rings, additionally comprising one to several heteroatoms, such as nitrogen, oxygen or sulphur atoms, in at least one of the rings, and at least one of the rings of which is aromatic. Mention may be made, as examples of polycyclic heteroaryl groups, of indole, benzofuran, benzimidazole, benzothiophene, benzotriazole, benzothiazole, benzoxazole, quinoline, isoquinoline, indazole, quinazoline, phthalazine, quinoxaline, naphthyridine, 2,3-dihydro-1H-indole, 2,3-dihydrobenzofuran, 2,3-dihydro-indene, tetrahydroquinoline, tetrahydroisoquinoline or tetrahydroisoquinazoline;
- a heterocycloalkyl: an optionally substituted saturated ring comprising from 3 to 8 atoms and comprising one to several heteroatoms, such as nitrogen, oxygen or sulphur atoms, in at least one of the rings, or several heteroatoms which are identical to or different from one another. For example, a heterocycloalkyl can be a pyrrolidine, a morpholine, a piperazine, a diazetidine, a dihydropyrrolidine, a piperidine, a piperadine, an azepan, an imidazolidine, a thiomorpholine, a tetrahydropyran, a tetrahydrothiopyran, a piperazine, a diazepan, and the like;
- hydroxyl: an —OH group;
- nitro: an —NO$_2$ group;
- oxo: a —C(O)— group;
- sulphonamide: group corresponding to the formula SO$_2$—N-alkyl or SO$_2$—N-cycloalkyl, alkyl and cycloalkyl being as defined above;
- trifluoromethylthio is defined by the formula —S—CF$_3$.

Furthermore, it is understood that, in the present description, when an atom or a group is substituted or optionally substituted by one or more defined group(s) or atom(s), the substituents can be identical to or different from one another and may be carried, if appropriate, by the same atom or different atoms.

Mention may be made, among the compounds which are a subject-matter of the invention, of a group of compounds of formula (I) in which A represents an aryl group, in particular a phenyl or heteroaryl, in particular a pyridyl group, and all the other substituents and indices are as defined in the general formula (I).

Mention may be made, among the compounds which are a subject-matter of the invention, of a group of compounds of formula (I) in which q=0, m and n=1, and all the other substituents and indices are as defined in the general formula (I).

Mention may be made, among the compounds which are a subject-matter of the invention, of a group of compounds of formula (I) in which $R_2$ represents a $(C_1-C_6)$ alkyl group, in particular a methyl, substituted by an —NHC(O)Rb group in which Rb and the other groups and indices are as defined for the compound of general formula (I).

Mention may be made, among the compounds which are a subject-matter of the invention, of a group of compounds of general formula (I) in which $R_2$ represents an —ORa group, the Ra group and all the other groups being as defined for the compound of formula (I).

Mention may be made, among the compounds which are a subject-matter of the invention, of a group of compounds of general formula (I) in which $R_2$ is a halogen atom or a cyano or a hydrogen or a hydroxyl optionally substituted by an —NH$_2$, or else by an —NHC(O)Rb group, the other groups being as defined for the compound of formula (I).

Mention may be made, among the compounds which are a subject-matter of the invention, of a group of compounds of general formula (I) in which A is a phenyl, $R_1$ is a —C(O)R group in which R represents a hydrogen atom, q is equal to 0, n and m have the value 1, and $R_2$ is —ORa, Ra being as defined in the general formula (I).

Mention may be made, among the compounds which are a subject-matter of the invention, of a group of compounds of general formula (I) in which A is a phenyl, $R_1$ is a —C(O)R group in which R represents a hydrogen atom, q is equal to 0, n and m have the value 1, p is equal to 2, one of the $R_2$ groups is —ORa, Ra being as defined in the general formula (I), and the other of the $R_2$ groups is a halogen atom.

Mention may be made, among the compounds which are a subject-matter of the invention, of a group of compounds of general formula (I) in which A is a phenyl, $R_1$ is a —C(O)R group in which R represents a hydrogen atom, q is equal to 0, n and m have the value 1 and $R_2$ is a methyl substituted by an —NH—CO—Rb group, Rb being as defined in the general formula (I).

Advantageously, in the compounds of formula (I), the $R_2$ group is in the 6 position of the 2,4-dioxo-1,2,3,4-tetrahydroquinazoline ring system. The compounds of formula (I) can also have an $R_2$ group in the 7 position of the 2,4-dioxo-1,2,3,4-tetrahydroquinazoline ring system.

Advantageously, in the compounds of formula (I), p=1 or 2.

In a specific form of the invention, when p'=2, then the two $R_3$ groups are in the 3 and 4 positions of the ring system A and can be different from one another.

The combinations of the groups of compounds of the invention mentioned above also come within the invention as embodiments according to the invention.-

Mention may be made, as examples of preferred compounds, of the following compounds:

No. 1: 2-{[3-(3,4-dimethoxybenzyl)-1-(1-formylpiperidin-4-yl)-2,4-dioxo-1,2,3,4-tetrahydroquinazolin-6-yl]oxy}propanenitrile No. 2: 1-(1-acetylpiperidin-4-yl)-3-(3,4-dimethoxybenzyl)-6-hydroxyquinazoline-2,4(1H,3H)-dione No. 3: {[1-(1-acetylpiperidin-4-yl)-3-(3,4-dimethoxybenzyl)-2,4-dioxo-1,2,3,4-tetrahydroquinazolin-6-yl]oxy}acetonitrile No. 4: 2-{[1-(1-acetylpiperidin-4-yl)-3-(3,4-dimethoxybenzyl)-2,4-dioxo-1,2,3,4-tetrahydroquinazolin-6-yl]oxy}propanenitrile No. 5: {[3-(3,4-dimethoxybenzyl)-1-(1-formylpiperidin-4-yl)-2,4-dioxo-1,2,3,4-tetrahydroquinazolin-6-yl]oxy}acetonitrile No. 11: 4-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde No. 12: 1-(1-acetylpiperidin-4-yl)-3-(3,4-dimethoxybenzyl)-6-[2-fluoro-1-(fluoromethyl)ethoxy]quinazoline-2,4(1H,3H)-dione No. 13: 4-[3-(3,4-dimethoxybenzyl)-2,4-dioxo-6-(2,2,2-trifluoroethoxy)-3,4-dihydroquinazolin-1(2H)-yl]piperidine-1-carbaldehyde No. 14: 1-(1-acetylpiperidin-4-yl)-6-(2,2-difluoroethoxy)-3-(3,4-dimethoxybenzyl)quinazoline-2,4(1H,3H)-dione No. 16: 4-[6-(2,2-difluoroethoxy)-3-(3,4-dimethoxybenzyl)-2,4-dioxo-3,4-dihydroquinazolin-1(2H)-yl]piperidine-1-carbaldehyde No. 20: N-{[3-(3,4-dimethoxybenzyl)-1-(1-formylpiperidin-4-yl)-2,4-dioxo-1,2,3,4-tetrahydroquinazolin-6-yl]methyl}acetamide No. 22: 1-(1-acetylpiperidin-4-yl)-6-(aminomethyl)-3-(3,4-dimethoxybenzyl)quinazoline-2,4(1H,3H)-dione hydrochloride No. 23: N-{[3-(3,4-dimethoxybenzyl)-1-(1-formylpiperidin-4-yl)-2,4-dioxo-1,2,3,4-tetrahydroquinazolin-6-yl]methyl}formamide No. 24: N-{[1-(1-acetylpiperidin-4-yl)-3-(3,4-dimethoxybenzyl)-2,4-dioxo-1,2,3,4-tetrahydroquinazoline-6-yl]methyl}formamide No. 25: N-{[1-(1-acetylpiperidin-4-yl)-3-(3,4-dimethoxybenzyl)-2,4-dioxo-1,2,3,4-tetrahydroquinazolin-6-yl]methyl}acetamide No. 32: 4-[6-(2,2-difluoroethoxy)-2,4-dioxo-3,4-dihydroquinazolin-1(2H)-yl]piperidine-1-carbaldehyde No. 33: 4-[3-(3,4-dichlorobenzyl)-6-(2,2-difluoroethoxy)-2,4-dioxo-3,4-dihydroquinazolin-1(2H)-yl]piperidine-1-carbaldehyde No. 34: 4-[3-(4-chlorobenzyl)-6-(2,2-difluoroethoxy)-2,4-dioxo-3,4-dihydroquinazolin-1(2H)-yl]piperidine-1-carbaldehyde No. 35: methyl 4-{[6-(2,2-difluoroethoxy)-1-(1-formylpiperidin-4-yl)-2,4-dioxo-1,4-dihydroquinazolin-3(2H)-yl]methyl}benzoate No. 36: 4-{[6-(2,2-difluoroethoxy)-1-(1-formylpiperidin-4-yl)-2,4-dioxo-1,4-dihydroquinazolin-3(2H)-yl]methyl}benzoic acid No. 37: 4-{[6-(2,2-difluoroethoxy)-1-(1-formylpiperidin-4-yl)-2,4-dioxo-1,4-dihydroquinazolin-3(2H)-yl]methyl}-N-(2-methoxyethyl)benzamide No. 38: 4-[3-(3,4-dimethoxybenzyl)-6-methyl-2,4-dioxo-3,4-dihydroquinazolin-1(2H)-yl]piperidine-1-carbaldehyde No. 39: 4-[6-(2,2-difluoroethoxy)-3-(3-hydroxy-4-methoxybenzyl)-2,4-dioxo-3,4-dihydroquinazolin-1(2H)-yl]piperidine-1-carbaldehyde No. 40: 4-[6-(2,2-difluoroethoxy)-3-[3-(2-hydroxyethoxy)-4-methoxybenzyl]-2,4-dioxo-3,4-dihydroquinazolin-1(2H)-yl]piperidine-1-carbaldehyde No. 41: 4-[6-(2,2-difluoroethoxy)-3-(3-ethoxy-4-methoxybenzyl)-2,4-dioxo-3,4-dihydroquinazolin-1(2H)-yl]piperidine-1-carbaldehyde No. 42: 4-[6-(2,2-difluoroethoxy)-3-[4-methoxy-3-(2-methoxyethoxy)benzyl]-2,4-dioxo-3,4-dihydroquinazolin-1(2H)-yl]piperidine-1-carbaldehyde No. 43: 4-[6-(2,2-difluoroethoxy)-3-(3,4-dimethoxybenzyl)-2,4-dioxo-3,4-dihydroquinazolin-1(2H)-yl]azepane-1-carbaldehyde No. 47: 4-[6-(2,2-difluoroethoxy)-3-[3-(3-hydroxypropoxy)-4-methoxybenzyl]-2,4-dioxo-3,4-dihydroquinazolin-1(2H)-yl]piperidine-1-carbaldehyde No. 48: 4-[5-chloro-3-(3,4-dimethoxybenzyl)-2,4-dioxo-3,4-dihydroquinazolin-1(2H)-yl]piperidine-1-carbaldehyde No. 49: 4-{3-[3-(cyclopentyloxy)-4-methoxybenzyl]-6-(2,2-difluoroethoxy)-2,4-dioxo-3,4-dihydroquinazolin-1(2H)-yl}piperidine-1-carbaldehyde No. 50: 2-(5-{[6-(2,2-difluoroethoxy)-1-(1-formylpiperidin-4-yl)-2,4-dioxo-1,4-dihydroquinazolin-3(2H)-yl]methyl}-2-methoxyphenoxy)acetamide No. 51: 4-[6-(2,2-difluoroethoxy)-3-(3,4-dimethoxybenzyl)-2,4-dioxo-3,4-dihydroquinazolin-1(2H)-yl]-3-methylpiperidine-1-carbaldehyde No. 52: 3-[6-(2,2-difluoroethoxy)-3-(3,4-dimethoxybenzyl)-2,4-dioxo-3,4-dihydroquinazolin-1(2H)-yl]-8-azabicyclo[3.2.1]octane-8-carbaldehyde No. 56: 4-{3-[4-(cyclopentyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 57: 4-[3-(3-chlorobenzyl)-6-[2-fluoro-1-(fluoromethyl)ethoxy]-2,4-dioxo-3,4-dihydroquinazolin-1(2H)-yl]piperidine-1-carbaldehyde No. 58: 4-[3-(4-chlorobenzyl)-6-[2-fluoro-1-(fluoromethyl)ethoxy]-2,4-dioxo-3,4-dihydroquinazolin-1(2H)-yl]piperidine-1-carbaldehyde No. 59: 4-{3-[3-(cyclopentyloxy)-4-methoxybenzyl]-6-[2-fluoro-1-(fluoromethyl)ethoxy]-2,4-dioxo-3,4-dihydroquinazolin-1(2H)-yl}piperidine-1-carbaldehyde No. 72: 4-[3-(3,4-dimethoxybenzyl)-6-(2-hydroxyethoxy)-2,4-dioxo-3,4-dihydroquinazolin-1(2H)-yl]piperidine-1-carbaldehyde No. 74: 4-[3-(3,4-dichlorobenzyl)-6-[2-fluoro-1-(fluoromethyl)ethoxy]-2,4-dioxo-3,4-dihydroquinazolin-1(2H)-yl]piperidine-1-carbaldehyde No. 76: 4-{3-[(6-chloropyridin-3-yl)methyl]-6-[2-fluoro-1-(fluoromethyl)ethoxy]-2,4-dioxo-3,4-dihydroquinazolin-1(2H)-yl}piperidine-1-carbaldehyde No. 78: 4-[3-(3-chloro-4-methoxybenzyl)-6-[2-fluoro-1-(fluoromethyl)ethoxy]-2,4-dioxo-3,4-dihydroquinazolin-1(2H)-yl]piperidine-1-carbaldehyde No. 79: 4-[3-(3,4-dimethoxybenzyl)-6-(2-fluoroethoxy)-2,4-dioxo-3,4-dihydroquinazolin-1(2H)-yl]piperidine-1-carbaldehyde No. 89: 2-[5-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]acetamide No. 90: 4-{6-[2-fluoro-1-(fluoromethyl)ethoxy]-3-(3-hydroxy-4-methoxybenzyl)-2,4-dioxo-3,4-dihydroquinazolin-1(2H)-yl}piperidine-1-carbaldehyde No. 91: 4-[3-(3,4-dimethoxybenzyl)-6-ethoxy-2,4-dioxo-3,4-dihydroquinazolin-1(2H)-yl]piperidine-1-carbaldehyde No. 97: 4-[5,7-dichloro-3-(3,4-dimethoxybenzyl)-2,4-dioxo-3,4-dihydroquinazolin-1(2H)-yl]piperidine-1-carbaldehyde No. 102: 4-[7-chloro-3-(3,4-dimethoxybenzyl)-2,4-dioxo-3,4-dihydroquinazolin-1(2H)-yl]piperidine-1-carbaldehyde No. 108: 4-{6-[2-fluoro-1-(fluoromethyl)ethoxy]-3-(3-fluoro-4-methoxybenzyl)-2,4-dioxo-3,4-dihydroquinazolin-1(2H)-yl}piperidine-1-carbaldehyde No. 111: 4-[6-(difluoromethoxy)-3-(3,4-dimethoxybenzyl)-2,4-dioxo-3,4-dihydroquinazolin-1(2H)-yl]piperidine-1-carbaldehyde No. 112: 4-[3-(3,4-dimethoxybenzyl)-6-(1-methylethoxy)-2,4-dioxo-3,4-dihydroquinazolin-1(2H)-yl]piperidine-1-carbaldehyde No. 114: 4-{6-[2-fluoro-1-(fluoromethyl)ethoxy]-3-[4-methoxy-3-(1-methylethoxy)benzyl]-2,4-dioxo-3,4-dihydroquinazolin-1(2H)-yl}piperidine-1-carbaldehyde No. 116: 4-{6-[2-fluoro-1-(fluoromethyl)ethoxy]-3-(3-methoxybenzyl)-2,4-dioxo-3,4-dihydroquinazolin-1(2H)-yl}piperidine-1-carbaldehyde No. 117: 4-{3-[3,5-bis(trifluoromethyl)benzyl]-6-[2-fluoro-1-(fluoromethyl)ethoxy]-2,4-dioxo-3,4-dihydroquinazolin-1(2H)-yl}piperidine-1-carbaldehyde No. 118: 4-[3-(3-ethoxybenzyl)-6-[2-fluoro-1-(fluoromethyl)ethoxy]-2,4-dioxo-3,4-dihydroquinazolin-1(2H)-yl]piperidine-1-carbaldehyde No. 124: 4-{3-[3-chloro-4-(2-methoxyethoxy)benzyl]-6-[2-fluoro-1-(fluoromethyl)ethoxy]-2,4-dioxo-3,4-dihydroquinazolin-1(2H)-yl}piperidine-1-carbaldehyde No. 130: 4-[3-(3,4-diethoxybenzyl)-6-[2-fluoro-1-(fluoromethyl)ethoxy]-2,4-dioxo-3,4-dihydroquinazolin-1(2H)-yl]piperidine-1-carbaldehyde No. 131: 4-[3-(4-ethoxy-3-methoxybenzyl)-6-[2-fluoro-1-(fluoromethyl)ethoxy]-2,4-dioxo-3,4-dihydroquinazolin-1(2H)-yl]piperidine-1-carbaldehyde No. 133: 4-{6-[2-fluoro-1-(fluoromethyl)ethoxy]-3-(4-methoxy-3-methylbenzyl)-2,4-dioxo-3,4-dihydroquinazolin-1(2H)-yl}piperidine-1-carbaldehyde No. 134: 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde No. 135: 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde No. 143: 4-{3-[4-(benzyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 145: 4-{6-[2-fluoro-1-(fluoromethyl)ethoxy]-3-(3-methoxy-4-nitrobenzyl)-2,4-dioxo-3,4-dihydroquinazolin-1(2H)-yl}piperidine-1-carbaldehyde No. 155: 4-[3-(4-ethoxybenzyl)-6-[2-fluoro-1-(fluoromethyl)ethoxy]-2,4-dioxo-3,4-dihydroquinazolin-1(2H)-yl]piperidine-1-carbaldehyde No. 158: 4-{6-[2-fluoro-1-(fluoromethyl)ethoxy]-3-[4-(morpholin-4-ylmethyl)benzyl]-2,4-dioxo-3,4-dihydroquinazolin-1(2H)-yl}piperidine-1-carbaldehyde No. 160: 4-{6-[2-fluoro-1-(fluoromethyl)ethoxy]-3-(4-morpholin-4-ylbenzyl)-2,4-dioxo-3,4-dihydroquinazolin-1(2H)-yl}piperidine-1-carbaldehyde No. 165: 4-[3-(biphenyl-4-ylmethyl)-6-[2-fluoro-1-(fluoromethyl)ethoxy]-2,4-dioxo-3,4-dihydroquinazolin-1(2H)-yl]piperidine-1-carbaldehyde No. 166: 4-{6-[2-fluoro-1-(fluoromethyl)ethoxy]-3-[4-(methylsulphanyl)benzyl]-2,4-dioxo-3,4-dihydroquinazolin-1(2H)-yl}piperidine-1-carbaldehyde No. 167: 4-{6-[2-fluoro-1-(fluoromethyl)ethoxy]-2,4-dioxo-3-(4-(pyridin-3-yl)benzyl)-3,4-dihydroquinazolin-1(2H)-yl}piperidine-1-carbaldehyde No. 170: 4-{6-[2-fluoro-1-(fluoromethyl)ethoxy]-3-(3-methoxy-4-methylbenzyl)-2,4-dioxo-3,4-dihydroquinazolin-1(2H)-yl}piperidine-1-carbaldehyde No. 175: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]acetamide No. 178: 4-{6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde No. 183: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylacetamide No. 184: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N,N-dimethylacetamide No. 185: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methoxy-N-methylacetamide No. 186: 4-{3-[4-(cyclopentyloxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde No. 188: 4-{3-[4-(cyclopentyloxy)-3-(1-methylethoxy)benzyl]-6-[2-fluoro-1-(fluoromethyl)ethoxy]-2,4-dioxo-3,4-dihydroquinazolin-1(2H)-yl}piperidine-1-carbaldehyde No. 189: 4-{3-[4-(cyclopentyloxy)-3-propoxybenzyl]-6-[2-fluoro-1-(fluoromethyl)ethoxy]-2,4-dioxo-3,4-dihydroquinazolin-1(2H)-yl}piperidine-1-carbaldehyde No. 190: 4-{3-[4-(cyclopentyloxy)-3-hydroxybenzyl]-6-[2-fluoro-1-(fluoromethyl)ethoxy]-2,4-dioxo-3,4-dihydroquinazolin-1(2H)-yl}piperidine-1-carbaldehyde No. 193: 4-{3-[4-(difluoromethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 194: 4-{3-[4-(difluoromethoxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde No. 200: 4-{6-[2-fluoro-1-(fluoromethyl)ethoxy]-2,4-dioxo-3-(4-(thiophen-3-yl)-benzyl)-3,4-dihydroquinazolin-1(2H)-yl}piperidine-1-carbaldehyde No. 201: 4-{6-[2-fluoro-1-(fluoromethyl)ethoxy]-2,4-dioxo-3-(4-(pyridin-4-yl)benzyl)-3,4-dihydroquinazolin-1(2H)-yl}piperidine-1-carbaldehyde No. 203: 4-{6-[2-fluoro-1-(fluoromethyl)ethoxy]-3-[(1-methyl-1H-indol-6-yl)methyl]-2,4-dioxo-3,4-dihydroquinazolin-1(2H)-yl}piperidine-1-carbaldehyde No. 206: 4-{3-[4-(cyclopropylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 207: 2-[4-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]-N-methylacetamide No. 212: 4-{6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde No. 213: 4-{6-[2-fluoro-1-(fluoromethyl)ethoxy]-2,4-dioxo-3-(4-(pyridin-2-yl)benzyl)-3,4-dihydroquinazolin-1(2H)-yl}piperidine-1-carbaldehyde No. 215: 4-{6-[2-fluoro-1-(fluoromethyl)ethoxy]-2,4-dioxo-3-(4-(thiophen-2-yl)-benzyl)-3,4-dihydroquinazolin-1(2H)-yl}piperidine-1-carbaldehyde No. 216: 4-{6-[2-fluoro-1-(fluoromethyl)ethoxy]-2,4-dioxo-3-(quinolin-7-ylmethyl)-3,4-dihydroquinazolin-1(2H)-yl}piperidine-1-carbaldehyde No. 218: 4-{6-[2-fluoro-1-(fluoromethyl)ethoxy]-3-[(6-methoxynaphthalen-2-yl)methyl]-2,4-dioxo-3,4-dihydroquinazolin-1(2H)-yl}piperidine-1-carbaldehyde No. 223: 4-{3-[4-(1H-benzimidazol-1-yl)benzyl]-6-[2-fluoro-1-(fluoromethyl)ethoxy]-2,4-dioxo-3,4-dihydroquinazolin-1(2H)-yl}piperidine-1-carbaldehyde No. 224: 4-{6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde No. 226: 4-{6-[2-fluoro-1-(fluoromethyl)ethoxy]-3-[3-methoxy-4-(tetrahydrofuran-3-yloxy)benzyl]-2,4-dioxo-3,4-dihydroquinazolin-1(2H)-yl}piperidine-1-carbaldehyde No. 228: 4-[3-{4-[(1-benzylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 230: 4-[3-(1-benzothiophen-5-ylmethyl)-6-[2-fluoro-1-(fluoromethyl)ethoxy]-2,4-dioxo-3,4-dihydroquinazolin-1(2H)-yl]piperidine-1-carbaldehyde No. 232: 4-{6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde No. 233: 4-[3-(3,4-dimethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 234: 4-[3-{4-[(1-acetylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 239: 4-[3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 240: 4-[3-{4-[(4-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 242: 4-[3-{4-[(3-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 243: 4-{6-[2-fluoro-1-(fluoromethyl)ethoxy]-2,4-dioxo-3-(3-(thiophen-3-yl)benzyl)-3,4-dihydroquinazolin-1(2H)-yl}piperidine-1-carbaldehyde No. 245: 4-[3-(4-ethoxy-3-methoxybenzyl)-6-(2-hydroxyethoxy)-2,4-dioxo-3,4-dihydroquinazolin-1(2H)-yl]piperidine-1-carbaldehyde No. 246: 4-[3-{4-[2-(2,3-dihydro-1H-indol-1-yl)-2-oxoethoxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 250: 4-[3-{4-[(3,4-dichlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 251: 4-{6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde No. 254: 4-{3-[3-ethoxy-4-(thiophen-2-ylmethoxy)benzyl]-6-[2-fluoro-1-(fluoromethyl)ethoxy]-2,4-dioxo-3,4-dihydroquinazolin-1(2H)-yl}piperidine-1-carbaldehyde No. 258: 4-[3-(3,4-dimethoxybenzyl)-6-[2-fluoro-1-(hydroxymethyl)ethoxy]-2,4-dioxo-3,4-dihydroquinazolin-1(2H)-yl]piperidine-1-carbaldehyde No. 263: (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid No. 264: 4-{6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde No. 270: 4-{6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde No. 275: 4-{6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde No. 276: 4-{6-[2-fluoro-1-(fluoromethyl)ethoxy]-3-[(1-methyl-3-phenyl-1H-pyrazol-5-yl)methyl]-2,4-dioxo-3,4-dihydroquinazolin-1(2H)-yl}piperidine-1-carbaldehyde No. 278: 4-{6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde No. 279: 4-{6-[2-fluoro-1-(fluoromethyl)ethoxy]-2,4-dioxo-3-[(2-(thiophen-2-yl)pyrimidin-5-yl)methyl]-3,4-dihydroquinazolin-1(2H)-yl}piperidine-1-carbaldehyde No. 280: 4-{6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde No. 282: 4-{6-[2-fluoro-1-(fluoromethyl)ethoxy]-3-[4-(3-methyl-1,2,4-oxadiazol-5-yl)benzyl]-2,4-dioxo-3,4-dihydroquinazolin-1(2H)-yl}piperidine-1-carbaldehyde No. 283: [2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]acetic acid No. 285: 4-{6-[2-fluoro-1-(fluoromethyl)ethoxy]-2,4-dioxo-3-(thieno[2,3-b]pyridin-2-ylmethyl)-3,4-dihydroquinazolin-1(2H)-yl}piperidine-1-carbaldehyde No. 286: 4-{6-[2-fluoro-1-(fluoromethyl)ethoxy]-2,4-dioxo-3-[(6-phenylpyridin-3-yl)methyl]-3,4-dihydroquinazolin-1(2H)-yl}piperidine-1-carbaldehyde No. 287: 4-{6-[2-fluoro-1-(fluoromethyl)ethoxy]-3-[(6-(morpholin-4-yl)pyridin-3-yl)methyl]-2,4-dioxo-3,4-dihydroquinazolin-1(2H)-yl}piperidine-1-carbaldehyde No. 289: 4-{6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde No. 292: 4-{6-[2-fluoro-1-(fluoromethyl)ethoxy]-3-[(1-methyl-5-phenyl-1H-pyrazol-3-yl)methyl]-2,4-dioxo-3,4-dihydroquinazolin-1(2H)-yl}piperidine-1-carbaldehyde No. 294: 4-({6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile No. 295: (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylpropanamide No. 297: 4-{7-fluoro-6-[2-fluoro-1-(fluoromethyl)ethoxy]-2,4-dioxo-3-(4-(thiophen-2-yl)benzyl)-3,4-dihydroquinazolin-1(2H)-yl}piperidine-1-carbaldehyde No. 298: 4-{6-[2-fluoro-1-(fluoromethyl)ethoxy]-3-[3-methoxy-4-(morpholin-4-ylmethyl)benzyl]-2,4-dioxo-3,4-dihydroquinazolin-1(2H)-yl}piperidine-1-carbaldehyde No. 299: 4-{6-[2-fluoro-1-(fluoromethyl)ethoxy]-3-[3-methoxy-4-(piperidin-1-ylmethyl)benzyl]-2,4-dioxo-3,4-dihydroquinazolin-1(2H)-yl}piperidine-1-carbaldehyde No. 300: 4-[3-{4-[(3,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 301: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-ethylacetamide No. 302: (2S)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy] propanoic acid No. 305: 4-{6-[2-fluoro-1-(fluoromethyl)ethoxy]-3-(3-methoxy-4-{[(3R)-2-oxo-1-phenylpyrrolidin-3-yl]oxy}benzyl)-2,4-dioxo-3,4-dihydroquinazolin-1(2H)-yl}piperidine-1-carbaldehyde No. 306: 4-{3-[4-(cyclobutylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 307: 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 308: 4-{7-fluoro-6-[2-fluoro-1-(fluoromethyl)ethoxy]-3-(4-hydroxy-3-methoxybenzyl)-2,4-dioxo-3,4-dihydroquinazolin-1(2H)-yl}piperidine-1-carbaldehyde No. 309: 4-{3-[4-(cyclopropylmethoxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 310: 4-{7-fluoro-6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde No. 311: 4-{7-fluoro-6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde No. 312: 4-[3-(4-ethoxy-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 315: 4-{7-fluoro-6-[2-fluoro-1-(fluoromethyl)ethoxy]-3-{[6-(3-methoxyphenyl)pyridin-3-yl]methyl}-2,4-dioxo-3,4-dihydroquinazolin-1(2H)-yl}piperidine-1-carbaldehyde No. 316: 4-{7-fluoro-6-[2-fluoro-1-(fluoromethyl)ethoxy]-3-{[6-(2-fluorophenyl)pyridin-3-yl]methyl}-2,4-dioxo-3,4-dihydroquinazolin-1(2H)-yl}piperidine-1-carbaldehyde No. 317: 4-{7-fluoro-6-[2-fluoro-1-(fluoromethyl)ethoxy]-3-{[6-(4-fluorophenyl)pyridin-3-yl]methyl}-2,4-dioxo-3,4-dihydroquinazolin-1(2H)-yl}piperidine-1-carbaldehyde No. 318: 4-{7-fluoro-6-[2-fluoro-1-(fluoromethyl)ethoxy]-3-{[6-(4-methoxyphenyl)pyridin-3-yl]methyl}-2,4-dioxo-3,4-dihydroquinazolin-1(2H)-yl}piperidine-1-carbaldehyde No. 319: 4-{7-fluoro-6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde No. 320: 4-{3-[3-ethoxy-4-(thiophen-2-ylmethoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde No. 321: 4-{7-fluoro-6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde No. 322: 4-{7-fluoro-6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde No. 323: 4-{7-fluoro-6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde No. 324: 4-{7-fluoro-6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde No. 325: 4-[3-{4-[2-(2,3-dihydro-1H-indol-1-yl)-2-oxoethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 326: 4-{7-fluoro-6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde No. 327: 4-[3-{4-[(3-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 328: 4-[3-{[6-(3,5-dichlorophenyl)pyridin-3-yl]methyl}-6-[2-fluoro-1-(fluoromethyl)ethoxy]-2,4-dioxo-3,4-dihydroquinazolin-1(2H)-yl]piperidine-1-carbaldehyde No. 329: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile No. 330: 4-{7-fluoro-6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde No. 331: 4-{7-fluoro-6-[2-fluoro-1-(fluoromethyl)ethoxy]-3-{[6-(3-fluorophenyl)pyridin-3-yl]methyl}-2,4-dioxo-3,4-dihydroquinazolin-1(2H)-yl}piperidine-1-carbaldehyde No. 332: 3-[5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)pyridin-2-yl]benzonitrile No. 333: 4-[3-(3,4-diethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 334: 4-[3-{4-[(4-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 335: 4-{7-fluoro-6-[2-fluoro-1-(fluoromethyl)ethoxy]-3-[4-(morpholin-4-ylmethyl)benzyl]-2,4-dioxo-3,4-dihydroquinazolin-1(2H)-yl}piperidine-1-carbaldehyde No. 336: 4-{7-fluoro-6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde No. 337: 4-{7-fluoro-6-[2-fluoro-1-(fluoromethyl)ethoxy]-3-(4-(morpholin-4-yl)-benzyl)-2,4-dioxo-3,4-dihydroquinazolin-1(2H)-yl}piperidine-1-carbaldehyde No. 338: 4-{7-fluoro-6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde No. 339: 4-{3-[4-(1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde No. 340: 5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxybenzonitrile No. 341: 3-(3,4-dimethoxybenzyl)-6-[2-fluoro-1-(fluoromethyl)ethoxy]-1-(1-formylpiperidin-4-yl)-2,4-dioxo-1,2,3,4-tetrahydroquinazoline-7-carbonitrile No. 342: 4-[3-(4-bromobenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 343: 4-[3-{4-[(3,4-dichlorobenzyl)oxy]-3-(2-methoxyethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde No. 344: 4-{3-[4-(benzyloxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde No. 345: 4-[3-{4-[(3,4-dichlorobenzyl)oxy]-3-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 349: 4-[3-{4-[(3,4-dichlorobenzyl)oxy]-3-(2-fluoroethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde No. 350: 4-[3-{4-[(2-chloro-4-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 351: 4-[3-{4-[(2,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 352: 4-[3-{4-[(2-chloro-6-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 353: 4-[3-{4-[(2,6-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 354: 4-[3-{4-[(2-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 355: 4-[7-fluoro-3-{4-[(2-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 357: 2-[(3,4-dichlorobenzyl)oxy]-5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzonitrile No. 358: 4-[3-{4-[(3,4-dichlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 360: 4-{7-fluoro-6-[2-fluoro-1-(fluoromethyl)ethoxy]-2,4-dioxo-3-[4-(2-phenylethyl)benzyl]-3,4-dihydroquinazolin-1(2H)-yl}piperidine-1-carbaldehyde No. 362: 4-[3-{4-[(4,5-dichloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 369: 4-[3-{4-[(4-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 371: 4-[3-{3-chloro-4-[(4-chlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 373: 4-[3-{3-chloro-4-[(2,4-dichlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 375: 4-[7-fluoro-3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 376: 4-[3-{4-[(3,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 377: 4-[3-(4-{[4-chloro-3-(trifluoromethyl)benzyl]oxy}-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 379: 4-[3-{4-[(3-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 380: 4-[3-{4-[(3,5-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 381: 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 382: 4-[3-{4-[(3-chloro-5-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 383: 4-{7-fluoro-6-[2-fluoro-1-(fluoromethyl)ethoxy]-3-(3-methoxy-4-{[4-(trifluoromethyl)benzyl]oxy}benzyl)-2,4-dioxo-3,4-dihydroquinazolin-1(2H)-yl}piperidine-1-carbaldehyde No. 384: 4-[3-{4-[(2,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 385: 4-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile No. 386: 3-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile No. 387: 4-[3-{4-[(4-chloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 388: 4-[3-{4-[1-(3,4-dichlorophenyl)ethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 389: 4-{7-fluoro-6-[2-fluoro-1-(fluoromethyl)ethoxy]-3-{4-[(3-hydroxybenzyl)oxy]-3-methoxybenzyl}-2,4-dioxo-3,4-dihydroquinazolin-1(2H)-yl}piperidine-1-carbaldehyde No. 390: 4-[7-fluoro-3-{4-[(3-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 391: 4-[3-{4-[(3,4-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 392: 4-{3-[4-(5,6-dichloro-1H-benzimidazol-1-yl)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 393: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)phenyl 3,4-dichlorobenzenesulphonate No. 394: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 3,4-dichlorobenzene-sulphonate No. 403: 3,4-dichloro-N-[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl]benzamide Another subject-matter of the present invention is processes for the preparation of a compound of general formula (I).

The compounds of the invention can be prepared by the methods illustrated in the following Schemes 1 to 4.

In that which follows, the term "leaving group" is understood to mean a group which can be easily substituted, with departure of an electron pair, by cleavage of a heterocyclic bond. This group can thus be easily replaced by another group, for example during a substitution reaction. Such leaving groups are, for example, halogens or an activated hydroxyl group, such as a mesylate, tosylate, triflate, and the like. Examples of leaving groups and references for their preparation are given in "Advanced Organic Chemistry", J. March, 3rd Edition, Wiley Interscience, pp. 310-316.

The term "protective group PG" is understood to mean a group which makes it possible to prevent the reactivity of a function group or position during a chemical reaction which may affect it and which restores the molecule after cleavage according to methods known to a person skilled in the art.

The term "temporary protective group for amines or alcohols" is understood to mean the protective groups such as those described in Protective Groups in Organic Synthesis, Greene T. W. and Wuts P. G. M., published by Wiley Intersciences, 1999, and in Protecting Groups, Kocienski P. J., 1994, Georg Thieme Verlag.

Mention may be made, for example, of temporary protective groups for amines: benzyls or carbamates (such as tert-butoxycarbonyl, cleavable in an acid medium, or benzyloxycarbonyl, cleavable by hydrogenolysis), temporary protective groups for carboxylic acids: hydrogenolysable alkyl esters (such as methyl or ethyl or tert-butyl esters which can be hydrolysed in a basic or acid medium) and benzyl esters, temporary protective groups for alcohols or phenols, such as tetrahydropyranyl, methyloxymethyl or methylethoxymethyl, tert-butyl and benzyl ethers, or temporary protective groups for carbonyl derivatives, such as linear or cyclic acetals, such as, for example, 1,3-dioxan-2-yl or 1,3-dioxolan-2-yl; and reference may be made to the well known general methods described in Protective Groups, cited above.

A person skilled in the art will be in the position to choose the appropriate protective groups according to the circumstances. The compounds of formula (I) can comprise precursor groups for other functional groups which are generated subsequently in one or more other stages.

In the general synthetic schemes which follow, the starting compounds and the reactants, when their method of preparation is not described, are commercially available or are described in the literature or else can be prepared according to methods which are described therein or which are known to a person skilled in the art.

The pure enantiomers of the compounds of the invention can be obtained from enantiomerically pure precursors or else by chiral phase chromatography or else, when the compounds comprise acid or amine functional groups, by selective crystallizations of diastereoisomeric salts obtained by reaction of the compounds (I) with chiral amines or chiral acids respectively.

According to one embodiment of the invention, the compounds of general formula (I) can be obtained according to the following Schemes 1 to 4. Out of concern for clarity, the group $R_4$ has been chosen as being a hydrogen, p and p' represent 1 and 2 respectively and the $R_2$ and $R_3$ groups have been set as indicated in the schemes. However, it is to be understood that $R_4$ can be as defined in the general formula (I), and $R_2$ and $R_3$ can have the positions indicated in the general formula (I) and that p and p' can be as defined in the general formula (I).

The synthetic routes described below serve solely as illustration and are under no circumstances limiting. A person skilled in the art can apply without difficulty the teaching below to the compounds of formula (I) for which R, $R_1$, $R_2$, $R_3$, $R_4$, Ra, Rb, Rc, m, n, p, p', and q are as defined in the general formula (I).

According to Scheme 1, the compound of formula (IV) is obtained by a reductive amination reaction by reacting a compound of formula (II), in which R' represents a $(C_1-C_6)$ alkyl group and $R_2$ is as defined for the compound of formula (I) with a compound of formula (III) in an acid medium and in the presence of a reducing agent, such as sodium triacetoxyborohydride. The PG group of the compound of formula (III) is a protective group for the amine functional group which may advantageously be tert-butoxycarbonyl (boc). The compound of formula (IV) thus formed is subsequently acylated, according to methods well known to a person skilled in the art, with an alkyl or aryl chloroformate to give the compound of formula (V) in which R" represents a $(C_1-C_6)$ alkyl group or an aryl group which is substituted. A hydrolysis reaction in a basic medium makes it possible to obtain the compounds of formula (VI) which, by a coupling reaction with a compound of formula (VII), in which $R_3$ is as defined for the compound of formula (I), results in the compounds of formula (VIII). An intramolecular cyclization reaction in the basic medium makes it possible to obtain the quinazolinedione derivatives of formula (IX). The protective group PG for the amine functional group is subsequently cleaved, for example in acid medium when PG is a boc, to give the compounds of formula (Ia) which give, by an acylation reaction, the compounds of formula (Ib).

The compounds of formula (Ia) are compounds of formula (I) and can act as intermediate for other compounds of formula (I), such as the compounds of formula (Ib).

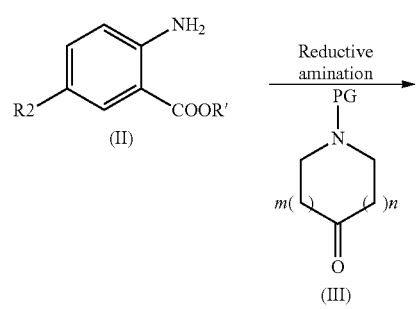

Scheme 1

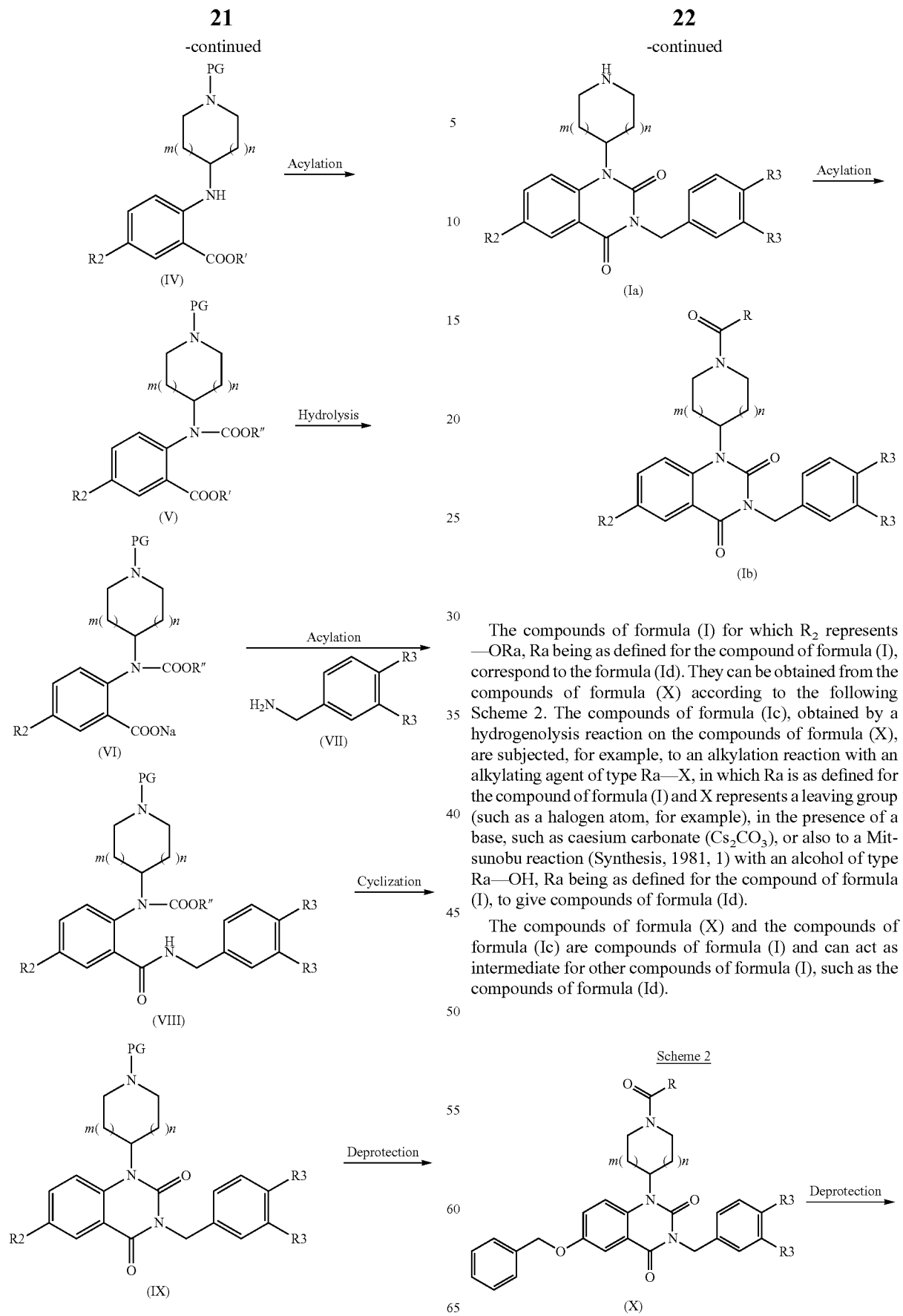

The compounds of formula (I) for which $R_2$ represents —ORa, Ra being as defined for the compound of formula (I), correspond to the formula (Id). They can be obtained from the compounds of formula (X) according to the following Scheme 2. The compounds of formula (Ic), obtained by a hydrogenolysis reaction on the compounds of formula (X), are subjected, for example, to an alkylation reaction with an alkylating agent of type Ra—X, in which Ra is as defined for the compound of formula (I) and X represents a leaving group (such as a halogen atom, for example), in the presence of a base, such as caesium carbonate ($Cs_2CO_3$), or also to a Mitsunobu reaction (Synthesis, 1981, 1) with an alcohol of type Ra—OH, Ra being as defined for the compound of formula (I), to give compounds of formula (Id).

The compounds of formula (X) and the compounds of formula (Ic) are compounds of formula (I) and can act as intermediate for other compounds of formula (I), such as the compounds of formula (Id).

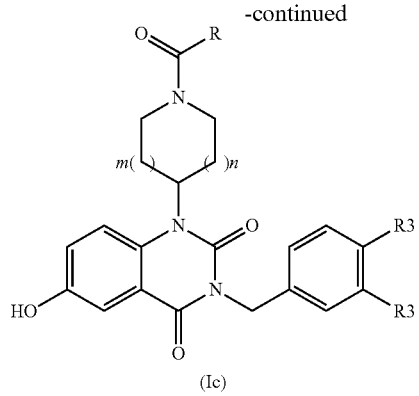

(Ic)

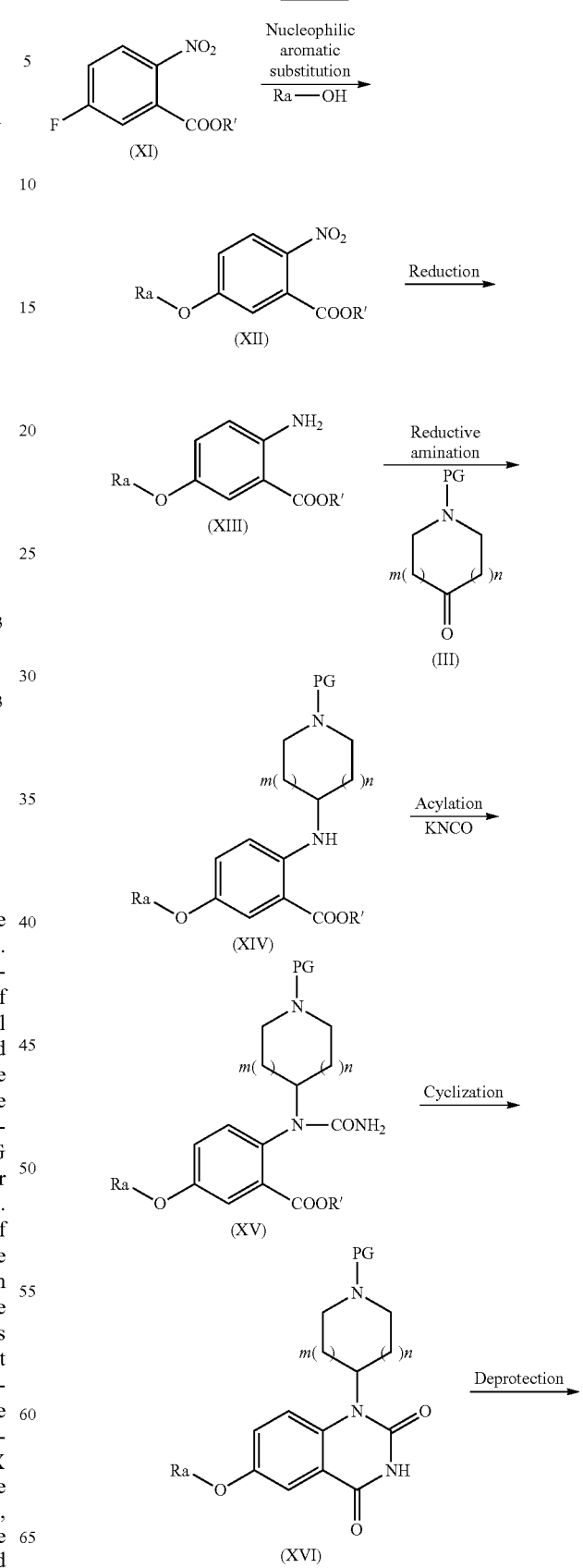

Alternatively, the compounds of formula (Id) can be obtained by following the procedure described in Scheme 3.

The compounds of formula (XII) are obtained by a nucleophilic aromatic substitution reaction involving a compound of formula (XI), in which R' is as defined above, and an alcohol of type Ra—OH, in which Ra is as defined for the compound of formula (I), in the presence of a base. The reduction of the nitro group of the compounds of formula (XII) results in the corresponding anilino derivatives (XIII). A reductive amination reaction with a compound of formula (III), in which PG is a protective group for amine functional groups, such as, for example, boc, results in the compounds of formula (XIV). The compounds of formula (XV) are obtained by reaction of a compound of formula (XIV) with potassium isocyanate (KNCO) in an acid medium. An intramolecular cyclization reaction in a basic medium makes it possible to obtain the compounds of formula (XVI). The protective group PG is cleaved by methods well known to a person skilled in the art to give the compounds of formula (XVII). An acylation reaction results in the compounds of formula (XVIII). Finally, the compounds of formula (Id) are obtained either by an alkylation reaction with a derivative of type (XIX), in which X represents a leaving group, such as a halogen atom, in the presence of a base, such as, for example, caesium carbonate, or also by a Mitsunobu reaction with a benzyl alcohol of type (XX). In the compounds (XIX) and (XX), $R_3$ is as defined above.

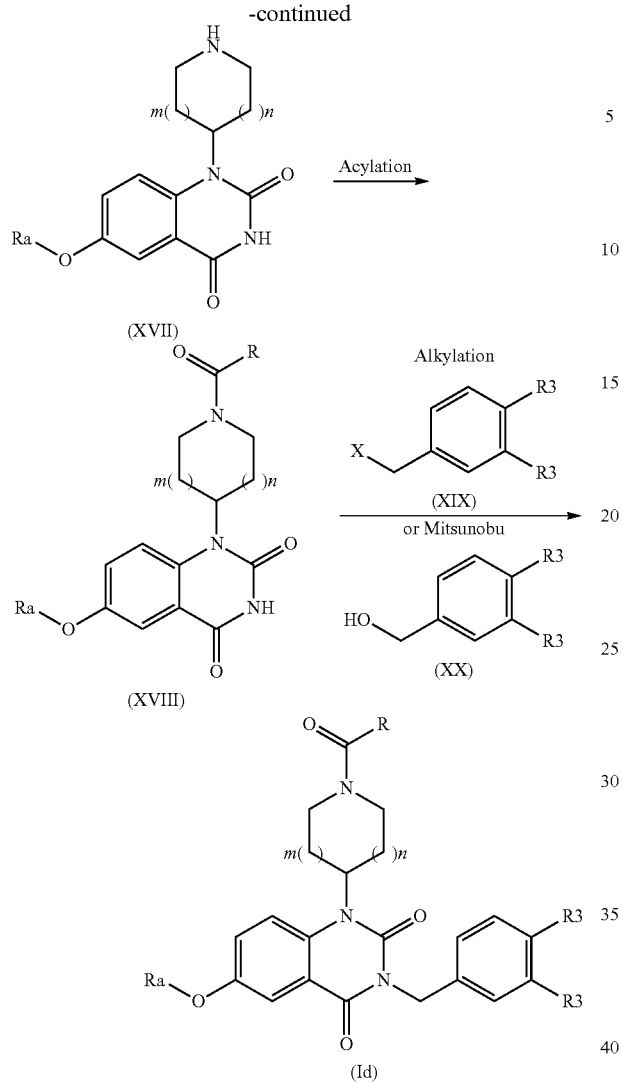

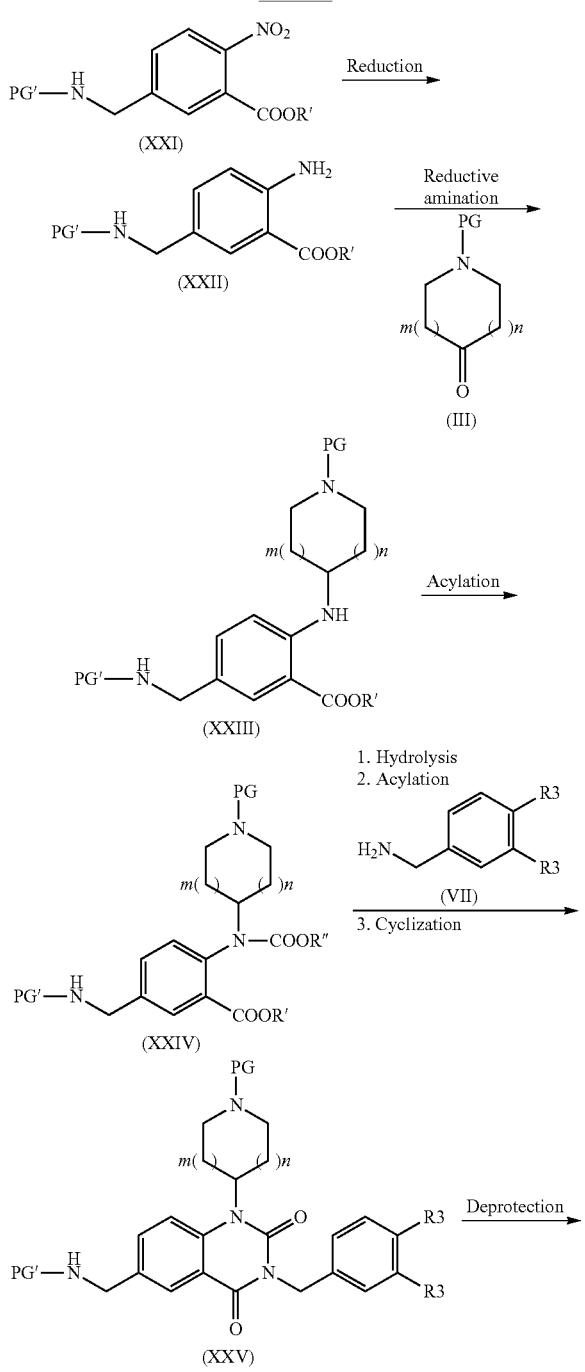

by a coupling reaction with a compound of formula (VII), in which $R_3$ is as defined for the compound of formula (I), followed by an intramolecular cyclization reaction in a basic medium. The PG' group (preferably a boc) is subsequently cleaved in an acid medium to result in the compounds of formula (XXVI) which, by acylation, give compounds of formula (XXVII), in which Rb is as defined for the compound of formula (I). The PG protective group of (XXVII) is cleaved by a hydrogenolysis reaction to give the compounds of formula (Ie). Finally, the compounds of formula (If) are obtained by an acylation reaction on the compounds of formula (Ie).

The compounds of formula (Ie) and (If), in which $R_2$ more particularly represents a group of type —$CH_2$—NHC(O)Rb, Rb being defined as in the compound of formula (I), can be prepared according to the following Scheme 4.

It is understood that, in Scheme 3, the $R_2$ group illustrated is of —O—Ra type and is in the 6 position of the quinoazolinedione structure (see, for example, compound (XVIII)) but that it is also possible to have a second $R_2$ group, as defined in the general formula (I), in the 7 position of the same quinazolinedione group.

The reduction of the nitro group of the compounds of type (XXI), in which R' and PG' are as defined above, the PG' group advantageously being boc, results in the corresponding anilino derivatives (XXII) which, by a reductive amination reaction in which they react in an acid medium and advantageously in the presence of a reducing agent, such as sodium triacetoxyborohydride, with a compound of formula (III), in which PG represents a benzyloxycarbonyl protective group for amines, give compounds of formula (XXIII). An acylation reaction with an alkyl or aryl chloroformate, in which R" represents a ($C_1$-$C_6$) alkyl group or an aryl group which is substituted, results in the compounds of formula (XXIV). The quinazolinedione analogues of formula (XXV) can be obtained by a hydrolysis reaction in a basic medium and then The following procedures and examples describe the preparation of some compounds in accordance with the invention. These procedures and examples are not limiting and serve only to illustrate the present invention.

In the procedures and examples below:

the mass spectra are produced on a quadrupole spectrometer of Platform LCZ type (Waters) or of ZQ 4000 type (Waters) in positive electrospray ionization mode;

the NMR (nuclear magnetic resonance) spectra are produced on a Fourier transform spectrometer (Bruker) at a temperature of 300° C. (exchangeable protons not recorded);

s=singlet, d=doublet, m=multiplet, br=broad signal t=triplet, q=quartet

DMSO-$d_6$=deuterated dimethyl sulphoxide, $CDCl_3$=deuterated chloroform.

The mixtures of solvents are quantified in volumetric ratios.

The NMR spectra and mass spectra confirm the structures of the compounds obtained according to the examples below.

In the examples which follow, the following abbreviations are used:

ACN: acetonitrile

AcOEt: ethyl acetate

AcOH: acetic acid

DBU: 1,8-diazabicyclo[5.4.0]undec-7-ene

DCM: dichloromethane

DCE: 1,2-dichloroethane

DIAD: diisopropyl azodicarboxylate

DIEA: diisopropylamine

DMF: N,N-dimethylformamide

EtOH: ethanol

HBTU: O-(benzotriazol-1-yl)-N,N,N',N'-tetramethyluronium hexafluorophosphate

IBCF: isobutyl chloroformate

MeOH: methanol $NaBH(OAc)_3$: sodium triacetoxyborohydride

AT: ambient temperature min: minute

THF: tetrahydrofuran $NEt_3$: triethylamine

TFA: trifluoroacetic acid

It is obvious that a person skilled in the art will be in a position to choose, in the light of his knowledge and the literature, other appropriate protective groups which make possible the introduction of all the groups described in the general formula (I).

When the compound of formula (I) comprises a bridged ring, it can be obtained without distinction by one of the synthetic routes described above.

EXAMPLES

The following examples describe the preparation of some compounds in accordance with the invention. These examples are not limiting and serve only to illustrate the present invention. The numbers of the compounds in the examples refer to those given in the table below, in which the

Example 1

Compound No. °6

Preparation of {[3-(3,4-dimethoxybenzyl)-1-(1-formylpiperidin-4-yl)-2,4-dioxo-1,2,3,4-tetrahydroquinazolin-6-yl]oxy}acetonitrile

Stage 1.1:

1,1-Dimethylethyl 4-{[4-(benzyloxy)-2-(methoxycarbonyl)phenyl]amino}piperidine-1-carboxylate

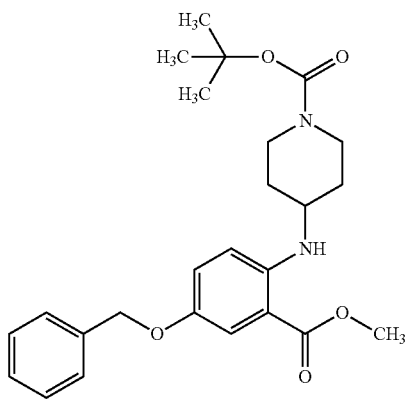

A mixture of 2 g of methyl 2-amino-5-(benzyloxy)benzoate, 3.1 g of 1,1-dimethylethyl 4-oxopiperidine-1-carboxylate and 3.29 g of NaBH(OAc)$_3$ in 10 ml of AcOH is irradiated under a microwave field (Biotage Initiator Sixty) at 110° C. for 20 min. The same reaction is repeated with two other lots of 2 g of methyl 2-amino-5-(benzyloxy)benzoate. The three reaction media are combined. The combined product is taken up in AcOEt. The organic phase is washed with water, with a saturated NH$_4$Cl solution and with a saturated NaHCO$_3$ solution, dried over Na$_2$SO$_4$ and filtered, and the solvent is evaporated under reduced pressure. The residue is chromatographed on silica gel, elution being carried out with an AcOEt/heptane mixture, (5/95, v/v) as far as (30/70, 10 v/v), to give 10.2 g of the expected product.

Stage 1.2:

1,1-Dimethylethyl 4-{[4-(benzyloxy)-2-(methoxycarbonyl)phenyl][(2-methyl-propoxy)carbonyl]amino}piperidine-1-carboxylate

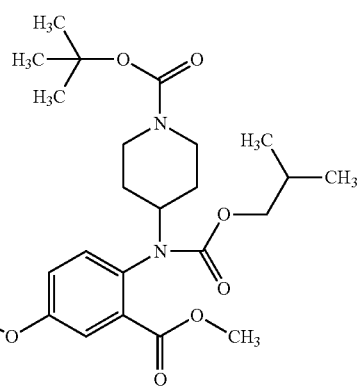

A mixture of 2 g of 1,1-dimethylethyl 4-{[4-(benzyloxy)-2-(methoxycarbonyl)phenyl]amino}piperidine-1-carboxylate obtained in stage 1.1, 0.87 ml of DIEA, 1.78 ml of IBCF and 1 g of NaOH in 10 ml of DCE is irradiated under a microwave field at 80° C. for 30 min. The same reaction is repeated with 4 other lots of 2 g of 1,1-dimethylethyl 4-{[4-(benzyloxy)-2-(methoxycarbonyl)phenyl]amino}piperidine-1-carboxylate. The 5 reaction media are combined. The combined product is taken up in AcOEt and filtered, and the filtrate is evaporated under reduced pressure. The residue is chromatographed on silica gel, elution being carried out with an AcOEt/heptane mixture, (10/90, v/v) as far as (50/50, v/v), to give 9.3 g of the expected product.

Stage 1.3:

Sodium salt of 5-(benzyloxy)-2-({1-[(1,1-dimethylethoxy)carbonyl]-piperidin-4-yl}[(2-methylpropoxy)carbonyl]amino)benzoic acid

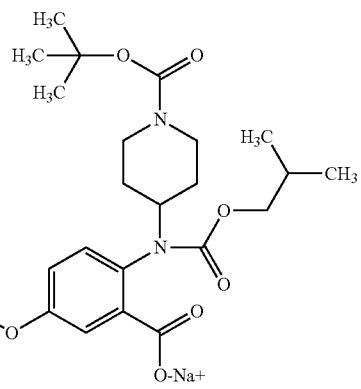

A mixture of 9.3 g of 1,1-dimethylethyl 4-{[4-(benzyloxy)-2-(methoxycarbonyl)phenyl][(2-methylpropoxy)carbonyl]amino}piperidine-1-carboxylate obtained in stage 1.2 and 34.4 ml of 2N NaOH in 57 ml of MeOH is heated at 100° C. for 3 h 00. The solution is evaporated under reduced pressure and DCM is added. Drying is carried out over Na₂SO₄, filtration is carried out and the solvent is evaporated under reduced pressure to give 8.7 g of the expected product.

Stage 1.4:

1,1-Dimethylethyl 4-[{4-(benzyloxy)-2-[(3,4-dimethoxybenzyl)carbamoyl]phenyl}(isobutoxycarbonyl)amino]piperidine-1-carboxylate

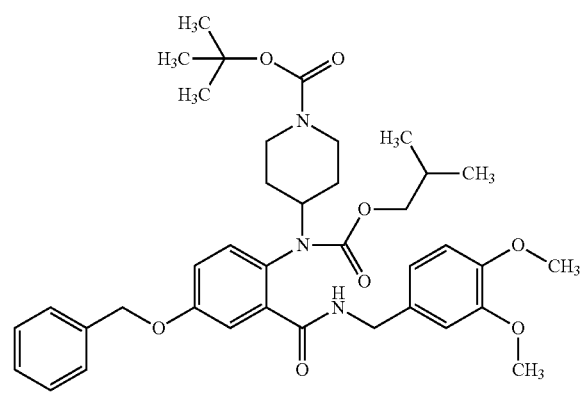

A mixture of 6 g of sodium salt of 5-(benzyloxy)-2-({1-[(1,1-dimethylethoxy)carbonyl]piperidin-4-yl}[(2-methylpropoxy)carbonyl]amino)benzoic acid obtained in stage 1.3 and 4.42 g of DIEA in 250 ml of DMF is stirred at AT for 15 min. 6.48 g of HBTU are added and the mixture is left stirring for 30 min. 2.48 g of veratrylamine are added and the reaction mixture is stirred for 48 h 00. It is evaporated under reduced pressure, the residue is taken up in AcOEt, washed with a saturated NH₄Cl solution and with a saturated NaHCO₃ solution, dried over Na₂SO₄ and filtered, and the solvent is evaporated under reduced pressure. The residue is chromatographed on silica gel, elution being carried out with an AcOEt/heptane mixture, (20/80, v/v) as far as (60/40, v/v), to give 7.5 g of expected product.

Stage 1.5:

1,1-Dimethylethyl 4-[6-(benzyloxy)-3-(3,4-dimethoxybenzyl)-2,4-dioxo-3,4-dihydroquinazolin-1(2H)-yl]piperidine-1-carboxylate

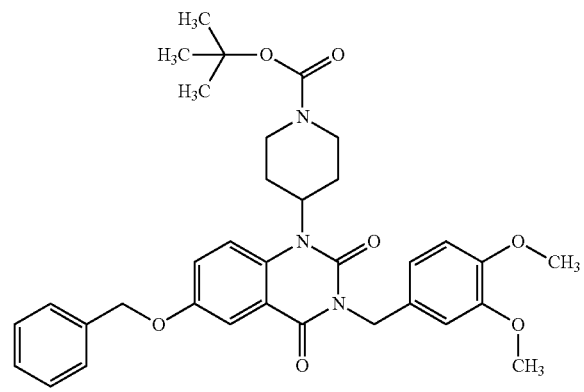

A mixture of 2.5 g of 1,1-dimethylethyl 4-[{4-(benzyloxy)-2-[(3,4-dimethoxybenzyl)carbamoyl]phenyl}(isobutoxycarbonyl)amino]piperidine-1-carboxylate obtained in stage 1.4 and 7.4 g of NaOH in 18.5 ml of DCE is irradiated under a microwave field at 110° C. for 30 min. The same reaction is repeated with 2 other lots of 2.5 g of 1,1-dimethylethyl 4-[{4-(benzyloxy)-2-[(3,4-dimethoxybenzyl)carbamoyl]phenyl}-(isobutoxycarbonyl)amino]piperidine-1-carboxylate. The 3 reaction media are combined. The combined product is taken up in DCM, washed with water, dried over Na₂SO₄ and filtered, and the solvent is evaporated under reduced pressure to give 6.6 g of expected product.

Stage 1.6:

6-(Benzyloxy)-3-(3,4-dimethoxybenzyl)-1-(piperidin-4-yl)quinazoline-2,4(1H,3H)-dione

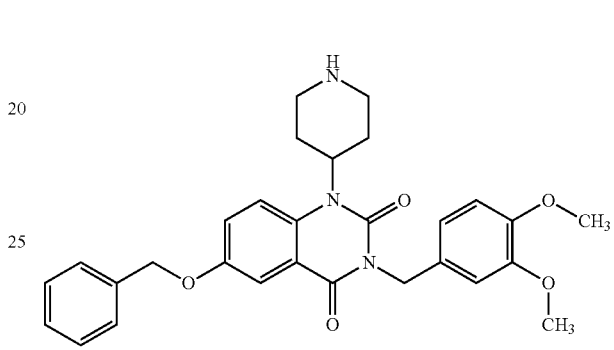

A mixture of 3.5 g of 1,1-dimethylethyl 4-[6-(benzyloxy)-3-(3,4-dimethoxybenzyl)-2,4-dioxo-3,4-dihydroquinazolin-1(2H)-yl]piperidine-1-carboxylate obtained in stage 1.5 and 25 ml of TFA in 50 ml of DCM is stirred at AT for 2 h 00. The mixture is neutralized with K₂CO₃. It is filtered and the filtrate is evaporated under reduced pressure. The residue is taken up in DCM and washed with a saturated NaHCO₃ solution and then with an 8% NaOH solution. The solution is dried over Na₂SO₄ and filtered, and the solvent is evaporated under reduced pressure to give 2.67 g of the expected product.

Stage 1.7:

4-[6-(Benzyloxy)-3-(3,4-dimethoxybenzyl)-2,4-dioxo-3,4-dihydroquinazolin-1(2H)-yl]piperidine-1-carbaldehyde

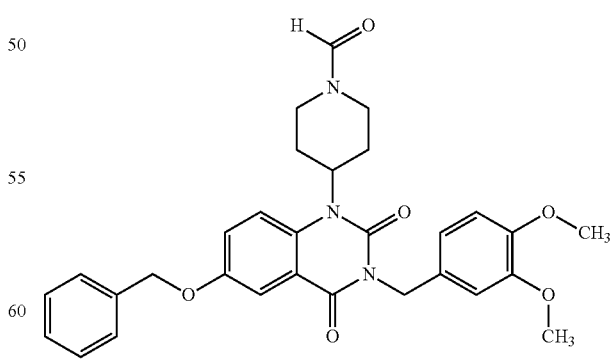

A mixture of 0.6 g of 6-(benzyloxy)-3-(3,4-dimethoxybenzyl)-1-(piperidin-4-yl)quinazoline-2,4(1H,3H)-dione obtained in stage 1.7 and 0.113 g of ammonium formate in 5 ml of ACN is irradiated under a microwave field at 140° C. for 1 h 00. The mixture is filtered and the filtrate is evaporated under reduced pressure to give 0.62 g of the expected product.

Stage 1.8: Compound No. 5:

4-[3-(3,4-Dimethoxybenzyl)-6-hydroxy-2,4-dioxo-3,4-dihydroquinazolin-1(2H)-yl]piperidine-1-carbaldehyde

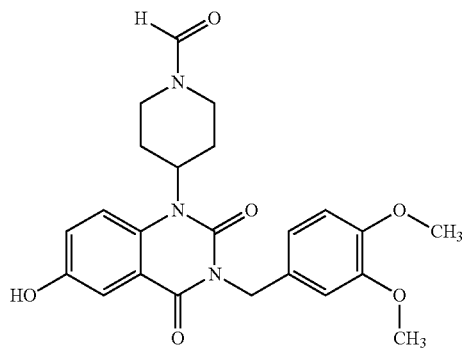

A mixture of 0.618 g of 4-[6-(benzyloxy)-3-(3,4-dimethoxybenzyl)-2,4-dioxo-3,4-dihydroquinazolin-1(2H)-yl]piperidine-1-carbaldehyde obtained in stage 1.7, 0.44 g of ammonium formate and 0.124 g of Pd/C (10%) in 10 ml of EtOH purged beforehand with nitrogen is irradiated under a microwave field at 80° C. for 2 h 00. The mixture is filtered and the filtrate is evaporated under reduced pressure to give 0.513 g of the expected product.

Stage 1.9: Compound No. 6

{[3-(3,4-Dimethoxybenzyl)-1-(1-formylpiperidin-4-yl)-2,4-dioxo-1,2,3,4-tetrahydroquinazolin-6-yl]oxy}acetonitrile

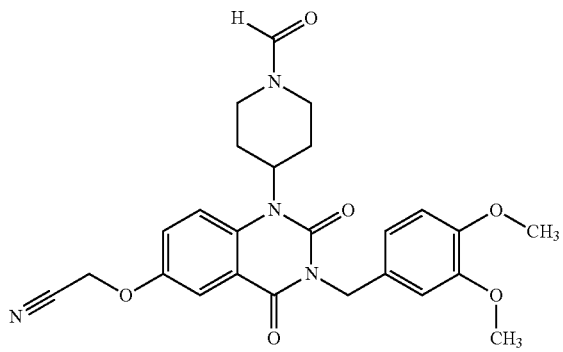

0.17 g of 4-[3-(3,4-dimethoxybenzyl)-6-hydroxy-2,4-dioxo-3,4-dihydroquinazolin-1(2H)-yl]piperidine-1-carbaldehyde obtained in stage 1.8 and 0.25 g of Cs₂CO₃ in 3 ml of DMF are stirred for 15 min at AT. 0.056 g of bromoacetonitrile is added and the reaction mixture is subsequently irradiated under a microwave field at 100° C. for 15 min. It is filtered and evaporated under reduced pressure. The residue is chromatographed on silica gel, elution being carried out with an MeOH/DCM mixture, (1/99, v/v) as far as (4/96, v/v), to give 0.112 g of the expected product.

Example 2

Compound No. 3

Preparation of {[1-(1-acetylpiperidin-4-yl)-3-(3,4-dimethoxybenzyl)-2,4-dioxo-1,2,3,4-tetrahydroquinazolin-6-yl]oxy}acetonitrile

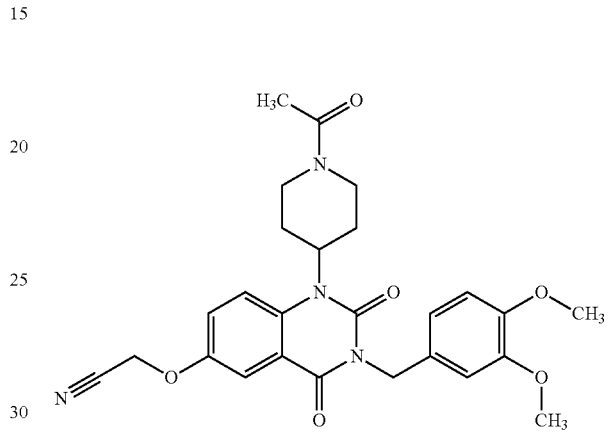

Stage 2.1:

1-(1-Acetylpiperidin-4-yl)-6-(benzyloxy)-3-(3,4-dimethoxybenzyl)quinazoline-2,4(1H,3H)-dione

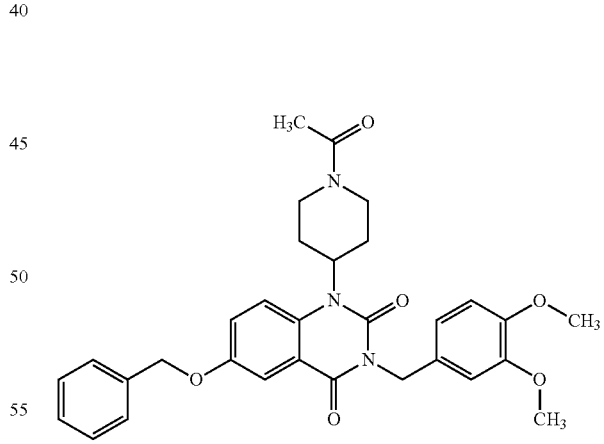

0.14 g of acetyl chloride is added to a mixture of 0.6 g of 6-(benzyloxy)-3-(3,4-dimethoxybenzyl)-1-(piperidin-4-yl)quinazoline-2,4(1H,3H)-dione obtained according to stage 1.6 and 0.24 g of NEt₃ in 10 ml of DCM cooled to 0° C. The mixture is stirred at AT overnight. It is washed twice with a saturated NH₄Cl solution and filtered, and then the filtrate is evaporated under reduced pressure to give 0.64 g of the expected product.

Stage 2.2: Compound No. 2

1-(1-Acetylpiperidin-4-yl)-3-(3,4-dimethoxybenzyl)-6-hydroxyquinazoline-2,4(1H,3H)-dione

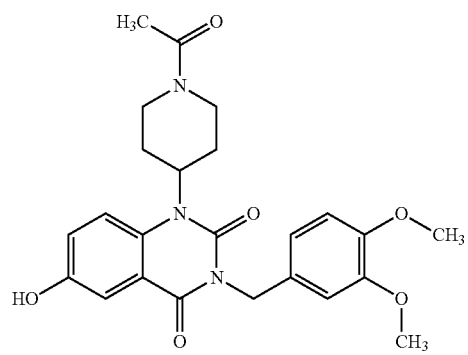

A mixture of 0.64 g of 1-(1-acetylpiperidin-4-yl)-6-(benzyloxy)-3-(3,4-dimethoxybenzyl)quinazoline-2,4(1H,3H)-dione obtained in stage 2.1, 0.44 g of ammonium formate and 0.125 g of Pd/C (10%) in 10 ml of EtOH purged beforehand with nitrogen is irradiated under a microwave field at 80° C. for 2 h. 00. The mixture is filtered and the filtrate is evaporated under reduced pressure to give 0.48 g of the expected product.

Stage 2.3: Compound No. 3

{[1-(1-Acetylpiperidin-4-yl)-3-(3,4-dimethoxybenzyl)-2,4-dioxo-1,2,3,4-tetrahydroquinazolin-6-yl]oxy}acetonitrile

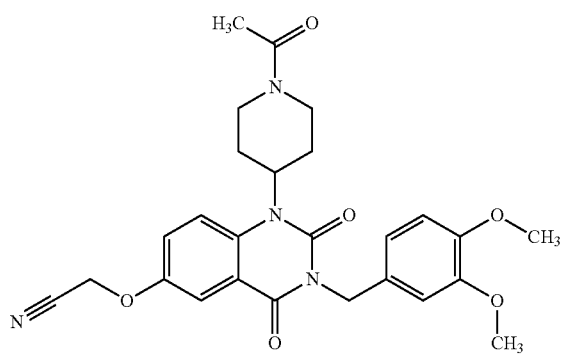

0.12 g of 1-(1-acetylpiperidin-4-yl)-3-(3,4-dimethoxybenzyl)-6-hydroxyquinazoline-2,4(1H,3H)-dione obtained in stage 2.2 and 0.172 g of $Cs_2CO_3$ in 3 ml of DMF are stirred for 15 min at AT. 0.038 g of bromoacetonitrile is added and the reaction mixture is subsequently irradiated under a microwave field at 100° C. for 15 min. It is filtered and the filtrate is evaporated under reduced pressure. The residue is chromatographed on silica gel, elution being carried out with an MeOH/DCM mixture, (1/99, v/v) as far as (4/96, v/v), to give 0.094 g of the expected product.

Example 3

Compound No. 34

Synthesis of 4-[3-(4-chlorobenzyl)-6-(2,2-difluoroethoxy)-2,4-dioxo-3,4-dihydroquinazolin-1(2H)-yl]piperidine-1-carbaldehyde

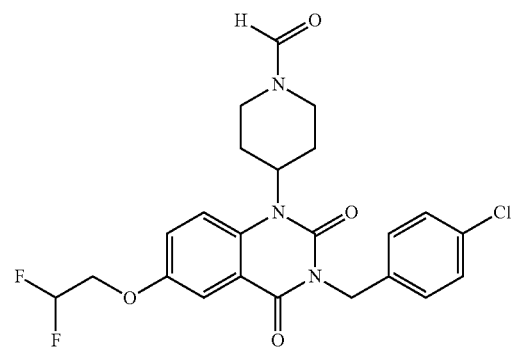

Stage 3.1:

Methyl 5-(2,2-difluoroethoxy)-2-nitrobenzoate

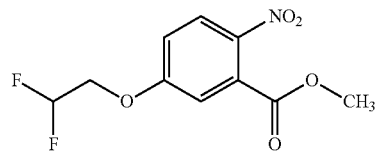

8.53 g of 2,2-difluoroethanol are added to a solution of 17.31 g of methyl 5-fluoro-2-nitrobenzoate, 9.64 g of $NEt_3$ and 32.71 g of 2,8,9-triisobutyl-2,5,8,9-tetraaza-1-phosphabicyclo[3.3.3]undecane in 250 ml of anhydrous THF. The mixture is stirred at AT for 30 min. The solvent is evaporated under reduced pressure. Water is added and extraction is carried out with AcOEt. The extract is washed with a 1N aqueous HCl solution, with water and then with a saturated NaCl solution. It is dried over $MgSO_4$ and filtered, and the solvent is evaporated under reduced pressure to give 21 g of the expected product.

Stage 3.2:

Methyl 2-amino-5-(2,2-difluoroethoxy)benzoate

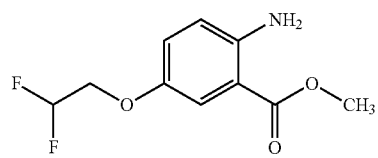

21 g of methyl 5-(2,2-difluoroethoxy)-2-nitrobenzoate obtained in stage 3.1 and 1 g of Pd/C (10%) in a mixture of 300 ml of AcOEt, 50 ml of EtOH and 5 ml of AcOH are stirred at AT under a hydrogen atmosphere for 24 h 00.

The mixture is filtered and evaporated under reduced pressure to give 18.6 g of the expected product.

Stage 3.3:

1,1-Dimethylethyl 4-{[4-(2,2-difluoroethoxy)-2-(methoxycarbonyl)phenyl]amino}piperidine-1-carboxylate

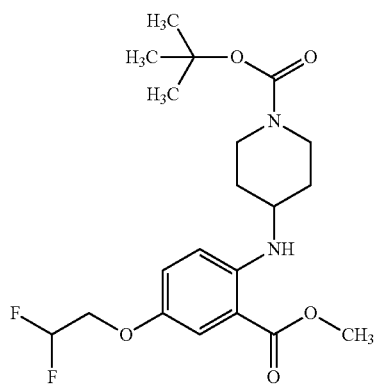

A mixture of 4 g of methyl 2-amino-5-(2,2-difluoroethoxy)benzoate and 6.88 g of 1,1-dimethylethyl 4-oxopiperidine-1-carboxylate obtained in stage 3.2 in 15 ml of AcOH is heated at 90° C. for 10 min. It is allowed to cool to AT and 7.3 g of NaBH(OAc)$_3$ are added. The mixture is left stirring at AT for 12 h 00. It is extracted with AcOEt and the extract is washed with a saturated K$_2$CO$_3$ solution and then with water. It is dried over MgSO$_4$, filtered and evaporated under reduced pressure to give 6.63 g of the expected product.

Stage 3.4:

1,1-Dimethylethyl 4-{carbamoyl[4-(2,2-difluoroethoxy)-2-(methoxycarbonyl)-phenyl]amino}piperidine-1-carboxylate

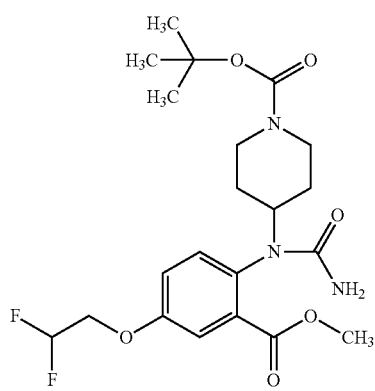

1.95 g of potassium isocyanate in solution of 4 ml of water are added to a solution of 6.63 g of 1,1-dimethylethyl 4-{[4-(2,2-difluoroethoxy)-2-(methoxycarbonyl)phenyl]amino}piperidine-1-carboxylate obtained in stage 3.3 in 40 ml of AcOH. The mixture is stirred at AT for 12 h 00. It is extracted with AcOEt and the extract is washed with a saturated K$_2$CO$_3$ solution and then with water. It is dried over MgSO$_4$, filtered and evaporated under reduced pressure to give 6.95 g of the expected product.

Stage 3.5:

1,1-Dimethylethyl 4-[6-(2,2-difluoroethoxy)-2,4-dioxo-3,4-dihydroquinazolin-1(2H)-yl]piperidine-1-carboxylate

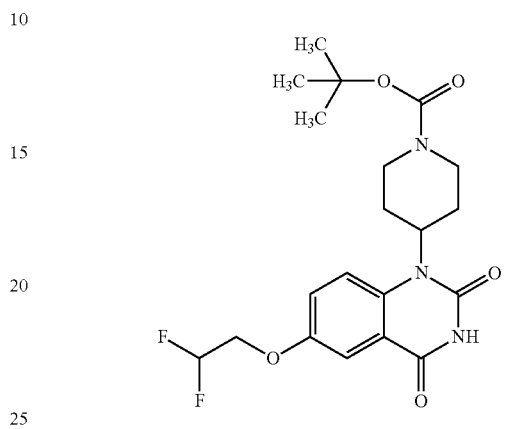

2.5 g of 1,1-dimethylethyl 4-{carbamoyl[4-(2,2-difluoroethoxy)-2-(methoxycarbonyl)phenyl]amino}piperidine-1-carboxylate obtained in stage 3.4 in solution in a mixture of 10 ml of dioxane and 5 ml of a 1N aqueous NaOH solution are irradiated under a microwave field at 130° C. for 30 min. Extraction is carried out with AcOEt and the extract is neutralized with a 1N aqueous HCl solution, washed with water, dried over MgSO$_4$, filtered and evaporated under reduced pressure. The residue obtained is triturated in an AcOEt/pentane mixture to give the expected product. The same reaction is reproduced with 2 other lots of 2.5 g of 1,1-dimethylethyl 4-{carbamoyl[4-(2,2-difluoroethoxy)-2-(methoxycarbonyl)phenyl]amino}piperidine-1-carboxylate obtained in stage 3.4 to give, in total, 5.63 g of expected product.

Stage 3.6:

6-(2,2-Difluoroethoxy)-1-(piperidin-4-yl)quinazoline-2,4(1H,3H)-dione

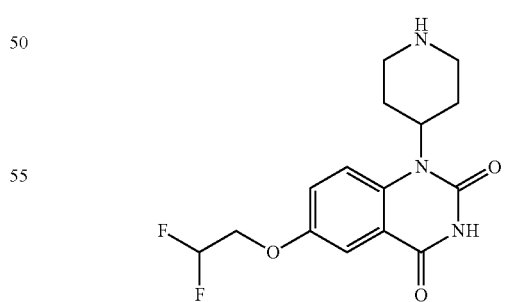

A solution of 5.63 g of 1,1-dimethylethyl 4-[6-(2,2-difluoroethoxy)-2,4-dioxo-3,4-dihydroquinazolin-1(2H)-yl]piperidine-1-carboxylate obtained in stage 3.5 in 70 ml of formic acid is stirred at AT for 2 h 00. The solvent is evaporated under reduced pressure to give 6.13 g of the expected product in the form of the formic acid salt.

Stage 3.7:

4-[6-(2,2-Difluoroethoxy)-2,4-dioxo-3,4-dihydro-quinazolin-1(2H)-yl]piperidine-1-carbaldehyde

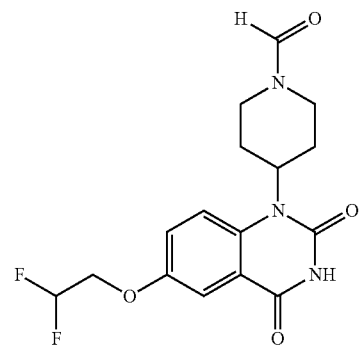

A mixture of 6.13 g of 6-(2,2-difluoroethoxy)-1-(piperidin-4-yl)quinazoline-2,4(1H,3H)-dione obtained in stage 3.6 and 3.12 g of ammonium formate in 28 ml of ACN and 28 ml of dioxane is irradiated under a microwave field at 140° C. for 1 h 00. The reaction mixture is run into water. The mixture is filtered and the precipitate is washed with water and then with ether to give 4.47 g of the expected product.

Stage 3.8: Compound No. 34

4-[3-(4-Chlorobenzyl)-6-(2,2-difluoroethoxy)-2,4-dioxo-3,4-dihydroquinazolin-1(2H)-yl]piperidine-1-carbaldehyde

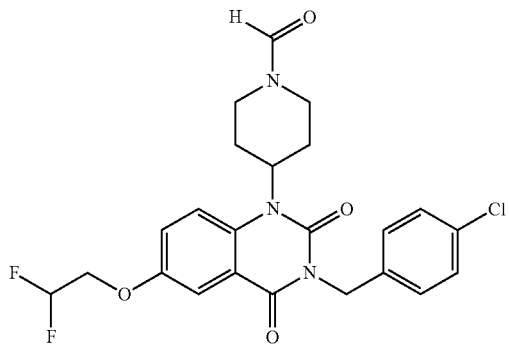

A mixture of 0.15 g of 4-[6-(2,2-difluoroethoxy)-2,4-dioxo-3,4-dihydroquinazolin-1(2H)-yl]piperidine-1-carbaldehyde obtained in stage 3.7, 0.096 g of 1-(bromomethyl)-4-chlorobenzene and 0.3 g of $Cs_2CO_3$ in 3 ml of DMF is stirred at AT for 1 h 00. AcOEt is added and washing is carried out with water and then with a saturated NaCl solution. The organic phase is dried over $MgSO_4$, filtered and evaporated under reduced pressure. The residue is chromatographed on silica gel, elution being carried out with AcOEt, to give 0.116 g of the expected product.

Example 4

Compound No. 49

Synthesis of 4-{3-[3-(cyclopentyloxy)-4-methoxybenzyl]-6-(2,2-difluoro-ethoxy)-2,4-dioxo-3,4-dihydroquinazolin-1(2H)-yl}piperidine-1-carbaldehyde

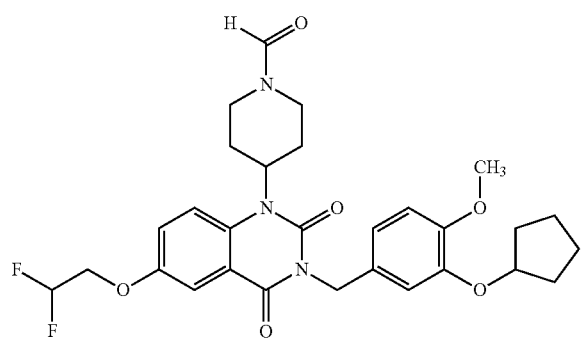

0.172 g of DIAD is added to a solution of 0.15 g of 4-[6-(2,2-difluoroethoxy)-2,4-dioxo-3,4-dihydroquinazolin-1(2H)-yl]piperidine-1-carbaldehyde obtained in stage 3.7, 0.142 g of [4-(cyclopentyloxy)-3-methoxyphenyl]methanol and 0.223 g of $PPh_3$ in 3 ml of anhydrous THF. The mixture is stirred at AT for 12 h 00 and then at 60° C. for 1 h 00. It is evaporated under reduced pressure and the residue is purified on silica gel, elution being carried out with AcOEt, to give 0.083 g of the expected product.

Example 5

Compound No. 20

Synthesis of N-{[3-(3,4-dimethoxybenzyl)-1-(1-formylpiperidin-4-yl)-2,4-dioxo-1,2,3,4-tetrahydro-quinazolin-6-yl]methyl}acetamide

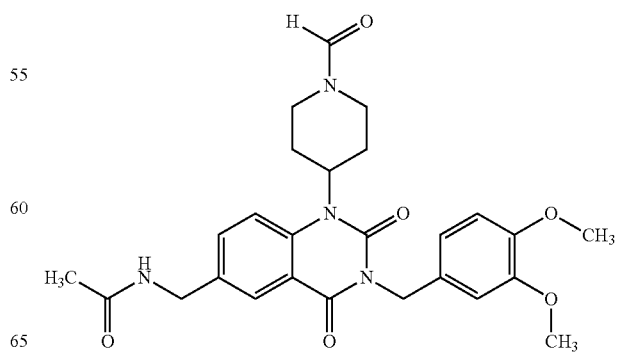

41

Stage 5.1:

Methyl 2-amino-5-({[(1,1-dimethylethoxy)carbonyl]amino}methyl)benzoate

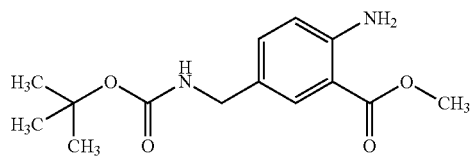

A mixture of 0.273 g of methyl 5-{[(tert-butoxycarbonyl)amino]methyl}-2-nitrobenzoate, 0.166 g of ammonium formate and 0.094 g of Pd/C (10%) in 10 ml of EtOH purged beforehand with nitrogen is irradiated under a microwave field at 120° C. for 5 min. The mixture is filtered and the filtrate is evaporated under reduced pressure. The residue is chromatographed on silica gel, elution being carried out with an AcOEt/heptane mixture, (5/95, v/v) as far as (30/70, v/v), to give 0.2 g of the expected product.

Stage 5.2:

Benzyl 4-{[4-({[(1,1-dimethylethoxy)carbonyl]amino}methyl)-2-(methoxy-carbonyl)phenyl]amino}piperidine-1-carboxylate

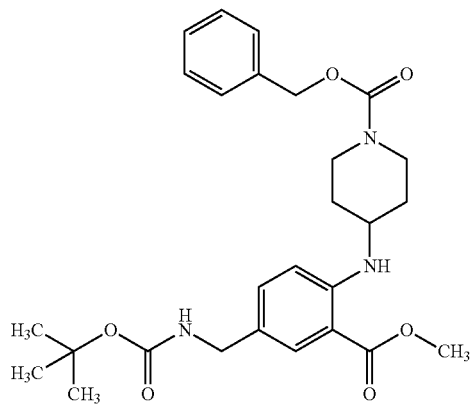

A solution of 1.66 g of benzyl 4-oxopiperidine-1-carboxylate and 1 g of methyl 2-amino-5-({[(1,1-dimethylethoxy)carbonyl]amino}methyl)benzoate obtained in stage 5.1 in 20 ml of DCM is added dropwise at AT to a suspension of 2.04 g of NaBH(OAc)$_3$ in a mixture of 20 ml of DCM and 0.41 ml of AcOH. The mixture is stirred at AT for 15 h 00 and then a further 2.04 g of NaBH(OAc)$_3$ are added. After stirring for 6 h 00, 1.66 g of benzyl 4-oxopiperidine-1-carboxylate are added and the mixture is stirred at AT for 48 h 00. A saturated NaHCO$_3$ solution is added and extraction is carried out with DCM. The organic phase is washed with a saturated NaHCO$_3$ solution and twice with a saturated NH$_4$Cl solution. It is dried over Na$_2$SO$_4$ and filtered, and the filtrate is evaporated under reduced pressure. The residue is chromatographed on silica gel, elution being carried out with an AcOEt/heptane mixture, (5/95, v/v) as far as (40/60, v/v), to give 1.6 g of the expected product.

42

Stage 5.3:

Benzyl 4-{[4-({[(1,1-dimethylethoxy)carbonyl]amino}methyl)-2-(methoxycarbonyl)phenyl]ethoxycarbonyl)amino}piperidine-1-carboxylate

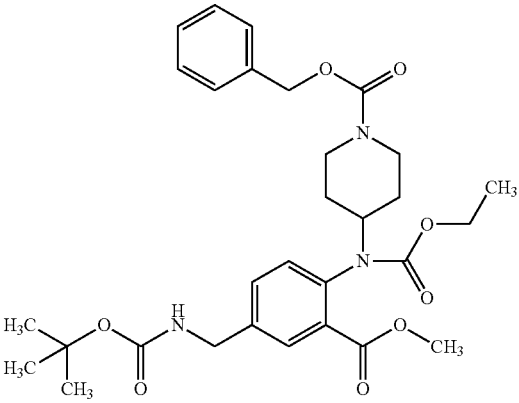

2.08 g of DIEA and then 1.745 g of ethyl chloroformate are added to a solution of 1.6 g of benzyl 4-{[4-({[(1,1-dimethylethoxy)carbonyl]amino}methyl)-2-(methoxy-carbonyl)phenyl]amino}piperidine-1-carboxylate obtained in stage 5.2 in 11 ml of DCM. The mixture is stirred at AT for 4 days. It is evaporated under reduced pressure. The residue is taken up in 10 ml of pyridine (10 ml) and 0.7 g of ethyl chloroformate is added. The mixture is stirred at AT for 4 h 00. It is evaporated under reduced pressure. The residue is chromatographed on silica gel, elution being carried out with an AcOEt/heptane mixture, (10/90, v/v) as far as (30/70, v/v), to give 0.875 g of the expected product.

Stage 5.4:

Benzyl 4-[3-(3,4-dimethoxybenzyl)-6-({[(1,1-dimethylethoxy)carbonyl]amino}-methyl)-2,4-dioxo-3,4-dihydroquinazolin-1(2H)-yl]piperidine-1-carboxylate

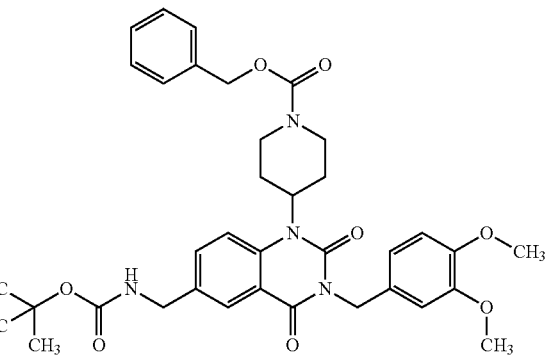

A mixture of 0.165 g of benzyl 4-{[4-({[(1,1-dimethylethoxy)carbonyl]amino}-methyl)-2-(methoxycarbonyl)phenyl](ethoxycarbonyl)amino}piperidine-1-carboxylate obtained in stage 5.3 and 0.028 g of LiOH in 5 ml of THF/H$_2$O (70/30) is stirred at AT for 15 h 00. The mixture is subsequently irradiated under a microwave field at 100° C. for 1 h 00. It is filtered and the filtrate is evaporated under reduced pressure. The residue is taken up in 5 ml of DMF. 0.108 g of DIEA is added and the mixture is stirred at AT for 10 min. 0.159 g of HBTU is added and the mixture is stirred at AT for 30 min. 0.061 g of veratrylamine is subsequently added and the mixture is stirred at AT for 1 h 00. 0.5 ml of DBU is added and the mixture is stirred at AT for 48 h 00. It is evaporated under reduced pressure and the residue is taken up in AcOEt. The solution is washed 3 times with a saturated NH$_4$Cl solution and twice with water. It is dried over Na$_2$SO$_4$ and filtered, and the filtrate is evaporated under reduced pressure. The residue is chromatographed on silica gel, elution being carried out with an AcOEt/DCM mixture, (10/90, v/v) as far as (20/80, v/v), to give 0.104 g of the expected product.

Stage 5.5:

Benzyl 4-[6-(aminomethyl)-3-(3,4-dimethoxybenzyl)-2,4-dioxo-3,4-dihydroquinazolin-1(2H)-yl]piperidine-1-carboxylate

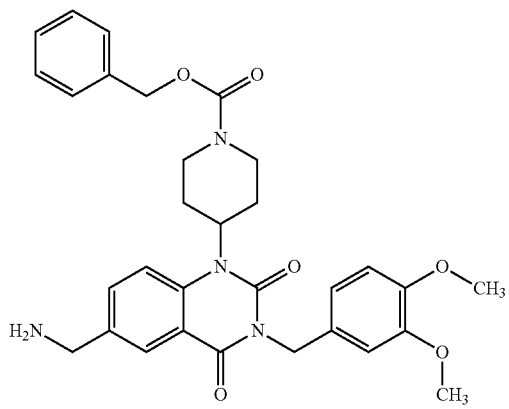

A solution of 0.102 g of benzyl 4-[3-(3,4-dimethoxybenzyl)-6-({[(1,1-dimethylethoxy)carbonyl]amino}methyl)-2,4-dioxo-3,4-dihydroquinazolin-1(2H)-yl]piperidine-1-carboxylate obtained in stage 5.4 and 0.5 ml of TFA in 9.5 ml of DCM is stirred at AT for 2 h 00. A saturated NaHCO$_3$ solution is added. The organic phase is dried over Na$_2$SO$_4$ and filtered, and the filtrate is evaporated under reduced pressure to give 0.09 g of the expected product.

Stage 5.6:

Benzyl 4-{6-[(acetylamino)methyl]-3-(3,4-dimethoxybenzyl)-2,4-dioxo-3,4-dihydroquinazolin-1(2H)-yl}piperidine-1-carboxylate

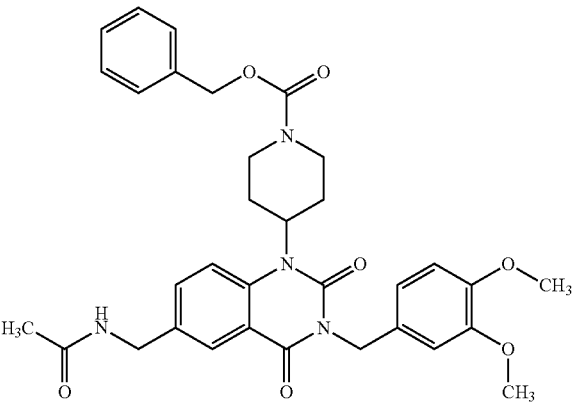

0.049 g of acetic anhydride is added to a solution of 0.09 g of benzyl 4-[6-(aminomethyl)-3-(3,4-dimethoxybenzyl)-2,4-dioxo-3,4-dihydroquinazolin-1(2H)-yl]piperidine-1-carboxylate obtained in stage 5.5 and 0.09 ml of NEt$_3$ in 3 ml of DCM and the mixture is stirred at AT for 1 h 00. DCM is added and the solution is washed with a saturated NH$_4$Cl solution, then with a 1N HCl solution, then with a 2N NaOH solution and then with water. The organic phase is dried over Na$_2$SO$_4$ and filtered, and the filtrate is evaporated under reduced pressure to give 0.104 g of the expected product.

Stage 5.7:

N-{[3-(3,4-Dimethoxybenzyl)-2,4-dioxo-1-(piperidin-4-yl)-1,2,3,4-tetrahydroquinazolin-6-yl]methyl}acetamide

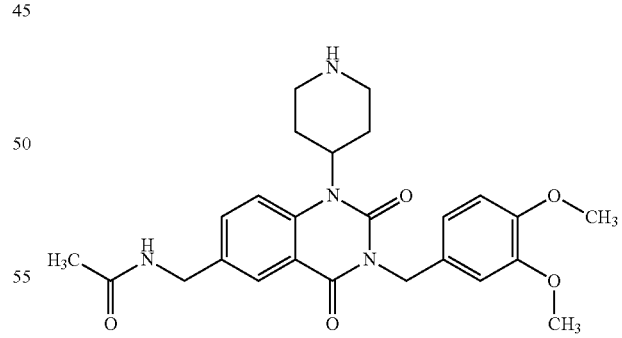

A mixture of 0.1 g of benzyl 4-{6-[(acetylamino)methyl]-3-(3,4-dimethoxybenzyl)-2,4-dioxo-3,4-dihydroquinazolin-1(2H)-yl}piperidine-1-carboxylate obtained in stage 5.6, 0.016 g of ammonium formate and 0.018 g of Pd/C (10%) in 2 ml of EtOH purged beforehand with nitrogen is irradiated under a microwave field at 80° C. for 30 min. The mixture is filtered and the filtrate is evaporated under reduced pressure to give 0.077 g of the expected product.

Stage 5.8: Compound No. 20

N-{[3-(3,4-Dimethoxybenzyl)-1-(1-formylpiperidin-4-yl)-2,4-dioxo-1,2,3,4-tetrahydroquinazolin-6-yl]methyl}acetamide

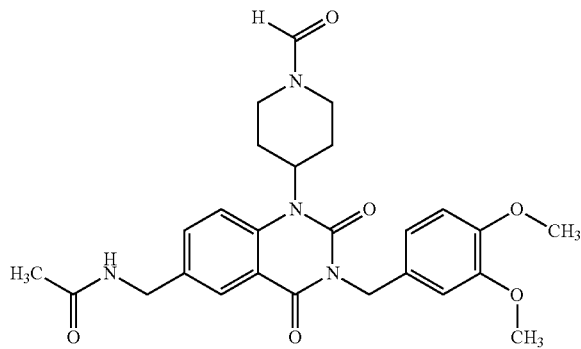

A mixture of 0.070 g of N-{[3-(3,4-dimethoxybenzyl)-2,4-dioxo-1-(piperidin-4-yl)-1,2,3,4-tetrahydroquinazolin-6-yl]methyl}acetamide obtained in stage 5.7 and 0.028 g of ammonium formate in 2 ml of ACN is irradiated under a microwave field at 140° C. for. 1 h 00. The mixture is filtered and the filtrate is evaporated under reduced pressure. The residue is chromatographed on silica gel, elution being carried out with an MeOH/DCM mixture, (0.5/99.5, v/v) as far as (7/93, v/v), to give 0.035 g of the expected product.

The chemical structures and the physical properties of compounds corresponding to the general formula (I) according to the invention, and also of some of their intermediates (in particular compounds 32, 55, 120 and 257), are illustrated in the following table.

| COMPOUND No. | STRUCTURE | NOMENCLATURE | NMR or MASS |
|---|---|---|---|
| 1 | 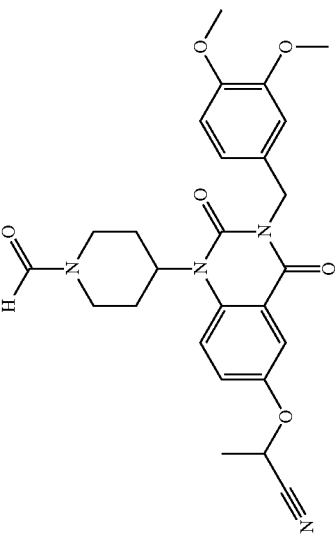 | 2-{[3-(3,4-dimethoxybenzyl)-1-(1-formylpiperidin-4-yl)-2,4-dioxo-1,2,3,4-tetrahydroquinazolin-6-yl]oxy}propanenitrile | $^1$H NMR (500 MHz, DMSO-d$_6$) δ ppm 1.71(d, 3H) 1.73(brdd, 2H) 2.41(dq, 1H) 2.53(dq, 1H) 2.80(td, 1H) 3.25(t, 1H) 3.70(s, 3H) 3.71(s, 3H) 3.80(d, 1H) 4.31(d, 1H) 4.77(brs, 1H) 5.03(s, 2H) 5.60(q, 1H) 6.83(dd, 1H) 6.85 (d, 1H) 6.98(s, 1H) 7.51(dd, 1H) 7.74(d, 1H) 7.84(d, 1H) 8.03(s, 1H) |
| 2 | 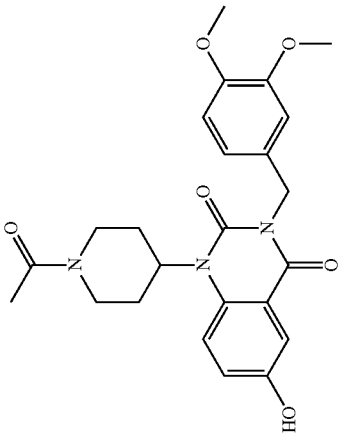 | 1-(1-acetylpiperidin-4-yl)-3-(3,4-dimethoxybenzyl)-6-hydroxyquinazoline-2,4(1H,3H)-dione | $^1$H NMR (500 MHz, DMSO-d$_6$) δ ppm 1.69(d, 1H) 1.74(d, 1H) 2.05(s, 3H) 2.42(dq, 1H) 2.57(dq, 1H) 2.70(t, 1H) 3.24(t, 1H) 3.70(br s, 3H) 3.71(s, 3H) 3.92(d, 1H) 4.51(d, 1H) 4.69(brs, 1H) 5.02(s, 2H) 6.81(dd, 1H) 6.86(d, 1H) 6.97(d, 1H) 7.21(dd, 1H) 7.44(d, 1H) 7.65(d, 1H) 9.88(brs, 1H) |

| | | |
|---|---|---|
| 3 | 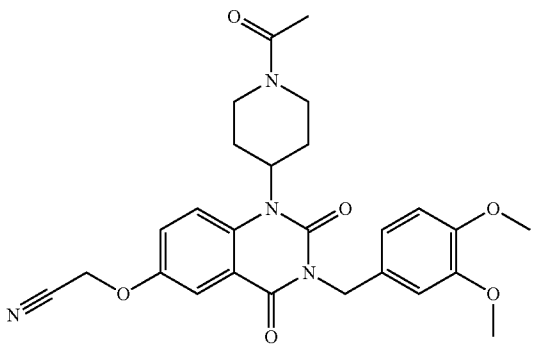{[1-{(1-acetylpiperidin-4-yl)-3-(3,4-dimethoxybenzyl)-2,4-dioxo-1,2,3,4-tetrahydroquinazolin-6-yl]oxy}acetonitrile | $^{1}$H NMR (500 MHz, DMSO-$d_6$) δ ppm 1.71(d, 1H) 1.76(d, 1H) 2.04(s, 3H) 2.41(dq, 1H) 2.56(dq, 1H) 2.70(t, 1H) 3.24(t, 1H) 3.70(s, 3H) 3.71(s, 3H) 3.92(d, 1H) 4.51(d, 1H) 4.73(brs, 1H) 5.04(s, 2H) 5.29(s, 2H) 6.82(dd, 1H) 6.85(d, 1H) 6.98(d, 1H) 7.50(dd, 1H) 7.70(d, 1H) 7.83(d, 1H) |
| 4 | 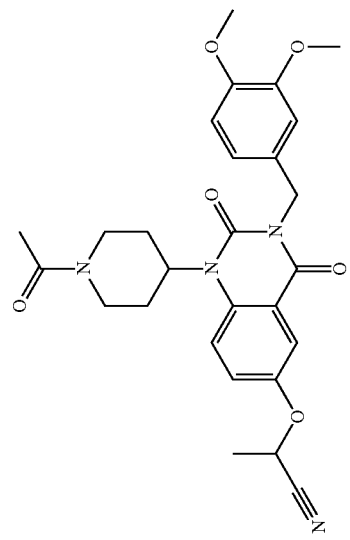2-{[1-(1-acetylpiperidin-4-yl)-3-(3,4-dimethoxybenzyl)-2,4-dioxo-1,2,3,4-tetrahydroquinazolin-6-yl]oxy}propanenitrile | $^{1}$H NMR (500 MHz, DMSO-$d_6$) δ ppm 1.71(d, 3H) 1.72(d, 2H) 1.77(d, 1H) 2.04(s, 3H) 2.41(qd, 1H) 2.56(dq, 1H) 2.70(d, 1H) 3.24(t, 1H) 3.70(s, 3H) 3.71(s, 3H) 3.92(d, 1H) 4.51(d, 1H) 4.73(brs, 1H) 5.03(s, 2H) 5.60(q, 1H) 6.83(d, 1H) 6.85(m, 1H) 6.98(d, 1H) 7.51(dd, 1H) 7.74(d, 1H) 7.83(d, 1H) |
| 5 | 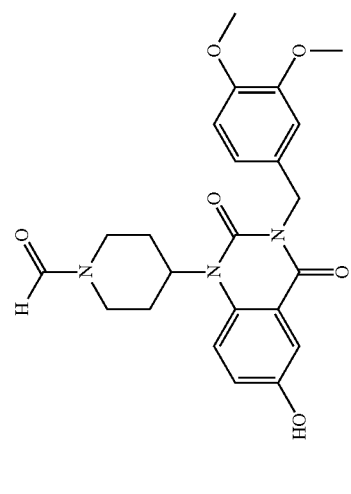4-[3-(3,4-dimethoxybenzyl)-6-hydroxy-2,4-dioxo-3,4-dihydroquinazolin-1(2H)-yl]piperidine-1-carbaldehyde | $^{1}$H NMR (500 MHz, DMSO-$d_6$) δ ppm 1.75(d, 1H) 1.78(d, 1H) 2.41 (qd, 1H) 2.53(qd, 1H) 2.79(td, 1H) 3.25(td, 1H) 3.70(s, 3H) 3.71(s, 3H) 3.80(d, 1H) 4.31(d, 1H) 4.72 (brs, 1H) 5.02(s, 2H) 6.82(dd, 1H) 6.86(d, 1H) 6.97(d, 1H) 7.21(dd, 1H) 7.44(d, 1H) 7.66(d, 1H) 8.03(s, 1H) 9.85(brs, 1H) |

| | | -continued | |
|---|---|---|---|
| 6 | 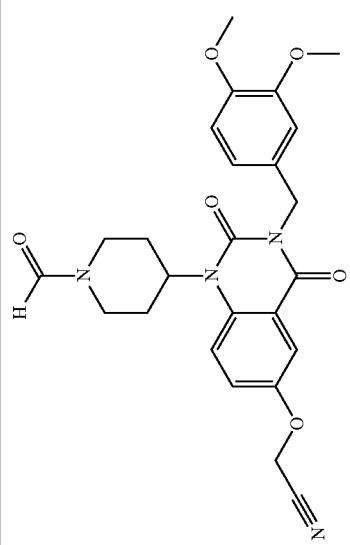 | {[3-(3,4-dimethoxybenzyl)-1-(1-formylpiperidin-4-yl)-2,4-dioxo-1,2,3,4-tetrahydroquinazolin-6-yl]oxy}acetonitrile | $^1$H NMR (500 MHz, DMSO-$d_6$) δ ppm 1.78(d, 1H) 1.81(d, 1H) 2.42(qd, 1H) 2.54(dt, 1H) 2.81(td, 4H) 3.26(dt, 1H) 3.71(s, 3H) 3.72(s, 3H) 3.81(d, 1H) 4.32(d, 1H) 4.77(brs, 1H) 5.05(s, 2H) 5.30(s, 2H) 6.84(dd, 1H) 6.87(d, 1H) 6.99(d, 1H) 7.51(dd, 1H) 7.71(d, 1H) 7.85(d, 1H) 8.04(s, 1H) |
| 7 | 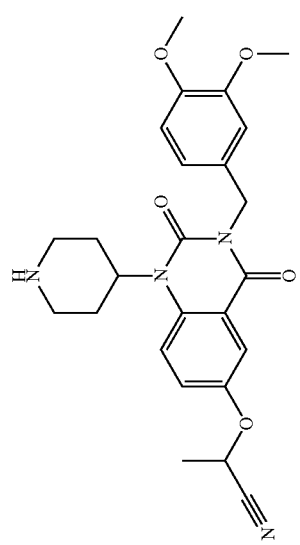 | 2-{[3-(3,4-dimethoxybenzyl)-2,4-dioxo-1-(piperidin-4-yl)-1,2,3,4-tetrahydroquinazolin-6-yl]oxy}propanenitrile | $^1$H NMR (500 MHz, DMSO-$d_6$) δ ppm 1.69(d, 3H) 1.75(d, 2H) 2.65(td, 2H) 2.87(t, 2H) 3.21(d, 2H) 3.69(s, 3H) 3.70(s, 3H) 4.68(brs, 1H) 5.04(s, 2H) 5.59(q, 1H) 6.84(m, 2H) 6.98(d, 1H) 7.50(dd, 1H) 7.73(d, 1H) 7.80(d, 1H) |
| 8 | 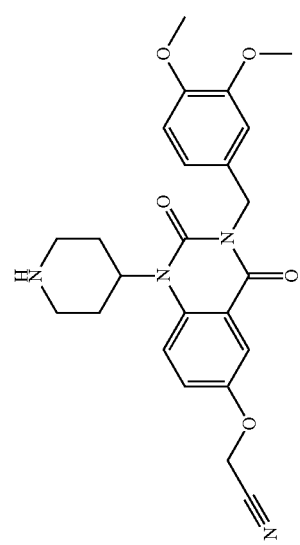 | {[3-(3,4-dimethoxybenzyl)-2,4-dioxo-1-(piperidin-4-yl)-1,2,3,4-tetrahydroquinazolin-6-yl]oxy}acetonitrile | $^1$H NMR (600 MHz, DMSO-$d_6$) δ ppm 1.77(d, 2H) 2.67(dt, 2H) 2.89(t, 2H) 3.23(d, 2H) 3.69(s, 3H) 3.70(s, 3H) 4.69(brs, 1H) 5.05(s, 2H) 5.28(s, 2H) 6.84(m, 2H) 6.99(s, 1H) 7.49(dd, 1H) 7.70(d, 1H) 7.80(d, 1H) |

| | | -continued | |
|---|---|---|---|
| 9 | 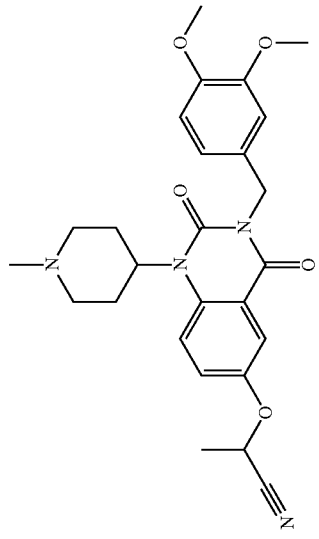 | 2-{[3-(3,4-dimethoxybenzyl)-1-(1-methylpiperidin-4-yl)-2,4-dioxo-1,2,3,4-tetrahydroquinazolin-6-yl]oxy}propanenitrile | 1H NMR (500 MHz, DMSO-d6) δ ppm 1.59(d, 2H) 1.66(d, 3H) 2.04(t, 2H) 2.16(s, 3H) 2.62(dt, 2H) 2.83(d, 2H) 3.66(s, 3H) 3.67(s, 3H) 4.43(brs, 1H) 5.01 (s, 2H) 5.54(q, 1H) 6.79(m, 1H) 6.82(d, 1H) 6.95(d, 1H) 7.45(dd, 1H) 7.68(d, 1H) 7.70(d, 1H) |
| 10 | 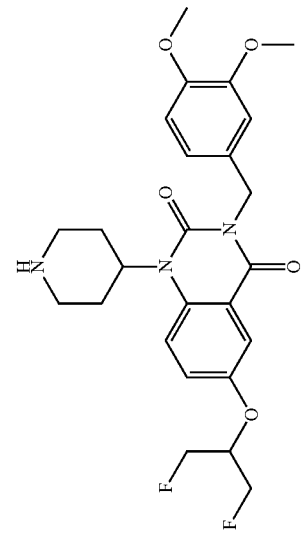 | 3-(3,4-dimethoxybenzyl)-6-[2-fluoro-1-(fluoromethyl)ethoxy]-1-piperidin-4-ylquinazoline-2,4(1H,3H)-dione | 1H NMR (500 MHz, DMSO-d6) δ ppm 1.85(d, 2H) 2.78(td, 2H) 3.04(t, 2H) 3.33(d, 2H) 3.71(s, 6H) 4.61-4.82(m, 4H) 5.04(brt, 1H) 5.05(s, 2H) 6.86(m, 2H) 6.99(s, 1H) 7.49(dd, 1H) 7.68(d, 1H) 7.76(d, 1H) 8.05(brs, 1H) |
| 11 | 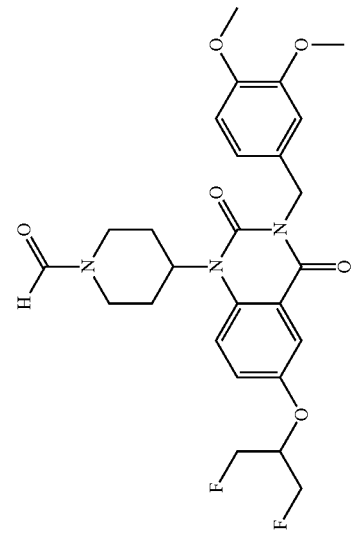 | 4-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde | 1H NMR (500 MHz, DMSO-d6) δ ppm 1.76(d, 1H) 1.80(d, 1H) 2.41(qd, 1H) 2.53(qd, 1H) 2.80(td, 1H) 3.25(dt, 1H) 3.70(s, 6H) 3.80(d, 1H) 4.31(d, 1H) 4.61-4.83(m, 5H) 5.02(m, 1H) 5.03(s, 2H) 6.83(dd, 1H) 6.85(d, 1H) 6.97 (d, 1H) 7.47(dd, 1H) 7.67(d, 1H) 7.77(d, 1H) 8.03(s, 1H) |

| | | | |
|---|---|---|---|
| 12 | 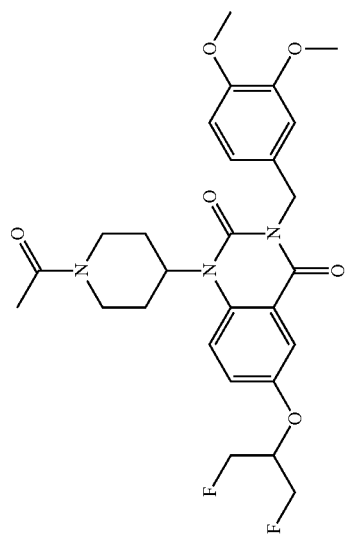 | 1-(1-acetylpiperidin-4-yl)-3-(3,4-dimethoxybenzyl)-6-[2-fluoro-1-(fluoromethyl)ethoxy]quinazoline-2,4(1H,3H)-dione | ¹H NMR (500 MHz, DMSO-d₆) δ ppm 1.70(d, 1H) 1.76(d, 1H) 2.04(s, 3H) 2.41(dq, 1H) 2.56(dq, 1H) 2.70(t, 1H) 3.25(t, 1H) 3.70(s, 3H) 3.71(s, 3H) 3.92(d, 1H) 4.51(d, 1H) 4.61–4.83(m, 5H) 5.02(m, 1H) 5.03(s, 2H) 6.82(dd, 1H) 6.85(m, 1H) 6.97(dd, 1H) 7.47(dd, 1H) 7.67(d, 1H) 7.77(d, 1H) |
| 13 | 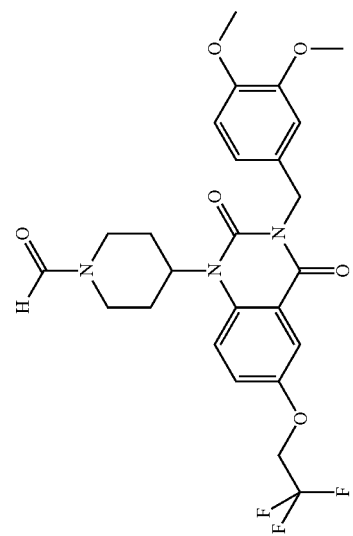 | 4-[3-(3,4-dimethoxybenzyl)-2,4-dioxo-6-(2,2,2-trifluoroethoxy)-3,4-dihydroquinazolin-1(2H)-yl]piperidine-1-carbaldehyde | ¹H NMR (600 MHz, DMSO-d₆) δ ppm 1.75(d, 1H) 1.79(d, 1H) 2.40(dq, 1H) 2.52(dq, 1H) 2.79(td, 1H) 3.25(td, 1H) 3.69(s, 6H) 3.79(d, 1H) 4.30(d, 1H) 4.75(brs, 1H) 4.88(q, 2H) 5.02(s, 2H) 6.82(d, 1H) 6.85(d, 1H) 6.97(s, 1H) 7.49(dd, 1H) 7.66(d, 1H) 7.79(d, 1H) 8.02(s, 1H) |
| 14 | 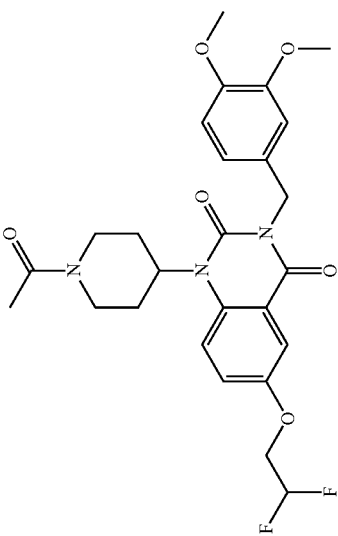 | 1-(1-acetylpiperidin-4-yl)-6-(2,2-difluoroethoxy)-3-(3,4-dimethoxybenzyl)quinazoline-2,4(1H,3H)-dione | ¹H NMR (500 MHz, DMSO-d₆) δ ppm 1.70(d, 1H) 1.74(d, 1H) 2.04(s, 3H) 2.41(qd, 1H) 2.56(qd, 1H) 2.70(t, 1H) 3.24(t, 1H) 3.70(s, 3H) 3.70(s, 3H) 3.91(d, 1H) 4.43(td, 2H) 4.50(d, 1H) 4.73(brs, 1H) 5.03 (s, 2H) 6.41(tt, 1H) 6.82(dd, 1H) 6.85(d, 1H) 6.97(dd, 1H) 7.46(dd, 1H) 7.60(d, 1H) 7.79(d, 1H) |

-continued

| | | | |
|---|---|---|---|
| 15 | 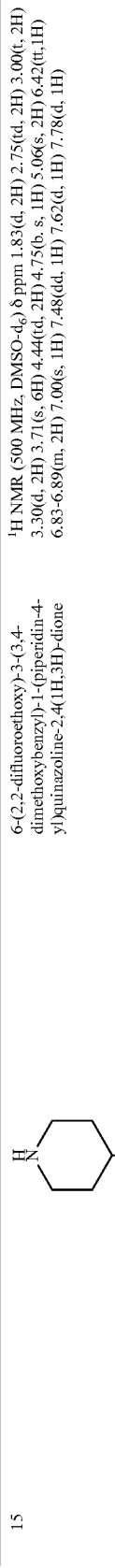 | 6-(2,2-difluoroethoxy)-3-(3,4-dimethoxybenzyl)-1-(piperidin-4-yl)quinazoline-2,4(1H,3H)-dione | $^1$H NMR (500 MHz, DMSO-$d_6$) δ ppm 1.83(d, 2H) 2.75(td, 2H) 3.00(t, 2H) 3.30(d, 2H) 3.71(s, 6H) 4.44(td, 2H) 4.75(b. s, 1H) 5.06(s, 2H) 6.42(tt,1H) 6.83-6.89(m, 2H) 7.00(s, 1H) 7.48(dd, 1H) 7.62(d, 1H) 7.78(d, 1H) |
| 16 | 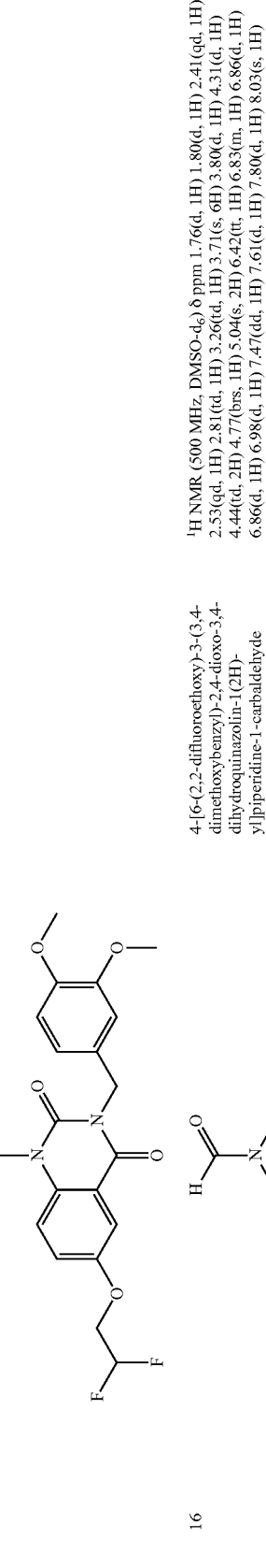 | 4-[6-(2,2-difluoroethoxy)-3-(3,4-dimethoxybenzyl)-2,4-dioxo-3,4-dihydroquinazolin-1(2H)-yl]piperidine-1-carbaldehyde | $^1$H NMR (500 MHz, DMSO-$d_6$) δ ppm 1.76(d, 1H) 1.80(d, 1H) 2.41(qd,1H) 2.53(qd, 1H) 2.81(td, 1H) 3.26(td, 1H) 3.71(s, 6H) 3.80(d, 1H) 4.31(d, 1H) 4.44(td, 2H) 4.77(brs, 1H) 5.04(s, 2H) 6.42(tt, 1H) 6.83(m, 1H) 6.86(d, 1H) 6.86(d, 1H) 6.98(d, 1H) 7.47(dd, 1H) 7.61(d, 1H) 7.80(d, 1H) 8.03(s, 1H) |
| 17 | 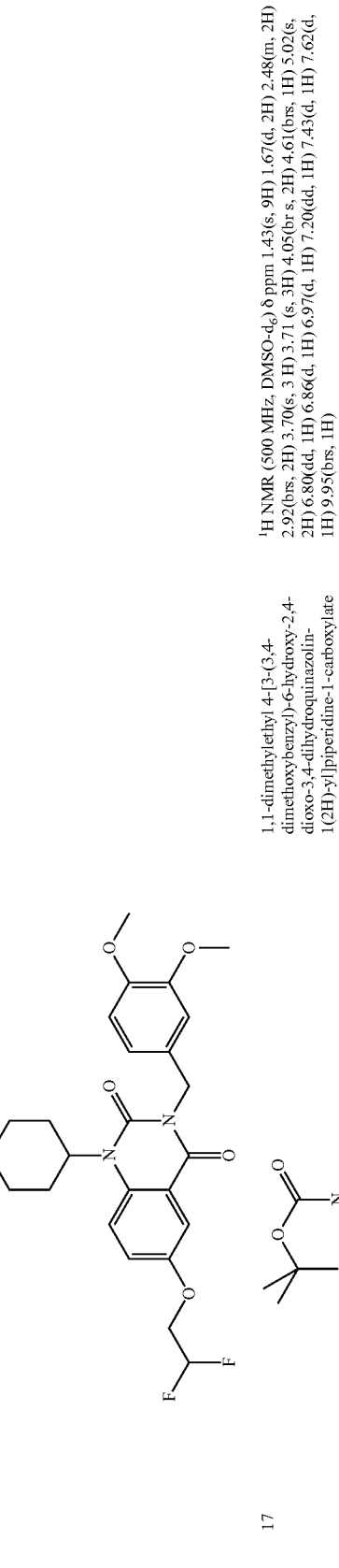 | 1,1-dimethylethyl 4-[3-(3,4-dimethoxybenzyl)-6-hydroxy-2,4-dioxo-3,4-dihydroquinazolin-1(2H)-yl]piperidine-1-carboxylate | $^1$H NMR (500 MHz, DMSO-$d_6$) δ ppm 1.43(s, 9H) 1.67(d, 2H) 2.48(m, 2H) 2.92(brs, 2H) 3.70(s, 3 H) 3.71 (s, 3H) 4.05(br s, 2H) 4.61(brs, 1H) 5.02(s, 2H) 6.80(dd, 1H) 6.86(d, 1H) 6.97(d, 1H) 7.20(dd, 1H) 7.43(d, 1H) 7.62(d, 1H) 9.95(brs, 1H) |

| | | | |
|---|---|---|---|
| 18 | 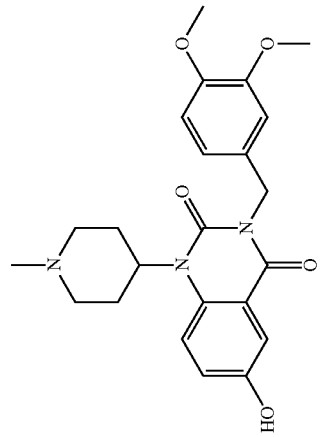 | 3-(3,4-dimethoxybenzyl)-6-hydroxy-1-(1-methylpiperidin-4-yl)quinazoline-2,4(1H,3H)-dione | ¹H NMR (500 MHz, DMSO-d₆) δ ppm 1.60(d, 2H) 2.06(td, 2H) 2.19(s, 3H) 2.65(qd, 2H) 2.85(d, 2H) 3.70(s, 3 H) 3.71(s, 3H) 4.43(brs, 1H) 5.02(s, 2H) 6.81(m, 1H) 6.85(d, 1H) 6.98(d, 1H) 7.19(dd, 1H) 7.41(d, 1H) 7.55(d, 1H) 9.82(s, 1H) |
| 19 | 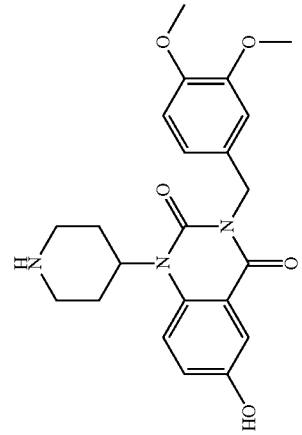 | 3-(3,4-dimethoxybenzyl)-6-hydroxy-1-(piperidin-4-yl)quinazoline-2,4(1H,3H)dione hydrochloride | ¹H NMR (500 MHz, DMSO-d₆) δ ppm 1.86(d, 2H) 2.83(m, 2H) 3.12(t, 2H) 3.37(m, 2H) 3.70(s, 6H) 4.76(brs, 1H) 5.03(s, 2H) 6.83(dd, 1H) 6.85(d, 1H) 6.98(d, 1H) 7.21(dd, 1H) 7.44(d, 1H) 7.70(d, 1H) 8.70(brs, 2H) 9.91(s, 1H) |
| 20 | 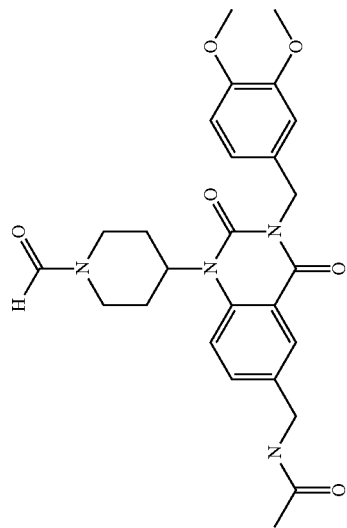 | N-{[3-(3,4-dimethoxybenzyl)-1-(1-formylpiperidin-4-yl)-2,4-dioxo-1,2,3,4-tetrahydroquinazolin-6-yl]methyl}acetamide | ¹H NMR (500 MHz, DMSO-d₆) δ pm1.75(d, 1H) 1.78(d, 1H) 1.86(s, 3H) 2.40(qd, 1H) 2.53(qd, 1H) 2.79(t, 1H) 3.25(t, 1H) 3.69(s, 3H) 3.70(s, 3H) 3.80(d, 1H) 4.29(d, 2H) 4.31(d, 1H) 4.77(brs, 1H) 5.02(s, 2H) 6.80(dd, 1H) 6.85(d, 1H) 6.96(d, 1H) 7.65(dd, 1H) 7.76(d, 1H) 7.96(d, 1H) 8.02(s, 1H) 8.46(t, 1H) |

| | | | | |
|---|---|---|---|---|
| 21 | [structure] | HCl | 6-(aminomethyl)-3-(3,4-dimethoxybenzyl)-1-(piperidin-4-yl)quinazoline-2,4(1H,3H)-dione hydrochloride | $^1$H NMR (500 MHz, DMSO-d$_6$) δ ppm 1.89(d, 2H) 2.83-2.92(m, 2H) 3.16(brs, 2H) 3.38-3.42(m, 2H) 3.71(s, 6H) 4.13(brs, 2H) 4.82-4.97(m, 1H) 5.07(s, 2H) 6.83-6.88(m, 2H) 7.00(s, 1H) 7.91-7.99(m, 2H) 8.24(s, 1H) 8.42(br s, 3H) 9.16(brs, 1H) |
| 22 | [structure] | HCl | 1-(1-acetylpiperidin-4-yl)-6-(aminomethyl)-3-(3,4-dimethoxybenzyl)quinazoline-2,4(1H,3H)-dione hydrochloride | $^1$H NMR (500 MHz, DMSO-d$_6$) δ ppm 1.67-1.79(m, 2H) 2.05(s, 3H) 2.36-2.47(m, 1H) 2.51-2.61(m, 1H) 2.73(t, 1H) 3.27(t, 1H) 3.71(s, 6H) 3.93(d, 1H) 4.11-4.15(m, 2H) 4.52(d, 1H) 4.78(brs, 1H) 5.05(s, 2H) 6.82(d, 1H) 6.86(d, 1H) 6.98(s, 1H) 7.87(s, 2H) 8.24(s, 1H) 8.32(brs, 3H) |
| 23 | [structure] | | N-{[3-(3,4-dimethoxybenzyl)-1-(1-formylpiperidin-4-yl)-2,4-dioxo-1,2,3,4-tetrahydroquinazolin-6-yl]methyl}formamide | $^1$H NMR (500 MHz, DMSO-d$_6$) δ ppm 1.73-1.83(m, 2H) 2.36-2.45(m, 1H) 2.48-2.57(m, 1H) 2.77-2.84(m, 1H) 3.23-3.29(m, 1H) 3.70(s, 1H) 3.71(s, 3H) 3.81(d, 1H) 4.31(d, 1H) 4.37(d, 2H) 4.77(brs, 1H) 5.04(s, 2H) 6.82(dd, 1H) 6.86(d, 1H) 6.98(d, 1H) 7.67(dd, 1H) 7.78(d, 1H) 7.99(d, 1H) 8.03(s, 1H) 8.16(s, 1H) 8.62(t, 1H) |

| | | | |
|---|---|---|---|
| 24 | 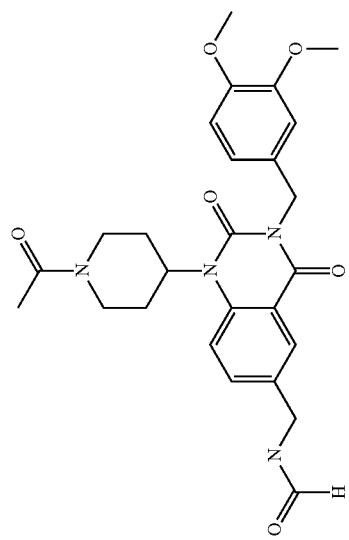 | N-{[1-(1-acetylpiperidin-4-yl)-3-(3,4-dimethoxybenzyl)-2,4-dioxo-1,2,3,4-tetrahydroquinazolin-6-yl]methyl}formamide | ¹H NMR (500 MHz, DMSO-d₆) δ ppm 1.67-1.78(m, 2H) 2.05(s, 3H) 2.35-2.48(m, 1H) 2.53-2.62(m, 1H) 2.72(t, 1H) 3.25(t, 1H) 3.70(s, 3H) 3.71(s, 3H) 3.93(d, 1H) 4.37(d, 2H) 4.52(d, 1H) 4.75(brs, 1H) 5.04(s, 2H) 6.82(dd, 1H) 6.86(d, 1H) 6.98(d, 1H) 7.67(dd, 1H) 7.78(d, 1H) 7.99(d, 1H) 8.16(s, 1H) 8.63(t, 1H) |
| 25 | 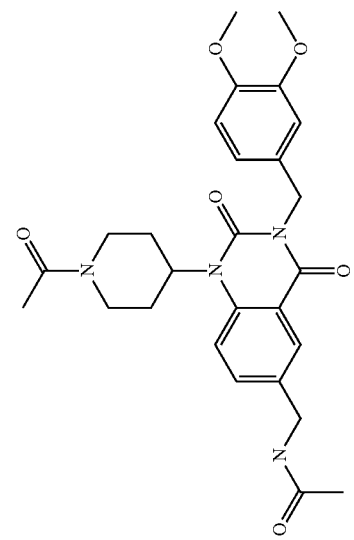 | N-{[1-(1-acetylpiperidin-4-yl)-3-(3,4-dimethoxybenzyl)-2,4-dioxo-1,2,3,4-tetrahydroquinazolin-6-yl]methyl}acetamide | ¹H NMR (500 MHz, DMSO-d₆) δ ppm 1.63-1.81(m, 2H) 1.87(s, 3H) 2.05(s, 3H) 2.32-2.42(m, 1H) 2.54-2.63(m, 1H) 2.71(dt, 1H) 3.25(dt, 1H) 3.70(s, 3H) 3.71(s, 3H) 3.93(d, 1H) 4.30(d, 2H) 4.52(d, 1H) 4.76(brs, 1H) 5.04(s, 2H) 6.81(dd, 1H) 6.86(d, 1H) 6.97(d, 1H) 7.65(dd, 1H) 7.76(d, 1H) 7.97(d, 1H) 8.47(t, 1H) |
| 26 | 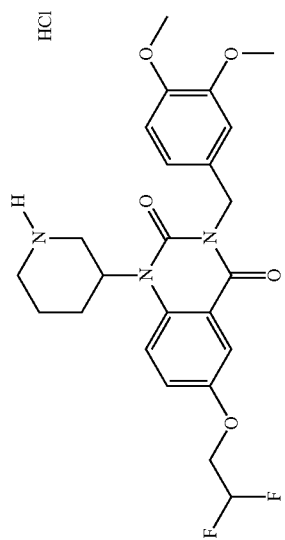 | 6-(2,2-difluoroethoxy)-3-(3,4-dimethoxybenzyl)-1-(piperidin-3-yl)quinazoline-2,4(1H,3H)-dione hydrochloride | ¹H NMR (600 MHz, DMSO-d₆) δ ppm 1.86-1.97(m, 3H) 2.54-2.62(m, 1H) 2.85-2.92(m, 1H) 3.31-3.35(m, 1H) 3.37-3.42(m, 1H) 3.71(s, 3H) 3.72(s, 3H) 3.73-3.78(m, 1H) 3.76(t, 1H) 4.45(td, 2H) 4.87(br s, 1H) 5.05(s, 2H) 6.41(tt, 1H) 6.83-6.88(m, 2H) 6.99(s, 1H) 7.52(dd, 1H) 7.63(d, 1H) 7.72(d, 1H) 8.95(brs, 1H) |

| | | | |
|---|---|---|---|
| 27 | HCl [structure] | 6-(2,2-difluoroethoxy)-3-(3,4-dimethoxybenzyl)-1-(pyrrolidin-3-yl)quinazoline-2,4(1H,3H)-dione hydrochloride | 1H NMR (500 MHz, DMSO-d6) δ ppm 2.25-2.32(m, 1H) 2.42-2.48(m, 1H) 3.11-3.19(m, 1H) 3.38-3.45(m, 1H) 3.58-3.64(m, 1H) 3.65-3.72(m, 1H) 3.73(s, 3H) 3.71(s, 3H) 4.45(td, 2H) 5.05-5.12(m, 2H) 5.47-5.54(m, 1H) 6.42(tt, 1H) 6.82-6.88(m, 2H) 7.01(s, 1H) 7.55(dd, 1H) 7.62(d, 1H) 7.71(d, 1H) 8.87(brs, 1H) |
| 28 | [structure] | 3-[6-(2,2-difluoroethoxy)-3-(3,4-dimethoxybenzyl)-2,4-dioxo-3,4-dihydroquinazolin-1(2H)-yl]piperidine-1-carbaldehyde | 1H NMR (600 MHz, DMSO-d6) mixture of two isomers δ ppm 1.52-1.62(m, 0.5H) 1.64-1.73(m, 0.5H) 1.75-1.84(m, 1H) 1.84-1.90(m, 1H) 2.54-2.67(m, 1.5H) 3.05(t, 0.5H) 3.59(t, 0.5H) 3.70(s, 3.5H) 3.77(dd, 0.5H) 4.06(t, 0.5H) 4.17-4.27(m, 1H) 4.31(brs, 0.5H) 4.42(td, 2H) 4.44(brs, 0.5H) 5.04(s, 2H) 6.38(tt, 1H) 6.80-6.84(m, 1H) 6.98(brs, 1H) 7.43(td, 1H) 7.60(brs, 1H) 7.62(d, 0.5H) 7.79(d, 0.5H) 7.99(s, 0.5H) 8.09(s, 0.5H) |
| 29 | [structure] | 1-(1-acetylpiperidin-3-yl)-6-(2,2-difluoroethoxy)-3-(3,4-dimethoxybenzyl)quinazoline-2,4(1H,3H)-dione | 1H NMR (500 MHz, DMSO-d6) mixture of two isomers δ ppm 1.55-1.65(m, 0.5H) 1.67-1.89(m, 2.5H) 1.99(s, 1.5H) 2.06(s, 1.5H) 2.52-2.65(m, 1H) 3.06(t, 0.5H) 3.30-3.37(m, 0.5H) 3.52(t, 0.5H) 3.70(s, 3H) 3.71(s, 3H) 3.52(t, 0.5H) 3.84(d, 0.5H) 3.91(d, 0.5H) 4.09(t, 0.5H) 4.28(brs, 0.5H) 4.39-4.48(m, 3H) 4.49(brs, 0.5H) 5.05(d, 2H) 6.41(tt, 1H) 6.81-6.89(m, 2H) 6.99(d, 1H) 7.44-7.48(m, 1H) 7.59-7.62(m, 1H) 7.64(d, 0.5H) 7.82(d, 0.5H) |

| | | |
|---|---|---|
| 30 | 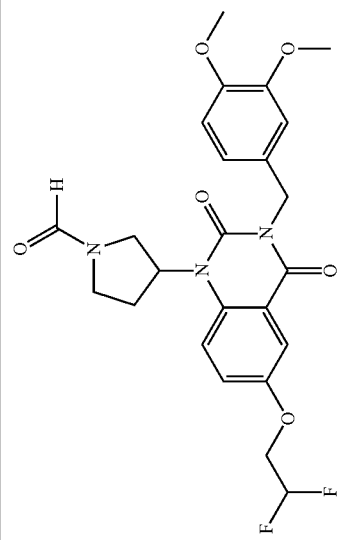<br>3-[6-(2,2-difluoroethoxy)-3-(3,4-dimethoxybenzyl)-2,4-dioxo-3,4-dihydroquinazolin-1(2H)-yl]pyrrolidine-1-carbaldehyde | $^1$H NMR (500 MHz, DMSO-d$_6$) mixture of two isomers δ ppm 2.18-2.27(m, 1H) 2.36-2.46(m, 1H) 3.41-3.48(m, 0.5H) 3.53-3.60(m, 0.5H) 3.63-3.73(m, 1.5H) 3.85-3.95(m, 1.5H) 4.43(td, 2H) 5.06(s, 2H) 5.38-5.45(m, 0.5H) 5.46-5.54(m, 0.5H) 6.41(tt, 1H) 6.82-6.88(m, 2H) 7.00(s, 1H) 7.46-7.51(m, 1H) 7.61(d, 0.5H) 7.66(d, 0.5H) 7.72(d, 0.5H) 8.16(s, 0.5H) 8.20(s, 0.5H) |
| 31 | 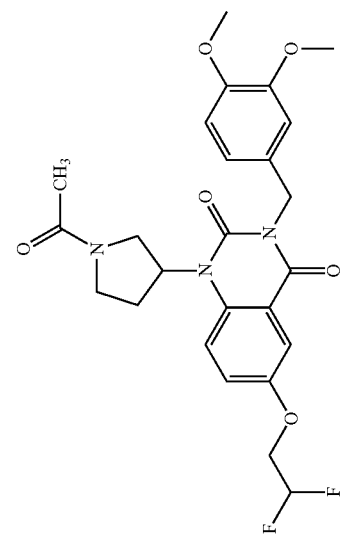<br>1-(1-acetylpyrrolidin-3-yl)-6-(2,2-difluoroethoxy)-3-(3,4-dimethoxybenzyl)quinazoline-2,4(1H,3H)-dione | $^1$H NMR (500 MHz, DMSO-d$_6$) mixture of two isomers δ ppm 1.98(s, 1.5H) 2.04(s, 1.5H) 2.17-2.25(m, 0.5H) 2.27-2.35(m, 0.5H) 2.57-2.66(m, 1H) 3.40-3.45(m, 0.5H) 3.56-3.61(m, 0.5H) 3.70-3.78(m, 1.5H) 3.82-3.95(m, 1.5H) 4.48(td, 2H) 5.10(d, 2H) 5.45-5.58(m, 2H) 6.46(tt, 1H) 6.87-6.92(m, 2H) 7.05(dd, 1H) 7.53(td, 1H) 7.66(t, 1H) 7.72 (dd, 1H) |
| 32 | 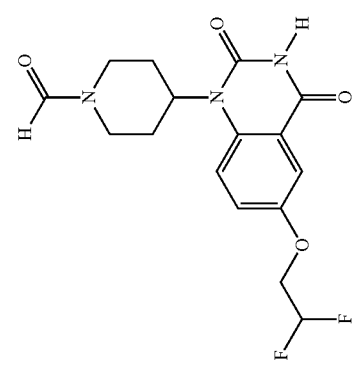<br>4-[6-(2,2-difluoroethoxy)-2,4-dioxo-3,4-dihydroquinazolin-1(2H)-yl]piperidine-1-carbaldehyde | $^1$H NMR (600 MHz, DMSO-d$_6$) δ ppm 1.72-1.82(m, 2H) 2.35-2.44(m, 1H) 2.47-2.55(m, 1H) 2.79(td, 1H) 3.25(td, 1H) 3.80(d, 1H) 4.32(d, 1H) 4.42(td, 2H) 4.71(brs, 1H) 6.40(tt, 1H) 7.43(dd, 1H) 7.55(d, 1H) 7.74(d, 1H) 8.03(s, 1H) |

| | -continued | | |
|---|---|---|---|
| 33 | 4-[3-(3,4-dichlorobenzyl)-6-(2,2-difluoroethoxy)-2,4-dioxo-3,4-dihydroquinazolin-1(2H)-yl]piperidine-1-carbaldehyde | ¹H NMR (500 MHz, DMSO-d₆) δ ppm 1.80(dd, 2H) 2.32-2.43(m, 1H) 2.44-2.52(m, 1H) 2.80(td, 1H) 3.26(dt, 1H) 3.80(brd, 1H) 4.31(br d, 1H) 4.44(td, 2H) 4.78(brs, 1H) 5.09(s, 2H) 6.41(tt, 1H) 7.30(dd, 1H) 7.49(dd, 1H) 7.58(d, 1H) 7.60(d, 1H) 7.62(d, 1H) 8.03(s, 1H) | |
| 34 | 4-[3-(4-chlorobenzyl)-6-(2,2-difluoroethoxy)-2,4-dioxo-3,4-dihydroquinazolin-1(2H)-yl]piperidine-1-carbaldehyde | ¹H NMR (500 MHz, DMSO-d₆) δ ppm 1.72-1.83(m, 2H) 2.32-2.44(m, 1H) 2.45-2.53(m, 1H) 2.80(dt, 1H) 3.25-3.30(dt, 1H) 3.80 (d, 1 H) 4.30 (d, 1 H) 4.44 (td, 2H) 4.78(brs, 1H) 5.09(s, 2H) 6.42 (tt, 1H) 7.32-7.40(m, 4H) 7.48(dd, 1H) 7.61(d, 1H) 8.03(s, 1H) | |
| 35 | Methyl 4-{[6-(2,2-difluoroethoxy)-1-(1-formylpiperidin-4-yl)-2,4-dioxo-1,4-dihydroquinazolin-3(2H)-yl]methyl}benzoate | ¹H NMR (500 MHz, DMSO-d₆) δ ppm 1.78(dd, 1H) 2.33-2.42(m, 1H) 2.44-2.52(m, 1H) 2.80(dt, 1H) 3.26(dt, 1H) 3.79(brd, 1H) 3.84(s, 3H) 4.30(brd, 1H) 4.45(td, 2H) 4.79(brs, 1H) 5.18(s, 2 H) 6.42(tt, 1H) 7.43(d, 2H) 7.49(dd, 1H) 7.62(d, 1H) 7.83(d, 1H) 7.91(d, 2H) 8.02(s, 1H) | |

| | | | |
|---|---|---|---|
| 36 | 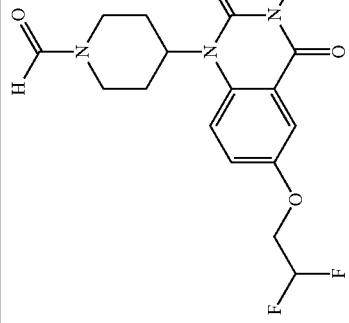 | 4-{[6-(2,2-difluoroethoxy)-1-(1-formylpiperidin-4-yl)-2,4-dioxo-1,4-dihydroquinazolin-3(2H)-yl]methyl}benzoic acid | 1H NMR (500 MHz, DMSO-d6) δ ppm 1.79(dd, 2H) 2.38(qd, 1H) 2.49(qd, 1H) 2.80(dt, 1H) 3.26(dt, 1H) 3.79(d, 1H) 4.31 (d, 1H) 4.45(td, 2H) 4.79(brs, 1H) 5.17(s, 2H) 6.42(tt, 1H) 7.40(d, 2H) 7.49(dd, 1H) 7.62(d, 1H) 7.83(d, 1H) 7.88(d, 2H) 8.02(s, 1H) 12.94(brs, 1H) |
| 37 | 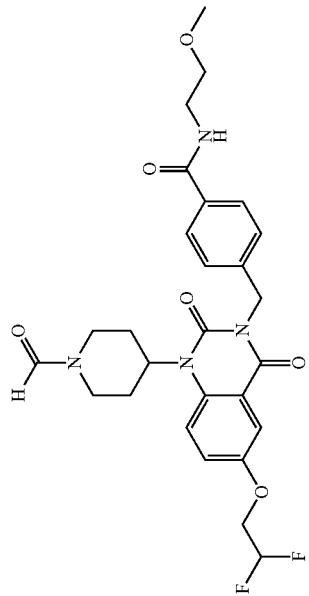 | 4-{[6-(2,2-difluoroethoxy)-1-(1-formylpiperidin-4-yl)-2,4-dioxo-1,4-dihydroquinazolin-3(2H)-yl]methyl}-N-(2-methoxyethyl)benzamide | 1H NMR (500 MHz, DMSO-d6) δ ppm 1.72-1.82(m, 2H) 2.32-2.42(m, 1H) 2.44-2.54(m, 1H) 2.75-2.83(m, 1H) 3.21-3.29(m, 4H) 3.37-3.45(m, 4H) 3.77(br.d, 1H) 4.29(br.d, 1H) 4.44(td, 2H) 4.78(brs., 1H) 5.14(s, 2H) 6.41 (tt, 1H) 7.35(m, 2H) 7.48(dd, 1H) 7.61 (d, 1H) 7.77(m, 2H) 7.81(d, 1H) 8.01(s, 1H) 8.47(t, 1H) |
| 38 | 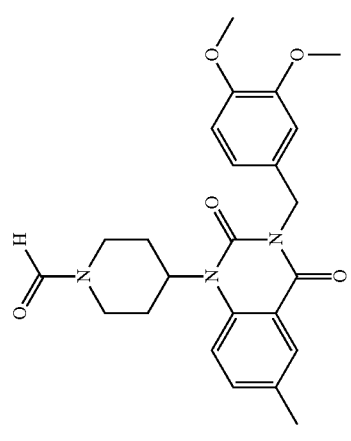 | 4-[3-(3,4-dimethoxybenzyl)-6-methyl-2,4-dioxo-3,4-dihydroquinazolin-1(2H)-yl]piperidine-1-carbaldehyde | 1H NMR (500 MHz, DMSO-d6) δ ppm 1.76(dd, 2H) 2.37(s, 3H) 2.39-2.42(m, 1H) 2.50-2.54(m, 1H) 2.77-2.82(m, 1H) 3.19-3.30(m, 1H) 3.70(s, 6H) 3.79(d, 1H) 4.30(d, 1H) 4.76(brs, 1H) 5.02(s, 2H) 6.82(dd, 1H) 6.85(d, 1H) 6.97(d, 1H) 7.60(dd, 1H) 7.71(d, 1H) 7.89(s, 1H) 8.03(s, 1H) |

| | | | |
|---|---|---|---|
| 39 | 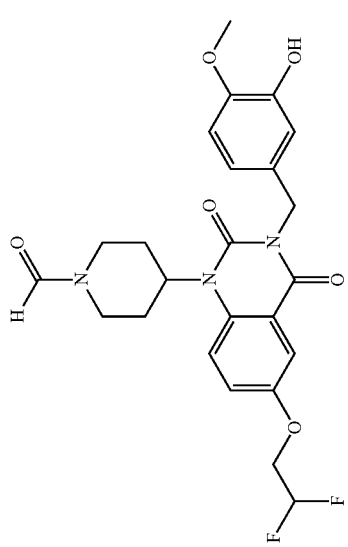 | 4-[6-(2,2-difluoroethoxy)-3-(3-hydroxy-4-methoxybenzyl)-2,4-dioxo-3,4-dihydroquinazolin-1(2H)-yl]piperidine-1-carbaldehyde | $^1$H NMR (500 MHz, DMSO-d$_6$) δ ppm 1.70-1.80(m, 2H) 2.35-1.45(m, 1H) 2.47-2.56(m, 1H) 2.80(dt, 1H) 3.25(dt, 1H) 3.70(s, 3H) 3.79(brd, 1H) 4.30(brd, 1H) 4.43(td, 2H) 4.77(brs, 1H) 4.96(s, 2H) 6.41(tt, 1H) 6.73(d, 1H) 6.78-6.82(m, 2H) 7.46(dd, 1H) 7.60(d, 1H) 7.79(d, 1H) 8.03(s, 1H) 8.95 (s, 1H) |
| 40 | 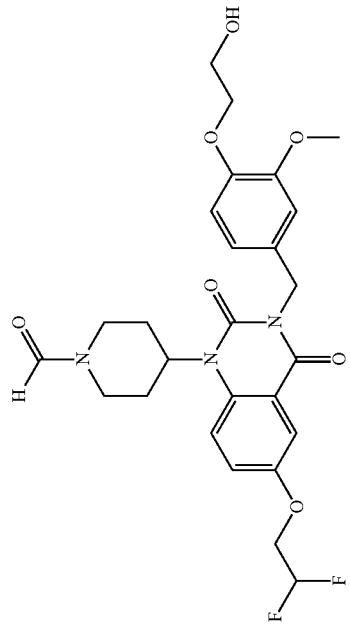 | 4-[6-(2,2-difluoroethoxy)-3-[2-hydroxyethoxy)-4-methoxybenzyl]-2,4-dioxo-3,4-dihydroquinazolin-1(2H)-yl]piperidine-1-carbaldehyde | $^1$H NMR (600 MHz, DMSO-d$_6$) δ ppm 1.76(dd, 2H) 2.35-2.45(m, 1H) 2.50-2.54(m, 1H) 2.79(dt, 1H) 3.25(dt, 1H) 3.68(dt, 2H) 3.70(s, 3H) 3.79(brd, 1H) 3.90(t, 2H) 4.30(brd, 1H) 4.42(td, 2H) 4.75(brs, 1H) 4.77(t, 1H) 5.01(s, 2H) 6.39(tt, 1H) 6.85(m, 2H) 6.97(s, 1H) 7.45(dd, 1H) 7.60(d, 1H) 7.77(d, 1H) 8.02(s, 1H) |
| 41 | 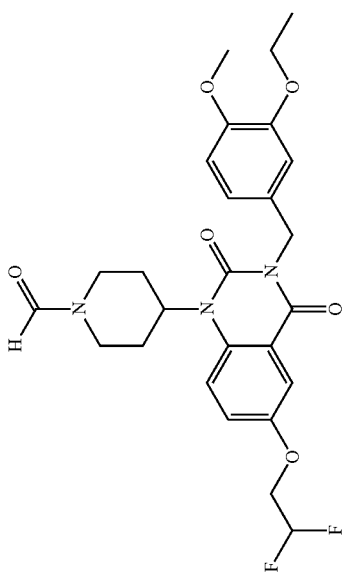 | 4-[6-ethoxy-3-(3-ethoxy-4-methoxybenzyl)-2,4-dioxo-3,4-dihydroquinazolin-1(2H)-yl]piperidine-1-carbaldehyde | $^1$H NMR (600 MHz, DMSO-d$_6$) δ ppm 1.29(t, 3H) 1.76(dd, 2H) 2.33-2.45(m, 1H) 2.50-2.56(m, 1H) 2.76-2.82(m, 1H) 3.21-3.31(m, 3H) 3.70(s, 3H) 3.79(brd, 1H) 3.94(q, 2H) 4.30(brd, 1 H) 4.41 (dt, 2H) 4.75(brs, 1H) 5.01(s, 2H) 6.39(tt, 1H) 6.81-6.86(m, 2H) 6.96(s, 1H) 7.45(dd, 1H) 7.60(d, 1H) 7.77(d, 1H) 8.02(s, 1H) |

| | | | |
|---|---|---|---|
| 42 | 4-[6-(2,2-difluoroethoxy)-3-[4-methoxy-3-(2-methoxyethoxy)benzyl]-2,4-dioxo-3,4-dihydroquinazolin-1(2H)-yl]piperidine-1-carbaldehyde | 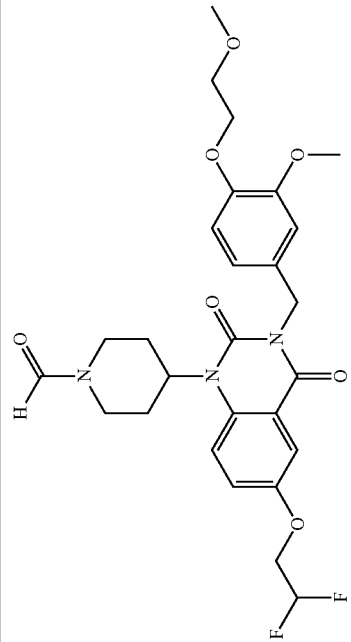 | $^1$H NMR (600 MHz, DMSO-$d_6$) δ ppm 1.69-1.82(m, 2H) 2.35-2.45(m, 1H) 2.45-2.55(m, 1H) 2.78(t, 1H) 3.21-3.28(m, 1H) 3.61(brs, 2H) 3.70(s, 3H) 3.78(d, 1H) 4.00(brs, 2H) 4.30(d, 1H) 4.42(t, 2H) 4.75(brs, 1H) 5.01(s, 2H) 6.39(t, 1H) 6.82-6.88(m, 2H) 6.97(s, 1H) 7.45(d, 1H) 7.59(s, 1H) 7.77(d, 1H) 8.02(s, 1H) |
| 43 | 4-[6-(2,2-difluoroethoxy)-3-(3,4-dimethoxybenzyl)-2,4-dioxo-3,4-dihydroquinazolin-1(2H)-yl]azepane-1-carbaldehyde | 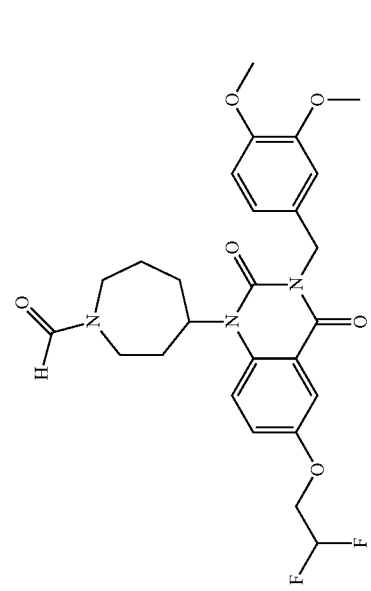 | $^1$H NMR (500 MHz, DMSO-$d_6$) mixture of two isomers δ ppm 1.72-1.81 (m, 1H) 1.85(brd, 1H) 1.86-2.03(m, 2H) 2.47(brs, 2H) 3.30-3.40(m, 1H) 3.42-3.52(m, 1H) 3.58-3.64(m, 2H) 3.70(s, 3H) 3.71(s, 3H) 4.42(td, 2H) 4.45(brs, 0.5H) 5.04(brs, 2H) 5.21(brs, 0.5H) 6.40(tt, 1H) 6.78-6.83(m, 1H) 6.86(d, 1H) 6.98(s, 1H) 7.38-7.48(m, 1H) 7.59(brs, 1H) 7.64-7.74(m, 1H) 8.08(brs, 0.5H) 8.12(s, 0.5H) |
| 44 | 3-(3,4-dimethoxybenzyl)-2,4-dioxo-1-(pyrrolidin-3-yl)-1,2,3,4-tetrahydroquinazoline-6-carbonitrile | 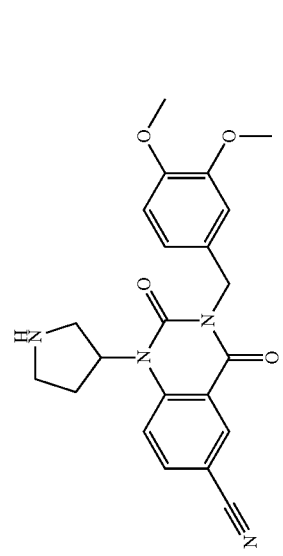 | $^1$H NMR (600 MHz, DMSO-$d_6$) δ ppm 1.96-2.09(m, 2H) 2.78-2.84(m, 1H) 3.05-3.12(m, 2H) 3.18-3.27(m, 1H) 3.70(s, 3H) 3.71(s, 3H) 5.04(s, 2H) 5.47-5.53(m, 1H) 6.83(brs, 2H) 6.99(s, 1H) 8.15(dd, 1H) 8.20(d, 1H) 8.47(s, 1H) |

| # | Name | Structure | NMR |
|---|---|---|---|
| 45 | 1-(1-acetylpyrrolidin-3-yl)-3-(3,4-dimethoxybenzyl)-2,4-dioxo-1,2,3,4-tetrahydroquinazoline-6-carbonitrile | 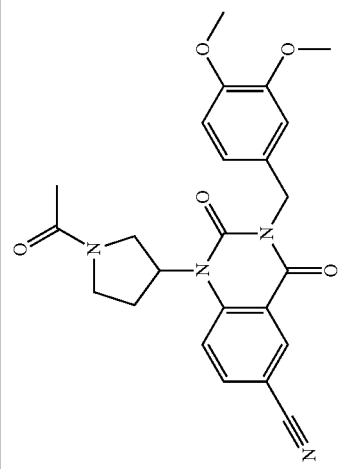 | $^1$H NMR (600 MHz, DMSO-$d_6$) mixture of two isomers δ ppm 1.91(s, 1.5H) 1.98(s, 1.5H) 2.14-2.22(m, 0.5H) 2.25-2.32(m, 0.5H) 2.43-2.50(m, 0.5H) 2.52-2.58(m, 0.5H) 3.31-3.39(m, 0.5H) 3.50-3.55(m, 0.5H) 3.63-3.73(m, 7.5H) 3.79-3.87(m, 1.5H) 5.00-5.06(m, 2H) 5.43-5.55(m, 1H) 6.82-6.90(m, 2H) 6.98(d, 1H) 7.84(dd, 1H) 8.17(dt, 1H) 8.43(dd, 1H) |
| 46 | 3-(3,4-dimethoxybenzyl)-1-(1-formylpyrrolidin-3-yl)-2,4-dioxo-1,2,3,4-tetrahydroquinazoline-6-carbonitrile | 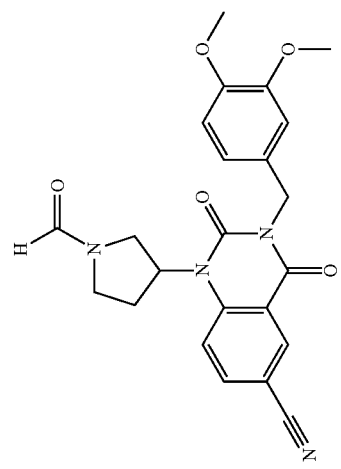 | $^1$H NMR (500 MHz, DMSO-$d_6$) mixture of two isomers δ ppm 2.19-2.27(m, 1H) 2.36-2.43(m, 1H) 3.43-3.47(m, 0.4H) 3.53-3.59(m, 0.6) 3.62-3.73(m, 1.6H) 3.70(s, 3H) 3.71 (s, 3H) 3.84-3.94(m, 1.4H) 5.04(s, 2H) 5.42-5.49(m, 0.4H) 5.50-5.56(m, 0.6H) 6.86(s, 2H) 6.99(s, 1H) 7.85(d, 0.6H) 7.90(d, 0.4H) 8.15-8.22(m, 2H) 8.45(s, 1H) |
| 47 | 4-[6-(2,2-difluoroethoxy)-3-[3-(3-hydroxypropoxy)-4-methoxybenzyl]-2,4-dioxo-3,4-dihydroquinazolin-1(2H)-yl]piperidine-1-carbaldehyde | 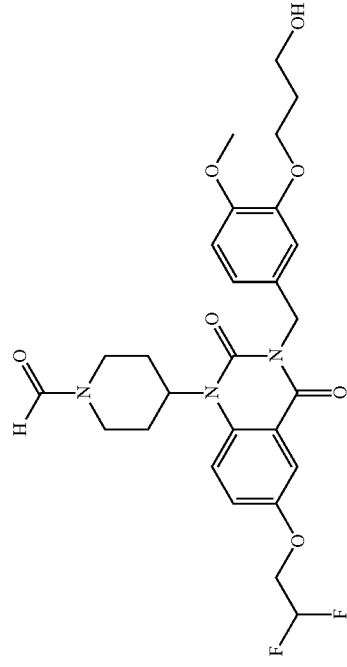 | $^1$H NMR (600 MHz, DMSO-$d_6$) δ ppm 1.72-1.79(m, 2H) 1.82(q, 2H) 2.36-2.44(m, 1H) 2.49-2.55(m, 1H) 2.78(td, 1H) 3.25(td, 1H) 3.51-3.54(m, 2H) 3.70(s, 3H) 3.76-3.80(m, 1H) 3.95(t, 2H) 4.28-4.32(m, 1H) 4.41 (td, 2H) 4.47(t, 1H) 4.75(s, 1H) 5.01(s, 2H) 6.39(tt, 1H) 6.81-6.86(m, 2H) 6.96-6.97(m, 1H) 7.45(dd, 1H) 7.59(d, 1H) 7.77(d, 1H) 8.02(s, 1H) |

| | -continued | | |
|---|---|---|---|
| 48 | 4-[5-chloro-3-(3,4-dimethoxybenzyl)-2,4-dioxo-3,4-dihydroquinazolin-1(2H)-yl]piperidine-1-carbaldehyde | 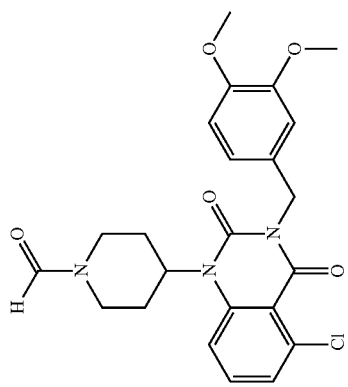 | ¹H NMR (500 MHz, DMSO-d₆) δ ppm 1.78-1.88(m, 2H) 2.34-2.44(m, 1H) 2.46-2.56(m, 1H) 2.80(t, 1H) 3.25(t, 1H) 3.71(s, 6H) 3.80(d, 1H) 4.31(d, 1H) 4.71(brs, 1H) 5.00(s, 2H) 6.83(d, 1H) 6.87(d, 1H) 6.97(s, 1H) 7.37(d, 1H) 7.69(dd, 1H) 7.77(d, 1H) 8.03(s, 1H) |
| 49 | 4-{3-[3-(cyclopentyloxy)-4-methoxybenzyl]-6-(2,2-difluoroethoxy)-2,4-dioxo-3,4-dihydroquinazolin-1(2H)-yl}piperidine-1-carbaldehyde | 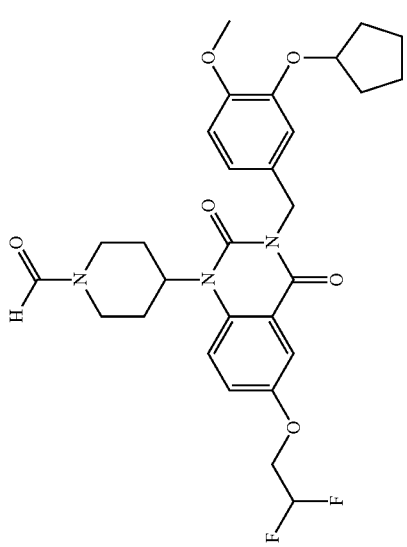 | ¹H NMR (500 MHz, DMSO-d₆) δ ppm 1.5-1.6(m, 2H) 1.63-1.71(m, 3H) 1.68-1.78(m, 1H) 1.78-1.98(m, 3H) 2.35-2.46(m, 1H) 2.47-2.57(m, 1H) 2.79(dt, 1H) 3.26(dt, 1H) 3.69(s, 3H) 3.79(br.d., 1H) 4.30(br.d, 1H) 4.43(td, 2H) 4.66-4.70(m, 1H) 4.76(brs., 1H) 5.01(s, 2H) 6.41(tt, 1H) 6.82-6.86(m, 2H) 6.96(s, 1H) 7.46(dd, 1H) 7.6(d, 1H) 7.80(d, 1H) 8.03(s, 1H) |
| 50 | 2-(5-{[6-(2,2-difluoroethoxy)-1-(1-formylpiperidin-4-yl)-2,4-dioxo-1,4-dihydroquinazolin-3(2H)-yl]methyl}-2-methoxyphenoxy)acetamide | 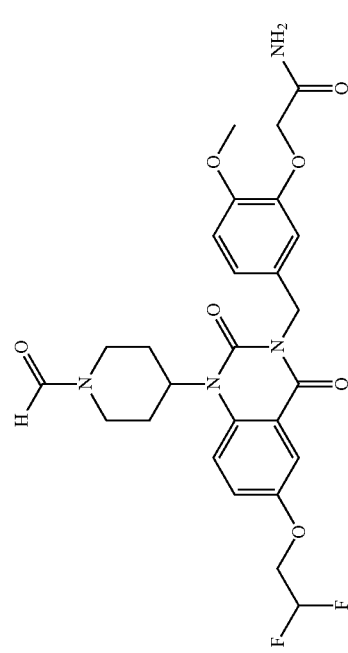 | ¹H NMR (500 MHz, DMSO-d₆) δ ppm 1.72-1.82(m, 2H) 2.35-2.45(m, 1H) 2.46-2.56(m, 1H) 2.79(td, 1H) 3.25(td, 1H) 3.79(d, 1H) 4.31(d, 1H) 4.35(s, 2H) 4.43(td, 2H) 4.76(brs, 1H) 5.00(s, 2H) 6.41(tt, 1H) 6.88-6.95(m, 3H) 7.31(brs, 1H) 7.37(brs, 1H) 7.46(dd, 1H) 7.59(d, 1H) 7.79(d, 1H) 8.02(s, 1H) |

| | | | |
|---|---|---|---|
| 51 | 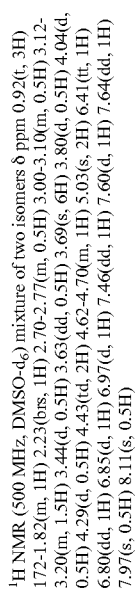 | 4-[6-(2,2-difluoroethoxy)-3-(3,4-dimethoxybenzyl)-2,4-dioxo-3,4-dihydroquinazolin-1(2H)-yl]-3-methylpiperidine-1-carbaldehyde | $^1$H NMR (500 MHz, DMSO-$d_6$) mixture of two isomers δ ppm 0.92(t, 3H) 1.72-1.82(m, 1H) 2.23(brs, 1H) 2.70-2.77(m, 0.5H) 3.00-3.10(m, 0.5H) 3.12-3.20(m, 1.5H) 3.44(d, 0.5H) 3.63(dd, 0.5H) 3.69(s, 6H) 3.80(d, 0.5H) 4.04(d, 0.5H) 4.29(d, 0.5H) 4.43(td, 2H) 4.62-4.70(m, 1H) 5.03(s, 2H) 6.41(tt, 1H) 6.80(d, 1H) 6.85(d, 1H) 6.97(d, 1H) 7.46(dd, 1H) 7.60(d, 1H) 7.64(dd, 1H) 7.97(s, 0.5H) 8.11(s, 0.5H) |
| 52 | 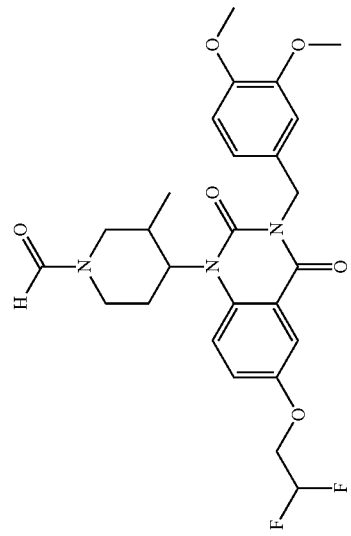 | 3-[6-(2,2-difluoroethoxy)-3-(3,4-dimethoxybenzyl)-2,4-dioxo-3,4-dihydroquinazolin-1(2H)-yl]-8-azabicyclo[3.2.1]octane-8-carbaldehyde | $^1$H NMR (600 MHz, DMSO-$d_6$) δ ppm 1.85-1.95(m, 4H) 2.18(t, 2H) 2.27-2.33(m, 1H) 2.34-2.41(m, 1H) 3.70(s, 1H) 3.71(s, 1H) 4.25-4.29(m, 1H) 4.40(td, 2H) 4.50-4.54(m, 1H) 4.55(brs., 1H) 5.05(s, 2H) 6.38(tt, H) 6.80(d, 1H) 6.85(d, 1H) 6.98(s, 1H) 7.45(dd, 1H) 7.56(d, 1H) 7.58(d, 1H) 8.12(s, 1H) |
| 53 | 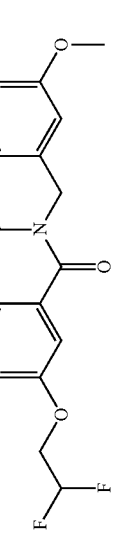 | 3-(3,4-dimethoxybenzyl)-1-(1-formylpiperidin-3-yl)-2,4-dioxo-1,2,3,4-tetrahydroquinazoline-6-carbonitrile | $^1$H NMR (500 MHz, DMSO-$d_6$) mixture of two isomers δ ppm 1.52-1.63(m, 0.5H) 1.65-1.73(m, 0.5H) 1.74-1.83(m, 1H) 1.87-1.93(m, 1H) 2.54-2.64(m, 1.5H) 3.06(dt, 0.5H) 3.57(t, 0.5H) 3.70(s, 3H) 3.71 (s, 3H) 3.79(dd, 0.5H) 4.03(t, 0.5H) 4.20(d, 0.5H) 4.30(d, 0.5H) 4.38(brs, 0.5H) 4.53(brs, 0.5H) 4.99-5.07(m, 2H) 6.84-6.88(m, 2H) 6.98(s, 1H) 7.86(d, 0.5H) 8.01(d, 0.5H) 7.98(s, 0.5H) 8.08(s, 0.5H) 8.14-8.18(m, 1H) 8.44(s, 1H) |

| | | | |
|---|---|---|---|
| 54 | 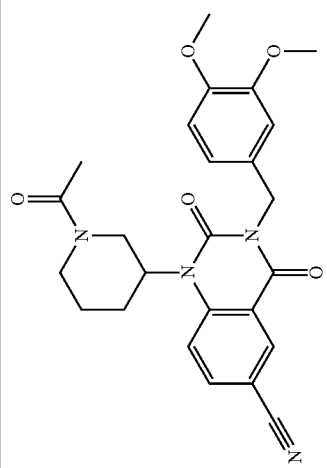 | 1-(1-acetylpiperidin-3-yl)-3-(3,4-dimethoxybenzyl)-2,4-dioxo-1,2,3,4-tetrahydroquinazoline-6-carbonitrile | 1H NMR (500 MHz, DMSO-d6) mixture of two isomers δ ppm 1.56-1.66(m, 0.5H) 1.70-1.82(m, 1.5H) 1.87(brd, 1H) 1.97(s, 1.5H) 2.05(s, 1.5H) 2.54(dd, 1H) 3.05(brt, 0.5H) 3.48(t, 0.5H) 3.70-3.72(m, 6H) 3.83(d, 1.5H) 3.94(brd, 0.5H) 4.04(t, 0.5H) 4.33(brs, 0.5H) 4.45(dd, 1H) 4.53(brs, 0.5H) 4.99-5.07(m, 2H) 6.83-6.87(m, 2H) 6.98(d, 1H) 7.84(d, 0.5H) 8.02(d, 0.5H) 8.16(dt, 1H) 8.44(dd, 1H) |
| 55 | 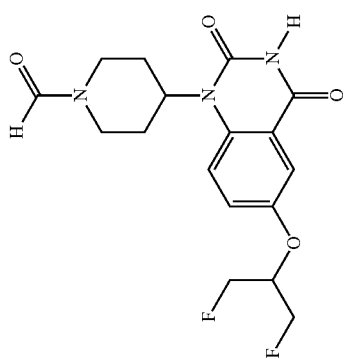 | 4-{6-[2-fluoro-1-(fluoromethyl)ethoxy]-2,4-dioxo-3,4-dihydroquinazolin-1(2H)-yl}piperidine-1-carbaldehyde | 1H NMR (600 MHz, DMSO-d6) δ ppm 1.73-1.82(m, 2H) 2.36-2.44(m, 1H) 2.44-2.55(m, 1H) 2.79(td, 1H) 3.25(td, 1H) 3.80(brd, 1H) 4.32(brd, 1H) 4.62-4.67(m, 1H) 4.68-4.76(m, 3H) 4.76-4.82(m, 1H) 4.96-5.06(m, 1H) 7.61(d, 1H) 7.73(d, 1H) 8.03(s, 1H) 11.46(brs, 1H) |
| 56 | 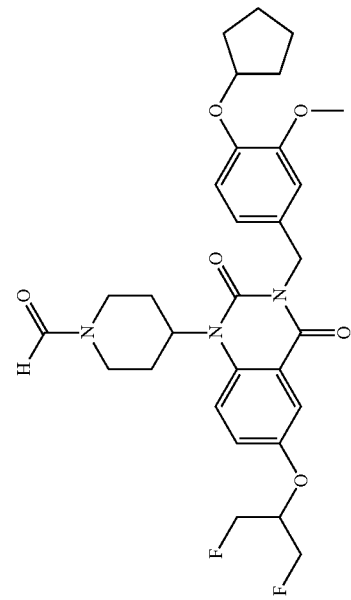 | 4-{3-[4-(cyclopentyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | LCMS m/z [MH]+ 572 |

| | | | |
|---|---|---|---|
| 57 | 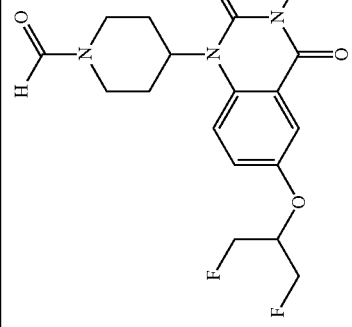 | 4-[3-(3-chlorobenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 492 |
| 58 | 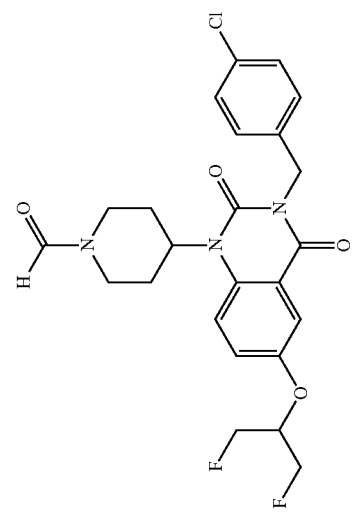 | 4-[3-(4-chlorobenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 492 |
| 59 | 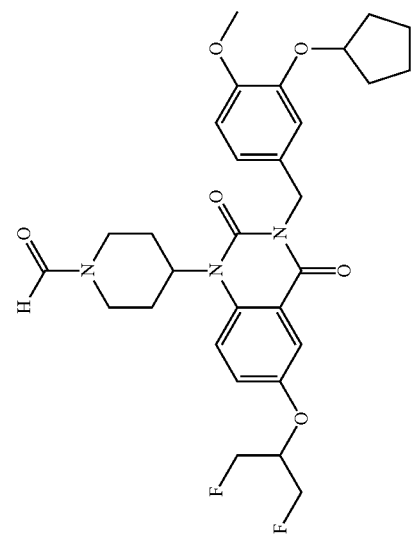 | 4-{3-[3-(cyclopentyloxy)-4-methoxybenzyl]-6-[2-fluoro-1-(fluoromethyl)ethoxy]-2,4-dioxo-3,4-dihydroquinazolin-1(2H)-yl}piperidine-1-carbaldehyde | LCMS m/z [MH]+ 572 |

| | | | |
|---|---|---|---|
| 60 | 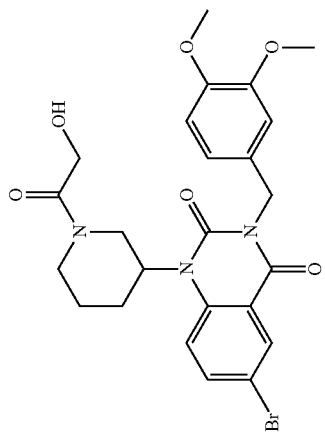 | 6-bromo-3-(3,4-dimethoxybenzyl)-1-[1-(hydroxyacetyl)piperidin-3-yl]quinazoline-2,4(1H,3H)-dione | LCMS m/z [MH]+ 532 |
| 61 | 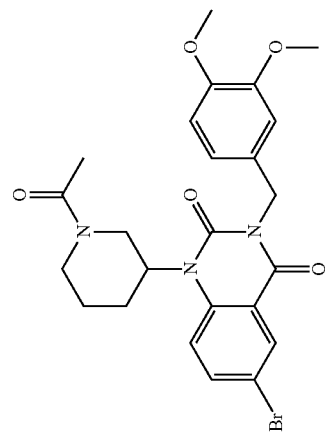 | 1-(1-acetylpiperidin-3-yl)-6-bromo-3-(3,4-dimethoxybenzyl)quinazoline-2,4(1H,3H)-dione | LCMS m/z [MH]+ 516 |
| 62 | 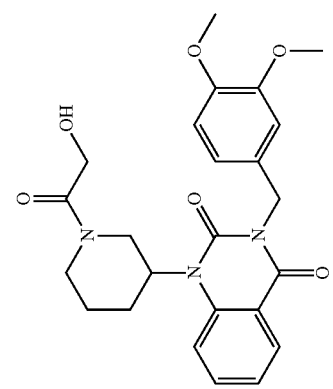 | 3-(3,4-dimethoxybenzyl)-1-[1-(hydroxyacetyl)piperidin-3-yl]quinazoline-2,4(1H,3H)-dione | LCMS m/z [MH]+ 454 |

| | | | |
|---|---|---|---|
| 63 |  | 6-bromo-3-(3,4-dimethoxybenzyl)-1-[piperidin-3-yl]quinazoline-2,4(1H,3H)-dione | LCMS m/z [MH]+ 474 |
| 64 | 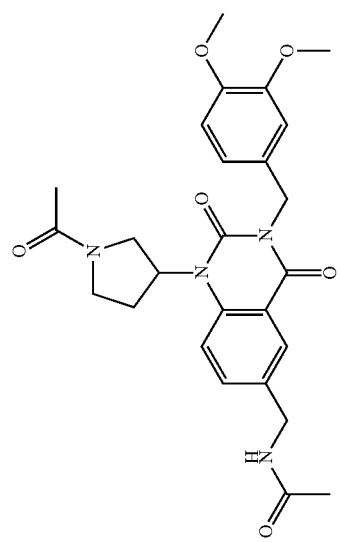 | N-{[1-(1-acetylpyrrolidin-3-yl)-3-(3,4-dimethoxybenzyl)-2,4-dioxo-1,2,3,4-tetrahydroquinazolin-6-yl]methyl}acetamide | LCMS m/z [MH]+ 495 |
| 65 | 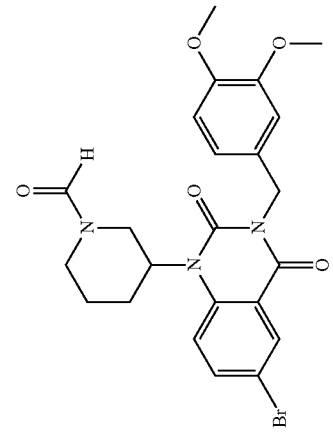 | 3-[6-bromo-3-(3,4-dimethoxybenzyl)-2,4-dioxo-3,4-dihydroquinazolin-1(2H)-yl]piperidine-1-carbaldehyde | LCMS m/z [MH]+ 502 |

-continued
| | | |
|---|---|---|
| 66 | 6-bromo-1-[1-(cyclopropyl-carbonyl)piperidin-3-yl]-3-(3,4-dimethoxybenzyl)quinazoline-2,4(1H,3H)-dione | LCMS m/z [MH]+ 542 |
| 67 | 1-{1-[(benzyloxy)acetyl]piperidin-3-yl}-6-bromo-3-(3,4-dimethoxybenzyl)quinazoline-2,4(1H,3H)-dione | LCMS m/z [MH]+ 622 |
| 68 | 1-{1-[(benzyloxy)acetyl]piperidin-3-yl}-3-(3,4-dimethoxybenzyl)-6-[2-fluoro-1-(fluoromethyl)ethoxy]quinazoline-2,4(1H,3H)-dione | LCMS m/z [MH]+ 638 |
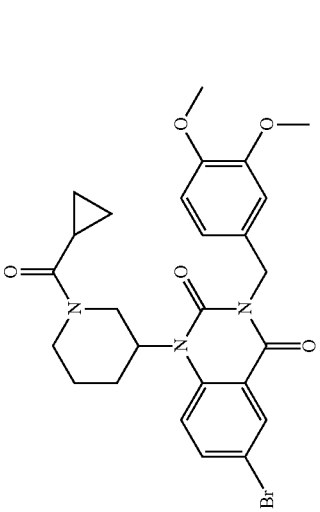
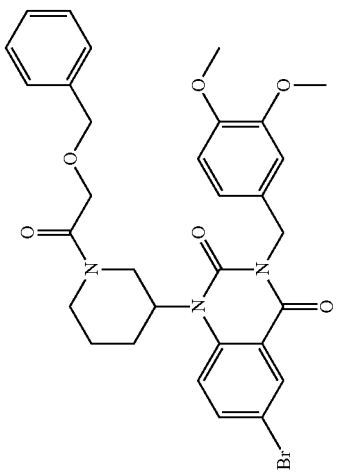
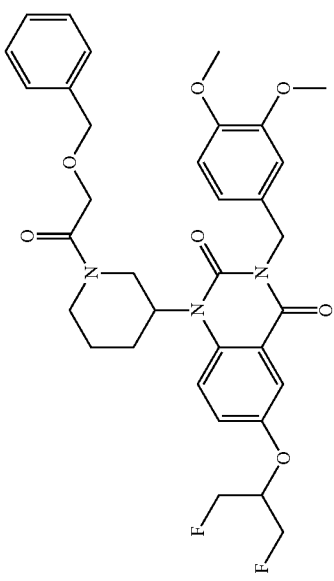

-continued
| | | | |
|---|---|---|---|
| 69 | 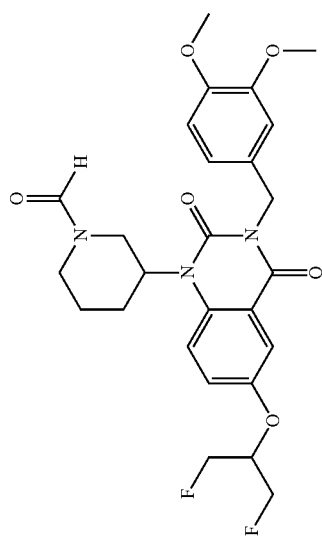 | 3-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 518 |
| 70 | 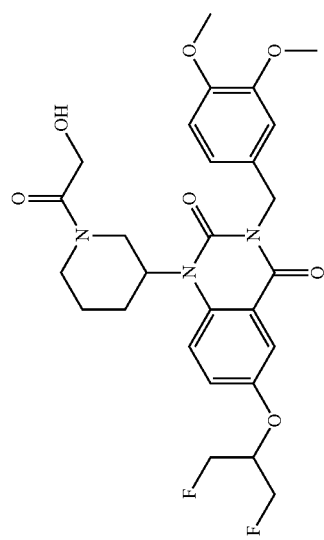 | 3-(3,4-dimethoxybenzyl)-6-[2-fluoro-1-(fluoromethyl)ethoxy]-1-[1-(hydroxyacetyl)piperidin-3-yl]quinazoline-2,4(1H,3H)-dione | LCMS m/z [MH]+ 548 |
| 71 | 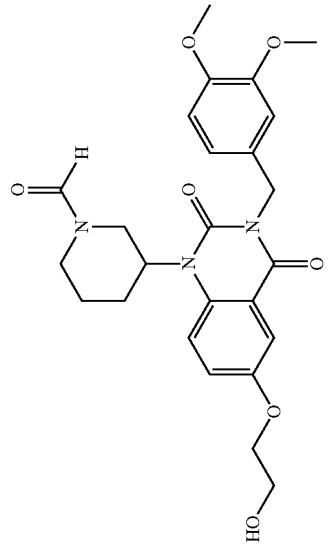 | 3-[3-(3,4-dimethoxybenzyl)-6-(2-hydroxyethoxy)-2,4-dioxo-3,4-dihydroquinazolin-1(2H)-yl]piperidine-1-carbaldehyde | LCMS m/z [MH]+ 484 |

| | | | |
|---|---|---|---|
| 72 | 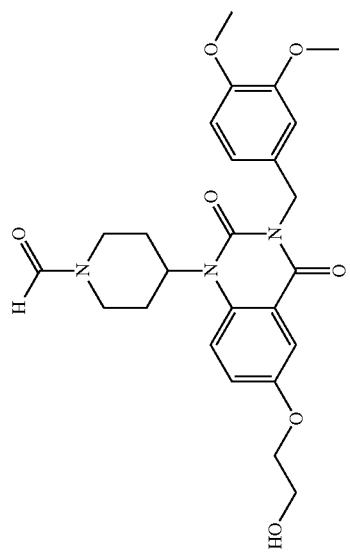 | 4-[3-(3,4-dimethoxybenzyl)-6-(2-hydroxyethoxy)-2,4-dioxo-3,4-dihydroquinazolin-1(2H)-yl]piperidine-1-carbaldehyde | LCMS m/z [MH]+ 484 |
| 73 | 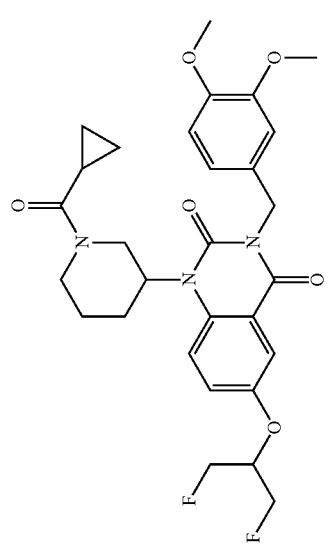 | 1-[1-(cyclopropylcarbonyl)-piperidin-3-yl]-3-(3,4-dimethoxybenzyl)-6-[2-fluoro-1-(fluoromethyl)ethoxy]quinazoline-2,4(1H,3H)-dione | LCMS m/z [MH]+ 558 |
| 74 | 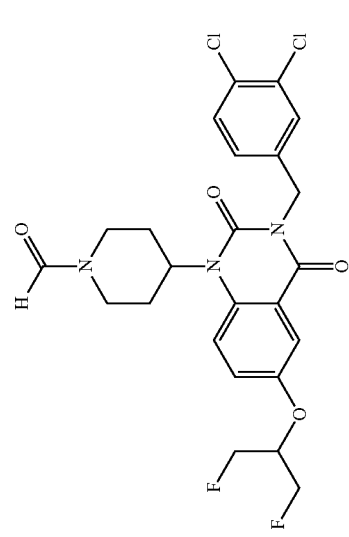 | 4-[3-(3,4-dichlorobenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 526 |

-continued
| | | | |
|---|---|---|---|
| 75 | 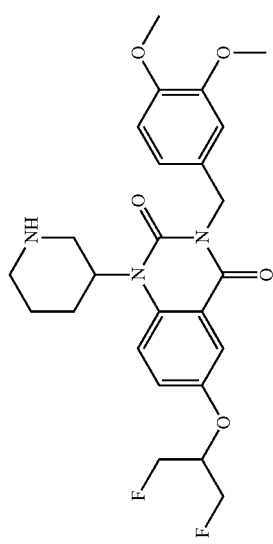 | 3-(3,4-dimethoxybenzyl)-6-[2-fluoro-1-(fluoromethyl)ethoxy]-1-(piperidin-3-yl)quinazoline-2,4(1H,3H)-dione | LCMS m/z [MH]+ 490 |
| 76 | 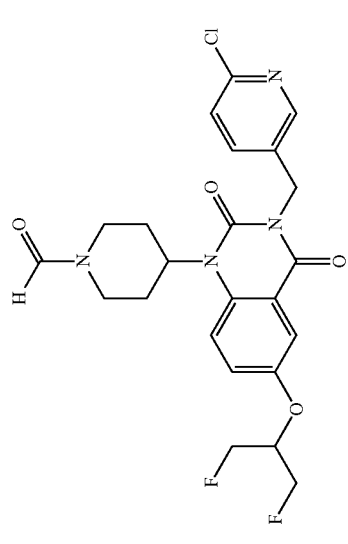 | 4-{3-[(6-chloropyridin-3-yl)methyl]-6-[2-fluoro-1-(fluoromethyl)ethoxy]-2,4-dioxo-3,4-dihydroquinazolin-1(2H)-yl}piperidine-1-carbaldehyde | LCMS m/z [MH]+ 493 |
| 77 | 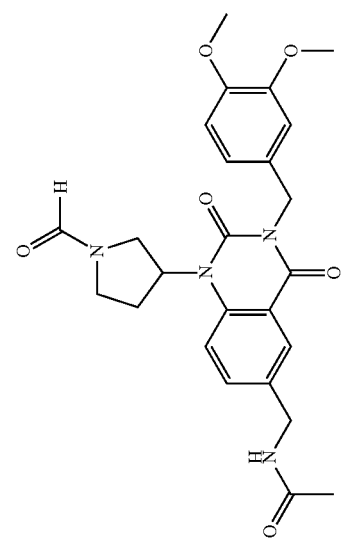 | N-{[3-(3,4-dimethoxybenzyl)-1-(1-formylpyrrolidin-3-yl)-2,4-dioxo-1,2,3,4-tetrahydroquinazolin-6-yl]methyl}acetamide | LCMS m/z [MH]+ 481 |

-continued
| | | |
|---|---|---|
| 78 | 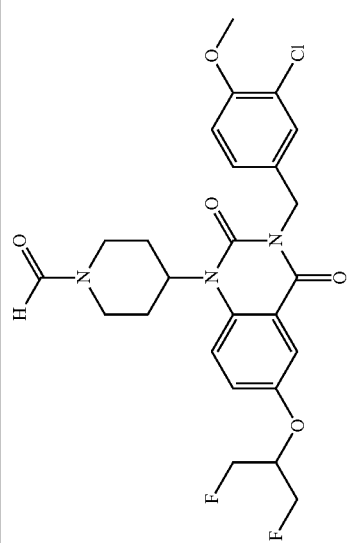 4-[3-(3-chloro-4-methoxybenzyl)-6-[2-fluoro-1-(fluoromethyl)-ethoxy]-2,4-dioxo-3,4-dihydroquinazolin-1(2H)-yl]piperidine-1-carbaldehyde | LCMS m/z [MH]+ 522 |
| 79 | 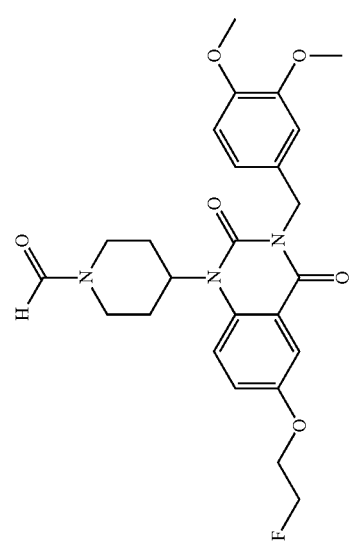 4-[3-(3,4-dimethoxybenzyl)-6-(2-fluoroethoxy)-2,4-dioxo-3,4-dihydroquinazolin-1(2H)-yl]piperidine-1-carbaldehyde | LCMS m/z [MH]+ 486 |
| 80 | 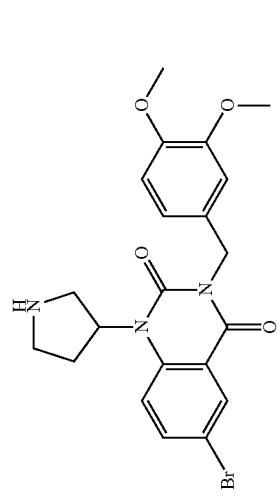 6-bromo-3-(3,4-dimethoxybenzyl)-1-[pyrrolidin-3-yl]quinazoline-2,4(1H,3H)-dione | LCMS m/z [MH]+ 460 |

-continued
| | | | |
|---|---|---|---|
| 81 | 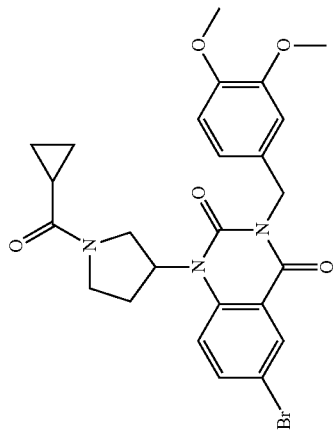 | 6-bromo-1-[1-(cyclopropyl-carbonyl)pyrrolidin-3-yl]-3-(3,4-dimethoxybenzyl)quinazoline-2,4(1H,3H)-dione | LCMS m/z [MH]+ 528 |
| 82 | 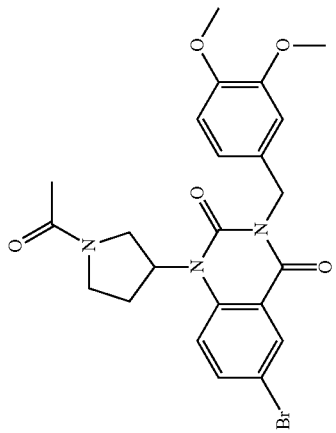 | 1-(1-acetylpyrrolidin-3-yl)-6-bromo-3-(3,4-dimethoxybenzyl)-quinazoline-2,4(1H,3H)-dione | LCMS m/z [MH]+ 502 |
| 83 | 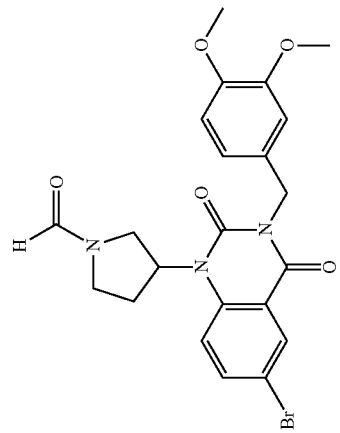 | 3-[6-bromo-3-(3,4-dimethoxy-benzyl)-2,4-dioxo-3,4-dihydroquinazolin-1(2H)-yl]pyrrolidine-1-carbaldehyde | LCMS m/z [MH]+ 488 |

| | | | |
|---|---|---|---|
| 84 | 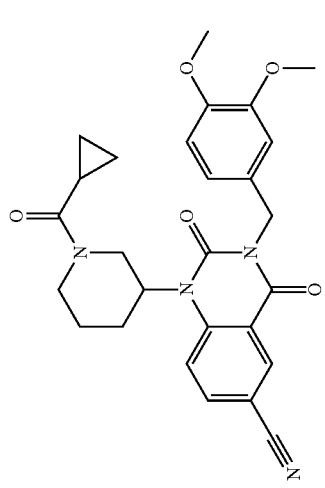 | 1-[1-(cyclopropylcarbonyl)-piperidin-3-yl]-3-(3,4-dimethoxybenzyl)-2,4-dioxo-1,2,3,4-tetrahydroquinazoline-6-carbonitrile | LCMS m/z [MH]+ 489 |
| 85 | 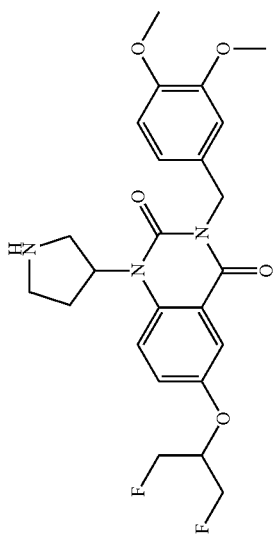 | 3-(3,4-dimethoxybenzyl)-6-[2-fluoro-1-(fluoromethyl)ethoxy]-1-(pyrrolidin-3-yl)quinazoline-2,4(1H,3H)-dione | LCMS m/z [MH]+ 476 |
| 86 | 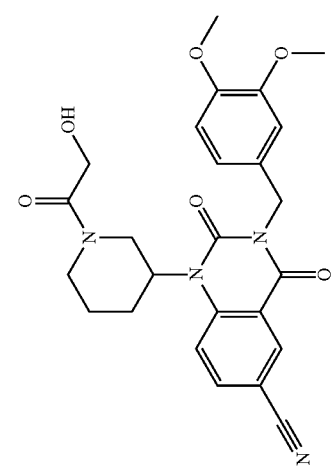 | 3-(3,4-dimethoxybenzyl)-1-[1-(hydroxyacetyl)piperidin-3-yl]-2,4-dioxo-1,2,3,4-tetrahydro-quinazoline-6-carbonitrile | LCMS m/z [MH]+ 479 |

| | -continued | | |
|---|---|---|---|
| 87 | 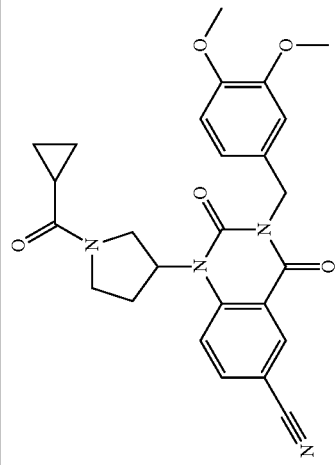 | 1-[1-(cyclopropylcarbonyl)-pyrrolidin-3-yl]-3-(3,4-dimethoxybenzyl)-2,4-dioxo-1,2,3,4-tetrahydroquinazoline-6-carbonitrile | LCMS m/z [MH]+ 475 |
| 88 | 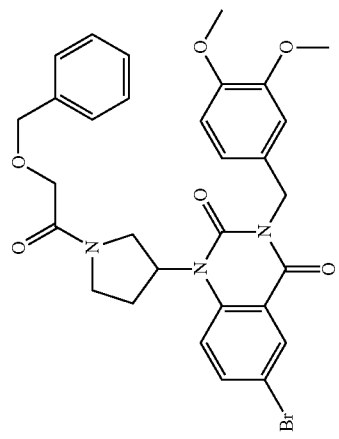 | 1-{1-[(benzyloxy)acetyl]pyrrolidin-3-yl}-6-bromo-3-(3,4-dimethoxybenzyl)quinazoline-2,4(1H,3H)-dione | LCMS m/z [MH]+ 608 |
| 89 | 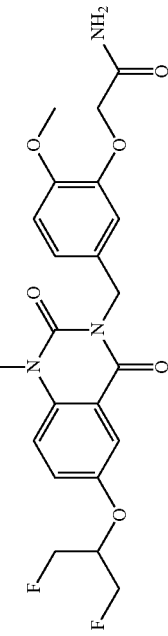 | 2-[5-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]acetamide | LCMS m/z [MH]+ 561 |

-continued
| | | |
|---|---|---|
| 90 | 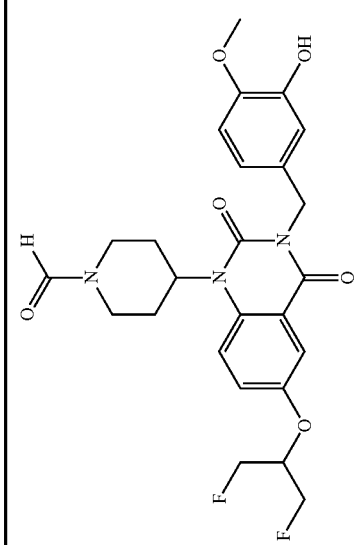 4-{6-[2-fluoro-1-(fluoromethyl)ethoxy]-3-(3-hydroxy-4-methoxybenzyl)-2,4-dioxo-3,4-dihydroquinazolin-1(2H)-yl}piperidine-1-carbaldehyde | LCMS m/z [MH]+ 504 |
| 91 | 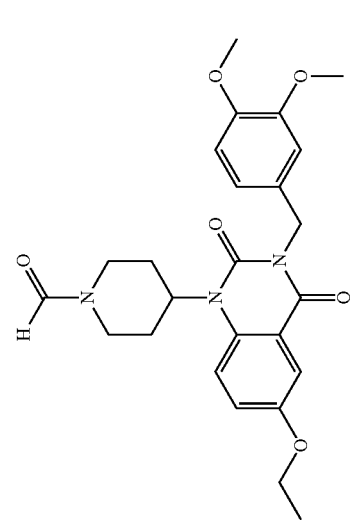 4-[3-(3,4-dimethoxybenzyl)-6-ethoxy-2,4-dioxo-3,4-dihydroquinazolin-1(2H)-yl]piperidine-1-carbaldehyde | LCMS m/z [MH]+ 468 |
| 92 | 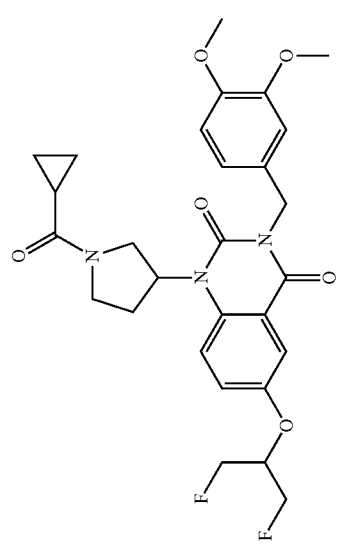 1-[1-(cyclopropylcarbonyl)-pyrrolidin-3-yl]-3-(3,4-dimethoxybenzyl)-6-[2-fluoro-1-(fluoromethyl)ethoxy]quinazoline-2,4(1H,3H)-dione | LCMS m/z [MH]+ 544 |

| | | -continued | |
|---|---|---|---|
| 93 | 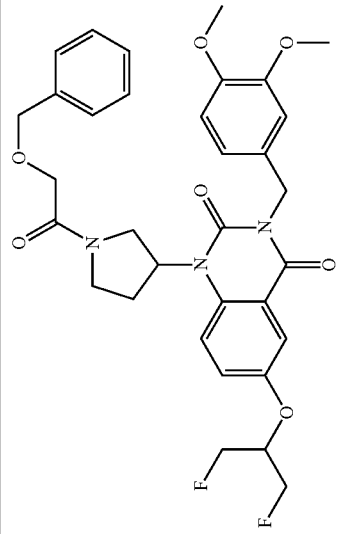 | 1-{1-[(benzyloxy)acetyl]-pyrrolidin-3-yl}-3-(3,4-dimethoxybenzyl)-6-[2-fluoro-1-(fluoromethyl)ethoxy]quinazoline-2,4(1H,3H)-dione | LCMS m/z [MH]+ 624 |
| 94 | 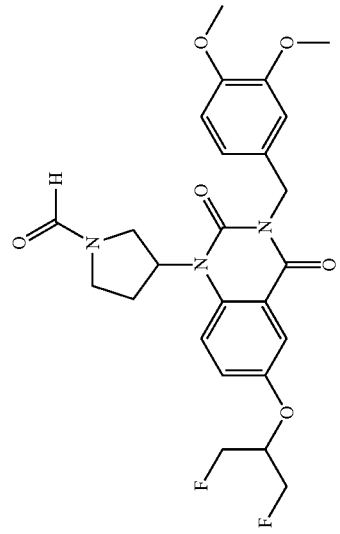 | 3-[3-(3,4-dimethoxybenzyl)-6-[2-fluoro-1-(fluoromethyl)ethoxy]-2,4-dioxo-3,4-dihydroquinazolin-1(2H)-yl]pyrrolidine-1-carbaldehyde | LCMS m/z [MH]+ 504 |
| 95 | 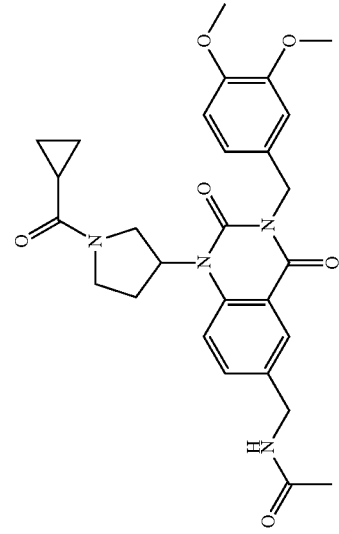 | N-({1-[1-(cyclopropylcarbonyl)-pyrrolidin-3-yl]-3-(3,4-dimethoxybenzyl)-2,4-dioxo-1,2,3,4-tetrahydroquinazolin-6-yl}methyl)acetamide | LCMS m/z [MH]+ 521 |

| | -continued | | |
|---|---|---|---|
| 96 | 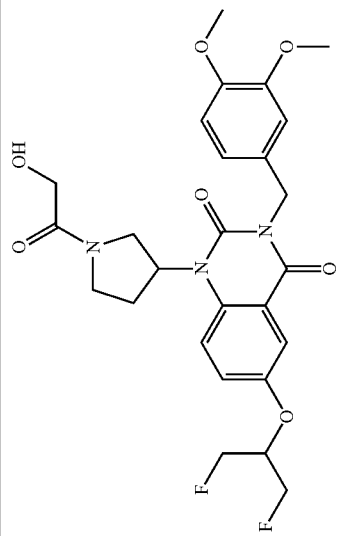 | 3-(3,4-dimethoxybenzyl)-6-[2-fluoro-1-(fluoromethyl)ethoxy]-1-[1-(hydroxyacetyl)pyrrolidin-3-yl]quinazoline-2,4(1H,3H)-dione | LCMS m/z [M + Na]+ 534 |
| 97 | 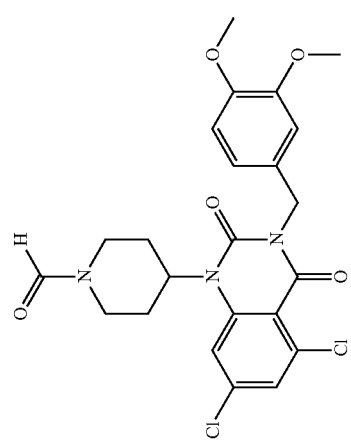 | 4-[5,7-dichloro-3-(3,4-dimethoxybenzyl)-2,4-dioxo-3,4-dihydroquinazolin-1(2H)-yl]piperidine-1-carbaldehyde | LCMS m/z [MH]+ 492 |
| 98 | 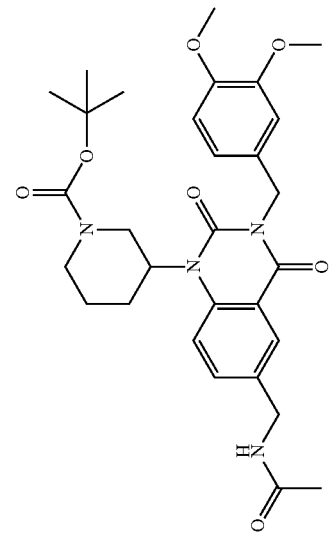 | 1,1-dimethylethyl 3-{6-[(acetylamino)methyl]-3-(3,4-dimethoxybenzyl)-2,4-dioxo-3,4-dihydroquinazolin-1(2H)-yl}piperidine-1-carboxylate | LCMS m/z [M + Na]+ 589 |

| | | -continued | |
|---|---|---|---|
| 99 | 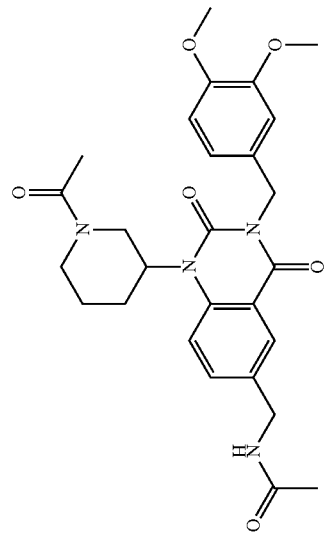 | N-{[3-(3,4-dimethoxybenzyl)-1-(1-formylpiperidin-3-yl)-2,4-dioxo-1,2,3,4-tetrahydroquinazolin-6-yl]methyl}acetamide | LCMS m/z [MH]+ 495 |
| 100 | 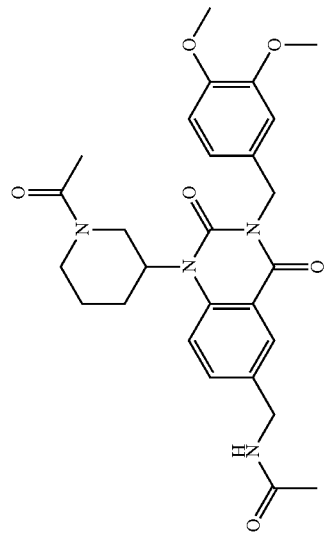 | N-{[1-(1-acetylpiperidin-3-yl)-3-(3,4-dimethoxybenzyl)-2,4-dioxo-1,2,3,4-tetrahydroquinazolin-6-yl]methyl}acetamide | LCMS m/z [MH]+ 509 |
| 101 | 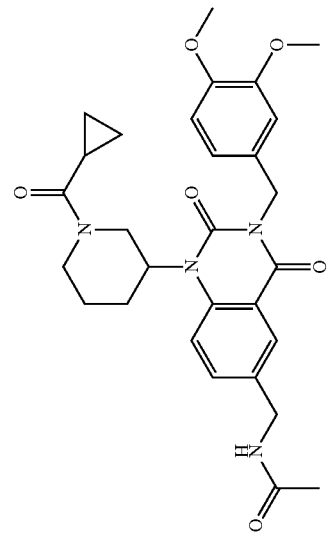 | N-({1-[1-(cyclopropylcarbonyl)-piperidin-3-yl]-3-(3,4-dimethoxybenzyl)-2,4-dioxo-1,2,3,4-tetrahydroquinazolin-6-yl}methyl)acetamide | LCMS m/z [MH]+ 535 |

-continued
| | | |
|---|---|---|
| 102 | 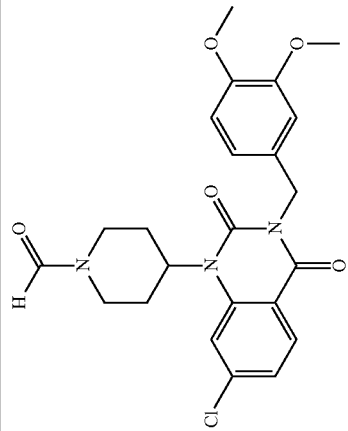 4-[7-chloro-3-(3,4-dimethoxybenzyl)-2,4-dioxo-3,4-dihydroquinazolin-1(2H)-yl]piperidine-1-carbaldehyde | LCMS m/z [MH]+ 458 |
| 103 | 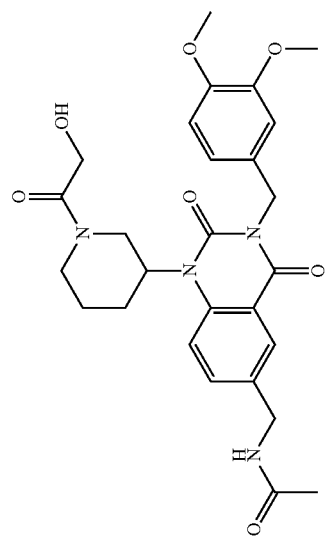 N-({3-(3,4-dimethoxybenzyl)-1-[1-(hydroxyacetyl)piperidin-3-yl]-2,4-dioxo-1,2,3,4-tetrahydroquinazolin-6-yl}methyl)acetamide | LCMS m/z [MH]+ 525 |
| 104 | 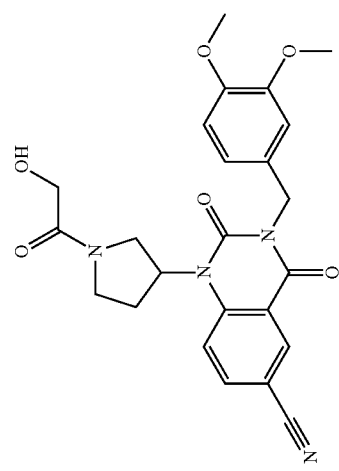 3-(3,4-dimethoxybenzyl)-1-[1-(hydroxyacetyl)pyrrolidin-3-yl]-2,4-dioxo-1,2,3,4-tetrahydroquinazoline-6-carbonitrile | LCMS m/z [MH]+ 465 |

-continued
| | | | |
|---|---|---|---|
| 105 |  | 6-bromo-3-(3,4-dimethoxybenzyl)-1-[1-(hydroxyacetyl)pyrrolidin-3-yl]quinazoline-2,4(1H,3H)-dione | LCMS m/z [MH]+ 518 |
| 106 | 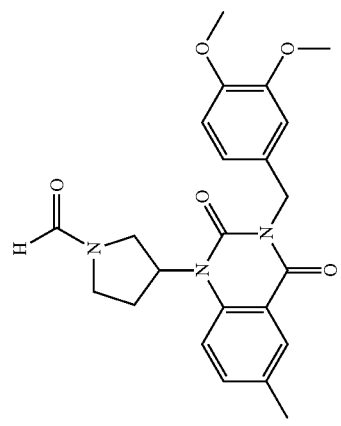 | 3-[3-(3,4-dimethoxybenzyl)-6-methyl-2,4-dioxo-3,4-dihydroquinazolin-1(2H)-yl]pyrrolidine-1-carbaldehyde | LCMS m/z [MH]+ 424 |
| 107 | 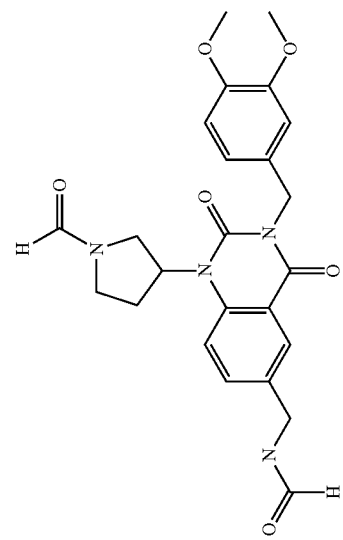 | N-{[3-(3,4-dimethoxybenzyl)-1-(1-formylpyrrolidin-3-yl)-2,4-dioxo-1,2,3,4-tetrahydroquinazolin-6-yl]methyl}formamide | LCMS m/z [MH]+ 467 |

| | | | |
|---|---|---|---|
| 108 | | 4-{6-[2-fluoro-1-(fluoromethyl)-ethoxy]-3-(3-fluoro-4-methoxybenzyl)-2,4-dioxo-3,4-dihydroquinazolin-1(2H)-yl}piperidine-1-carbaldehyde | LCMS m/z [MH]+ 506 |
| 109 | | 4-[6-(benzyloxy)-3-(3,4-dimethoxybenzyl)-2,4-dioxo-3,4-dihydroquinazolin-1(2H)-yl]piperidine-1-carbaldehyde | LCMS m/z [MH]+ 530 |
| 110 | | 1,1-dimethylethyl 3-[6-(benzyloxy)-3-(3,4-dimethoxybenzyl)-2,4-dioxo-3,4-dihydroquinazolin-1(2H)-yl]azetidine-1-carboxylate | LCMS m/z [MH]+ 574 |

-continued
| | | | |
|---|---|---|---|
| 111 | 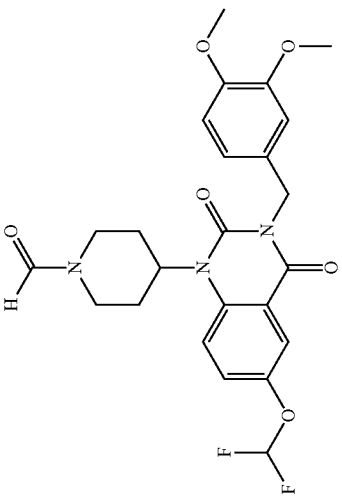 | 4-[6-(difluoromethoxy)-3-(3,4-dimethoxybenzyl)-2,4-dioxo-3,4-dihydroquinazolin-1(2H)-yl]piperidine-1-carbaldehyde | LCMS m/z [MH]+ 490 |
| 112 | 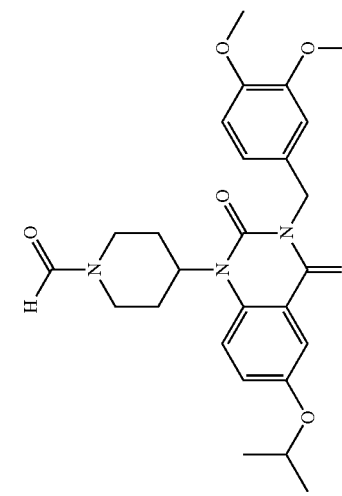 | 4-[3-(3,4-dimethoxybenzyl)-6-(1-methylethoxy)-2,4-dioxo-3,4-dihydroquinazolin-1(2H)-yl]piperidine-1-carbaldehyde | LCMS m/z [MH]+ 482 |
| 113 | 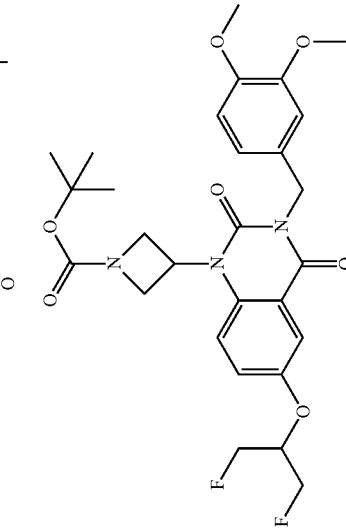 | 1,1-dimethylethyl 3-[3-(3,4-dimethoxybenzyl)-6-[2-fluoro-1-(fluoromethyl)ethoxy]-2,4-dioxo-3,4-dihydroquinazolin-1(2H)-yl]azetidine-1-carboxylate | LCMS m/z [MH]+ 562 |

| | | |
|---|---|---|
| 114 | 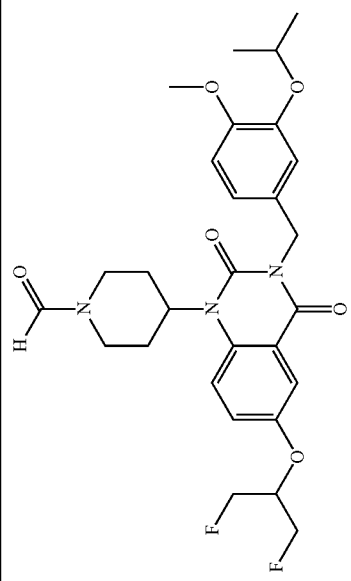 4-{6-[2-fluoro-1-(fluoromethyl)ethoxy]-3-[4-methoxy-3-(1-methylethoxy)-benzyl]-2,4-dioxo-3,4-dihydroquinazolin-1(2H)-yl}piperidine-1-carbaldehyde | LCMS m/z [MH]+ 546 |
| 115 | 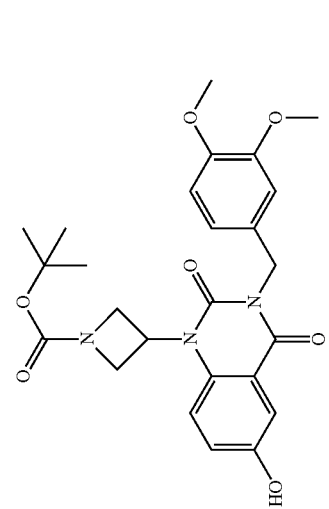 1,1-dimethylethyl 3-[3-(3,4-dimethoxybenzyl)-6-hydroxy-2,4-dioxo-3,4-dihydroquinazolin-1(2H)-yl]azetidine-1-carboxylate | LCMS m/z [MH]+ 484 |
| 116 | 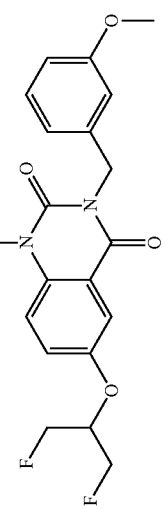 4-{6-[2-fluoro-1-(fluoromethyl)ethoxy]-3-(3-methoxybenzyl)-2,4-dioxo-3,4-dihydroquinazolin-1(2H)-yl}piperidine-1-carbaldehyde | LCMS m/z [MH]+ 488 |

| | | | |
|---|---|---|---|
| 117 | 4-{3-[3,5-bis(trifluoromethyl)benzyl]-6-[2-fluoro-1-(fluoromethyl)ethoxy]-2,4-dioxo-3,4-dihydroquinazolin-1(2H)-yl}piperidine-1-carbaldehyde | 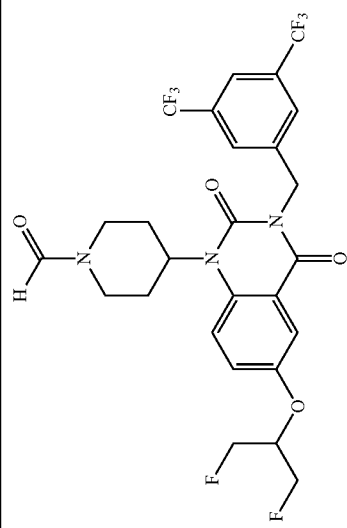 | LCMS m/z [MH]+ 564 |
| 118 | 4-[3-(3-ethoxybenzyl)-6-[2-fluoro-1-(fluoromethyl)ethoxy]-2,4-dioxo-3,4-dihydroquinazolin-1(2H)-yl]piperidine-1-carbaldehyde | 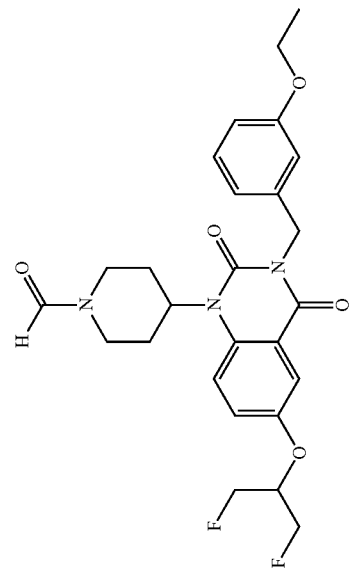 | LCMS m/z [MH]+ 502 |

-continued
| COMPOUND No. | STRUCTURE | NOMENCLATURE | MASS LCUVMS MH+ |
|---|---|---|---|
| 119 | 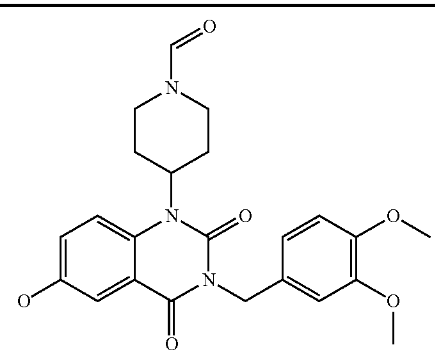 | 4-[3-(3,4-dimethoxybenzyl)-6-hydroxy-2,4-dioxo-3,4-dihydroquinazolin-1(2H)-yl]piperidine-1-carbaldehyde | 440 |
| 120 | 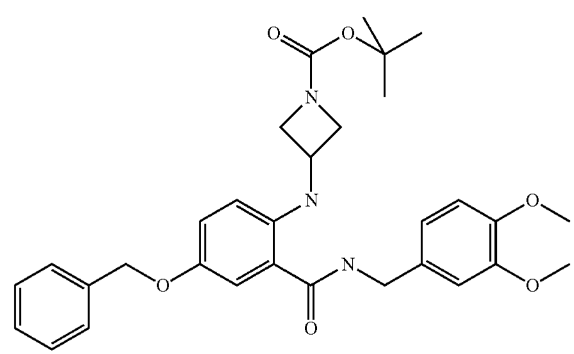 | 1,1-dimethylethyl 3-({4-(benzyloxy)-2-[(3,4-dimethoxybenzyl)carbamoyl]phenyl}amino)azetidine-1-carboxylate | 548 |

-continued
| | | |
|---|---|---|
| 121 | 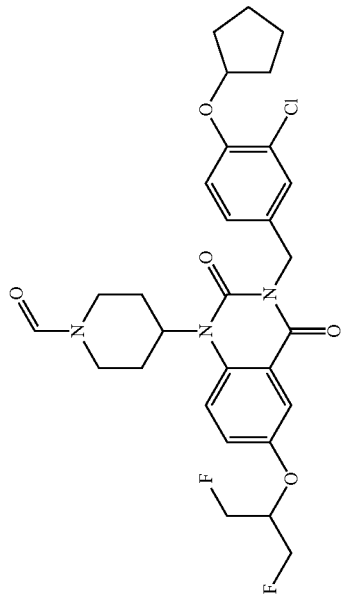 4-{3-[3-chloro-4-(cyclopentyloxy)benzyl]-6-[2-fluoro-1-(fluoromethyl)ethoxy]-2,4-dioxo-3,4-dihydroquinazolin-1(2H)-yl}piperidine-1-carbaldehyde | 576 |
| 122 | 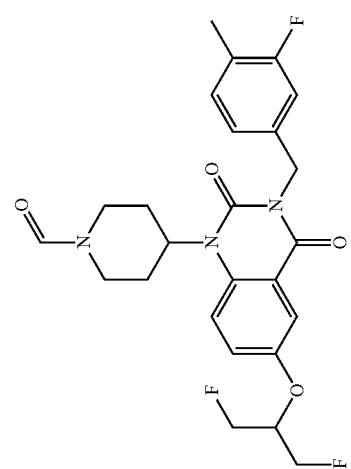 4-{6-[2-fluoro-1-(fluoromethyl)ethoxy]-3-(3-fluoro-4-methylbenzyl)-2,4-dioxo-3,4-dihydroquinazolin-1(2H)-yl}piperidine-1-carbaldehyde | 490 |
| 123 | 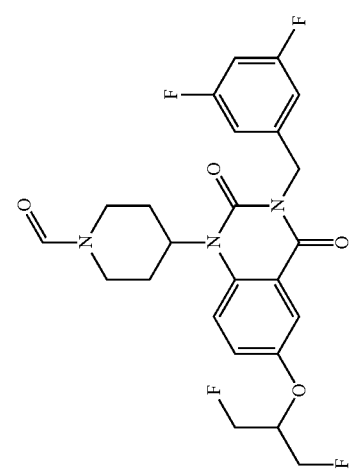 4-[3-(3,5-difluorobenzyl)-6-[2-fluoro-1-(fluoromethyl)ethoxy]-2,4-dioxo-3,4-dihydroquinazolin-1(2H)-yl]piperidine-1-carbaldehyde | 494 |

| | | |
|---|---|---|
| 124 | 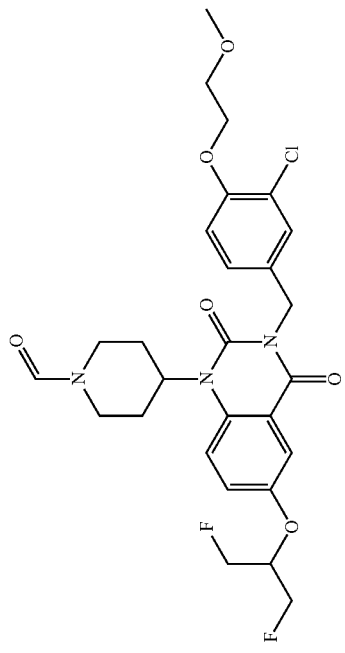 4-{3-[3-chloro-4-(2-methoxyethoxy)benzyl]-6-[2-fluoro-1-(fluoromethyl)ethoxy]-2,4-dioxo-3,4-dihydroquinazolin-1(2H)-yl}piperidine-1-carbaldehyde | 566 |
| 125 | 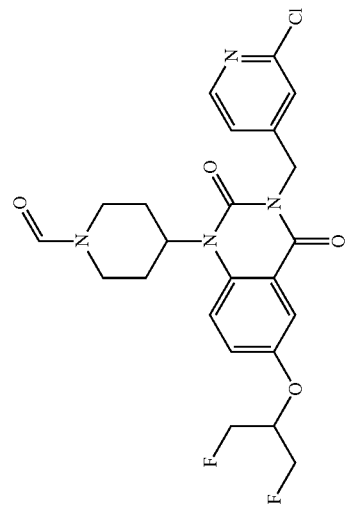 4-{3-[(2-chloropyridin-4-yl)methyl]-6-[2-fluoro-1-(fluoromethyl)ethoxy]-2,4-dioxo-3,4-dihydroquinazolin-1(2H)-yl}piperidine-1-carbaldehyde | 493 |
| 126 | 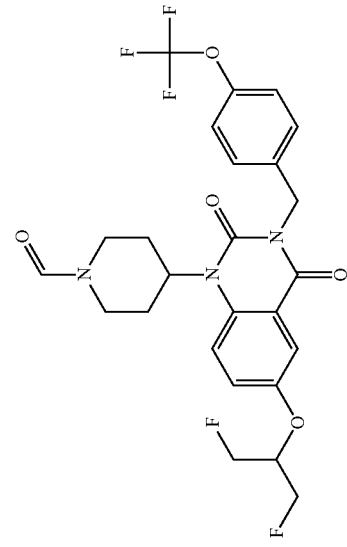 4-{6-[2-fluoro-1-(fluoromethyl)ethoxy]-2,4-dioxo-3-[4-(trifluoromethoxy)benzyl]-3,4-dihydroquinazolin-1(2H)-yl}piperidine-1-carbaldehyde | 542 |

-continued
| | | | |
|---|---|---|---|
| 127 | 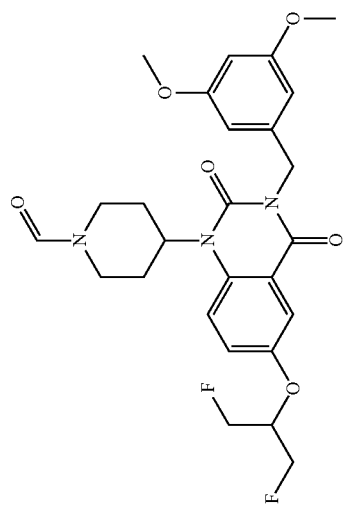 | 4-[3-(3,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 518 |
| 128 | 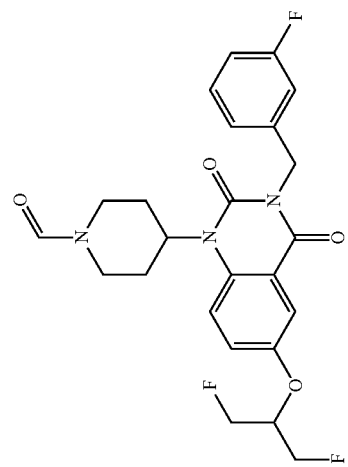 | 4-[3-(3-fluorobenzyl)-6-[2-fluoro-1-(fluoromethyl)ethoxy]-2,4-dioxo-3,4-dihydroquinazolin-1(2H)-yl]piperidine-1-carbaldehyde | 476 |
| 129 | 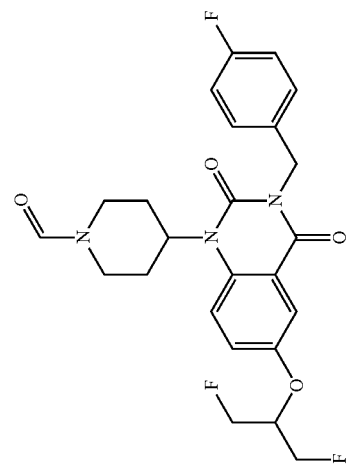 | 4-[3-(4-fluorobenzyl)-6-[2-fluoro-1-(fluoromethyl)ethoxy]-2,4-dioxo-3,4-dihydroquinazolin-1(2H)-yl]piperidine-1-carbaldehyde | 476 |

-continued
| | | |
|---|---|---|
| 130 | 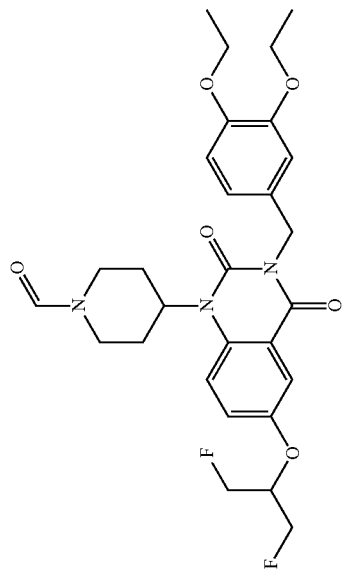 | 4-[3-(3,4-diethoxybenzyl)-6-[2-fluoro-1-(fluoromethyl)ethoxy]-2,4-dioxo-3,4-dihydroquinazolin-1(2H)-yl]piperidine-1-carbaldehyde | 546 |
| 131 | 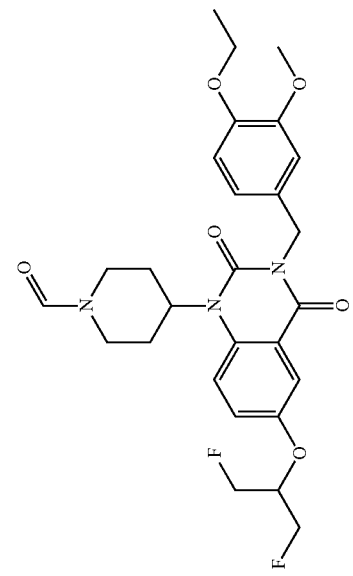 | 4-[3-(4-ethoxy-3-methoxybenzyl)-6-[2-fluoro-1-(fluoromethyl)ethoxy]-2,4-dioxo-3,4-dihydroquinazolin-1(2H)-yl]piperidine-1-carbaldehyde | 532 |
| 132 | 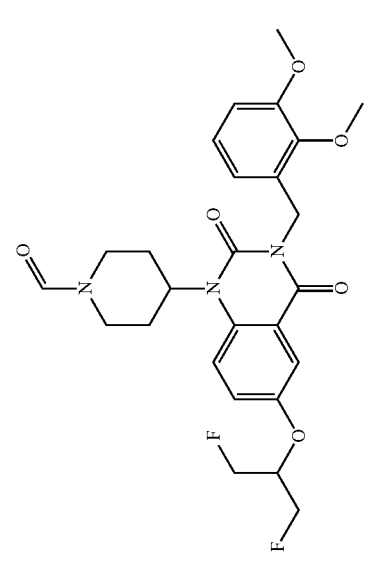 | 4-[3-(2,3-dimethoxybenzyl)-6-[2-fluoro-1-(fluoromethyl)ethoxy]-2,4-dioxo-3,4-dihydroquinazolin-1(2H)-yl]piperidine-1-carbaldehyde | 518 |

| | | |
|---|---|---|
| 133 | 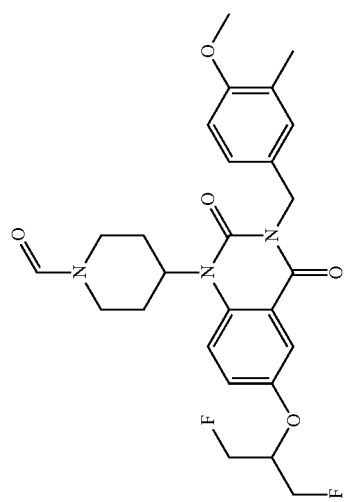 | 4-{6-[2-fluoro-1-(fluoromethyl)ethoxy]-3-(4-methoxy-3-methylbenzyl)-2,4-dioxo-3,4-dihydroquinazolin-1(2H)-yl}piperidine-1-carbaldehyde | 502 |
| 134 | 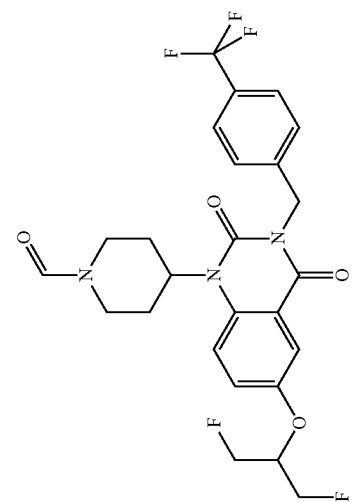 | 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde | 526 |
| 135 | 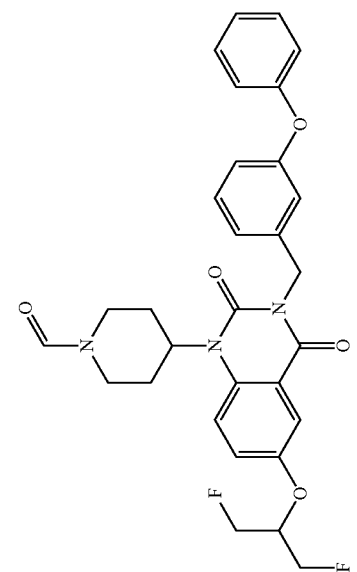 | 4-{6-[2-fluoro-1-(fluoromethyl)ethoxy]-2,4-dioxo-3-(3-phenoxybenzyl)-3,4-dihydroquinazolin-1(2H)-yl}piperidine-1-carbaldehyde | 550 |

| | | |
|---|---|---|
| 136 | 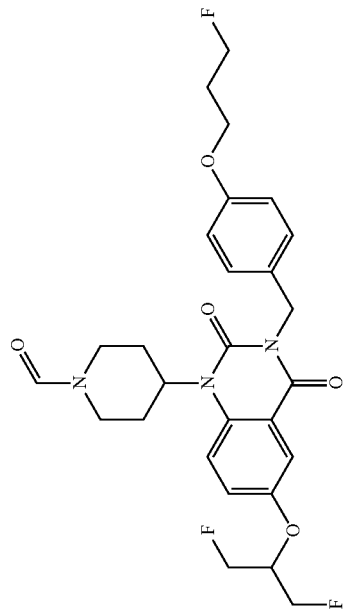 4-{6-[2-fluoro-1-(fluoromethyl)ethoxy]-3-[4-(3-fluoropropoxy)benzyl]-2,4-dioxo-3,4-dihydroquinazolin-1(2H)-yl}piperidine-1-carbaldehyde | 534 |
| 137 | 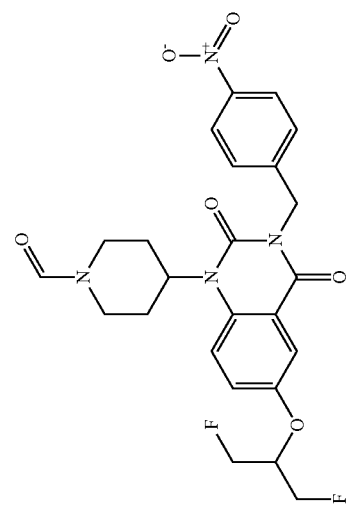 4-{6-[2-fluoro-1-(fluoromethyl)ethoxy]-3-(4-nitrobenzyl)-2,4-dioxo-3,4-dihydroquinazolin-1(2H)-yl}piperidine-1-carbaldehyde | 503 |
| 138 | 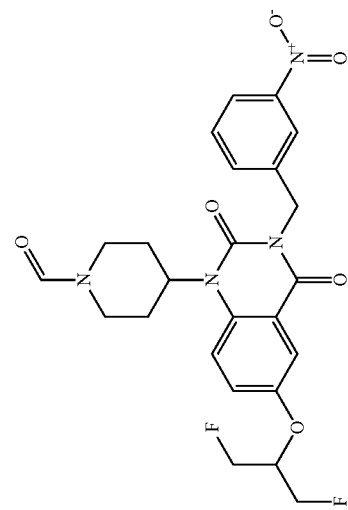 4-{6-[2-fluoro-1-(fluoromethyl)ethoxy]-3-(3-nitrobenzyl)-2,4-dioxo-3,4-dihydroquinazolin-1(2H)-yl}piperidine-1-carbaldehyde | 503 |

-continued
| | | | |
|---|---|---|---|
| 139 | 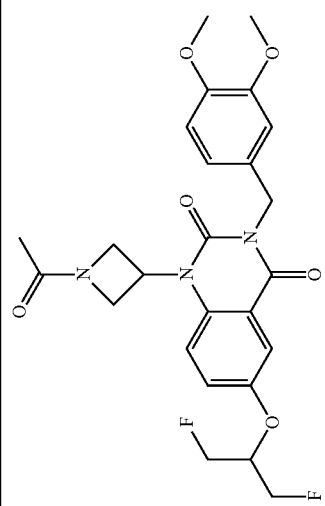 | 1-(1-acetylazetidin-3-yl)-3-(3,4-dimethoxybenzyl)-6-[2-fluoro-1-(fluoromethyl)ethoxy]quinazoline-2,4(1H,3H)-dione | 504 |
| 140 | 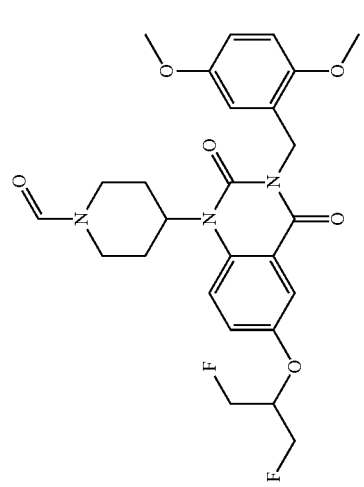 | 4-[3-(2,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 518 |
| 141 | 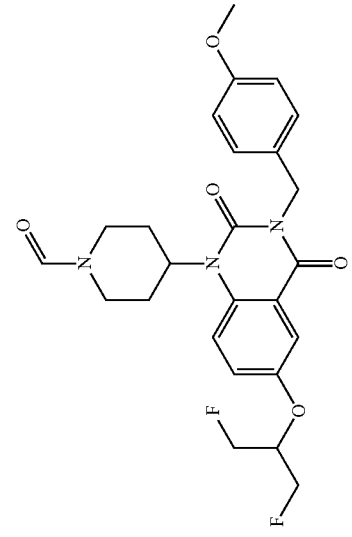 | 4-{6-[2-fluoro-1-(fluoromethyl)ethoxy]-3-(4-methoxybenzyl)-2,4-dioxo-3,4-dihydroquinazolin-1(2H)-yl}piperidine-1-carbaldehyde | 488 |

| | | |
|---|---|---|
| 142 | 4-{3-[3-(benzyloxy)benzyl]-6-[2-fluoro-1-(fluoromethyl)ethoxy]-2,4-dioxo-3,4-dihydroquinazolin-1(2H)-yl}piperidine-1-carbaldehyde 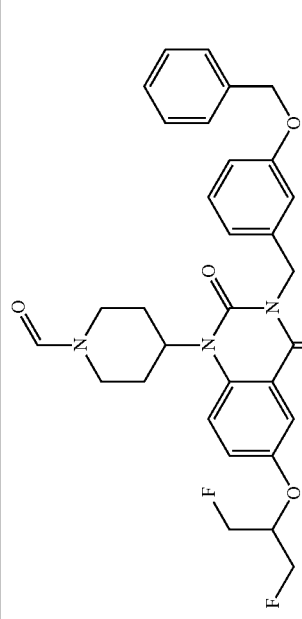 | 564 |
| 143 | 4-{3-[4-(benzyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde 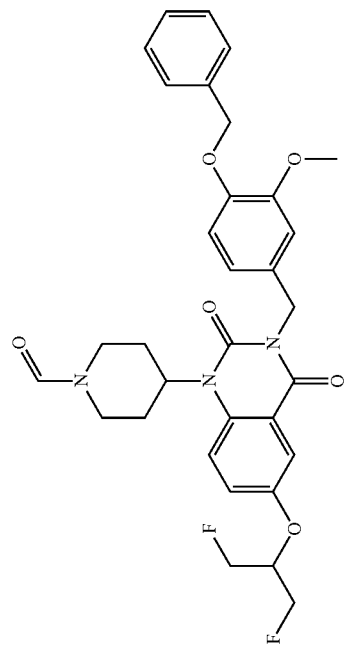 | 594 |
| 144 | 4-[3-(3,5-dichlorobenzyl)-6-[2-fluoro-1-(fluoromethyl)ethoxy]-2,4-dioxo-3,4-dihydroquinazolin-1(2H)-yl]piperidine-1-carbaldehyde 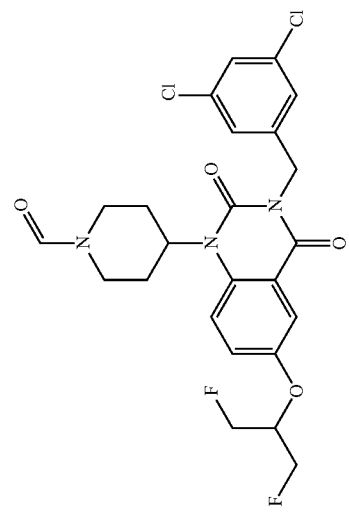 | 526 |

| | | |
|---|---|---|
| 145 | 4-{6-[2-fluoro-1-(fluoromethyl)ethoxy]-3-(3-methoxy-4-nitrobenzyl)-2,4-dioxo-3,4-dihydroquinazolin-1(2H)-yl}piperidine-1-carbaldehyde | 533 |
| | 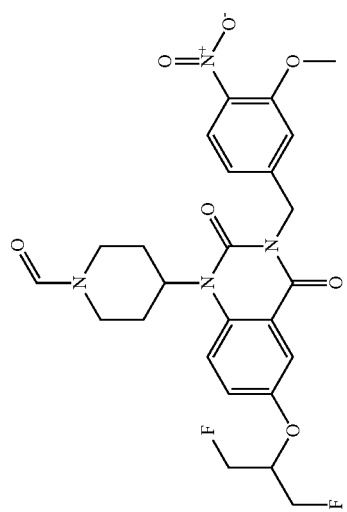 | |
| 146 | 4-{6-[2-fluoro-1-(fluoromethyl)ethoxy]-2,4-dioxo-3-{4-[(trifluoromethyl)sulphanyl]benzyl}-3,4-dihydroquinazolin-1(2H)-yl}piperidine-1-carbaldehyde | 558 |
| | 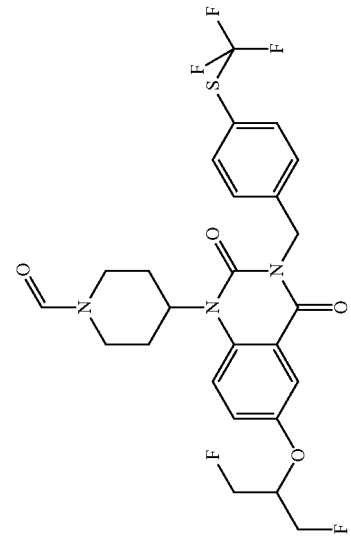 | |
| 147 | 4-{6-[2-fluoro-1-(fluoromethyl)ethoxy]-2,4-dioxo-3-[4-(pyrrolidin-1-ylmethyl)benzyl]-3,4-dihydroquinazolin-1(2H)-yl}piperidine-1-carbaldehyde | 541 |
| | 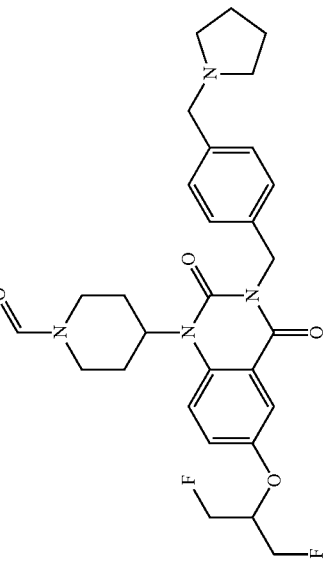 | |

| | | |
|---|---|---|
| 148 | 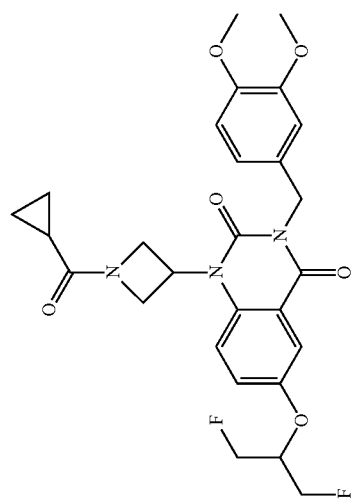 1-[1-(cyclopropylcarbonyl)azetidin-3-yl]-3-(3,4-dimethoxybenzyl)-6-[2-fluoro-1-(fluoromethyl)ethoxy]quinazoline-2,4(1H,3H)-dione | 530 |
| 149 | 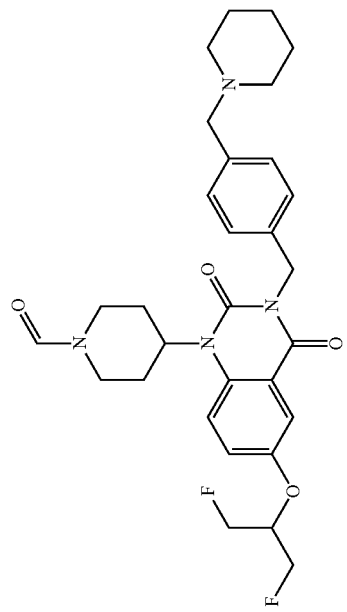 4-{6-[2-fluoro-1-(fluoromethyl)ethoxy]-2,4-dioxo-3-[4-(piperidin-1-ylmethyl)benzyl]-3,4-dihydroquinazolin-1(2H)-yl}piperidine-1-carbaldehyde | 555 |
| 150 | 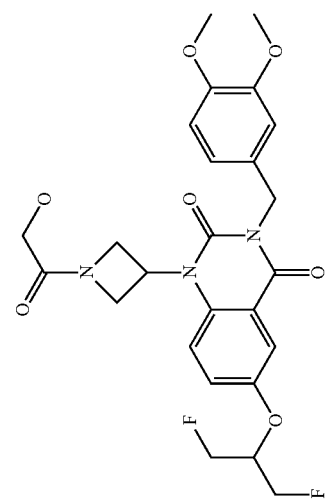 3-(3,4-dimethoxybenzyl)-6-[2-fluoro-1-(fluoromethyl)ethoxy]-1-[1-(hydroxyacetyl)azetidin-3-yl]quinazoline-2,4(1H,3H)-dione | 520 |

| | | |
|---|---|---|
| 151 | 4-({6-[2-fluoro-1-(fluoromethyl)ethoxy]-1-(1-formylpiperidin-4-yl)-2,4-dioxo-1,4-dihydroquinazolin-3(2H)-yl}methyl)benzonitrile 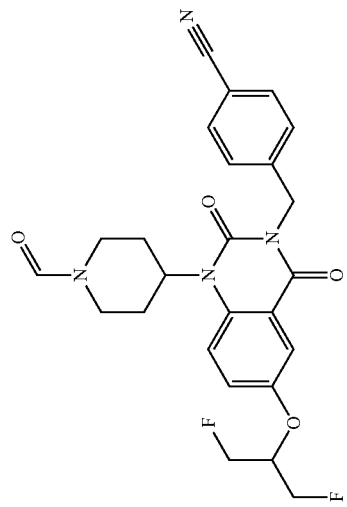 | 483 |
| 152 | 4-{6-[2-fluoro-1-(fluoromethyl)ethoxy]-2,4-dioxo-3-[3-(trifluoromethyl)benzyl]-3,4-dihydroquinazolin-1(2H)-yl}piperidine-1-carbaldehyde 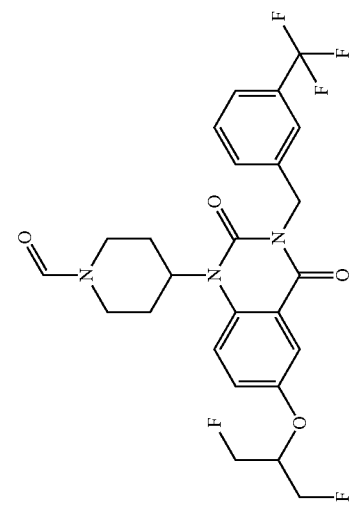 | 526 |
| 153 | 3-[3-(3,4-dimethoxybenzyl)-6-[2-fluoro-1-(fluoromethyl)ethoxy]-2,4-dioxo-3,4-dihydroquinazolin-1(2H)-yl]azetidine-1-carbaldehyde 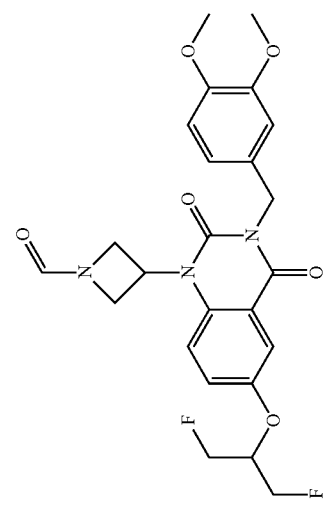 | 490 |

| | | | |
|---|---|---|---|
| 154 | 1-{1-[(benzyloxy)acetyl]azetidin-3-yl}-3-(3,4-dimethoxybenzyl)-6-[2-fluoro-1-(fluoromethyl)ethoxy]quinazoline-2,4(1H,3H)-dione | 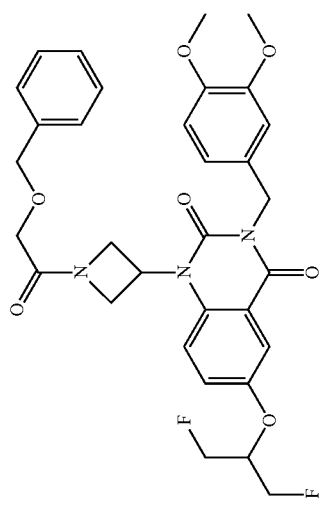 | 610 |
| 155 | 4-[3-(4-ethoxybenzyl)-6-[2-fluoro-1-(fluoromethyl)ethoxy]-2,4-dioxo-3,4-dihydroquinazolin-1(2H)-yl]piperidine-1-carbaldehyde | 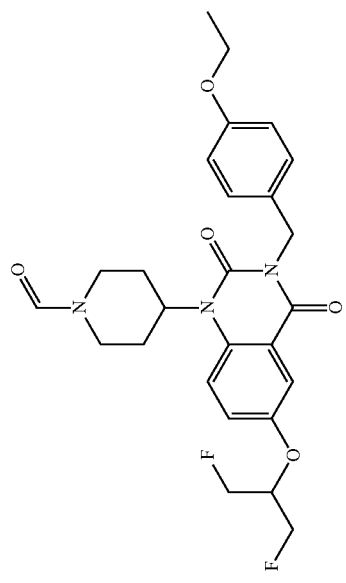 | 502 |
| 156 | 4-{6-[2-fluoro-1-(fluoromethyl)ethoxy]-2,4-dioxo-3-[3-(piperidin-1-ylmethyl)benzyl]-3,4-dihydroquinazolin-1(2H)-yl}piperidine-1-carbaldehyde | 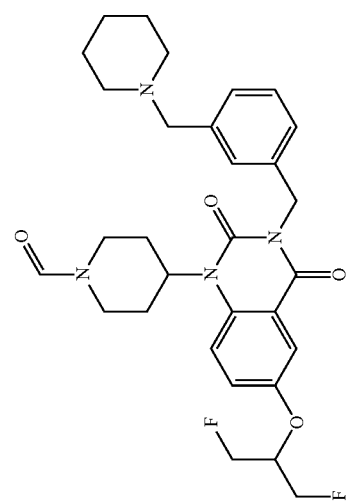 | 555 |

| | | |
|---|---|---|
| 157 | 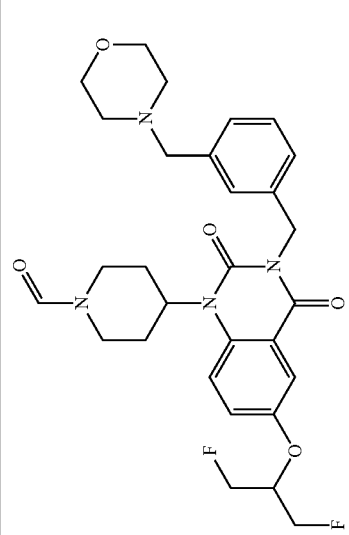 | 4-{6-[2-fluoro-1-(fluoromethyl)ethoxy]-3-[3-(morpholin-4-ylmethyl)benzyl]-2,4-dioxo-3,4-dihydroquinazolin-1(2H)-yl}piperidine-1-carbaldehyde — 557 |
| 158 | 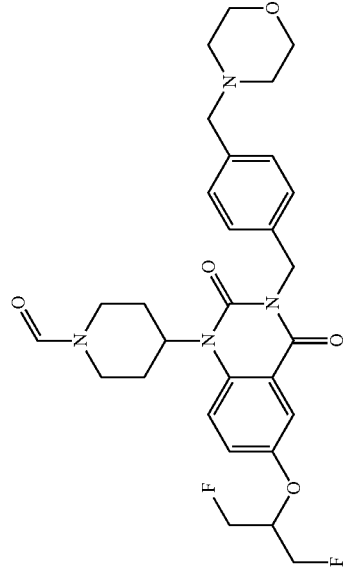 | 4-{6-[2-fluoro-1-(fluoromethyl)ethoxy)-3-[4-(morpholin-4-ylmethyl)benzyl]-2,4-dioxo-3,4-dihydroquinazolin-1(2H)-yl}piperidine-1-carbaldehyde — 557 |
| 159 | 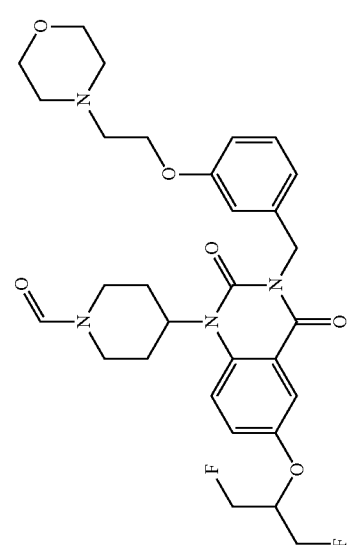 | 4-{6-[2-fluoro-1-(fluoromethyl)ethoxy]-3-[3-(2-(morpholin-4-yl)ethoxy)benzyl]-2,4-dioxo-3,4-dihydroquinazolin-1(2H)-yl}piperidine-1-carbaldehyde — 587 |

| | | |
|---|---|---|
| 160 | 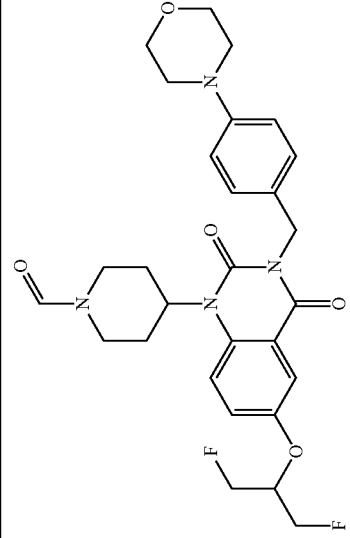 | 4-[6-[2-fluoro-1-(fluoromethyl)ethoxy]-3-(4-(morpholin-4-yl)benzyl)-2,4-dioxo-3,4-dihydroquinazolin-1(2H)-yl]piperidine-1-carbaldehyde  543 |
| 161 | 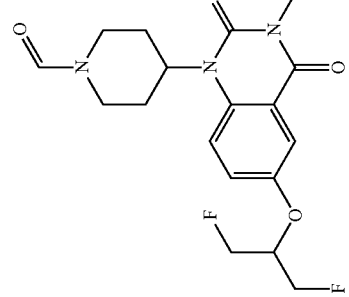 | 4-[3-(1-benzofur-6-ylmethyl)-6-[2-fluoro-1-(fluoromethyl)ethoxy]-2,4-dioxo-3,4-dihydroquinazolin-1(2H)-yl]piperidine-1-carbaldehyde  498 |
| 162 | 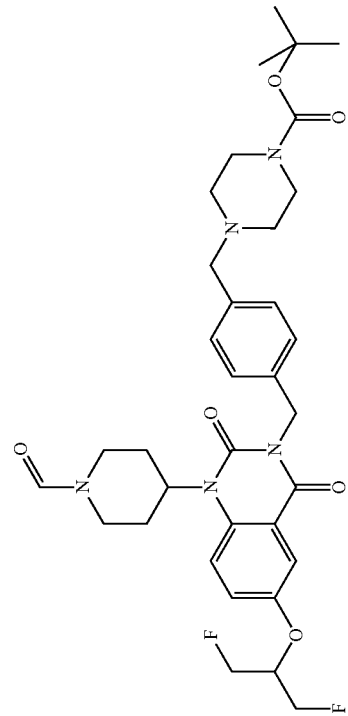 | 1,1-dimethylethyl 4-[4-({6-[2-fluoro-1-(fluoromethyl)ethoxy]-1-(1-formylpiperidin-4-yl)-2,4-dioxo-1,4-dihydroquinazolin-3(2H)-yl}methyl)benzyl]piperazine-1-carboxylate  656 |

| | | |
|---|---|---|
| 163 | 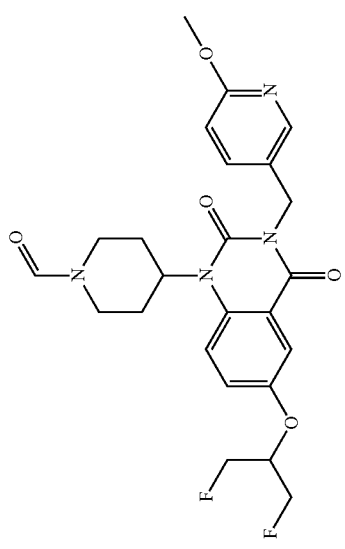 | 4-{6-[2-fluoro-1-(fluoromethyl)ethoxy]-3-[(6-methoxypyridin-3-yl)methyl]-2,4-dioxo-3,4-dihydroquinazolin-1(2H)-yl}piperidine-1-carbaldehyde | 489 |
| 164 | 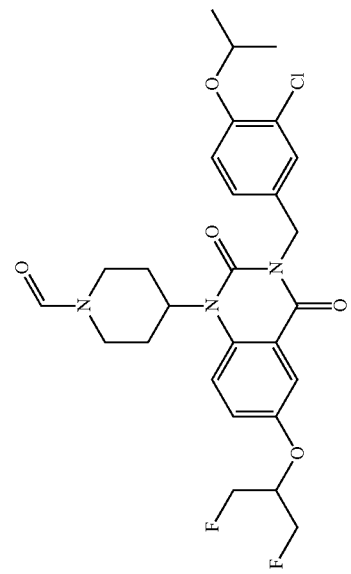 | 4-{3-[3-chloro-4-(1-methylethoxy)benzyl]-6-[2-fluoro-1-(fluoromethyl)ethoxy]-2,4-dioxo-3,4-dihydroquinazolin-1(2H)-yl}piperidine-1-carbaldehyde | 550 |
| 165 | 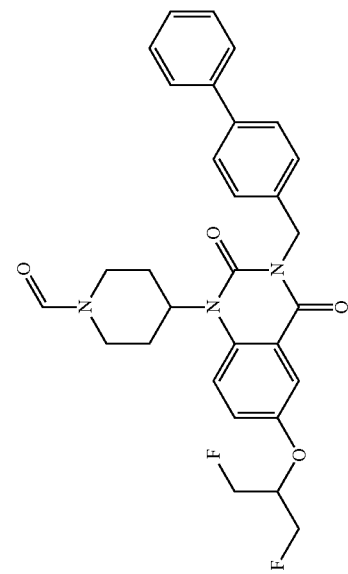 | 4-[3-(biphenyl-4-ylmethyl)-6-[2-fluoro-1-(fluoromethyl)ethoxy]-2,4-dioxo-3,4-dihydroquinazolin-1(2H)-yl]piperidine-1-carbaldehyde | 534 |

| 166 | 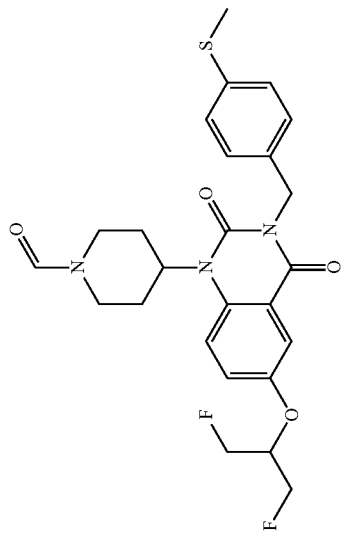 | 4-{6-[2-fluoro-1-(fluoromethyl)ethoxy]-3-[4-(methylsulphanyl)benzyl]-2,4-dioxo-3,4-dihydroquinazolin-1(2H)-yl}piperidine-1-carbaldehyde | 504 |
| --- | --- | --- | --- |
| 167 | 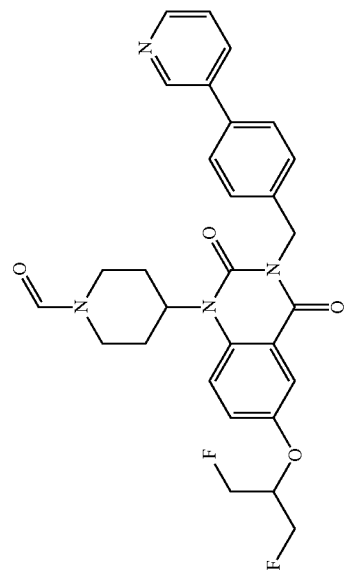 | 4-{6-[2-fluoro-1-(fluoromethyl)ethoxy]-2,4-dioxo-3-(4-(pyridin-3-yl)benzyl)-3,4-dihydroquinazolin-1(2H)-yl}piperidine-1-carbaldehyde | 535 |
| 168 | 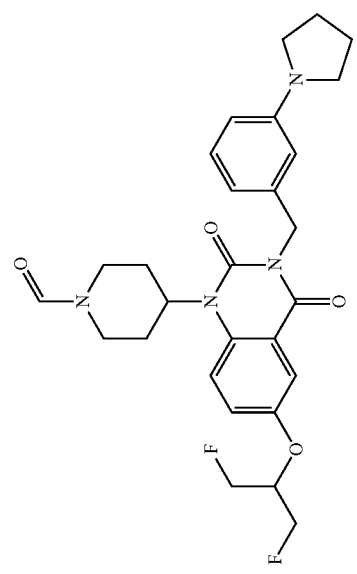 | 4-{6-[2-fluoro-1-(fluoromethyl)ethoxy]-2,4-dioxo-3-(3-(pyrrolidin-1-yl)benzyl)-3,4-dihydroquinazolin-1(2H)-yl}piperidine-1-carbaldehyde | 527 |

| | | |
|---|---|---|
| 169 | 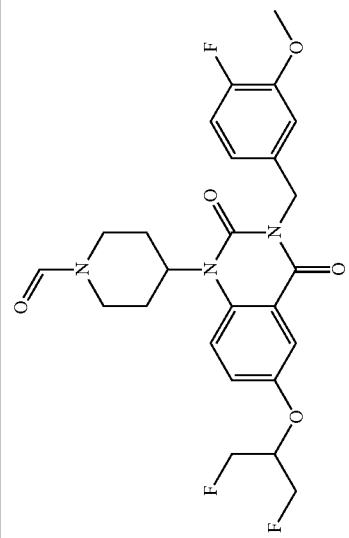 4-{6-[2-fluoro-1-(fluoromethyl)ethoxy]-3-(4-fluoro-3-methoxybenzyl)-2,4-dioxo-3,4-dihydroquinazolin-1(2H)-yl}piperidine-1-carbaldehyde | 506 |
| 170 | 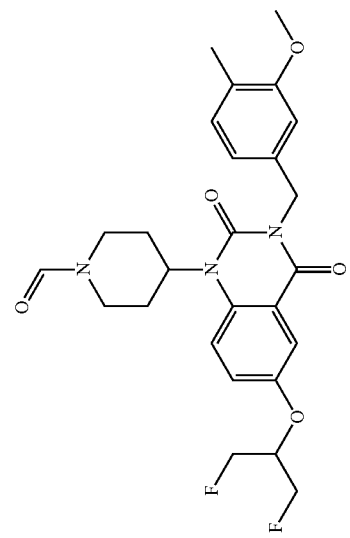 4-{6-[2-fluoro-1-(fluoromethyl)ethoxy]-3-(3-methoxy-4-methylbenzyl)-2,4-dioxo-3,4-dihydroquinazolin-1(2H)-yl}piperidine-1-carbaldehyde | 502 |
| 171 | 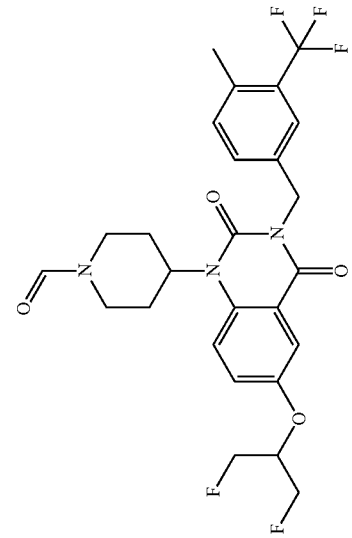 4-{6-[2-fluoro-1-(fluoromethyl)ethoxy]-3-[4-methyl-3-(trifluoromethyl)benzyl]-2,4-dioxo-3,4-dihydroquinazolin-1(2H)-yl}piperidine-1-carbaldehyde | 540 |

| 172 | 4-{6-[2-fluoro-1-(fluoromethyl)ethoxy]-3-{4-[(4-methylpiperazin-1-yl)methyl]benzyl}-2,4-dioxo-3,4-dihydroquinazolin-1(2H)-yl}piperidine-1-carbaldehyde | 570 | 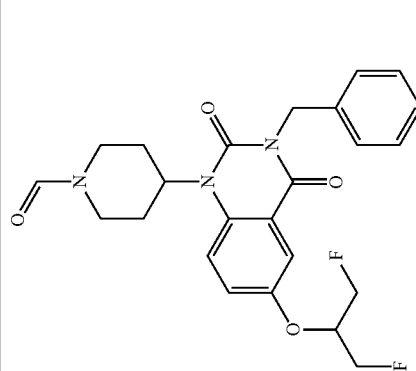 |
| --- | --- | --- | --- |
| 173 | 4-[3-{4-(cyclopentyloxy)-3-[2-fluoro-1-(fluoromethyl)ethoxy]benzyl}-6-[2-fluoro-1-(fluoromethyl)ethoxy]-2,4-dioxo-3,4-dihydroquinazolin-1(2H)-yl]piperidine-1-carbaldehyde | 636 | 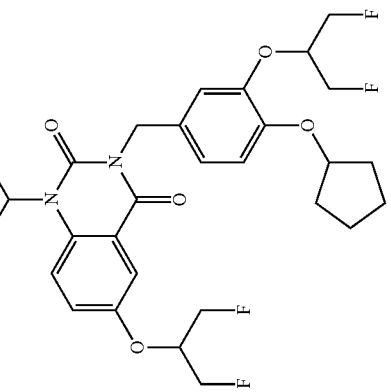 |

| 174 | 3-[3,4-bis(cyclopentyloxy)benzyl]-1-(1-ethenylpiperidin-4-yl)-6-[2-fluoro-1-(fluoromethyl)ethoxy]quinazoline-2,4(1H,3H)-dione | 626 |
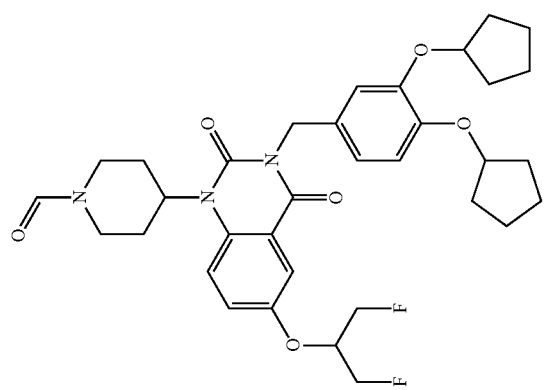
| 175 | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]acetamide | 615 |
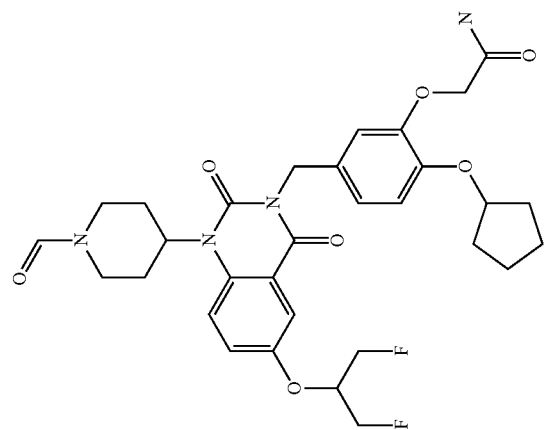

| | | |
|---|---|---|
| 176 | 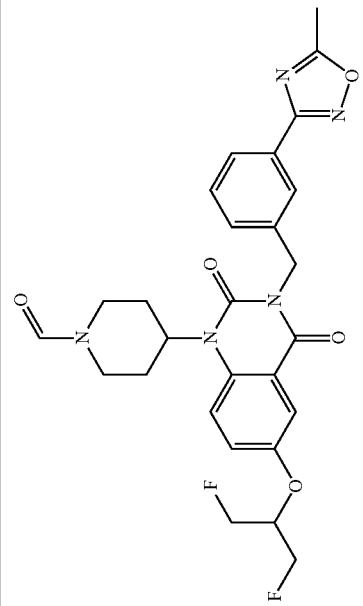 | 4-{6-[2-fluoro-1-(fluoromethyl)ethoxy]-3-[3-(5-methyl-1,2,4-oxadiazol-3-yl)benzyl]-2,4-dioxo-3,4-dihydroquinazolin-1(2H)-yl}piperidine-1-carbaldehyde | 540 |
| 177 | 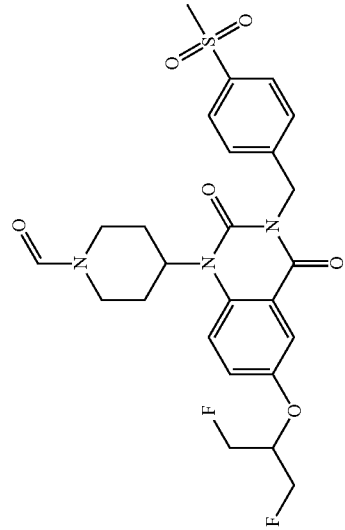 | 4-{6-[2-fluoro-1-(fluoromethyl)ethoxy]-3-[4-(methylsulphonyl)benzyl]-2,4-dioxo-3,4-dihydroquinazolin-1(2H)-yl}piperidine-1-carbaldehyde | 536 |
| 178 | 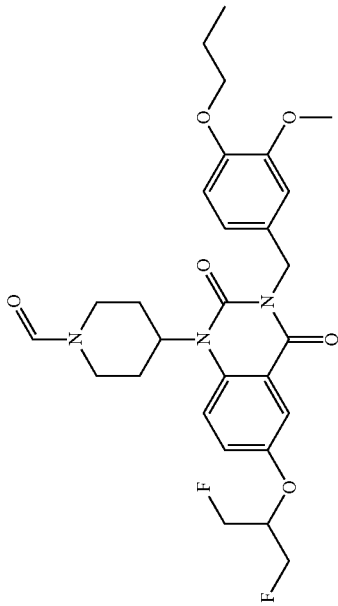 | 4-{6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde | 546 |

| | | |
|---|---|---|
| 179 | 4-[3-(3-chloro-4-ethoxybenzyl)-6-[2-fluoro-1-(fluoromethyl)ethoxy]-2,4-dioxo-3,4-dihydroquinazolin-1(2H)-yl]piperidine-1-carbaldehyde 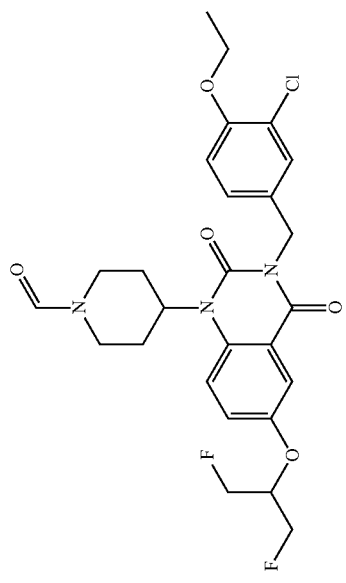 | 536 |
| 180 | 4-{3-[4-(1,1-dimethylethoxy)benzyl]-6-[2-fluoro-1-(fluoromethyl)ethoxy]-2,4-dioxo-3,4-dihydroquinazolin-1(2H)-yl}piperidine-1-carbaldehyde 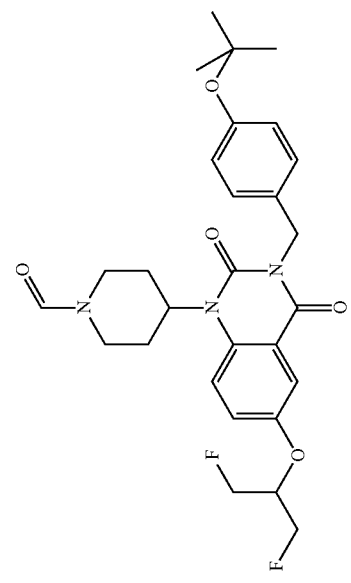 | 530 |
| 181 | 4-{6-[2-fluoro-1-(fluoromethyl)ethoxy]-2,4-dioxo-3-[3-(trifluoromethoxy)benzyl]-3,4-dihydroquinazolin-1(2H)-yl}piperidine-1-carbaldehyde 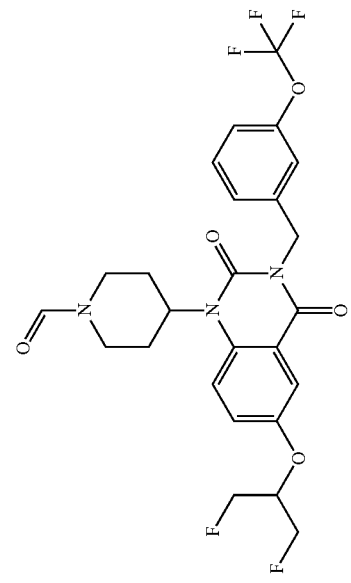 | 542 |

| | | |
|---|---|---|
| 182 | 4-{6-[2-fluoro-1-(fluoromethyl)ethoxy]-3-[3-fluoro-4-(trifluoromethyl)benzyl]-2,4-dioxo-3,4-dihydroquinazolin-1(2H)-yl}piperidine-1-carbaldehyde | 544 |
| | 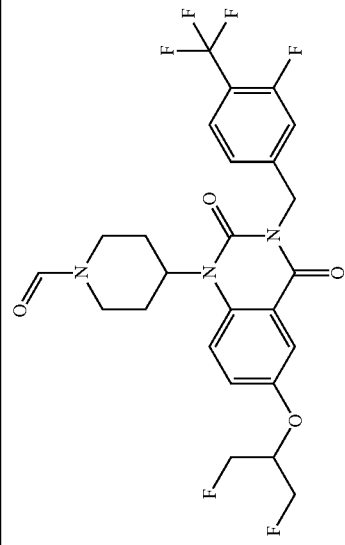 | |
| 183 | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylacetamide | 629 |
| | 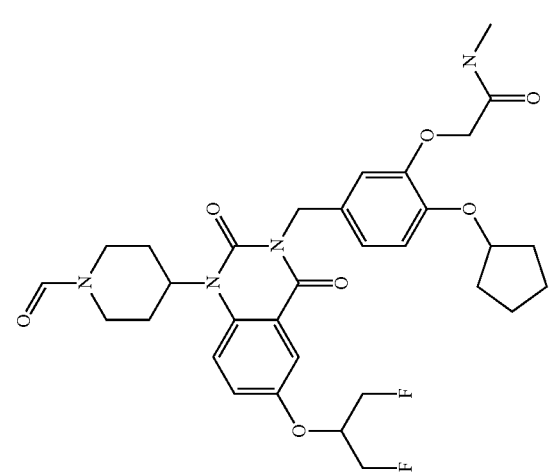 | |

| | | |
|---|---|---|
| 184 | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N,N-dimethylacetamide 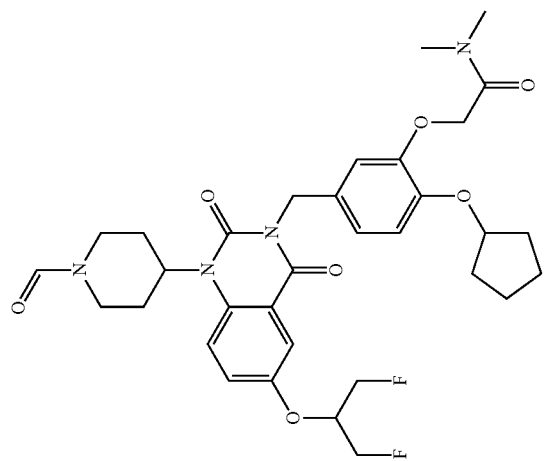 | 643 |
| 185 | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methoxy-N-methylacetamide 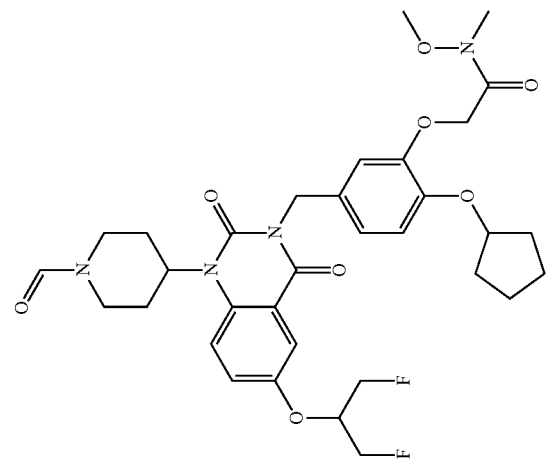 | 659 |

| | | |
|---|---|---|
| 186 | 4-{3-[4-(cyclopentyloxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde | 586 |
| | 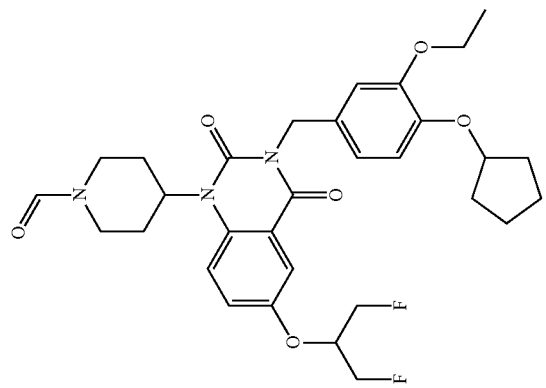 | |
| 187 | 4-{3-[3-(cyclobutylmethoxy)-4-(cyclopentyloxy)benzyl]-6-[2-fluoro-1-(fluoromethyl)ethoxy]-2,4-dioxo-3,4-dihydroquinazolin-1(2H)-yl}piperidine-1-carbaldehyde | 626 |
| | 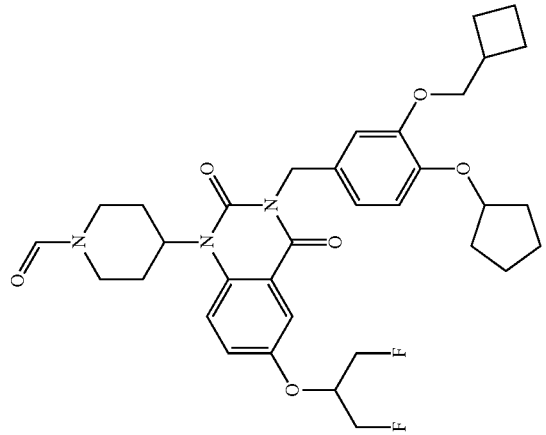 | |

-continued
| 188 | 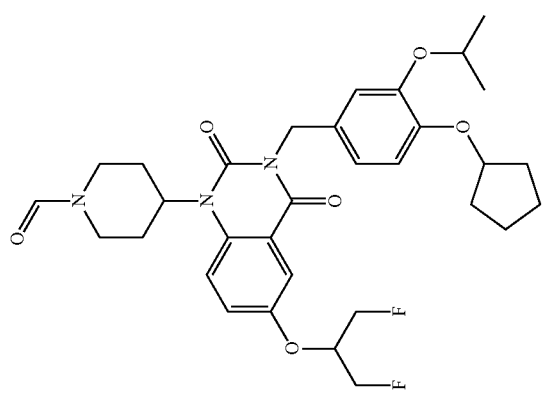 | 4-{3-[4-(cyclopentyloxy)-3-(1-methylethoxy)benzyl]-6-[2-fluoro-1-(fluoromethyl)ethoxy]-2,4-dioxo-3,4-dihydroquinazolin-1(2H)-yl}piperidine-1-carbaldehyde | 600 |
| 189 | 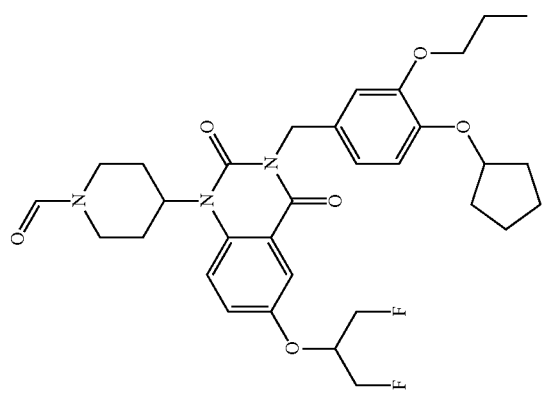 | 4-{3-[4-(cyclopentyloxy)-3-propoxybenzyl]-6-[2-fluoro-1-(fluoromethyl)ethoxy]-2,4-dioxo-3,4-dihydroquinazolin-1(2H)-yl}piperidine-1-carbaldehyde | 600 |

| | | |
|---|---|---|
| 190 | 4-{3-[4-(cyclopentyloxy)-3-hydroxybenzyl]-6-[2-fluoro-1-(fluoromethyl)ethoxy]-2,4-dioxo-3,4-dihydroquinazolin-1(2H)-yl}piperidine-1-carbaldehyde 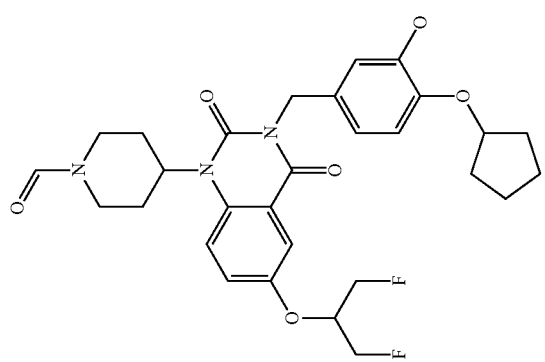 | 558 |
| 191 | 4-{3-[4-(cyclopentyloxy)-3-(2-methylpropoxy)benzyl]-6-(2-fluoro-1-(fluoromethyl)ethoxy]-2,4-dioxo-3,4-dihydroquinazolin-1(2H)-yl}piperidine-1-carbaldehyde 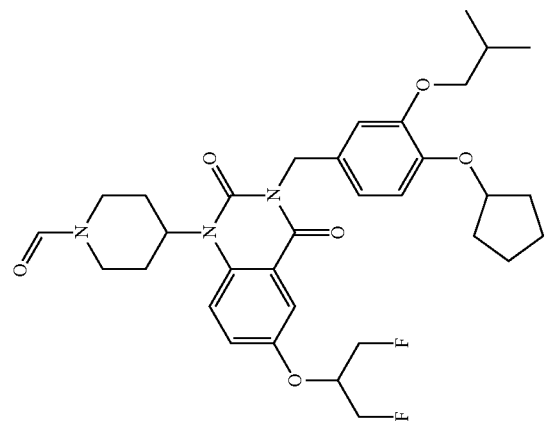 | 614 |

| | | |
|---|---|---|
| 192 | 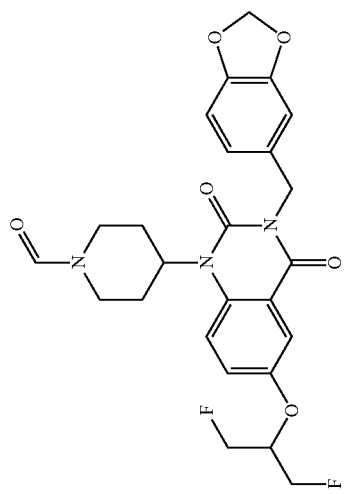 | 4-[3-(1,3-benzodioxol-5-ylmethyl)-6-[2-fluoro-1-(fluoromethyl)ethoxy]-2,4-dioxo-3,4-dihydroquinazolin-1(2H)-yl]piperidine-1-carbaldehyde | 502 |
| 193 | 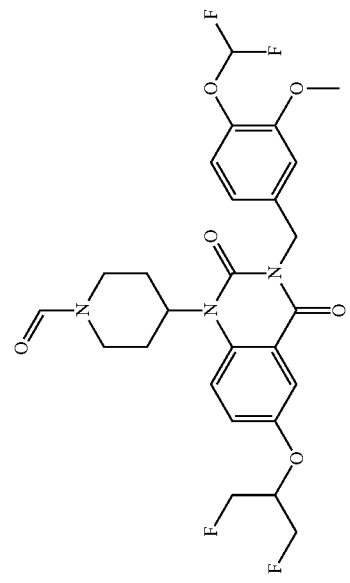 | 4-{3-[4-(difluoromethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | 554 |
| 194 | 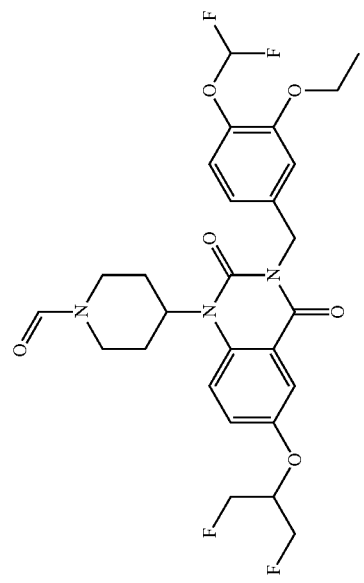 | 4-{3-[4-(difluoromethoxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde | 568 |

-continued
| | | | |
|---|---|---|---|
| 195 | 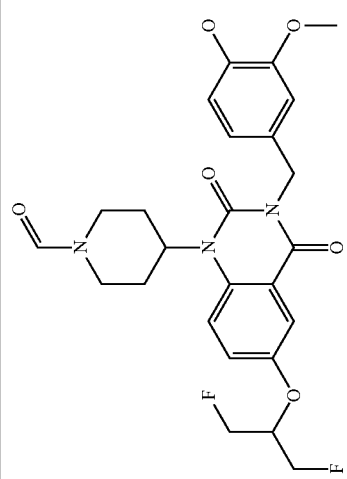 | 4-{6-[2-fluoro-1-(fluoromethyl)ethoxy]-3-(4-hydroxy-3-methoxybenzyl)-2,4-dioxo-3,4-dihydroquinazolin-1(2H)-yl]piperidine-1-carbaldehyde | 504 |
| 196 | 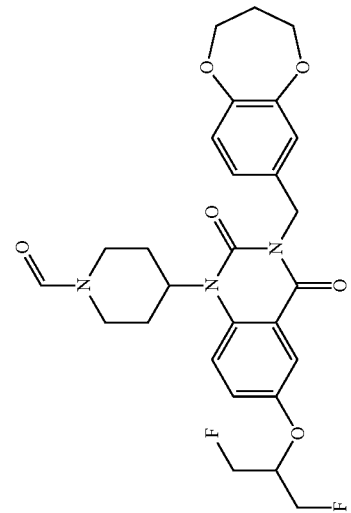 | 4-[3-(3,4-dihydro-2H-1,5-benzodioxepin-7-ylmethyl)-6-[2-fluoro-1-(fluoromethyl)ethoxy]-2,4-dioxo-3,4-dihydroquinazolin-1(2H)-yl]piperidine-1-carbaldehyde | 530 |
| 197 | 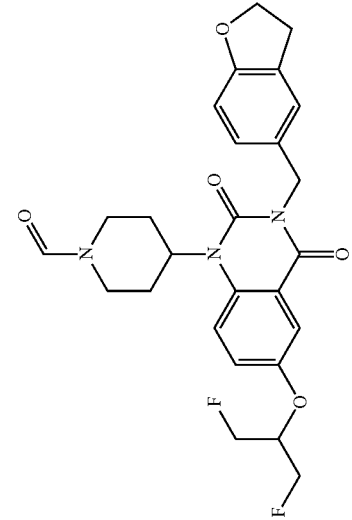 | 4-[3-(2,3-dihydro-1-benzofuran-5-ylmethyl)-6-[2-fluoro-1-(fluoromethyl)ethoxy]-2,4-dioxo-3,4-dihydroquinazolin-1(2H)-yl]piperidine-1-carbaldehyde | 500 |

| | | |
|---|---|---|
| 198 | 4-{6-[2-fluoro-1-(fluoromethyl)ethoxy]-3-[3-fluoro-5-(trifluoromethyl)benzyl]-2,4-dioxo-3,4-dihydroquinazolin-1(2H)-yl}piperidine-1-carbaldehyde 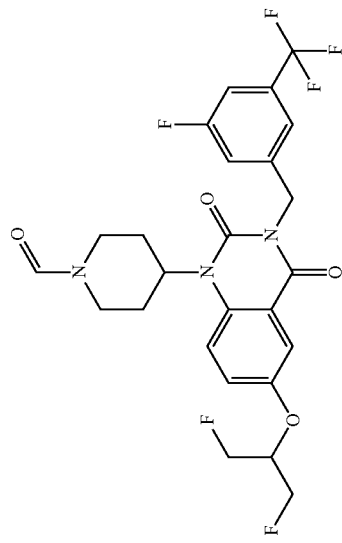 | 544 |
| 199 | 4-{6-[2-fluoro-1-fluoromethyl)ethoxy]-3-[(1-methyl-1H-benzotriazol-5-yl)methyl]-2,4-dioxo-3,4-dihydroquinazolin-1(2H)-yl}piperidine-1-carbaldehyde 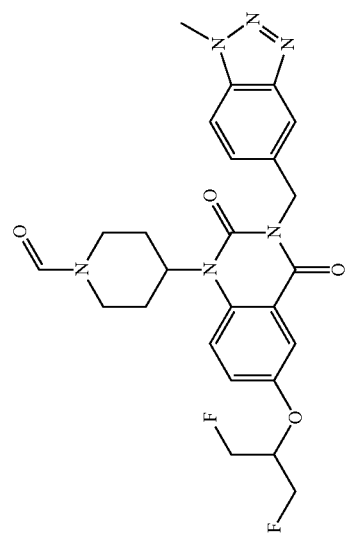 | 513 |
| 200 | 4-{6-[2-fluoro-1-(fluoromethyl)ethoxy]-2,4-dioxo-3-(4-(thiophen-3-yl)benzyl)-3,4-dihydroquinazolin-1(2H)-yl}piperidine-1-carbaldehyde 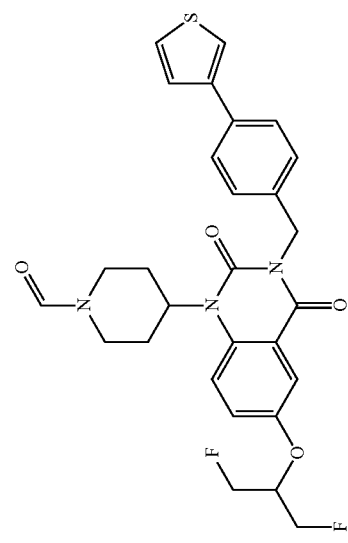 | 540 |

-continued
| | | |
|---|---|---|
| 201 | 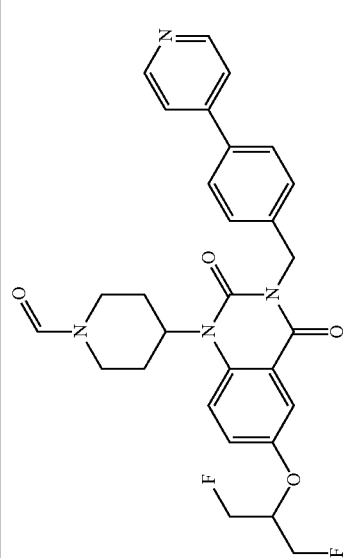 4-{6-[2-fluoro-1-(fluoromethyl)ethoxy]-2,4-dioxo-3-(4-(pyridin-4-yl)benzyl)-3,4-dihydroquinazolin-1(2H)-yl}piperidine-1-carbaldehyde | 535 |
| 202 | 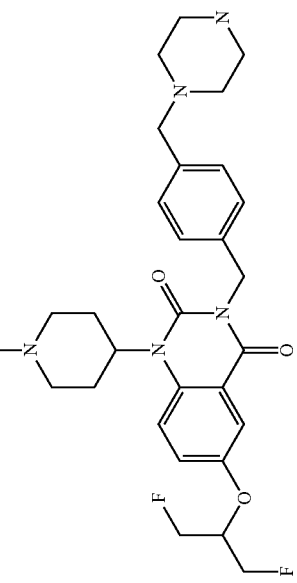 4-{6-[2-fluoro-1-(fluoromethyl)ethoxy]-2,4-dioxo-3-[4-(piperazin-1-ylmethyl)benzyl]-3,4-dihydroquinazolin-1(2H)-yl}piperidine-1-carbaldehyde | 555 |
| 203 | 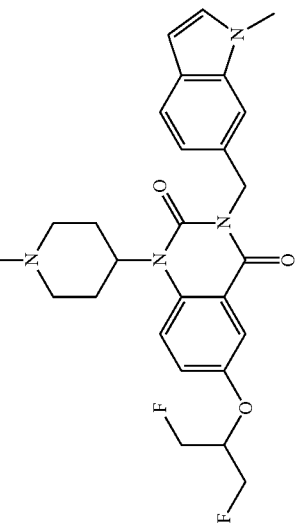 4-{6-[2-fluoro-1-(fluoromethyl)ethoxy]-3-[(1-methyl-1H-indol-6-yl)methyl]-2,4-dioxo-3,4-dihydroquinazolin-1(2H)-yl}piperidine-1-carbaldehyde | 511 |

| | | | |
|---|---|---|---|
| 204 | 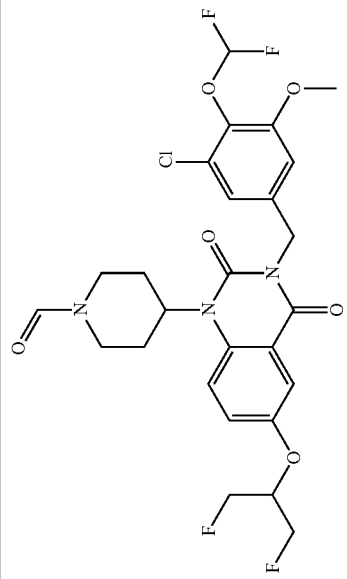 | 4-{3-[3-chloro-4-(difluoromethoxy)-5-methoxybenzyl]-6-[2-fluoro-1-(fluoromethyl)ethoxy]-2,4-dioxo-3,4-dihydroquinazolin-1(2H)-yl}piperidine-1-carbaldehyde | 588 |
| 205 | 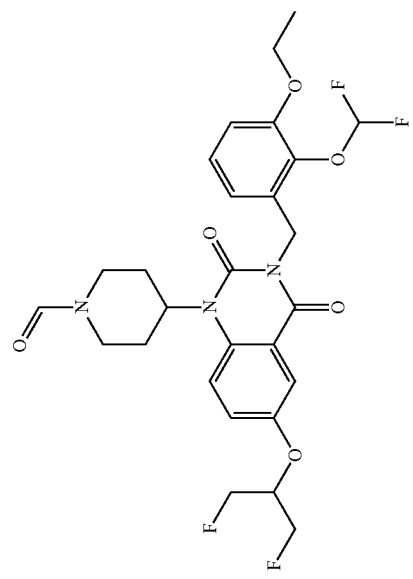 | 4-{3-[2-(difluoromethoxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde | 568 |
| 206 | 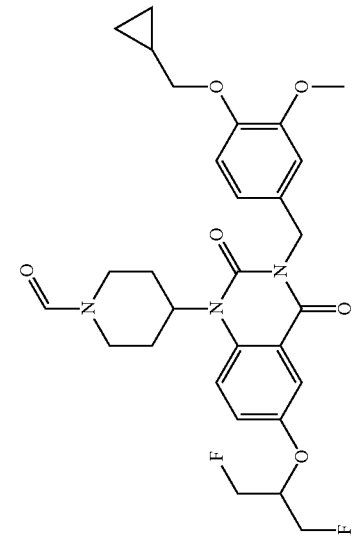 | 4-{3-[4-(cyclopropylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | 558 |

| | | |
|---|---|---|
| 207 | 2-[4-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]-N-methylacetamide 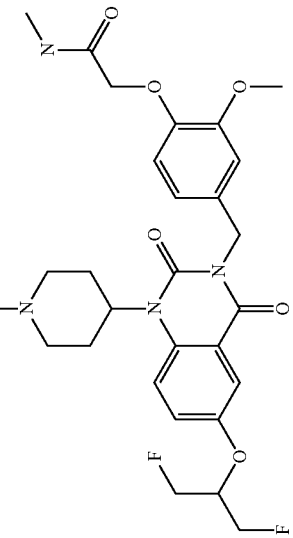 | 575 |
| 208 | 4-[3-(biphenyl-3-ylmethyl)-6-[2-fluoro-1-(fluoromethyl)ethoxy]-2,4-dioxo-3,4-dihydroquinazolin-1(2H)-yl]piperidine-1-carbaldehyde 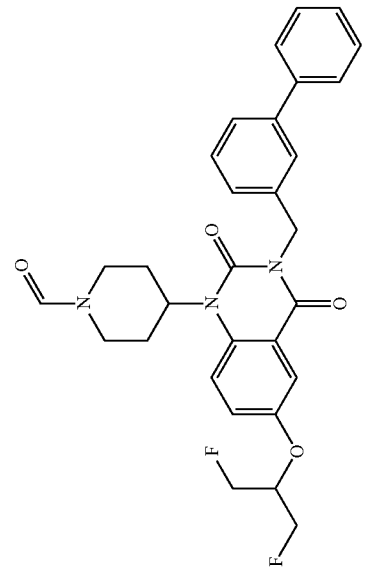 | 534 |
| 209 | 4-{6-[2-fluoro-1-(fluoromethyl)ethoxy]-3-{3-[(4-methylpiperazin-1-yl)methyl]benzyl}-2,4-dioxo-3,4-dihydroquinazolin-1(2H)-yl}piperidine-1-carbaldehyde 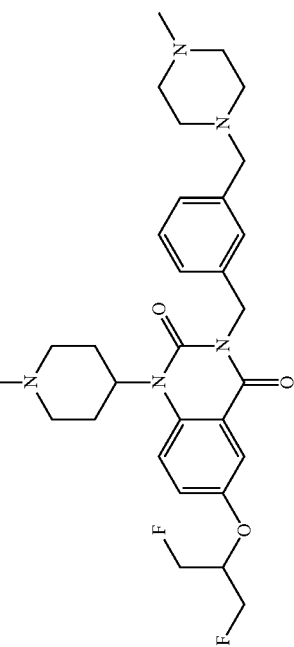 | 570 |

| | -continued | |
|---|---|---|
| 210 | 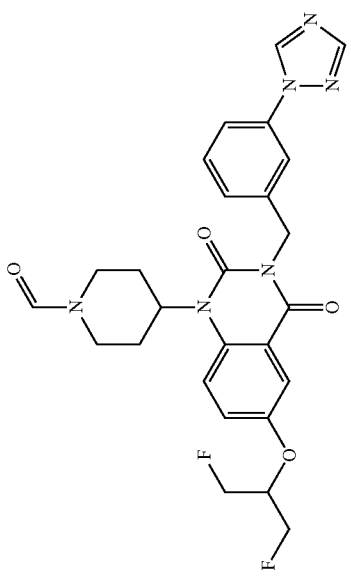 | 4-{6-[2-fluoro-1-(fluoromethyl)ethoxy]-2,4-dioxo-3-[3-(1H-1,2,4-triazol-1-yl)benzyl]-3,4-dihydroquinazolin-1(2H)-yl}piperidine-1-carbaldehyde — 525 |
| 211 | 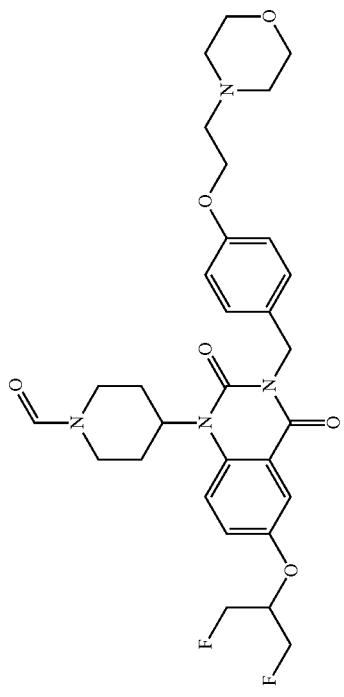 | 4-{6-[2-fluoro-1-(fluoromethyl)ethoxy]-3-[4-(2-(morpholin-4-yl)ethoxy)benzyl]-2,4-dioxo-3,4-dihydroquinazolin-1(2H)-yl}piperidine-1-carbaldehyde — 587 |
| 212 | 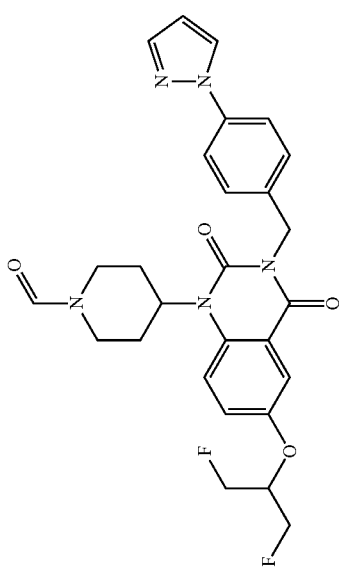 | 4-{6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde — 524 |

| | | |
|---|---|---|
| 213 | 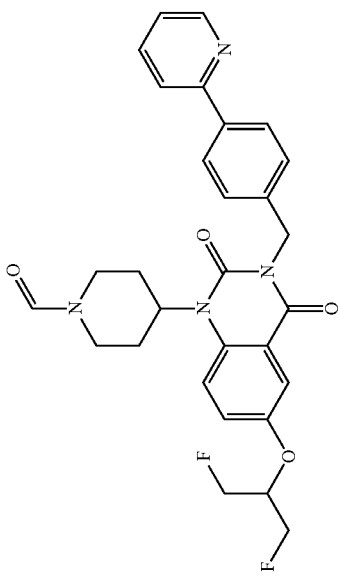 | 535 4-{6-[2-fluoro-1-(fluoromethyl)ethoxy]-2,4-dioxo-3-(4-(pyridin-2-yl)benzyl)-3,4-dihydroquinazolin-1(2H)-yl}piperidine-1-carbaldehyde |
| 214 | 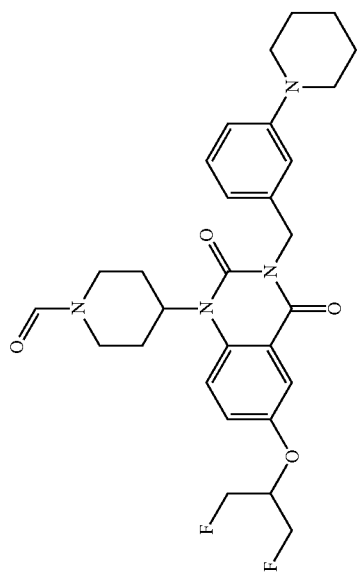 | 541 4-{6-[2-fluoro-1-(fluoromethyl)ethoxy]-2,4-dioxo-3-(3-(piperidin-1-yl)benzyl)-3,4-dihydroquinazolin-1(2H)-yl}piperidine-1-carbaldehyde |
| 215 | 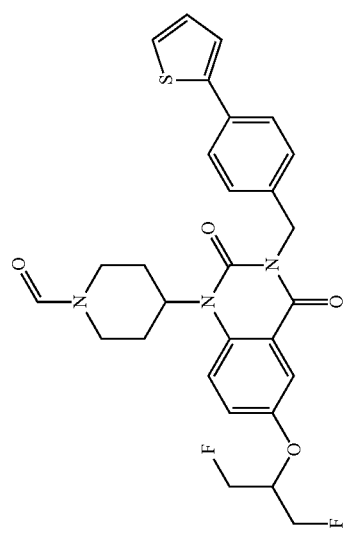 | 540 4-{6-[2-fluoro-1-(fluoromethyl)ethoxy]-2,4-dioxo-3-(4-(thiophen-2-yl)benzyl)-3,4-dihydroquinazolin-1(2H)-yl}piperidine-1-carbaldehyde |

| 216 | 4-{6-[2-fluoro-1-(fluoromethyl)ethoxy]-2,4-dioxo-3-(quinolin-7-ylmethyl)-3,4-dihydroquinazolin-1(2H)-yl}piperidine-1-carbaldehyde | 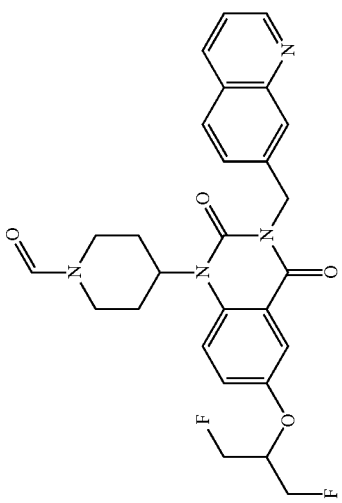 | 509 |
| 217 | 4-{3-[4-(difluoromethoxy)benzyl]-6-[2-fluoro-1-(fluoromethyl)ethoxy]-2,4-dioxo-3,4-dihydroquinazolin-1(2H)-yl}piperidine-1-carbaldehyde | 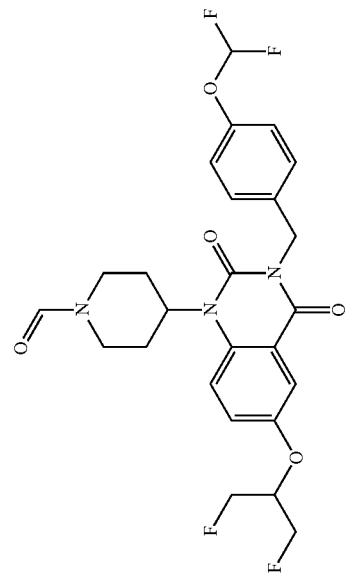 | 524 |
| 218 | 4-{6-[2-fluoro-1-(fluoromethyl)ethoxy]-3-[(6-methoxynaphth-2-yl)methyl]-2,4-dioxo-3,4-dihydroquinazolin-1(2H)-yl}piperidine-1-carbaldehyde | 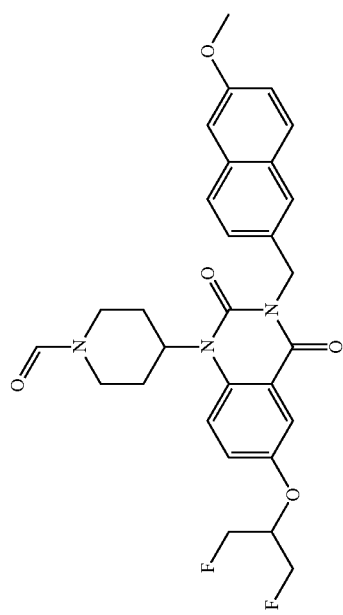 | 538 |

| | | |
|---|---|---|
| 219 | 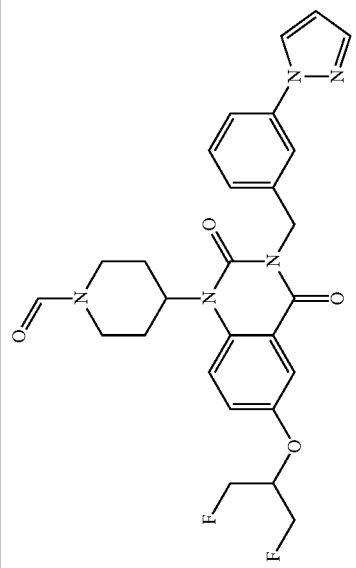 4-{6-[2-fluoro-1-(fluoromethyl)ethoxy]-2,4-dioxo-3-[3-(1H-pyrazol-1-yl)benzyl]-3,4-dihydroquinazolin-1(2H)-yl}piperidine-1-carbaldehyde | 524 |
| 220 | 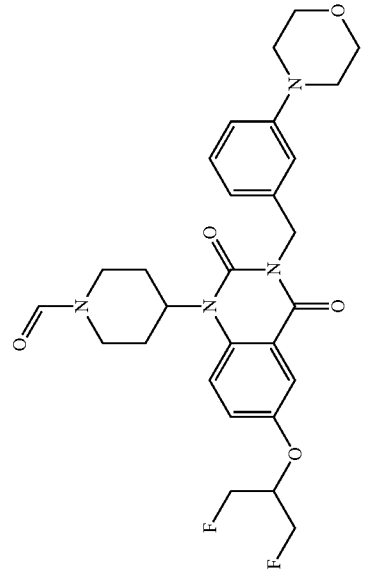 4-{6-[2-fluoro-1-(fluoromethyl)ethoxy]-3-(3-(morpholin-4-yl)benzyl)-2,4-dioxo-3,4-dihydroquinazolin-1(2H)-yl}piperidine-1-carbaldehyde | 543 |
| 221 | 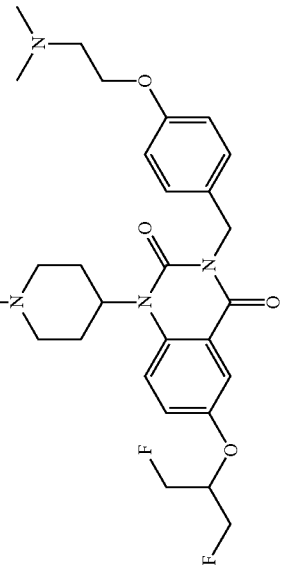 4-[3-{4-[2-(dimethylamino)ethoxy]benzyl}-6-[2-fluoro-1-(fluoromethyl)ethoxy]-2,4-dioxo-3,4-dihydroquinazolin-1(2H)-yl]piperidine-1-carbaldehyde | 545 |

| | | |
|---|---|---|
| 222 | 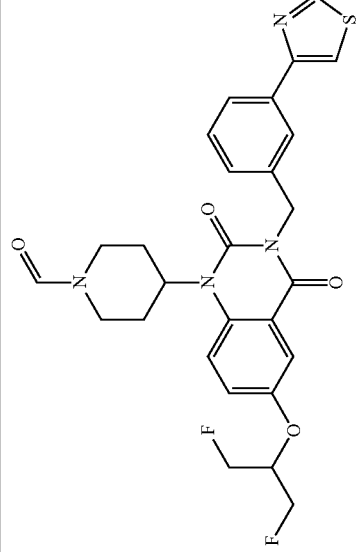 4-{6-[2-fluoro-1-(fluoromethyl)ethoxy]-3-[3-(2-methyl-1,3-thiazol-4-yl)benzyl]-2,4-dioxo-3,4-dihydroquinazolin-1(2H)-yl}piperidine-1-carbaldehyde | 555 |
| 223 | 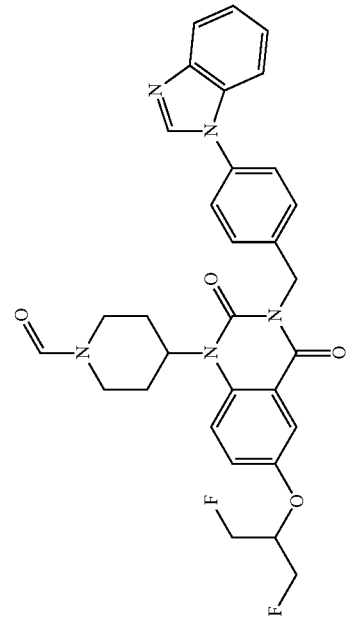 4-{3-[4-(1H-benzimidazol-1-yl)benzyl]-6-[2-fluoro-1-(fluoromethyl)ethoxy]-2,4-dioxo-3,4-dihydroquinazolin-1(2H)-yl}piperidine-1-carbaldehyde | 574 |
| 224 | 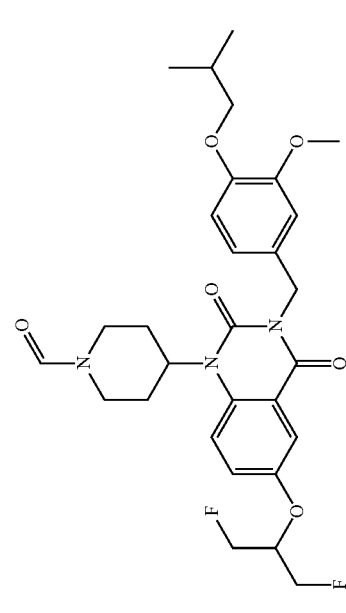 4-{6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde | 560 |

-continued
| | | |
|---|---|---|
| 225 | 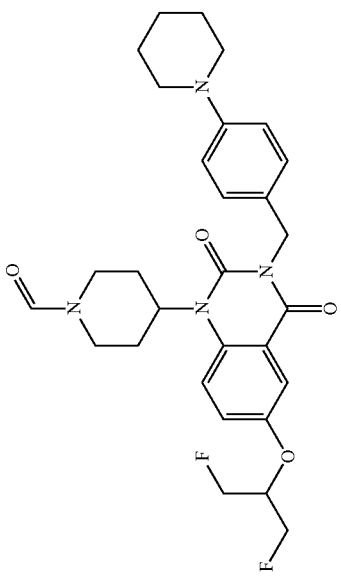 4-{6-[2-fluoro-1-(fluoromethyl)ethoxy]-2,4-dioxo-3-(4-(piperidin-1-yl)benzyl)-3,4-dihydroquinazolin-1(2H)-yl}piperidine-1-carbaldehyde | 541 |
| 226 | 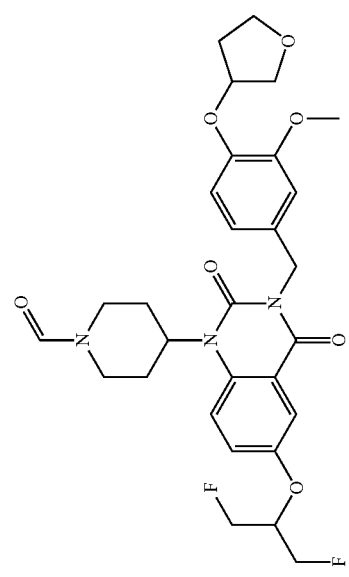 4-{6-[2-fluoro-1-(fluoromethyl)ethoxy]-3-[3-methoxy-4-(tetrahydrofuran-3-yloxy)benzyl]-2,4-dioxo-3,4-dihydroquinazolin-1(2H)-yl}piperidine-1-carbaldehyde | 574 |
| 227 | 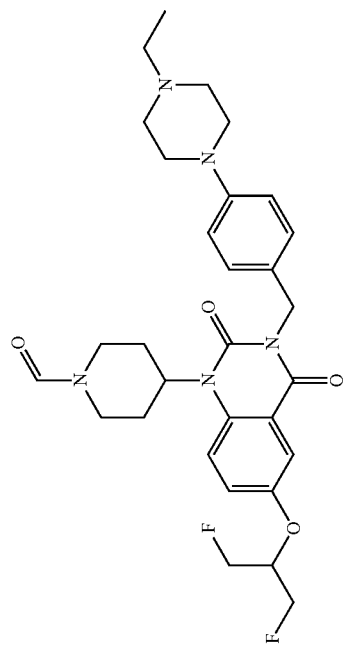 4-{3-[4-(4-ethylpiperazin-1-yl)benzyl]-6-[2-fluoro-1-(fluoromethyl)ethoxy]-2,4-dioxo-3,4-dihydroquinazolin-1(2H)-yl}piperidine-1-carbaldehyde | 570 |

| | | |
|---|---|---|
| 228 | 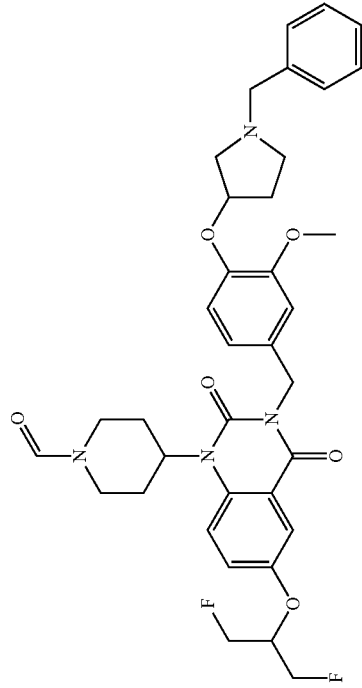 4-[3-{4-[(1-benzylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 663 |
| 229 | 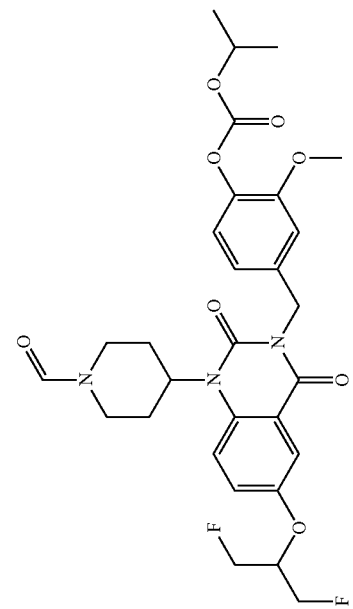 4-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 1-methylethyl carbonate | 590 |
| 230 | 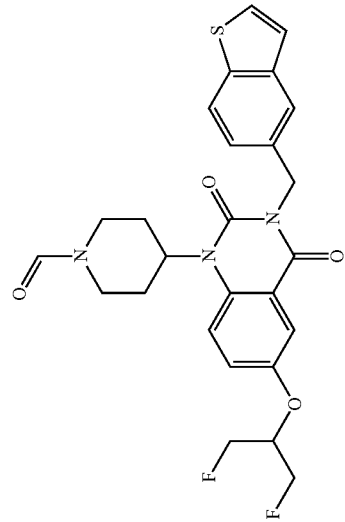 4-[3-(1-benzothiophen-5-ylmethyl)-6-[2-fluoro-1-(fluoromethyl)ethoxy]-2,4-dioxo-3,4-dihydroquinazolin-1(2H)-yl]piperidine-1-carbaldehyde | 514 |

| | | |
|---|---|---|
| 231 | 4-{6-[2-fluoro-1-(fluoromethyl)ethoxy]-3-[3-methoxy-4-(pyrrolidin-3-yloxy)benzyl]-2,4-dioxo-3,4-dihydroquinazolin-1(2H)-yl}piperidine-1-carbaldehyde 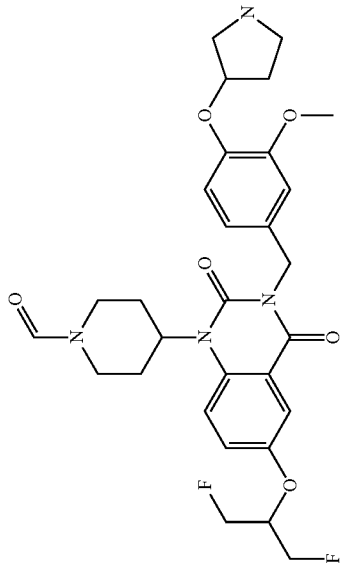 | 573 |
| 232 | 4-{6-[2-fluoro-1-(fluoromethyl)ethoxy]-3-[3-methoxy-4-(1-methylethyoxy)benzyl]-2,4-dioxo-3,4-dihydroquinazolin-1(2H)-yl}piperidine-1-carbaldehyde 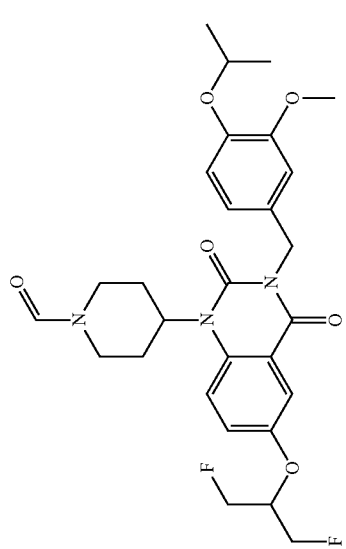 | 546 |
| 233 | 4-[3-(3,4-dimethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde 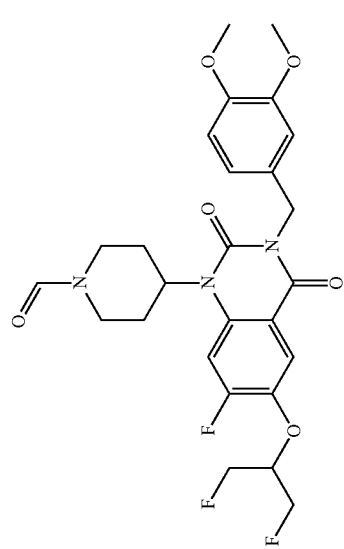 | 536 |

| | | |
|---|---|---|
| 234 | 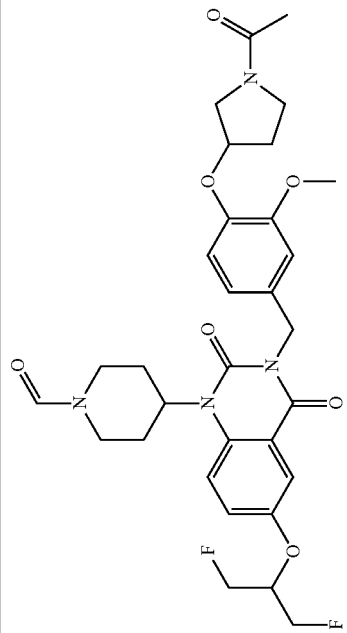 4-[3-{4-[(1-acetylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 615 |
| 235 | 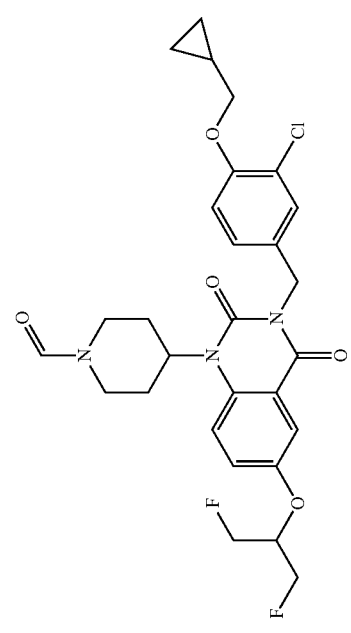 4-{3-[3-chloro-4-(cyclopropylmethoxy)benzyl]-6-[2-fluoro-1-(fluoromethyl)ethoxy]-2,4-dioxo-3,4-dihydroquinazolin-1(2H)-yl}piperidine-1-carbaldehyde | 562 |
| 236 | 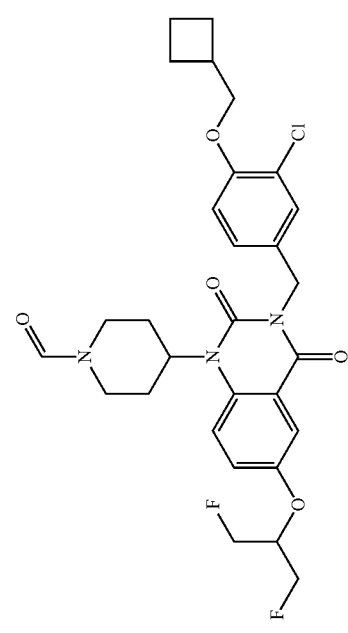 4-{3-[3-chloro-4-(cyclobutylmethoxy)benzyl]-6-[2-fluoro-1-(fluoromethyl)ethoxy]-2,4-dioxo-3,4-dihydroquinazolin-1(2H)-yl}piperidine-1-carbaldehyde | 576 |

| | | |
|---|---|---|
| 237 | 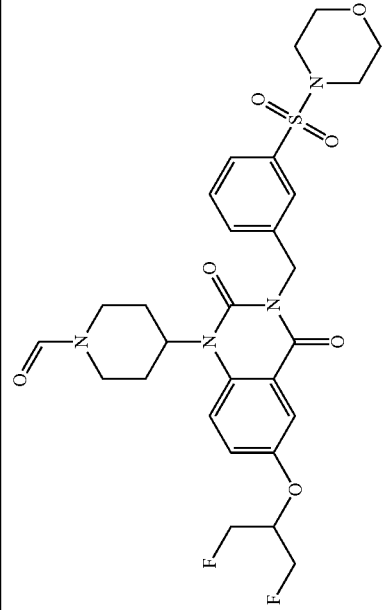 4-{6-[2-fluoro-1-(fluoromethyl)ethoxy]-3-[3-(morpholin-4-ylsulphonyl)benzyl]-2,4-dioxo-3,4-dihydroquinazolin-1(2H)-yl}piperidine-1-carbaldehyde | 607 |
| 238 | 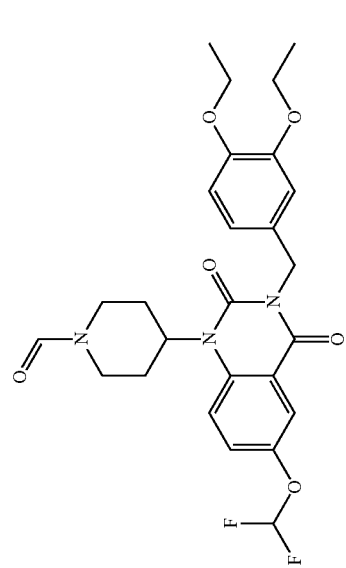 4-[3-(3,4-diethoxybenzyl)-6-(difluoromethoxy)-2,4-dioxo-3,4-dihydroquinazolin-1(2H)-yl]piperidine-1-carbaldehyde | 518 |
| 239 | 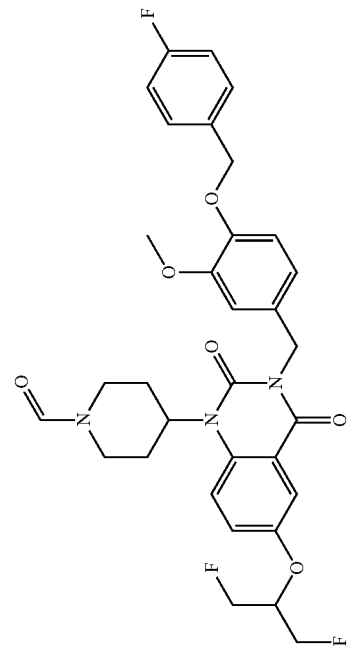 4-[3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 612 |

-continued
| 240 | 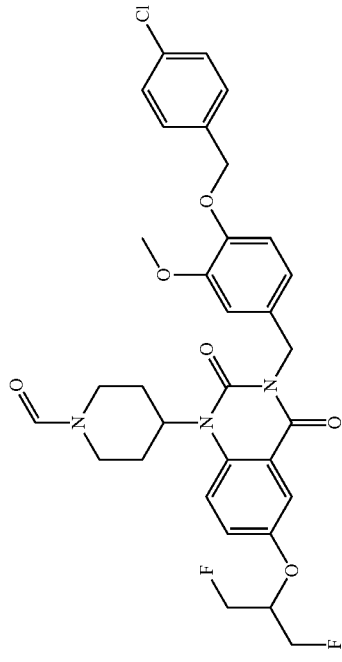 | 4-[3-[4-[(4-chlorobenzyl)oxy]-3-methoxybenzyl]-6-[2-fluoro-1-(fluoromethyl)ethoxy]-2,4-dioxo-3,4-dihydroquinazolin-1(2H)-yl]piperidine-1-carbaldehyde | 628 |
| --- | --- | --- | --- |
| 241 | 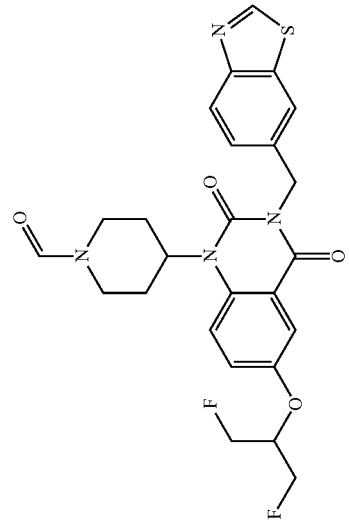 | 4-[3-(1,3-benzothiazol-6-ylmethyl)-6-[2-fluoro-1-(fluoromethyl)ethoxy]-2,4-dioxo-3,4-dihydroquinazolin-1(2H)-yl]piperidine-1-carbaldehyde | 515 |
| 242 | 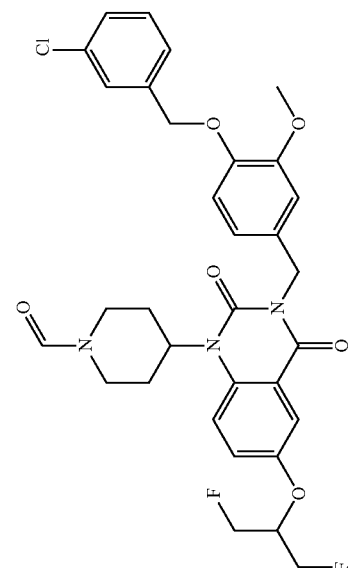 | 4-[3-[4-[(3-chlorobenzyl)oxy]-3-methoxybenzyl]-6-[2-fluoro-1-(fluoromethyl)ethoxy]-2,4-dioxo-3,4-dihydroquinazolin-1(2H)-yl]piperidine-1-carbaldehyde | 628 |

| | | |
|---|---|---|
| 243 | 4-{6-[2-fluoro-1-(fluoromethyl)ethoxy]-2,4-dioxo-3-(3-(thiophen-3-yl)benzyl)-3,4-dihydroquinazolin-1(2H)-yl]piperidine-1-carbaldehyde 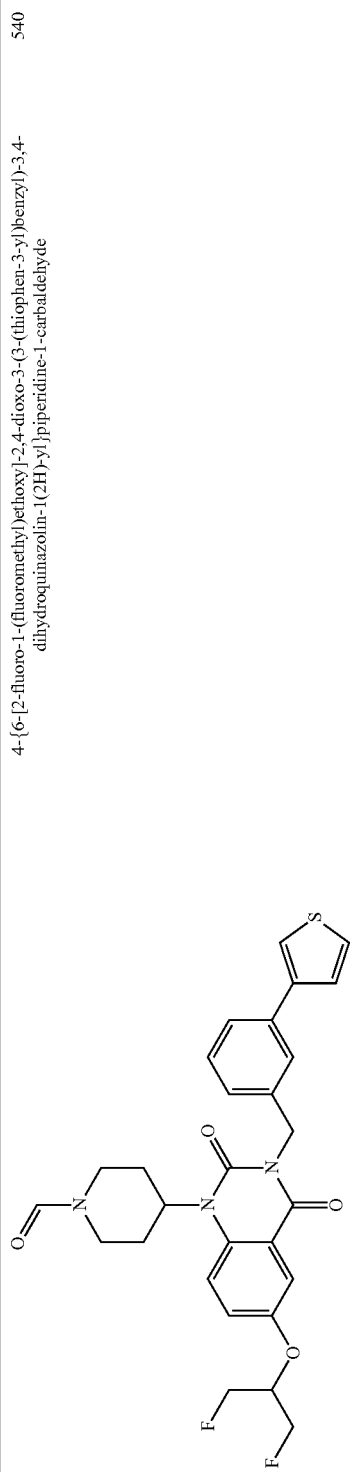 | 540 |
| 244 | 4-[3-(3,4-diethoxybenzyl)-6-(2,2-difluoroethoxy)-2,4-dioxo-3,4-dihydroquinazolin-1(2H)-yl]piperidine-1-carbaldehyde 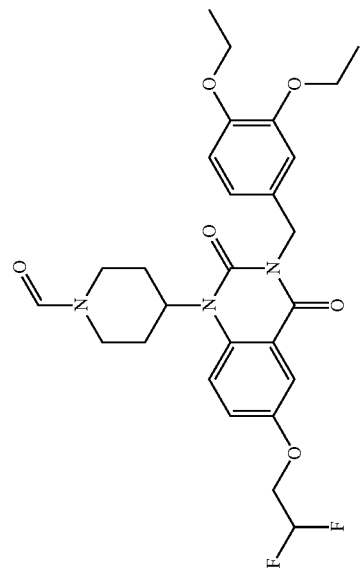 | 532 |
| 245 | 4-[3-(4-ethoxy-3-methoxybenzyl)-6-(2-hydroxyethoxy)-2,4-dioxo-3,4-dihydroquinazolin-1(2H)-yl]piperidine-1-carbaldehyde 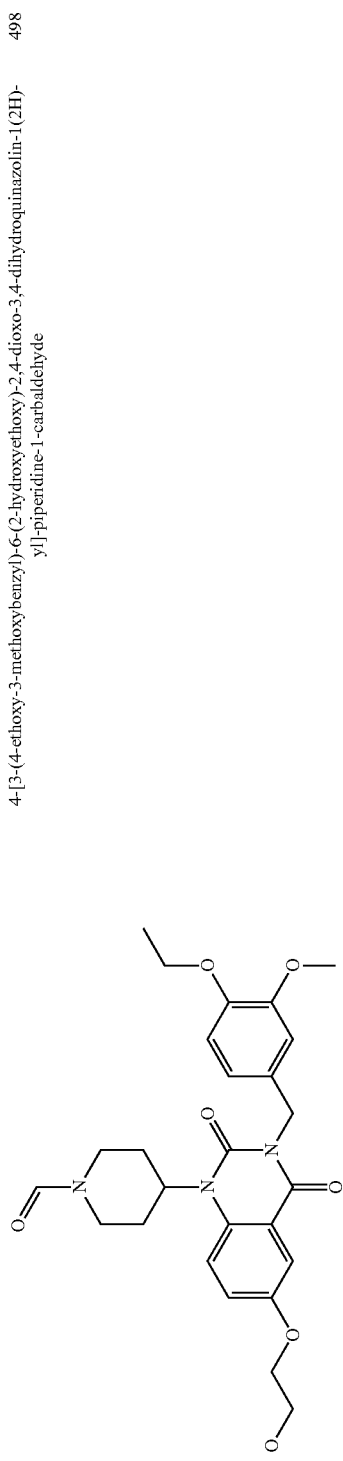 | 498 |

| 246 | 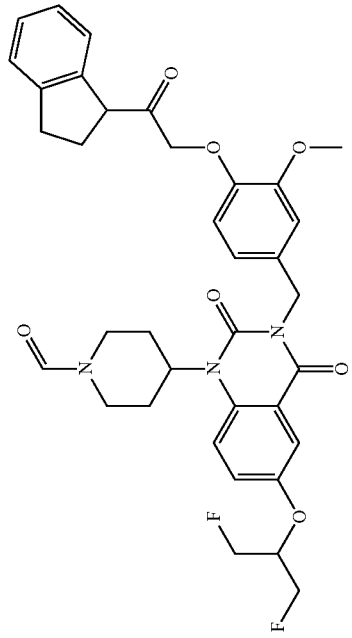 | 4-[3-{4-[2-(2,3-dihydro-1H-indol-1-yl)-2-oxoethoxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 663 |
| 247 | 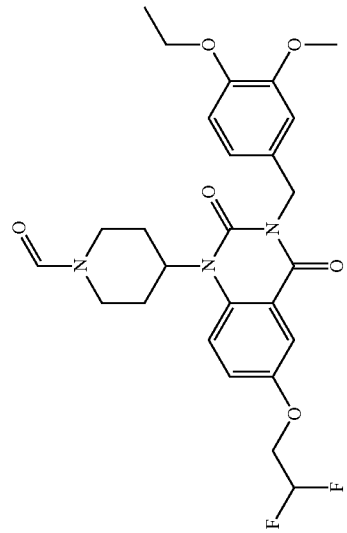 | 4-[6-(2,2-difluoroethoxy)-3-(4-ethoxy-3-methoxybenzyl)-2,4-dioxo-3,4-dihydroquinazolin-1(2H)-yl]piperidine-1-carbaldehyde | 518 |
| 248 | 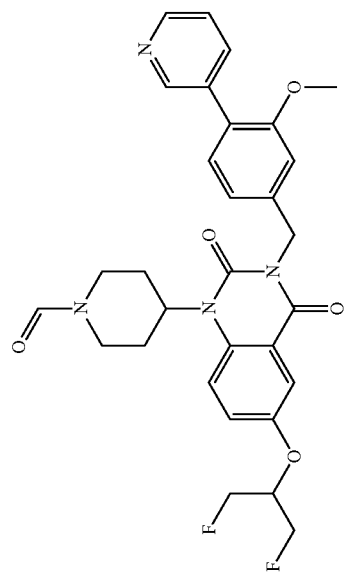 | 4-{6-[2-fluoro-1-(fluoromethyl)ethoxy]-3-(3-methoxy-4-(pyridin-3-yl)benzyl)-2,4-dioxo-3,4-dihydroquinazolin-1(2H)-yl}piperidine-1-carbaldehyde | 565 |

| | | |
|---|---|---|
| 249 | methyl 4-({6-[2-fluoro-1-(fluoromethyl)ethoxy]-1-(1-formylpiperidin-4-yl)-2,4-dioxo-1,4-dihydroquinazolin-3(2H)-yl}methyl)benzoate 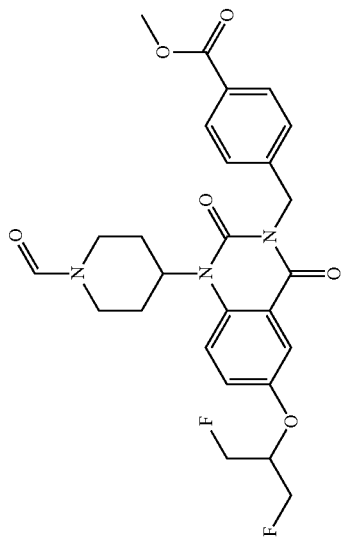 | 516 |
| 250 | 4-[3-{4-[(3,4-dichlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde 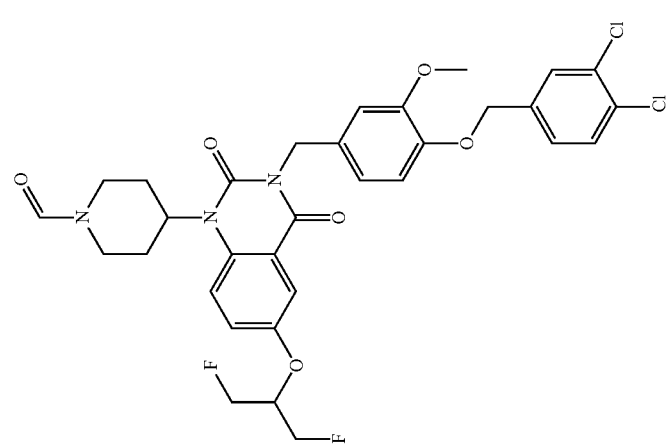 | 662 |

-continued

| | | | |
|---|---|---|---|
| 251 | 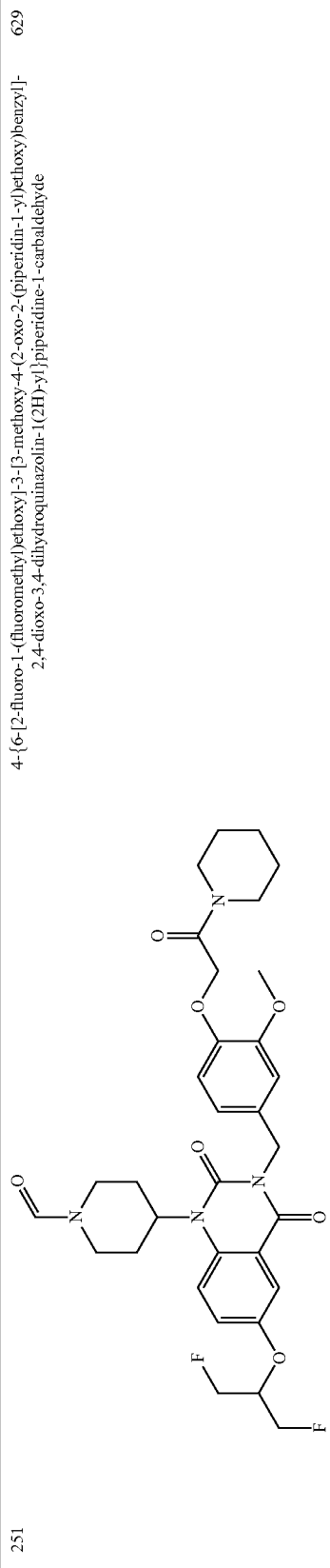 | 4-{6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde | 629 |
| 252 | 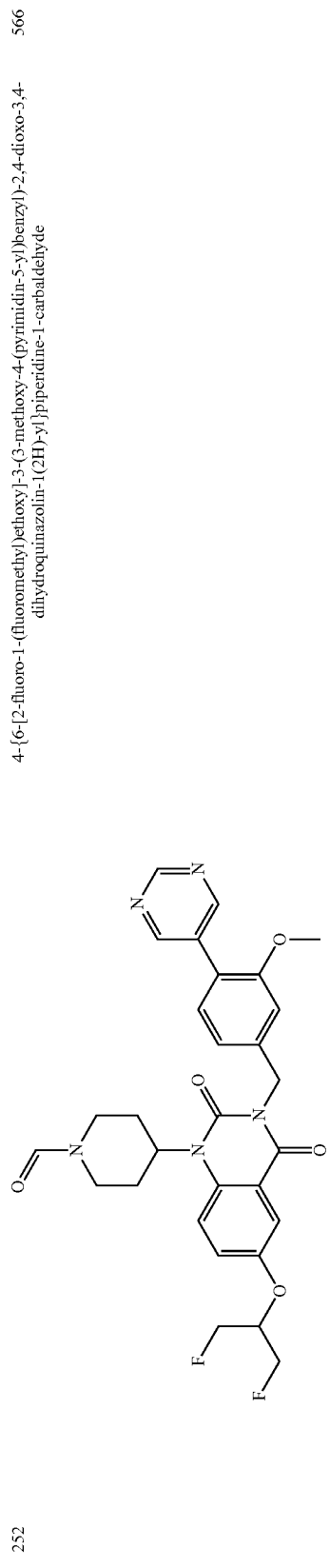 | 4-{6-[2-fluoro-1-(fluoromethyl)ethoxy]-3-(3-methoxy-4-(pyrimidin-5-yl)benzyl)-2,4-dioxo-3,4-dihydroquinazolin-1(2H)-yl}piperidine-1-carbaldehyde | 566 |
| 253 | 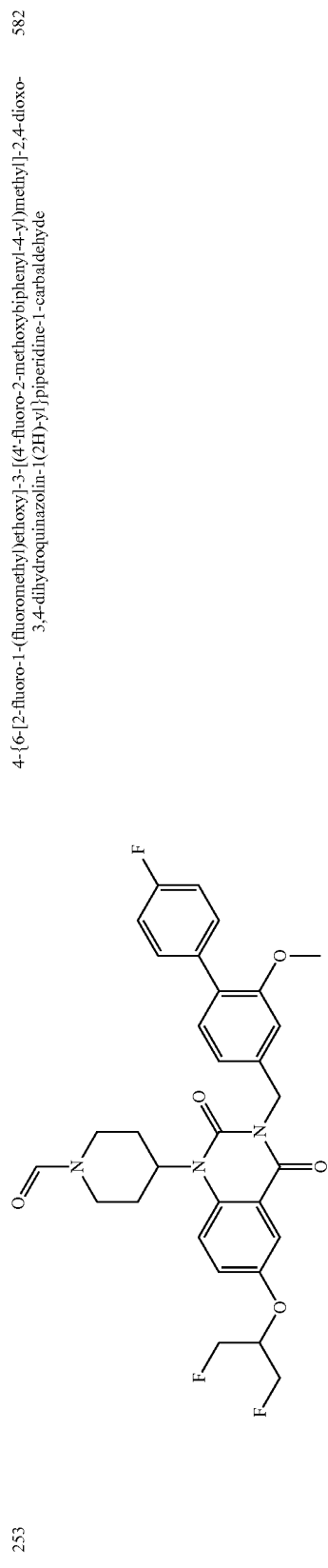 | 4-{6-[2-fluoro-1-(fluoromethyl)ethoxy]-3-[(4'-fluoro-2-methoxybiphenyl-4-yl)methyl]-2,4-dioxo-3,4-dihydroquinazolin-1(2H)-yl}piperidine-1-carbaldehyde | 582 |

| | | |
|---|---|---|
| 254 | 4-{3-[3-ethoxy-4-(thiophen-2-ylmethoxy)benzyl]-6-[2-fluoro-1-(fluoromethyl)ethoxy]-2,4-dioxo-3,4-dihydroquinazolin-1(2H)-yl}piperidine-1-carbaldehyde 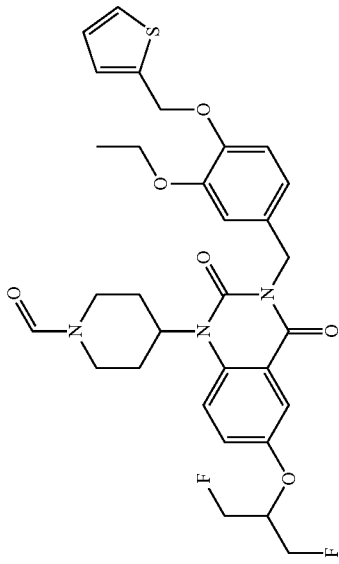 | 614 |
| 255 | 4-[3-(3,4-diethoxybenzyl)-6-(2-fluoroethoxy)-2,4-dioxo-3,4-dihydroquinazolin-1(2H)-yl]piperidine-1-carbaldehyde 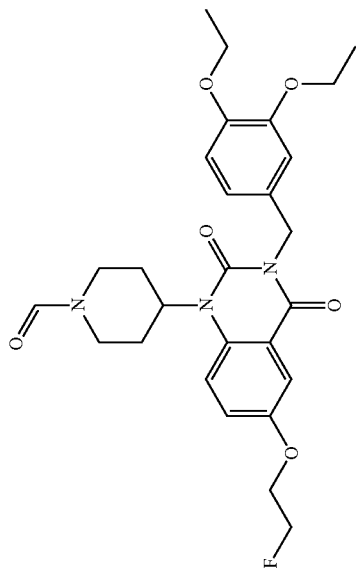 | 514 |

| | | |
|---|---|---|
| 256 | 4-[3-(3,4-dimethoxybenzyl)-6-(3-fluoro-2-hydroxypropoxy)-2,4-dioxo-3,4-dihydroquinazolin-1(2H)-yl]piperidine-1-carbaldehyde 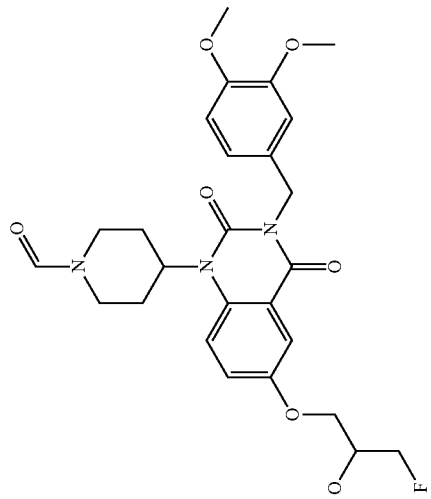 | 516 |
| 257 | 1,1-dimethylethyl 4-({4-[2-fluoro-1-(fluoromethyl)ethoxy]-2-(methoxycarbonyl)phenyl}amino)piperidine-1-carboxylate 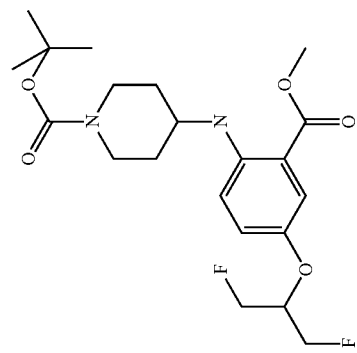 | 429 |

| | | |
|---|---|---|
| 258 | 4-[3-(3,4-dimethoxybenzyl)-6-[2-fluoro-1-(hydroxymethyl)ethoxy]-2,4-dioxo-3,4-dihydroquinazolin-1(2H)-yl]piperidine-1-carbaldehyde 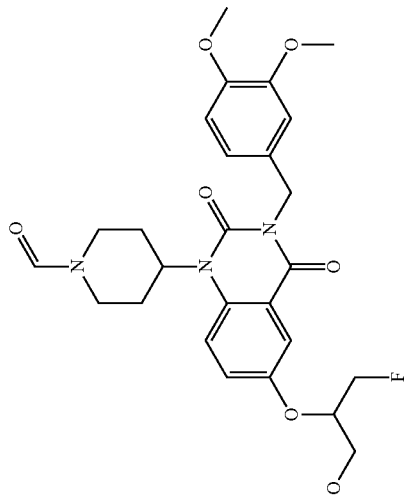 | 516 |
| 259 | 4-{6-[2-fluoro-1-(fluoromethyl)ethoxy]-2,4-dioxo-3-[3-(1H-pyrazol-1-ylmethyl)benzyl]-3,4-dihydroquinazolin-1(2H)-yl}piperidine-1-carbaldehyde 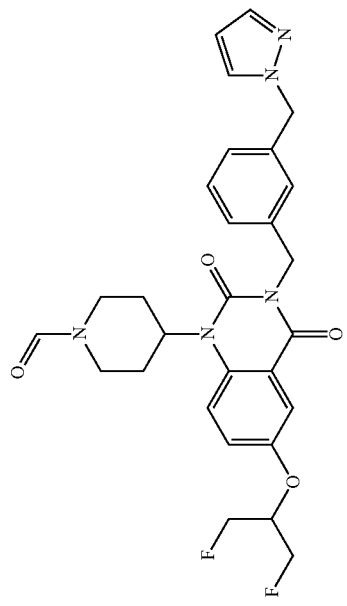 | 538 |
| 260 | 4-{6-[2-fluoro-1-(fluoromethyl)ethoxy]-3-(3-methoxy-4-(thiophen-2-yl)benzyl)-2,4-dioxo-3,4-dihydroquinazolin-1(2H)-yl}piperidine-1-carbaldehyde 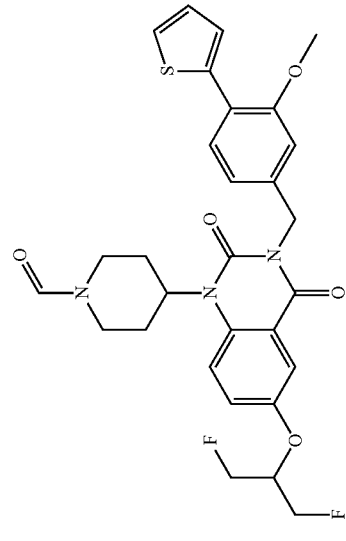 | 570 |

| 261 | 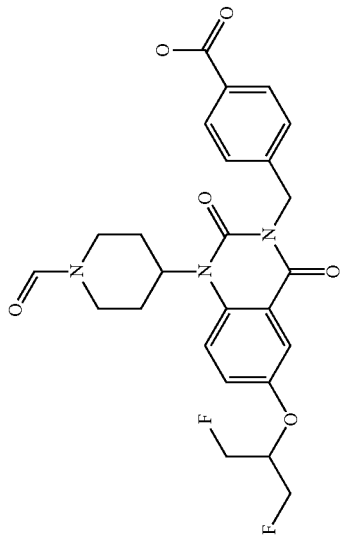 | 4-({6-[2-fluoro-1-(fluoromethyl)ethoxy]-1-(1-formylpiperidin-4-yl)-2,4-dioxo-1,4-dihydroquinazolin-3(2H)-yl}methyl)benzoic acid | 502 |
| --- | --- | --- | --- |
| 262 | 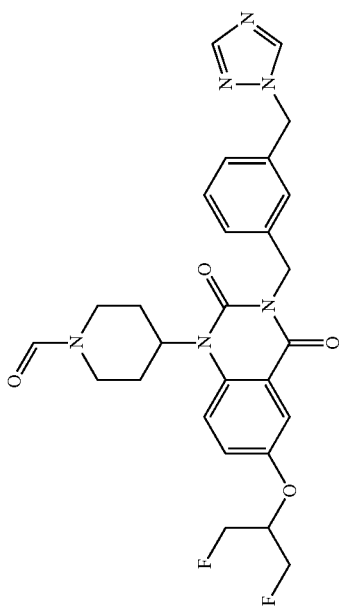 | 4-{6-[2-fluoro-1-(fluoromethyl)ethoxy]-2,4-dioxo-3-[3-(1H-1,2,4-triazol-1-ylmethyl)benzyl]-3,4-dihydroquinazolin-1(2H)-yl}piperidine-1-carbaldehyde | 539 |
| 263 | 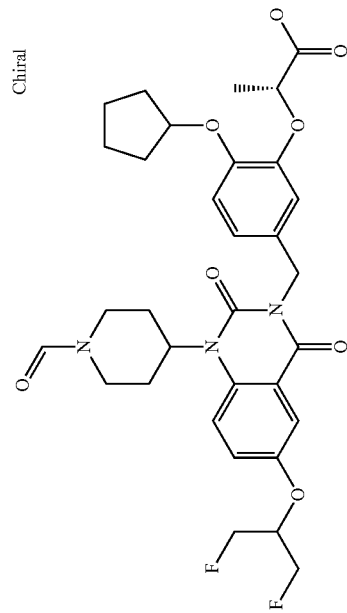 | (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid | 630 |

-continued

| | | |
|---|---|---|
| 264 | 4-{6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde | 544 |
| | 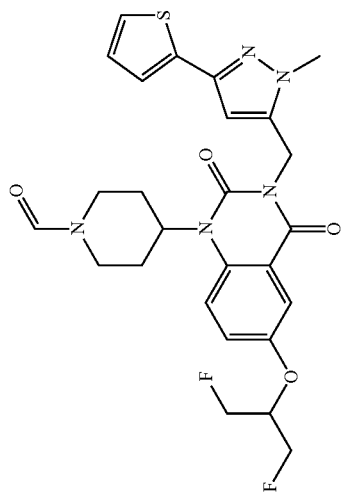 | |
| 265 | 4-{6-[2-fluoro-1-(fluoromethyl)ethoxy]-2,4-dioxo-3-[4-(1H-1,2,4-triazol-1-ylmethyl)benzyl]-3,4-dihydroquinazolin-1(2H)-yl}piperidine-1-carbaldehyde | 539 |
| | 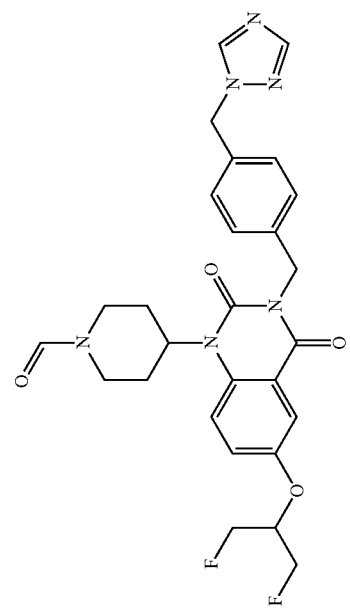 | |
| 266 | 4-({6-[2-fluoro-1-(fluoromethyl)ethoxy]-1-(1-formyl)piperidin-4-yl)-2,4-dioxo-1,4-dihydroquinazolin-3(2H)-yl}methyl)-N-(2-(morpholin-4-yl)ethyl)benzamide | 614 |
| | 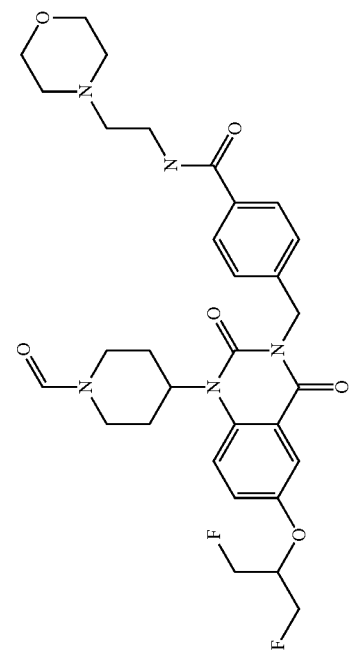 | |

| # | Structure | Name | MW |
|---|---|---|---|
| 267 | 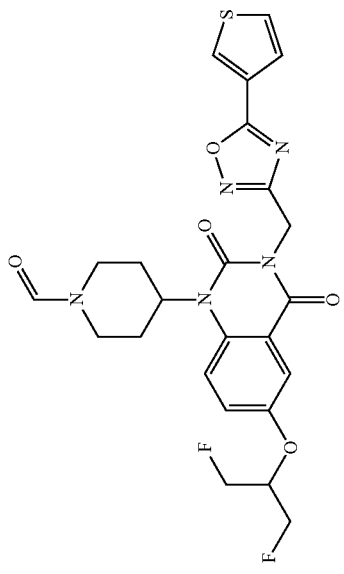 | 4-{6-[2-fluoro-1-(fluoromethyl)ethoxy]-2,4-dioxo-3-[(5-(thiophen-3-yl)-1,2,4-oxadiazol-3-yl)methyl]-3,4-dihydroquinazolin-1(2H)-yl}piperidine-1-carbaldehyde | 532 |
| 268 | 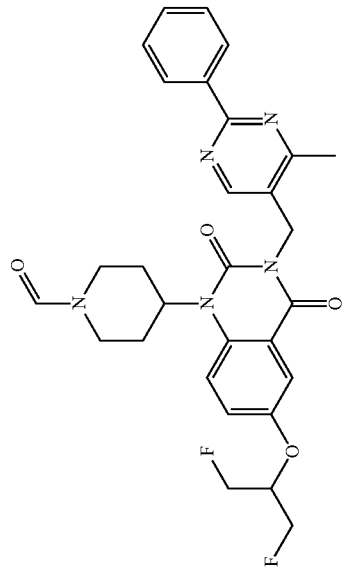 | 4-{6-[2-fluoro-1-(fluoromethyl)ethoxy]-3-[(4-methyl-2-phenylpyrimidin-5-yl)methyl]-2,4-dioxo-3,4-dihydroquinazolin-1(2H)-yl}piperidine-1-carbaldehyde | 550 |
| 269 | 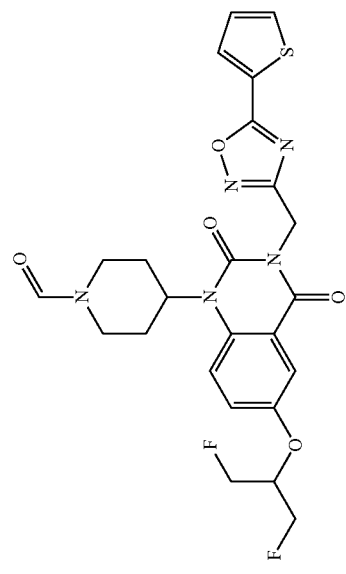 | 4-{6-[2-fluoro-1-(fluoromethyl)ethoxy]-2,4-dioxo-3-[(5-(thiophen-2-yl)-1,2,4-oxadiazol-3-yl)methyl]-3,4-dihydroquinazolin-1(2H)-yl}piperidine-1-carbaldehyde | 532 |

| | | |
|---|---|---|
| 270 | 4-{6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde | 540 |
| | 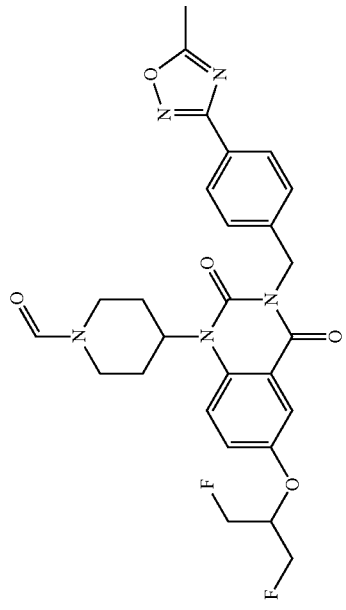 | |
| 271 | 4-{6-[2-fluoro-1-(fluoromethyl)ethoxy]-2,4-dioxo-3-[(2-(thiophen-2-yl)-1,3-thiazol-4-yl)methyl]-3,4-dihydroquinazolin-1(2H)-yl}piperidine-1-carbaldehyde | 547 |
| | 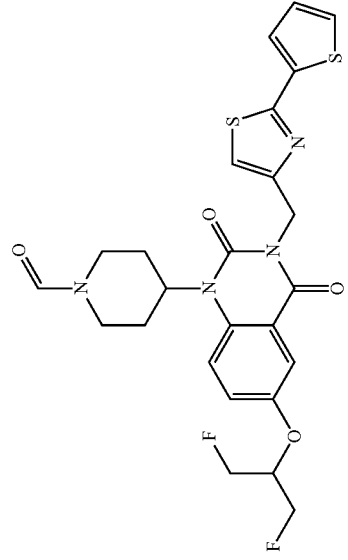 | |
| 272 | 4-{6-[2-fluoro-1-(fluoromethyl)ethoxy]-3-(2-fluoro-4-(thiophen-2-yl)benzyl)-2,4-dioxo-3,4-dihydroquinazolin-1(2H)-yl}piperidine-1-carbaldehyde | 558 |
| | 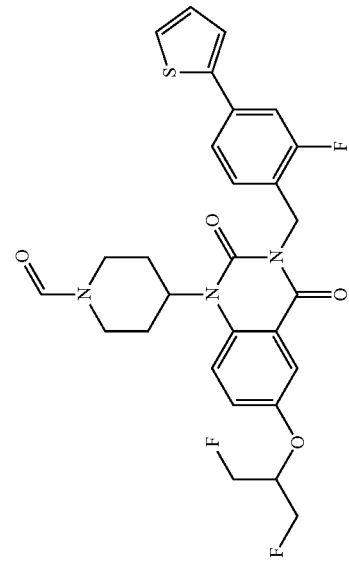 | |

| | | |
|---|---|---|
| 273 | 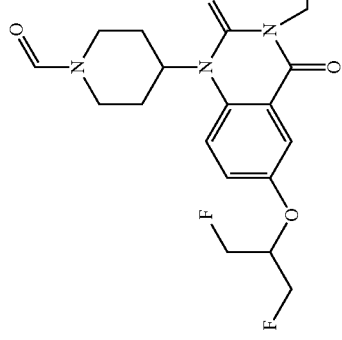 | 4-{6-[2-fluoro-1-(fluoromethyl)ethoxy]-3-[(1-methyl-5-(thiophen-2-yl)-1H-pyrazol-3-yl)methyl]-2,4-dioxo-3,4-dihydroquinazolin-1(2H)-yl}piperidine-1-carbaldehyde 544 |
| 274 | 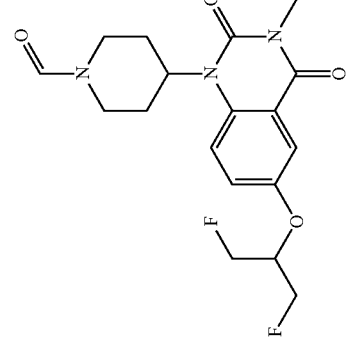 | 4-{6-[2-fluoro-1-(fluoromethyl)ethoxy]-2,4-dioxo-3-[(3-(thiophen-2-yl)-1,2,4-oxadiazol-5-yl)methyl]-3,4-dihydroquinazolin-1(2H)-yl}piperidine-1-carbaldehyde 532 |
| 275 | 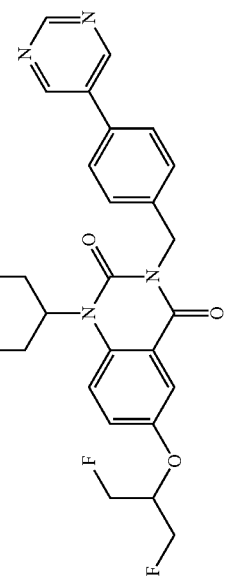 | 4-{6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde 536 |

| | | |
|---|---|---|
| 276 | 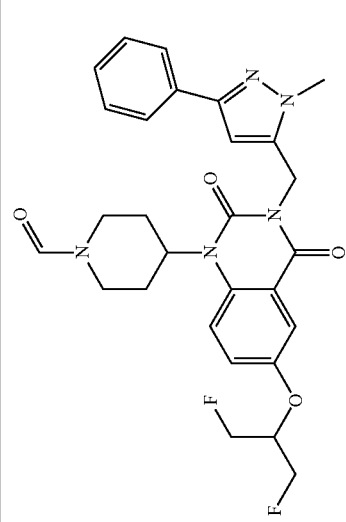 4-{6-[2-fluoro-1-(fluoromethyl)ethoxy]-3-[(1-methyl-3-phenyl-1H-pyrazol-5-yl)methyl]-2,4-dioxo-3,4-dihydroquinazolin-1(2H)-yl}piperidine-1-carbaldehyde | 538 |
| 277 | 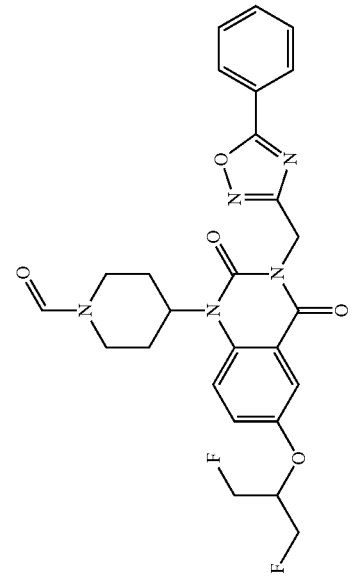 4-{6-[2-fluoro-1-(fluoromethyl)ethoxy]-2,4-dioxo-3-[(5-phenyl-1,2,4-oxadiazol-3-yl)methyl]-3,4-dihydroquinazolin-1(2H)-yl}piperidine-1-carbaldehyde | 526 |
| 278 | 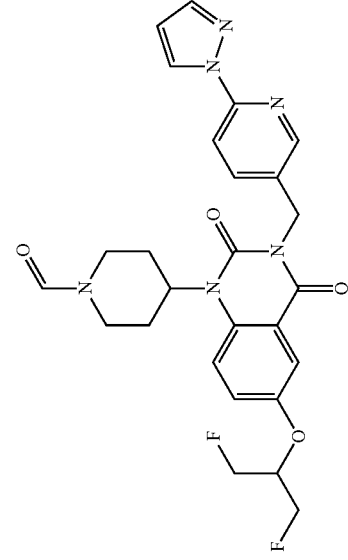 4-{6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde | 525 |

| | | | |
|---|---|---|---|
| 279 | 4-{6-[2-fluoro-1-(fluoromethyl)ethoxy]-2,4-dioxo-3-[(2-(thiophen-2-yl)pyrimidin-5-yl)methyl]-3,4-dihydroquinazolin-1(2H)-yl}piperidine-1-carbaldehyde | 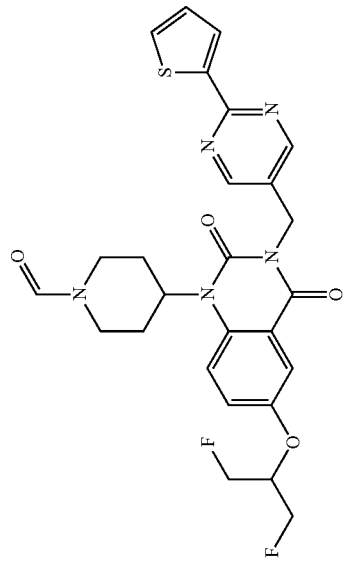 | 542 |
| 280 | 4-{6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde | 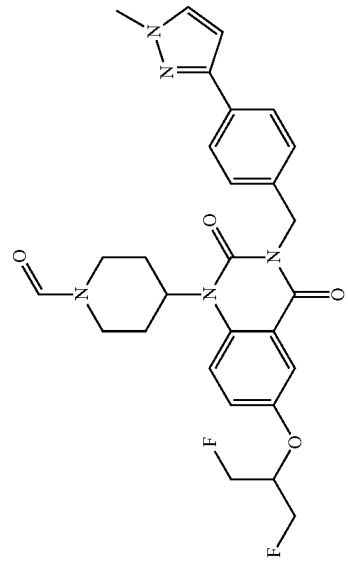 | 538 |
| 281 | 4-{6-[2-fluoro-1-(fluoromethyl)ethoxy]-3-(imidazo[1,2-a]pyridin-7-ylmethyl)-2,4-dioxo-3,4-dihydroquinazolin-1(2H)-yl}piperidine-1-carbaldehyde | 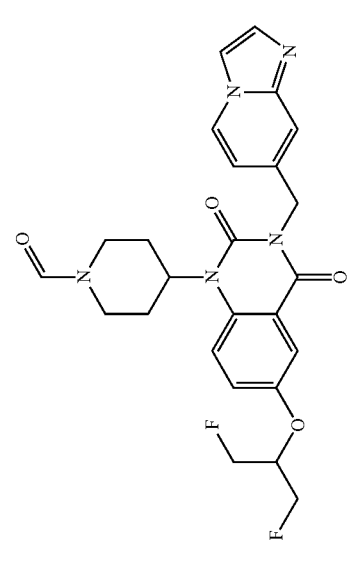 | 598 |

-continued

| | | |
|---|---|---|
| 282 | 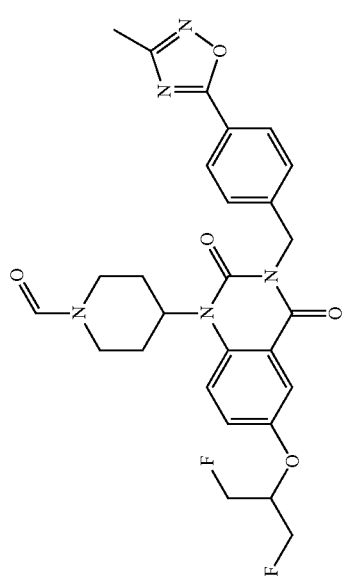 4-{6-[2-fluoro-1-(fluoromethyl)ethoxy]-3-[4-(3-methyl-1,2,4-oxadiazol-5-yl)benzyl]-2,4-dioxo-3,4-dihydroquinazolin-1(2H)-yl}piperidine-1-carbaldehyde | 540 |
| 283 | 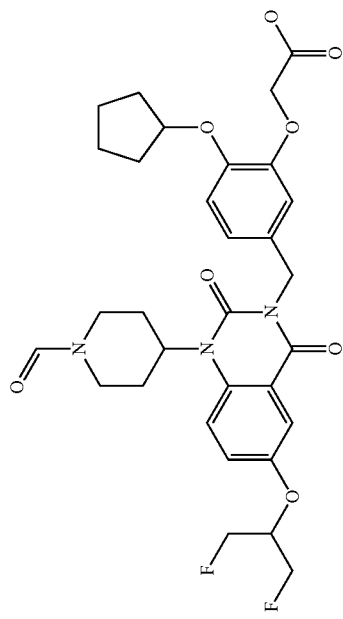 [2-(cyclopentyloxy)-5-(({6-[2-fluoro-1-(fluoromethyl)ethoxy]-1-(1-formyl)piperidin-4-yl)-2,4-dioxo-1,4-dihydroquinazolin-3(2H)-yl}methyl)phenoxy]acetic acid | 616 |
| 284 | 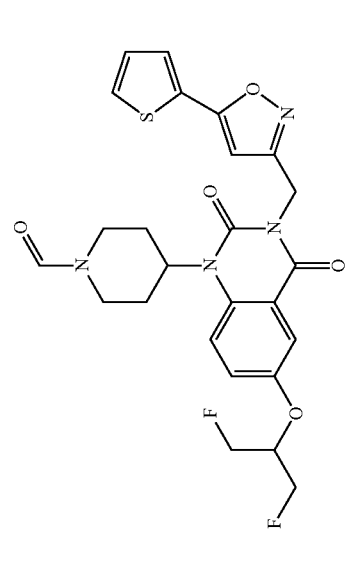 4-{6-[2-fluoro-1-(fluoromethyl)ethoxy]-2,4-dioxo-3-[(5-(thiophen-2-yl)isoxazol-3-yl)methyl]-3,4-dihydroquinazolin-1(2H)-yl}piperidine-1-carbaldehyde | 531 |

| 285 | 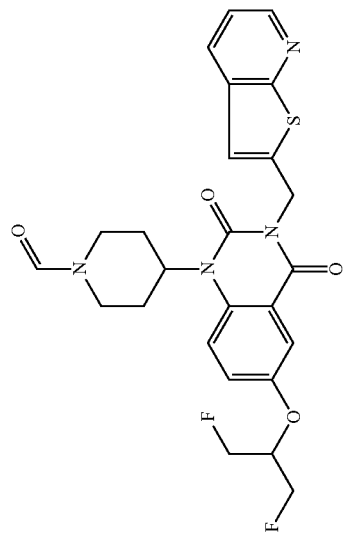 | 4-{6-[2-fluoro-1-(fluoromethyl)ethoxy]-2,4-dioxo-3-(thieno[2,3-b]pyridin-2-ylmethyl)-3,4-dihydroquinazolin-1(2H)-yl}piperidine-1-carbaldehyde | 514 |
| 286 | 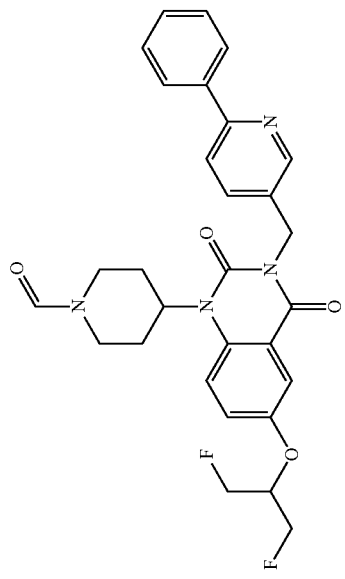 | 4-{6-[2-fluoro-1-(fluoromethyl)ethoxy]-2,4-dioxo-3-[(6-phenylpyridin-3-yl)methyl]-3,4-dihydroquinazolin-1(2H)-yl}piperidine-1-carbaldehyde | 535 |
| 287 | 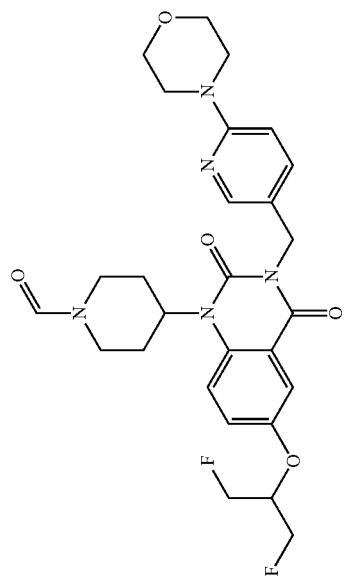 | 4-{6-[2-fluoro-1-(fluoromethyl)ethoxy]-3-[(6-(morpholin-4-yl)pyridin-3-yl)methyl]-2,4-dioxo-3,4-dihydroquinazolin-1(2H)-yl}piperidine-1-carbaldehyde | 544 |

| | | | |
|---|---|---|---|
| 288 | 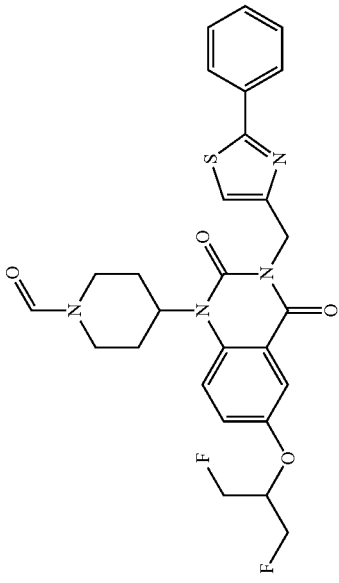 | 4-{6-[2-fluoro-1-(fluoromethyl)ethoxy]-2,4-dioxo-3-[(2-phenyl-1,3-thiazol-4-yl)methyl]-3,4-dihydroquinazolin-1(2H)-yl}piperidine-1-carbaldehyde | 541 |
| 289 | 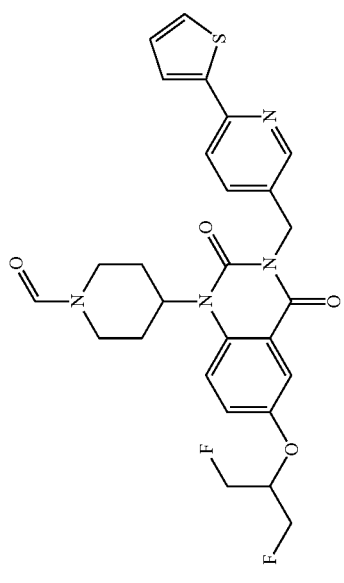 | 4-{6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde | 541 |
| 290 | 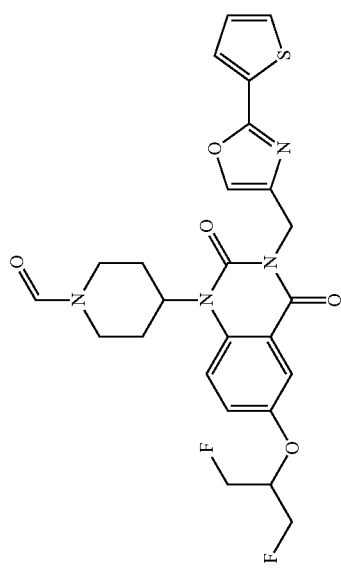 | 4-{6-[2-fluoro-1-(fluoromethyl)ethoxy]-2,4-dioxo-3-[(2-thiophen-2-yl)-1,3-oxazol-4-yl)methyl]-3,4-dihydroquinazolin-1(2H)-yl}piperidine-1-carbaldehyde | 531 |

-continued

| | | |
|---|---|---|
| 291 | 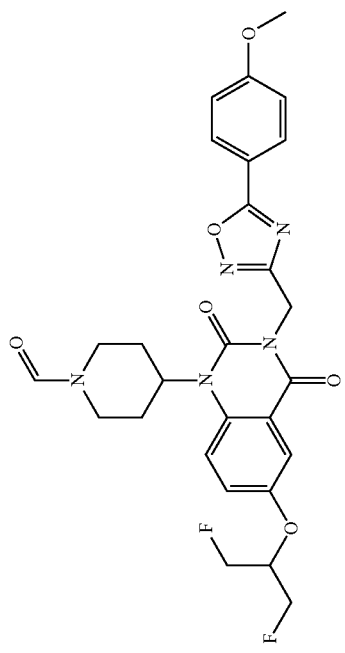 | 4-{6-[2-fluoro-1-(fluoromethyl)ethoxy]-3-{[5-(4-methoxyphenyl)-1,2,4-oxadiazol-3-yl]methyl}-2,4-dioxo-3,4-dihydroquinazolin-1(2H)-yl}piperidine-1-carbaldehyde 556 |
| 292 | 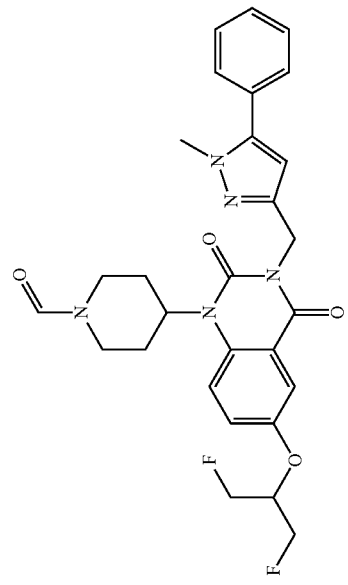 | 4-{6-[2-fluoro-1-(fluoromethyl)ethoxy]-3-[(1-methyl-5-phenyl-1H-pyrazol-3-yl)methyl]-2,4-dioxo-3,4-dihydroquinazolin-1(2H)-yl}piperidine-1-carbaldehyde 538 |
| 293 | 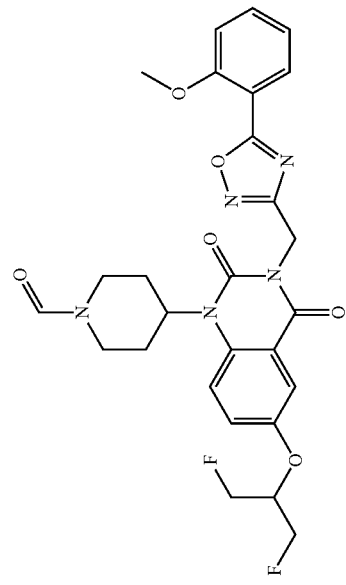 | 4-{6-[2-fluoro-1-(fluoromethyl)ethoxy]-3-{[5-(2-methoxyphenyl)-1,2,4-oxadiazol-3-yl]methyl}-2,4-dioxo-3,4-dihydroquinazolin-1(2H)-yl}piperidine-1-carbaldehyde 556 |

| | | |
|---|---|---|
| 294 | 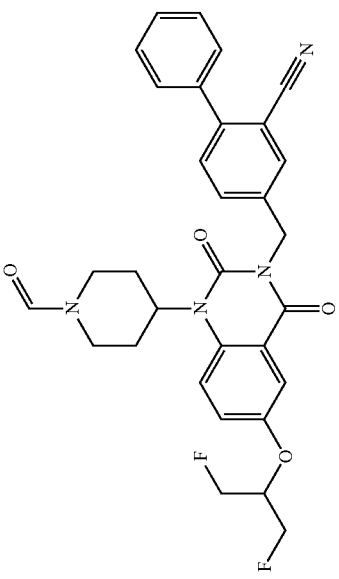 4-({6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile | 559 |
| 295 | Chiral 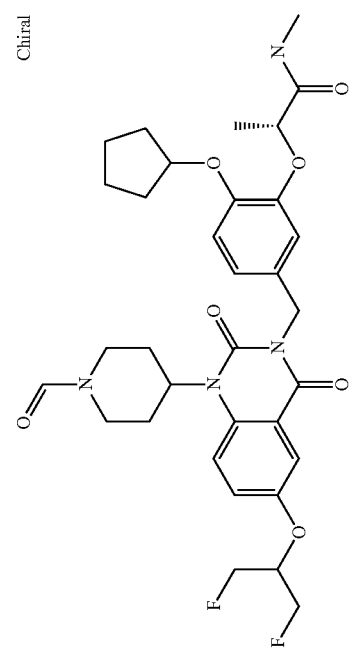 (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylpropanamide | 643 |
| 296 | Chiral 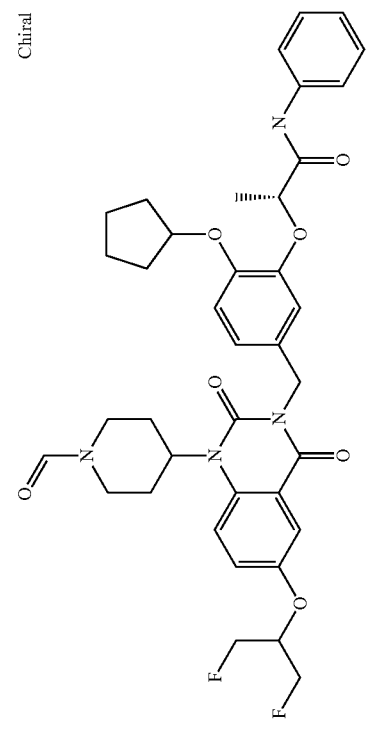 (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-phenylpropanamide | 705 |

| 297 | 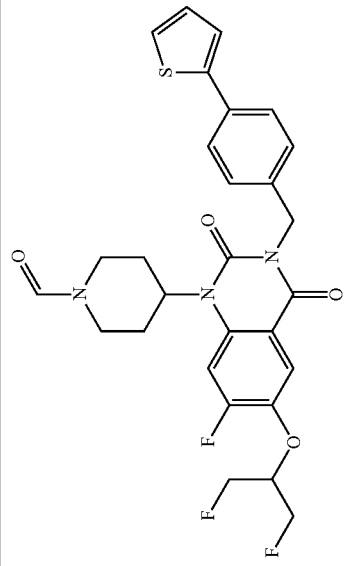 | 4-{7-fluoro-6-[2-fluoro-1-(fluoromethyl)ethoxy]-2,4-dioxo-3-(4-(thiophen-2-yl)benzyl)-3,4-dihydroquinazolin-1(2H)-yl}piperidine-1-carbaldehyde | 558 |
| 298 | 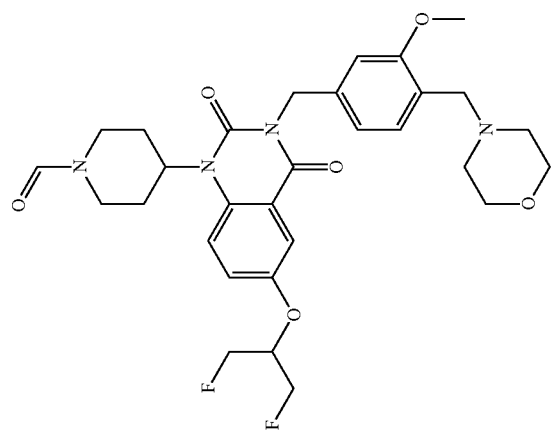 | 4-{6-[2-fluoro-1-(fluoromethyl)ethoxy]-3-[3-methoxy-4-(morpholin-4-ylmethyl)benzyl]-2,4-dioxo-3,4-dihydroquinazolin-1(2H)-yl}piperidine-1-carbaldehyde | 587 |

| 299 | 4-{6-[2-fluoro-1-(fluoromethyl)ethoxy]-3-[3-methoxy-4-(piperidin-1-ylmethyl)benzyl]-2,4-dioxo-3,4-dihydroquinazolin-1(2H)-yl}piperidine-1-carbaldehyde | 585 |
|---|---|---|
| | 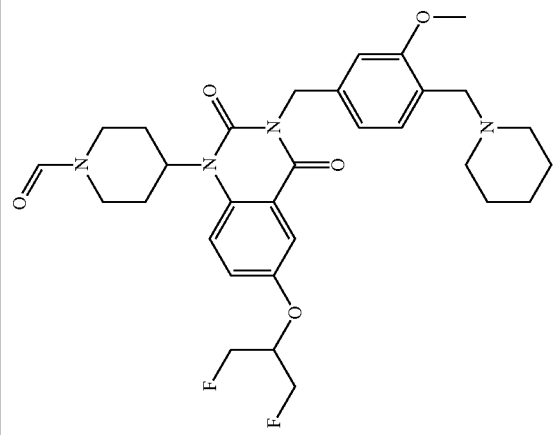 | |
| 300 | 4-[3-{4-[(3,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| | 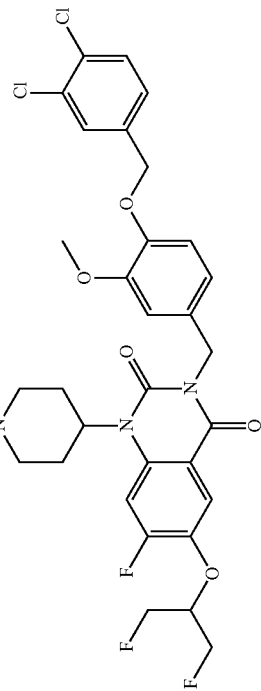 | |

| | | |
|---|---|---|
| 301 | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-ethylacetamide 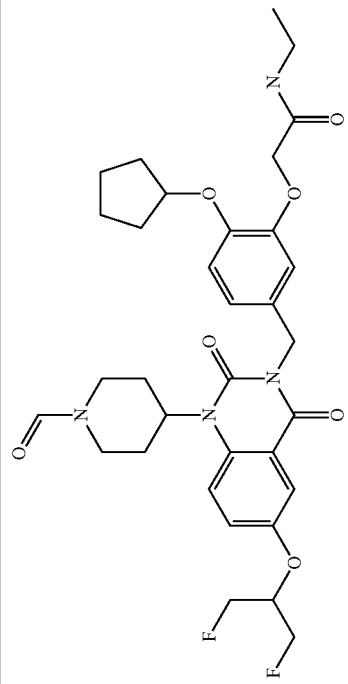 | 643 |
| 302 | (2S)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid Chiral 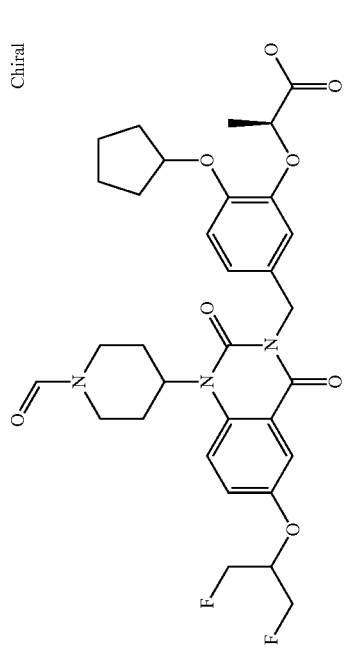 | 630 |
| 303 | 4-[3-(3-fluoro-4,5-dimethoxybenzyl)-6-[2-fluoro-1-(fluoromethyl)ethoxy]-2,4-dioxo-3,4-dihydroquinazolin-1(2H)-yl]piperidine-1-carbaldehyde 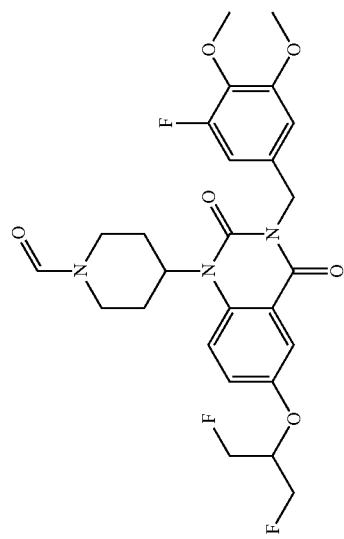 | 536 |

-continued

| 304 | 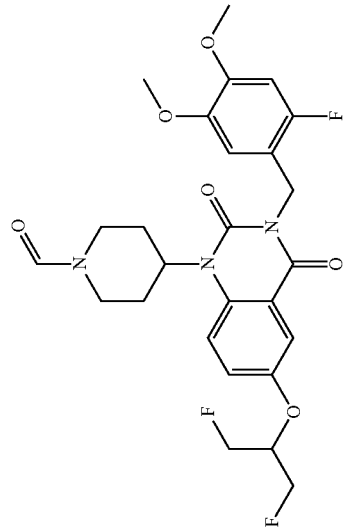 | 4-[3-(2-fluoro-4,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 536 |
| 305 | Chiral 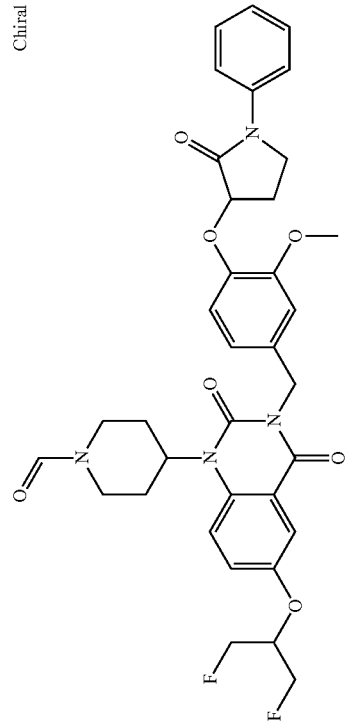 | 4-{6-[2-fluoro-1-(fluoromethyl)ethoxy]-3-(3-methoxy-4-{[(3R)-2-oxo-1-phenylpyrrolidin-3-yl]oxy}benzyl)-2,4-dioxo-3,4-dihydroquinazolin-1(2H)-yl}piperidine-1-carbaldehyde | 663 |
| 306 | 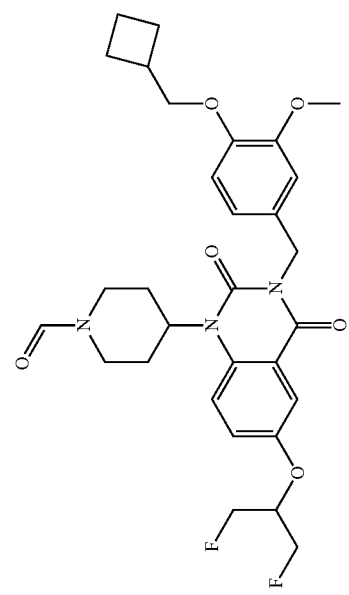 | 4-{3-[4-(cyclobutylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | 572 |

| 307 | 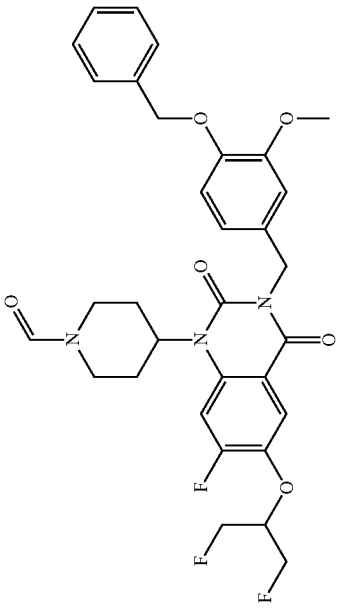 | 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 612 |
| 308 | 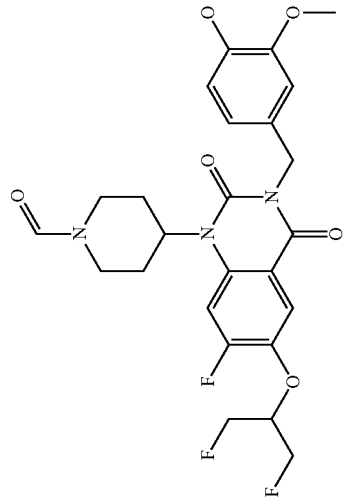 | 4-{7-fluoro-6-[2-fluoro-1-(fluoromethyl)ethoxy]-3-(4-hydroxy-3-methoxybenzyl)-2,4-dioxo-3,4-dihydroquinazolin-1(2H)-yl}piperidine-1-carbaldehyde | 522 |
| 309 | 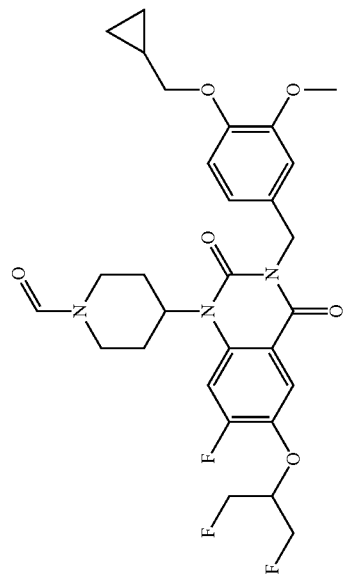 | 4-{3-[4-(cyclopropylmethoxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 576 |

| | | | |
|---|---|---|---|
| 310 | 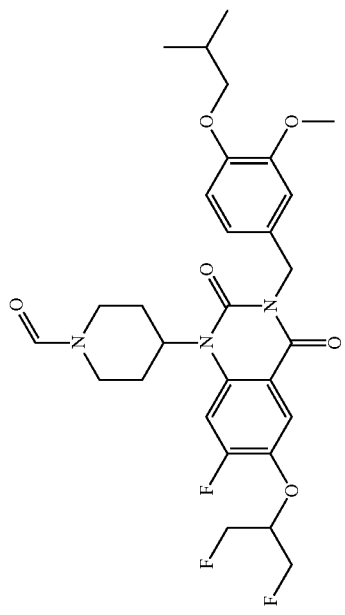 | 4-{7-fluoro-6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde | 578 |
| 311 | 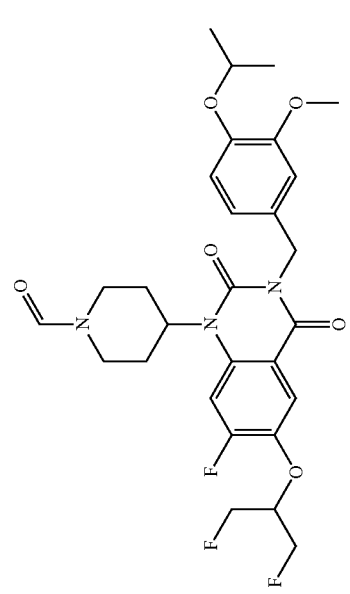 | 4-{7-fluoro-6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde | 564 |
| 312 | 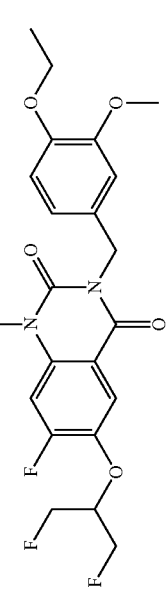 | 4-[3-(4-ethoxy-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde | 550 |

| | | |
|---|---|---|
| 313 | 3-(3,4-dimethoxybenzyl)-6-[2-fluoro-1-(fluoromethyl)ethoxy]-1-(6-oxopiperidin-3-yl)quinazoline-2,4(1H,3H)-dione 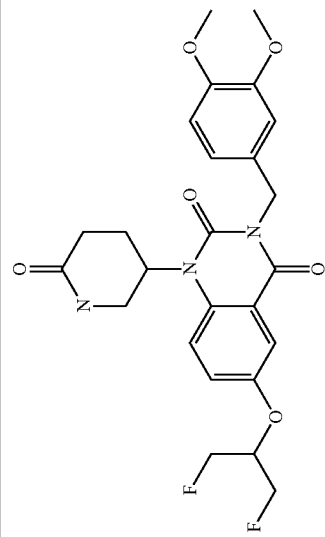 | 504 |
| 314 | 4-{6-[2-fluoro-1-(fluoromethyl)ethoxy]-3-[(5-methoxy-1-methyl-4-oxo-1,4-dihydropyridin-2-yl)methyl]-2,4-dioxo-3,4-dihydroquinazolin-1(2H)-yl}piperidine-1-carbaldehyde 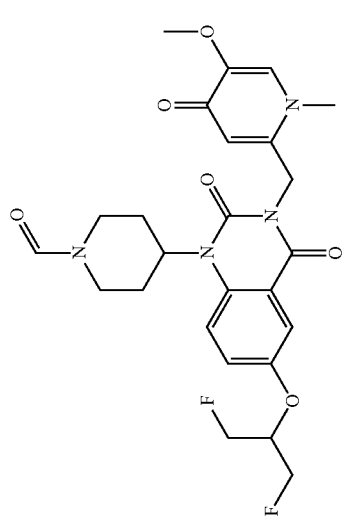 | 519 |
| 315 | 4-{7-fluoro-6-[2-fluoro-1-(fluoromethyl)ethoxy]-3-{[6-(3-methoxyphenyl)pyridin-3-yl]methyl}-2,4-dioxo-3,4-dihydroquinazolin-1(2H)-yl}piperidine-1-carbaldehyde 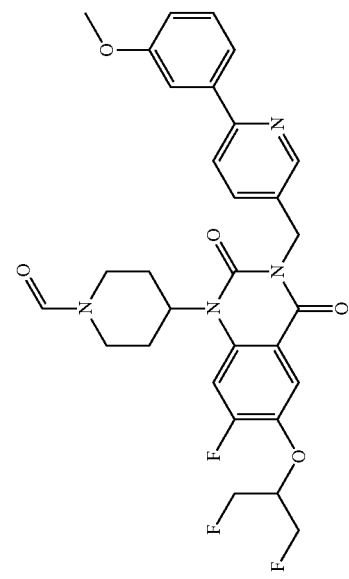 | 583 |

-continued

| | | |
|---|---|---|
| 316 | 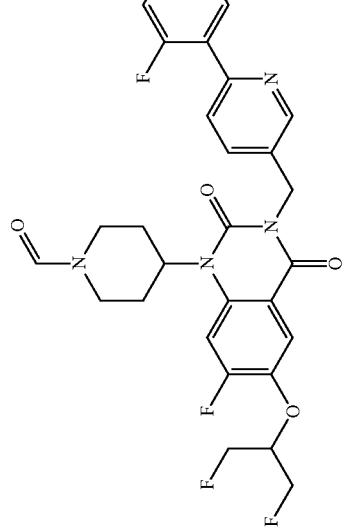 | 4-{7-fluoro-6-[2-fluoro-1-(fluoromethyl)ethoxy]-3-{[6-(2-fluorophenyl)pyridin-3-yl]methyl}-2,4-dioxo-3,4-dihydroquinazolin-1(2H)-yl}piperidine-1-carbaldehyde — 571 |
| 317 | 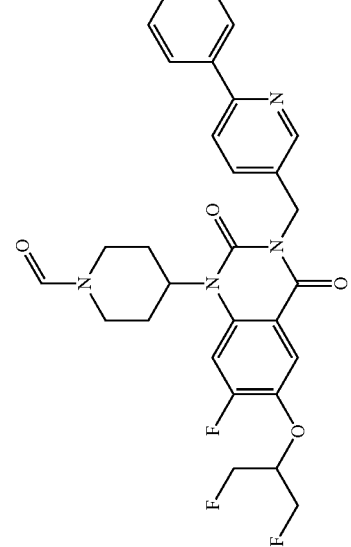 | 4-{7-fluoro-6-[2-fluoro-1-(fluoromethyl)ethoxy]-3-{[6-(4-fluorophenyl)pyridin-3-yl]methyl}-2,4-dioxo-3,4-dihydroquinazolin-1(2H)-yl}piperidine-1-carbaldehyde — 571 |
| 318 | 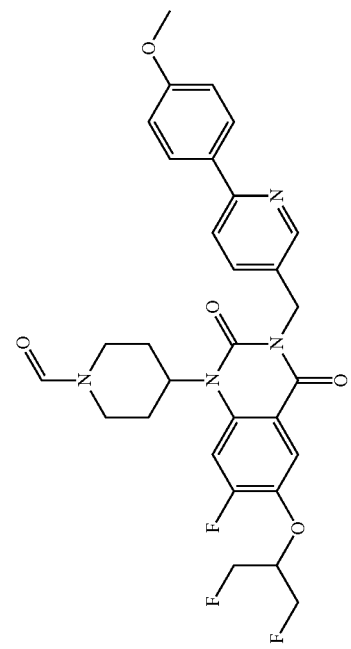 | 4-{7-fluoro-6-[2-fluoro-1-(fluoromethyl)ethoxy]-3-{[6-(4-methoxyphenyl)pyridin-3-yl]methyl}-2,4-dioxo-3,4-dihydroquinazolin-1(2H)-yl}piperidine-1-carbaldehyde — 583 |

| | | |
|---|---|---|
| 319 | 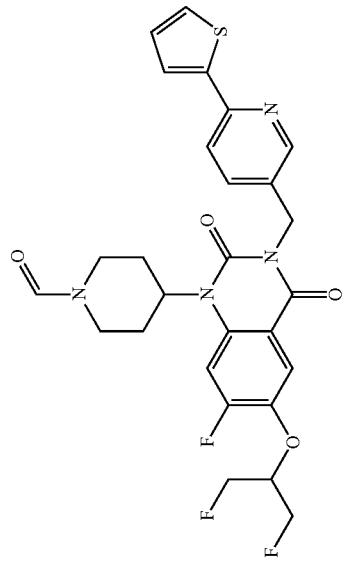 4-{7-fluoro-6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde | 559 |
| 320 | 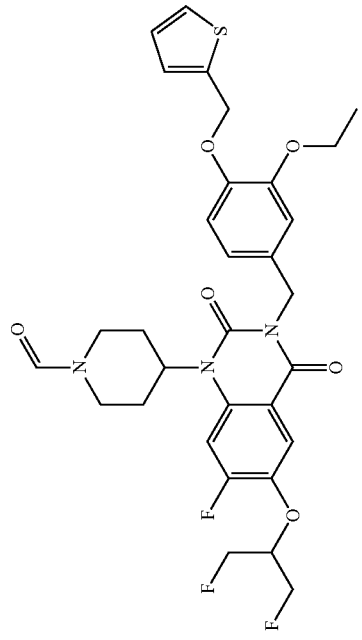 4-{3-[3-ethoxy-4-(thiophen-2-ylmethoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 632 |
| 321 | 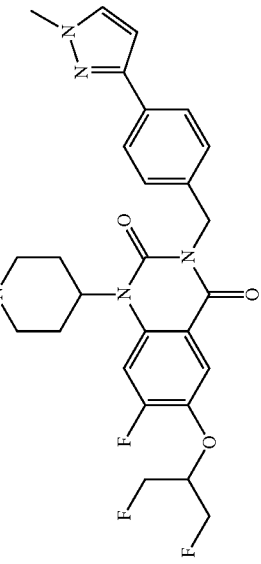 4-{7-fluoro-6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde | 556 |

-continued

| | | |
|---|---|---|
| 322 | 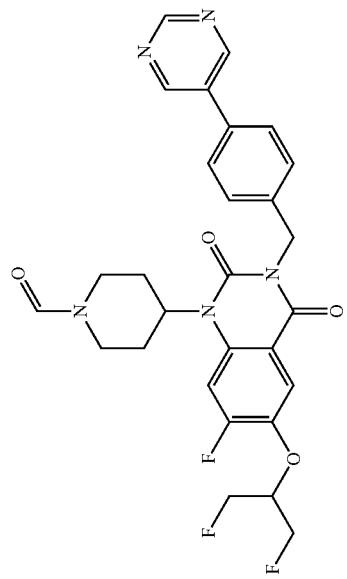 | 4-{7-fluoro-6-[2-fluoro-1-(fluoromethyl)ethoxy]-2,4-dioxo-3-(4-pyrimidin-5-yl)benzyl)-3,4-dihydroquinazolin-1(2H)-yl}piperidine-1-carbaldehyde 554 |
| 323 | 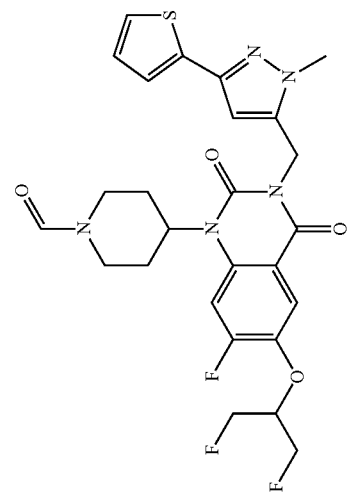 | 4-{7-fluoro-6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde 562 |
| 324 | 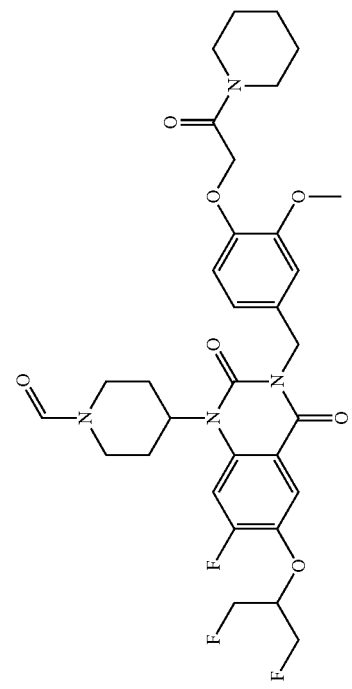 | 4-{7-fluoro-6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde 647 |

-continued

| | | |
|---|---|---|
| 325 | 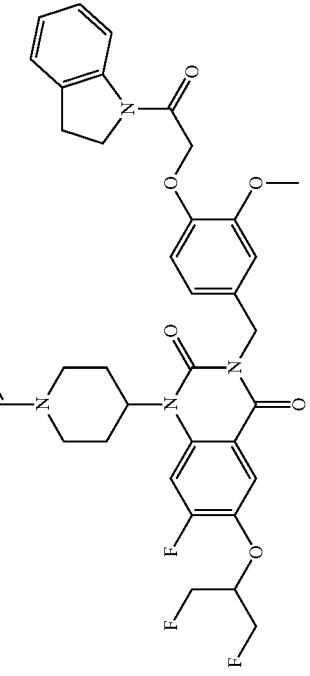 | 4-[3-{4-[2-(2,3-dihydro-1H-indol-1-yl)-2-oxoethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 681 |
| 326 | 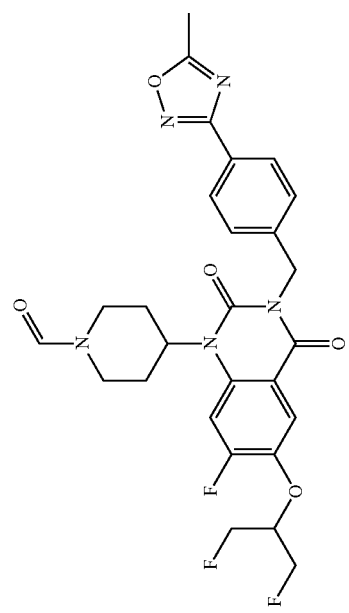 | 4-{7-fluoro-6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde | 558 |
| 327 | 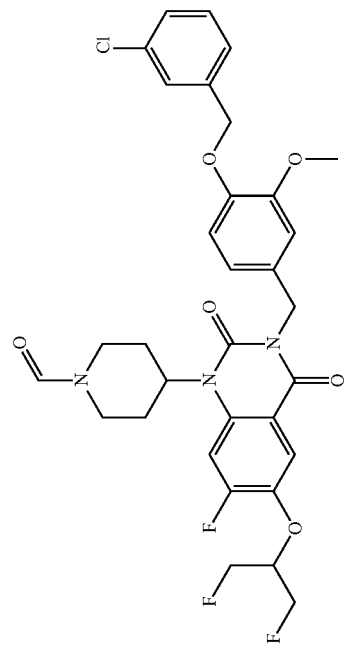 | 4-[3-{4-[(3-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |

| | | |
|---|---|---|
| 328 | 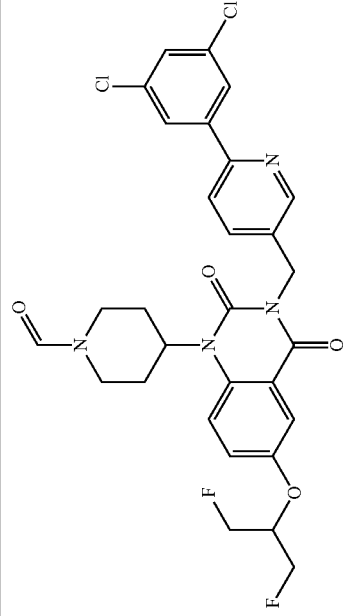 | 4-[3-{[6-(3,5-dichlorophenyl)pyridin-3-yl]methyl}-6-[2-fluoro-1-(fluoromethyl)ethoxy]-2,4-dioxo-3,4-dihydroquinazolin-1(2H)-yl]piperidine-1-carbaldehyde | 603 |
| 329 | 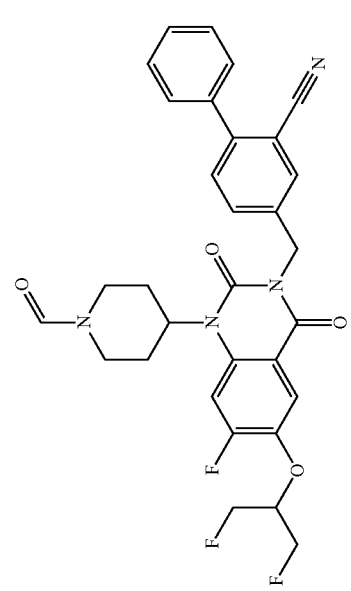 | 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile | 577 |
| 330 | 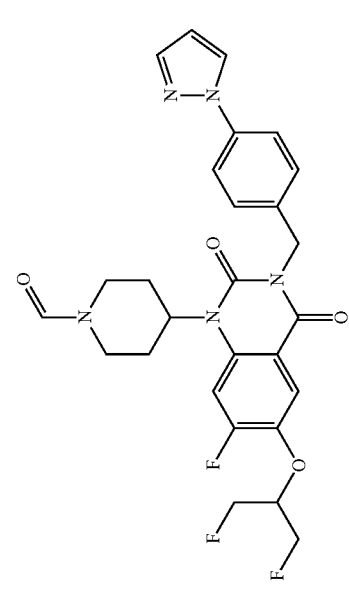 | 4-{7-fluoro-6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde | 542 |

-continued

| | | | |
|---|---|---|---|
| 331 | 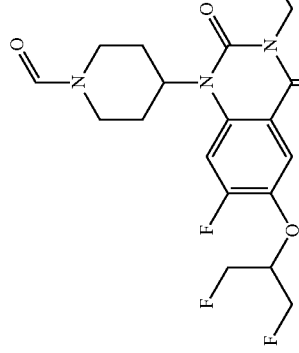 | 4-{7-fluoro-6-[2-fluoro-1-(fluoromethyl)ethoxy]-3-{[6-(3-fluorophenyl)pyridin-3-yl]methyl}-2,4-dioxo-3,4-dihydroquinazolin-1(2H)-yl]piperidine-1-carbaldehyde | 571 |
| 332 | 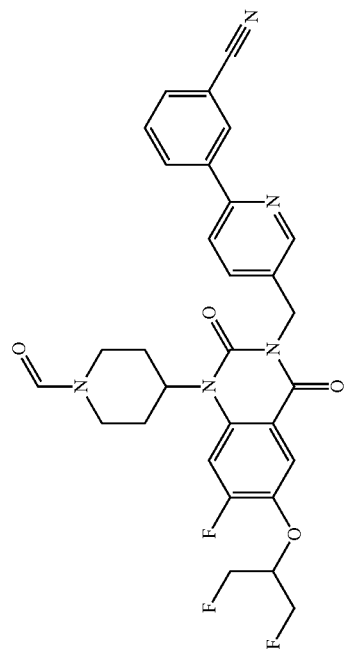 | 3-[5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)pyridin-2-yl]benzonitrile | 578 |
| 333 | 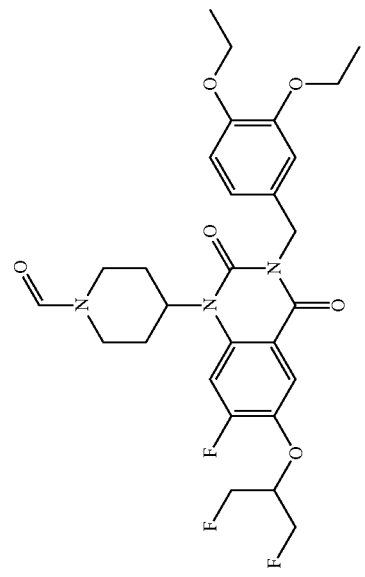 | 4-[3-(3,4-diethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde | 564 |

-continued

| | | |
|---|---|---|
| 334 | 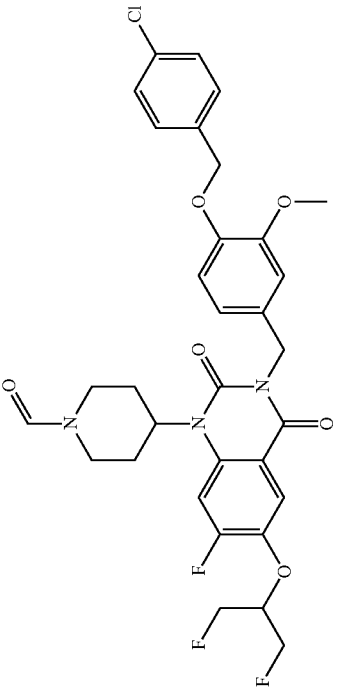 4-[3-{4-[(4-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |
| 335 | 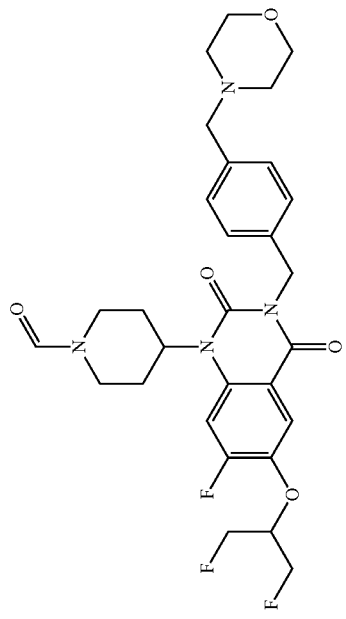 4-{7-fluoro-6-[2-fluoro-1-(fluoromethyl)ethoxy]-3-[4-(morpholin-4-ylmethyl)benzyl]-2,4-dioxo-3,4-dihydroquinazolin-1(2H)-yl}piperidine-1-carbaldehyde | 575 |
| 336 | 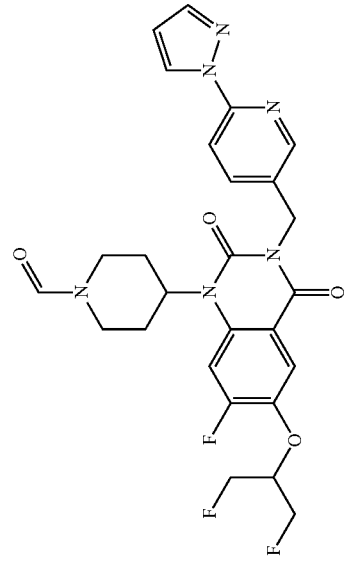 4-{7-fluoro-6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde | 543 |

| | | |
|---|---|---|
| 337 | 4-{7-fluoro-6-[2-fluoro-1-(fluoromethyl)ethoxy]-3-(4-(morpholin-4-yl)benzyl)-2,4-dioxo-3,4-dihydroquinazolin-1(2H)-yl}piperidine-1-carbaldehyde | 561 |
| | 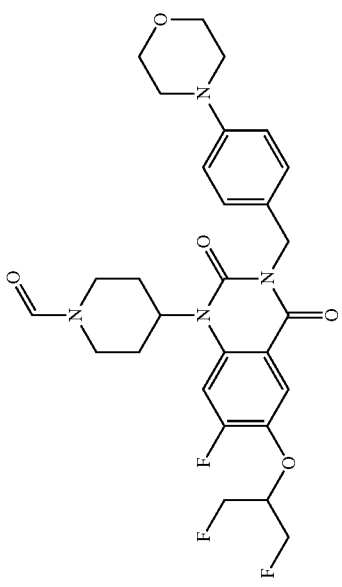 | |
| 338 | 4-{7-fluoro-6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde | 564 |
| | 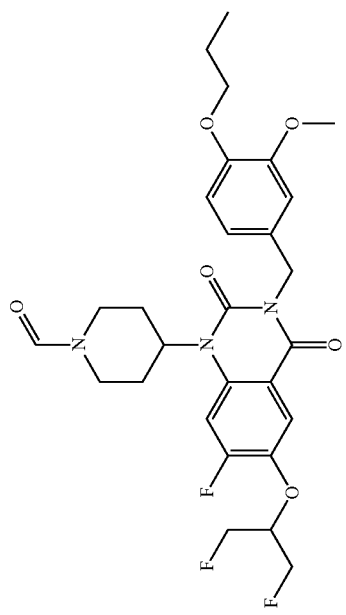 | |
| 339 | 4-{3-[4-(1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 592 |
| | 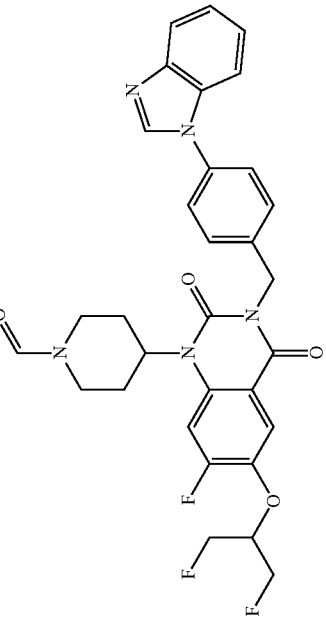 | |

-continued
| | | |
|---|---|---|
| 340 | 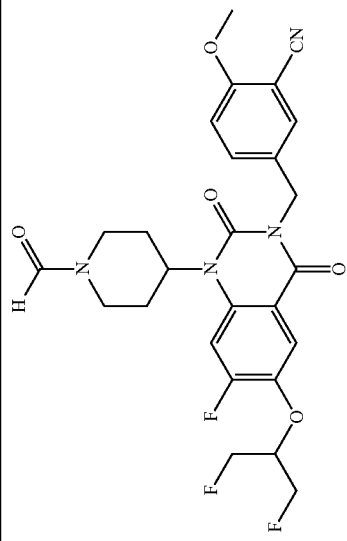 5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxybenzonitrile | 531 |
| 341 | 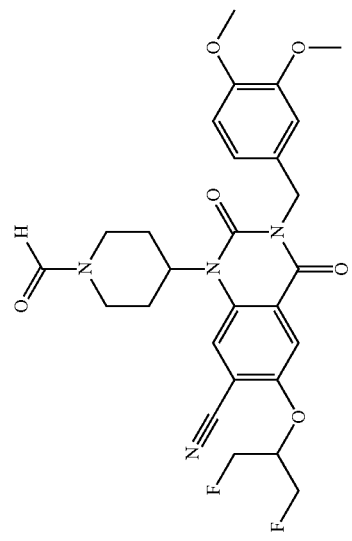 3-(3,4-dimethoxybenzyl)-6-[2-fluoro-1-(fluoromethyl)ethoxy]-1-(1-formylpiperidin-4-yl)-2,4-dioxo-1,2,3,4-tetrahydroquinazoline-7-carbonitrile | 543 |
| 342 | 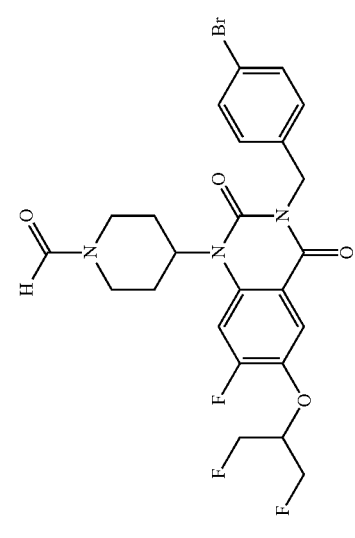 4-[3-(4-bromobenzyl)-7-fluoro-6-[2-fluoro-1-(fluoromethyl)ethoxy]-2,4-dioxo-3,4-dihydroquinazolin-1(2H)-yl]piperidine-1-carbaldehyde | 554 |

| | | |
|---|---|---|
| 343 | 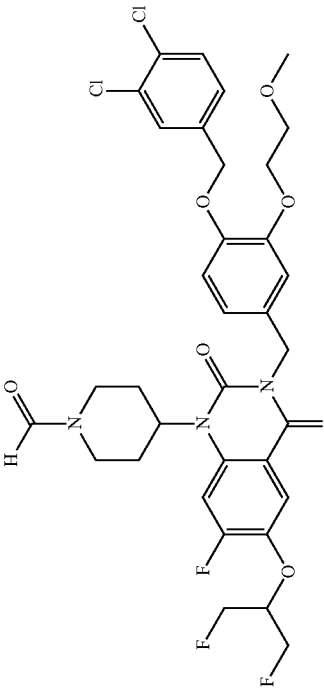 4-[3-{4-[(3,4-dichlorobenzyl)oxy]-3-(2-methoxyethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde | 724 |
| 344 | 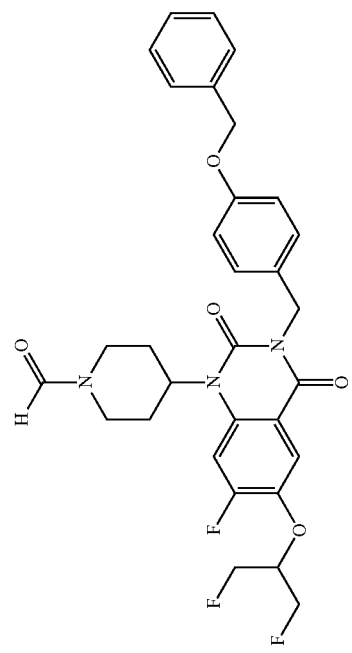 4-{3-[4-(benzyloxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 582 |
| 345 | 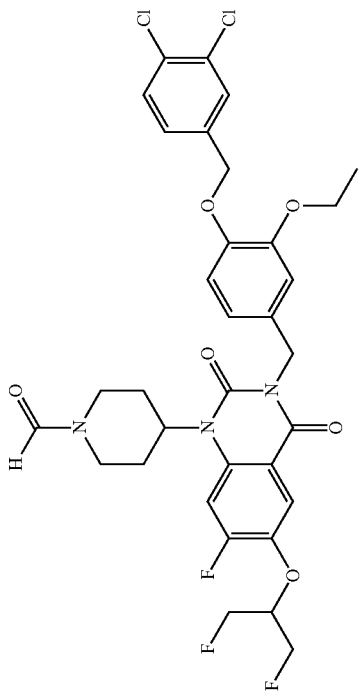 4-[3-{4-[(3,4-dichlorobenzyl)oxy]-3-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 694 |

-continued

| | | |
|---|---|---|
| 346 | 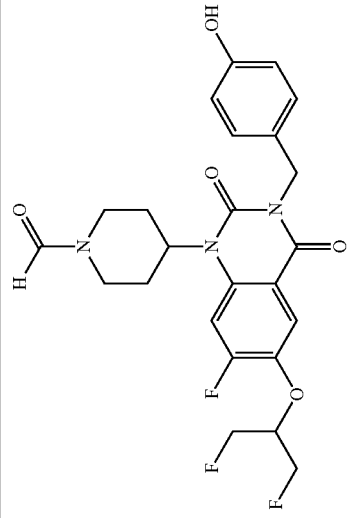 4-{7-fluoro-6-[2-fluoro-1-(fluoromethyl)ethoxy]-3-(4-hydroxybenzyl)-2,4-dioxo-3,4-dihydroquinazolin-1(2H)-yl}piperidine-1-carbaldehyde | 492 |
| 347 | 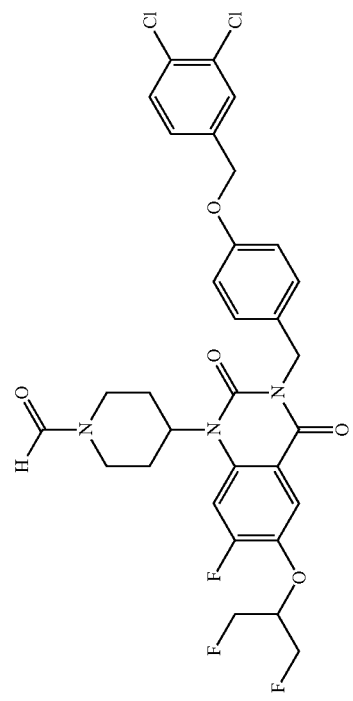 4-[3-{4-[(3,4-dichlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 650 |
| 348 | 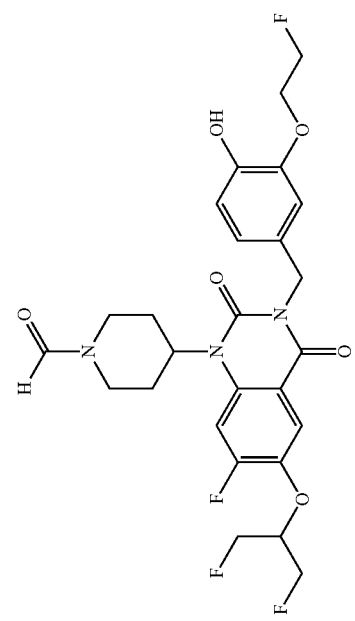 4-{7-fluoro-3-[3-(2-fluoroethoxy)-4-hydroxybenzyl]-6-[2-fluoro-1-(fluoromethyl)ethoxy]-2,4-dioxo-3,4-dihydroquinazolin-1(2H)-yl}piperidine-1-carbaldehyde | 554 |

| 349 | 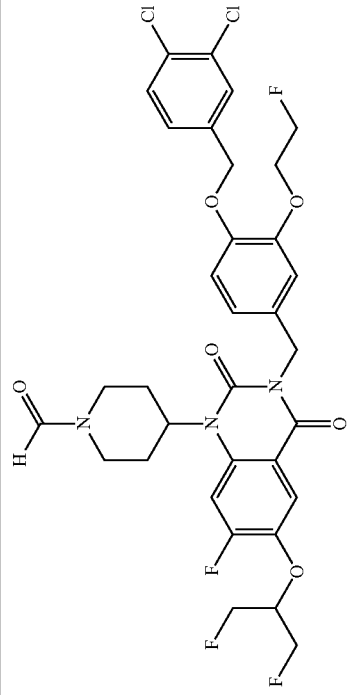 | 4-[3-{4-[(3,4-dichlorobenzyl)oxy]-3-(2-fluoroethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde | 712 |
| 350 | 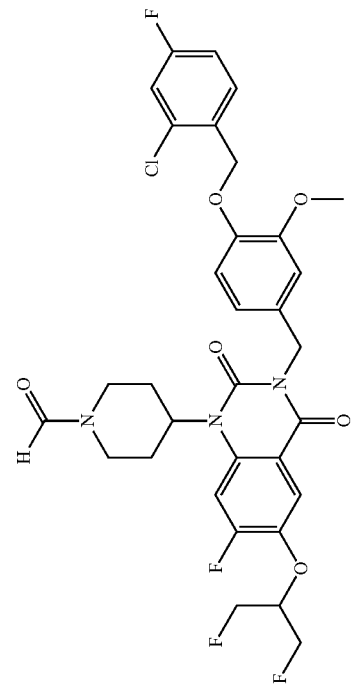 | 4-[3-{4-[(2-chloro-4-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 664 |
| 351 | 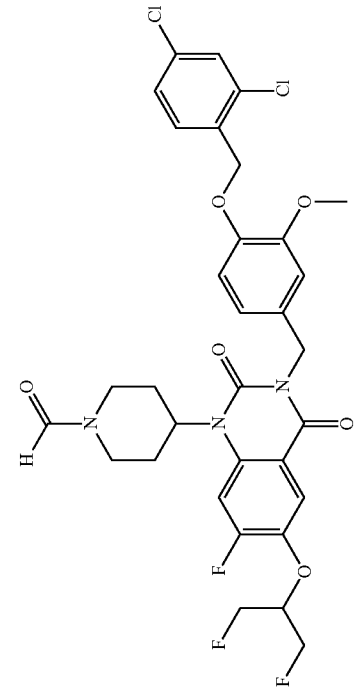 | 4-[3-{4-[(2,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |

| | | |
|---|---|---|
| 352 | 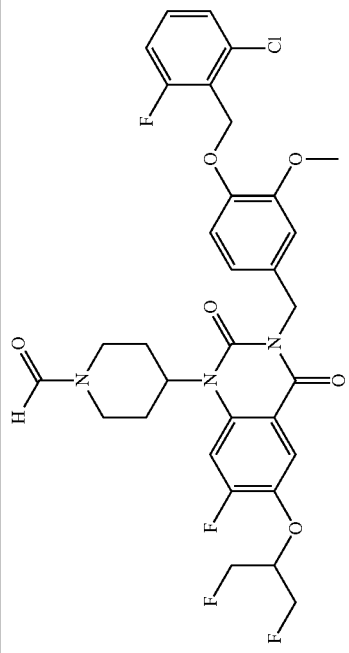 4-[3-{4-[(2-chloro-6-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 664 |
| 353 | 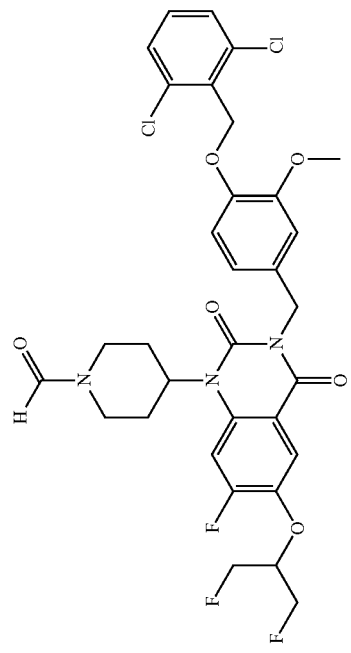 4-[3-{4-[(2,6-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 354 | 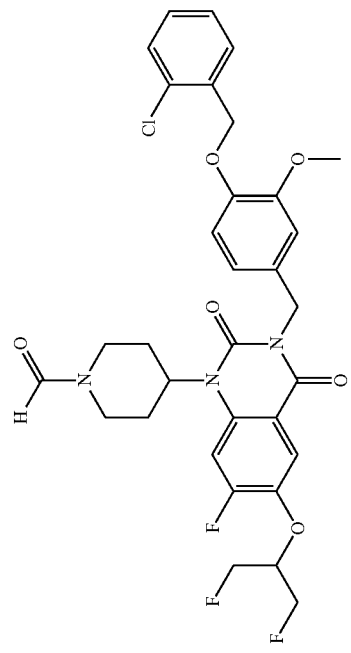 4-[3-{4-[(2-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |

| | | |
|---|---|---|
| 355 | 4-[7-fluoro-3-{4-[(2-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde 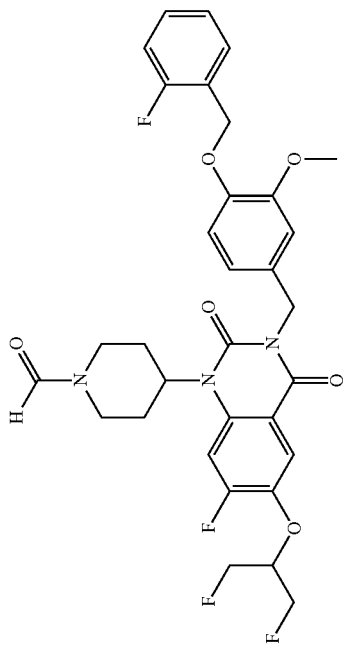 | 630 |
| 356 | 4-[3-{3-[(3,4-dichlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde 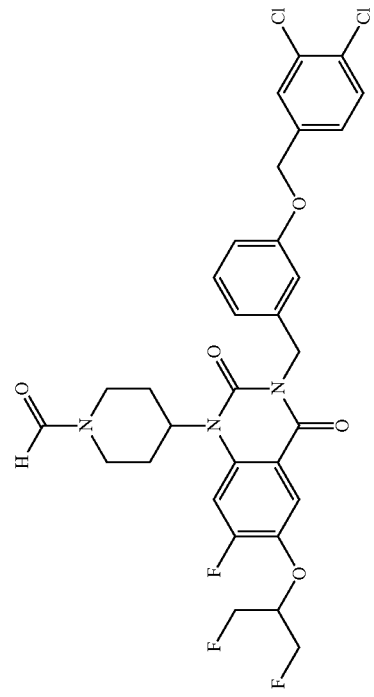 | 650 |
| 357 | 2-[(3,4-dichlorobenzyl)oxy]-5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzonitrile 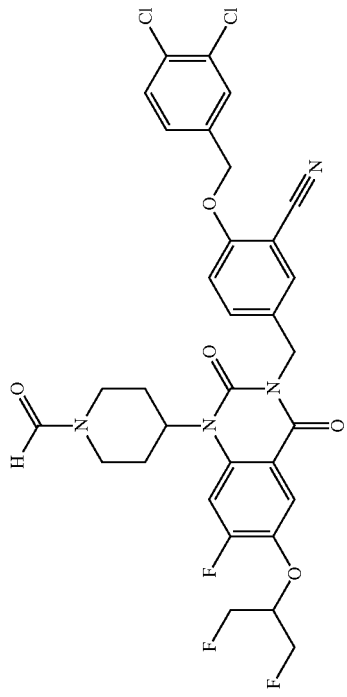 | 675 |

| # | Structure | Name | MS |
|---|---|---|---|
| 358 | 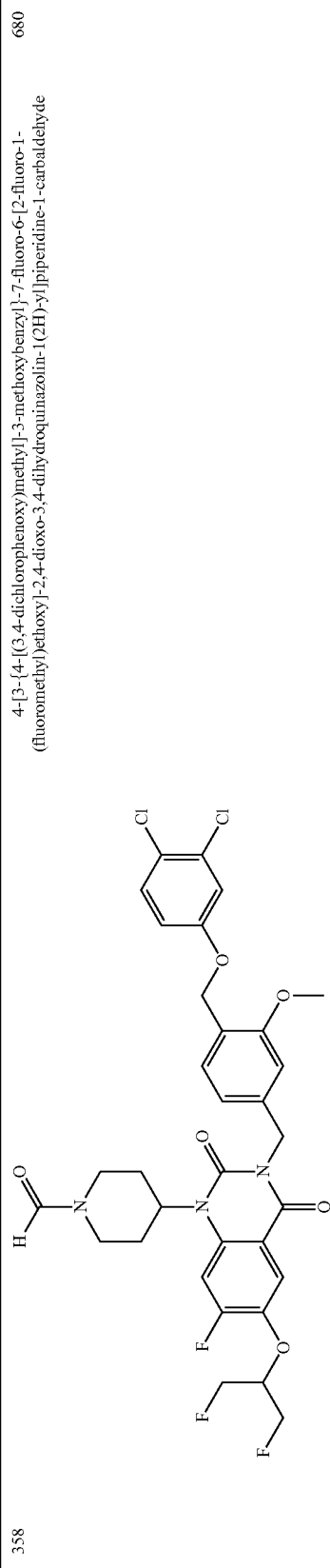 | 4-[3-[4-[(3,4-dichlorophenoxy)methyl]-3-methoxybenzyl]-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 359 | 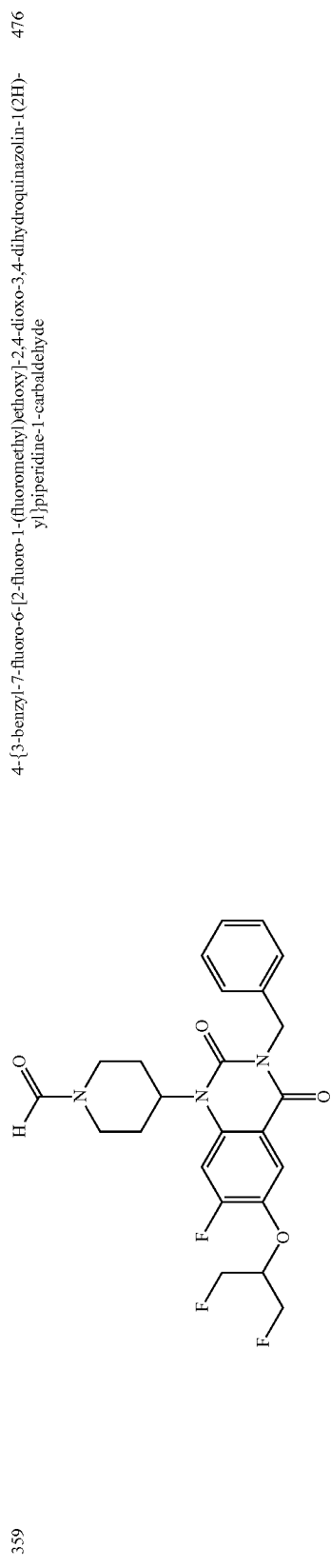 | 4-{3-benzyl-7-fluoro-6-[2-fluoro-1-(fluoromethyl)ethoxy]-2,4-dioxo-3,4-dihydroquinazolin-1(2H)-yl}piperidine-1-carbaldehyde | 476 |
| 360 | 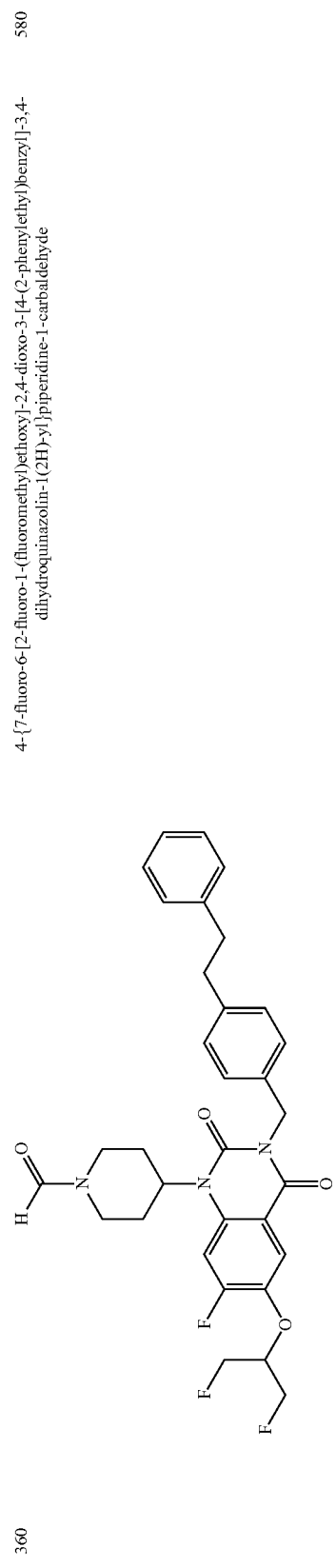 | 4-{7-fluoro-6-[2-fluoro-1-(fluoromethyl)ethoxy]-2,4-dioxo-3-[4-(2-phenylethyl)benzyl]-3,4-dihydroquinazolin-1(2H)-yl}piperidine-1-carbaldehyde | 580 |

| | | |
|---|---|---|
| 361 | 4-[3-(2-chloro-4,5-dimethoxybenzyl)-6-[2-fluoro-1-(fluoromethyl)ethoxy]-2,4-dioxo-3,4-dihydroquinazolin-1(2H)-yl]piperidine-1-carbaldehyde 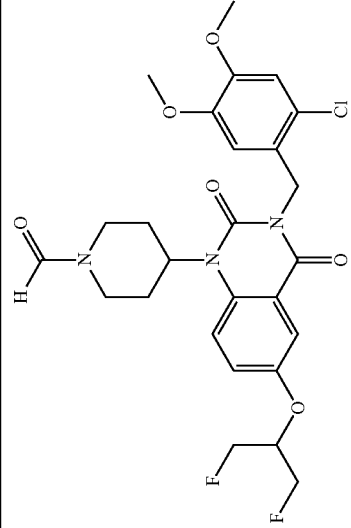 | 552 |
| 362 | 4-[3-[4-[(4,5-dichloro-2-fluorobenzyl)oxy]-3-methoxybenzyl]-7-fluoro-6-[2-fluoro-1-(fluoromethyl)ethoxy]-2,4-dioxo-3,4-dihydroquinazolin-1(2H)-yl]piperidine-1-carbaldehyde 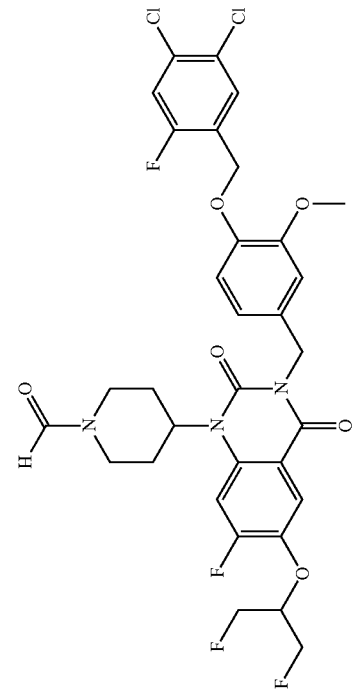 | 698 |
| 363 | 4-[3-{3-[(3,4-dichlorobenzyl)oxy]-4-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde 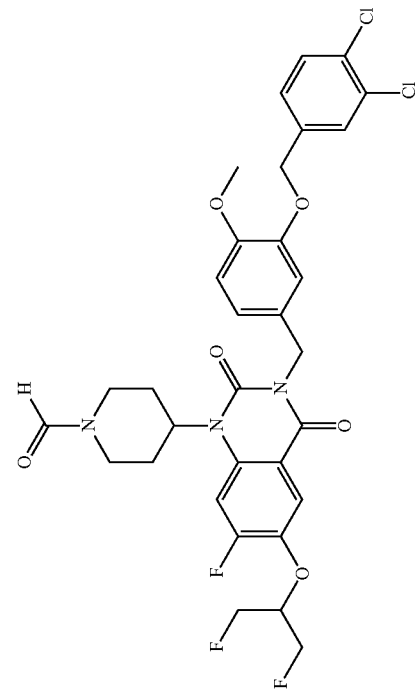 | 680 |

| | | | |
|---|---|---|---|
| 364 | 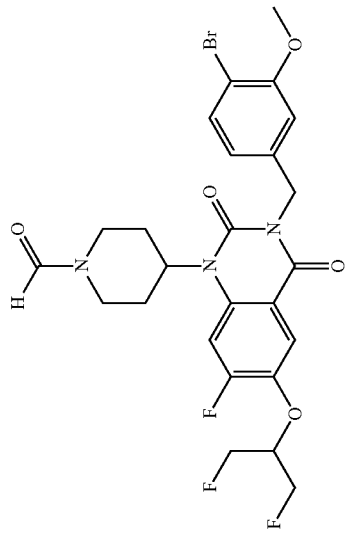 | 4-[3-(4-bromo-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde | 584 |
| 365 | 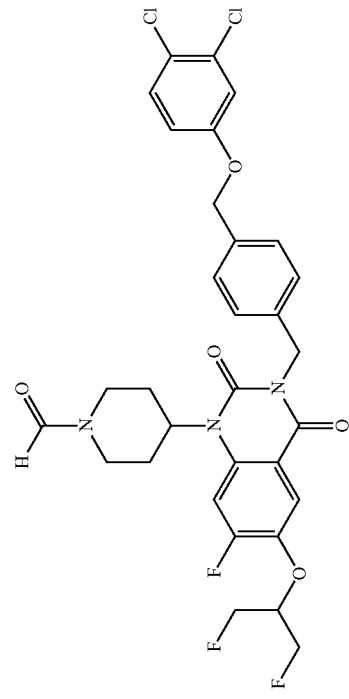 | 4-[3-{4-[(3,4-dichlorophenoxy)methyl]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 650 |
| 366 | 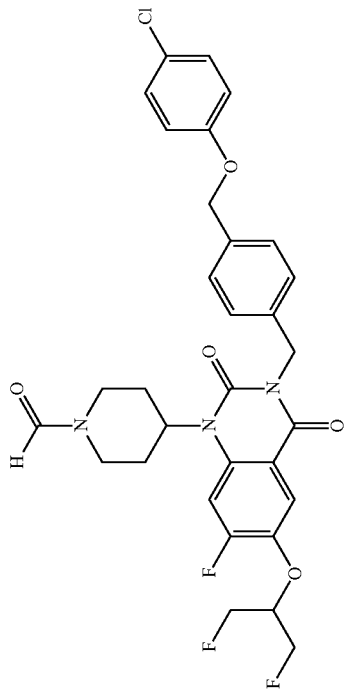 | 4-[3-{4-[(4-chlorophenoxy)methyl]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |

| | | |
|---|---|---|
| 367 | 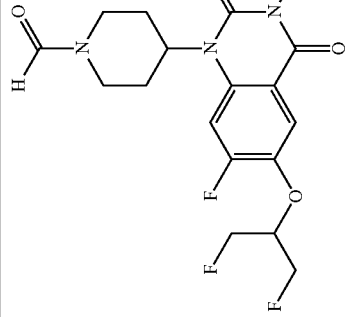 4-{7-fluoro-6-[2-fluoro-1-(fluoromethyl)ethoxy]-3-[3-methoxy-4-(2-phenylethyl)benzyl]-2,4-dioxo-3,4-dihydroquinazolin-1(2H)-yl}piperidine-1-carbaldehyde | 610 |
| 368 | 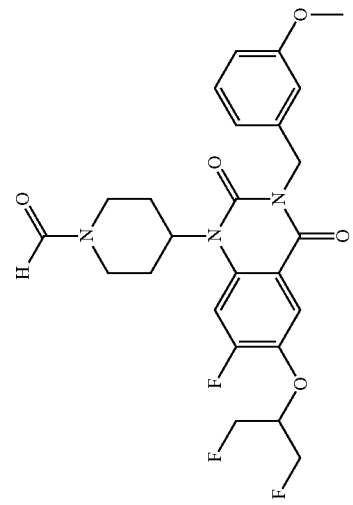 4-{7-fluoro-6-[2-fluoro-1-(fluoromethyl)ethoxy]-3-(3-methoxybenzyl)-2,4-dioxo-3,4-dihydroquinazolin-1(2H)-yl}piperidine-1-carbaldehyde | 506 |
| 369 | 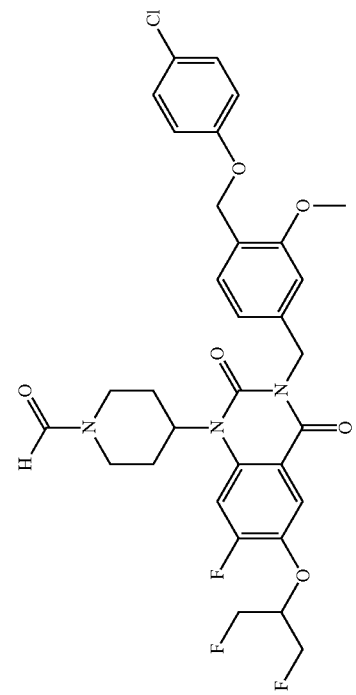 4-[3-{4-[(4-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |

-continued

| | | |
|---|---|---|
| 370 | 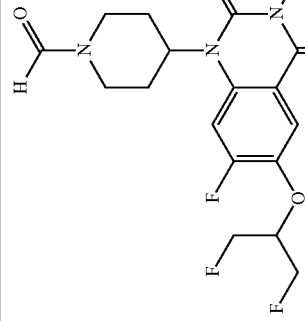 4-{3-[4-(benzyloxy)-3-chlorobenzyl]-7-fluoro-6-[2-fluoro-1-(fluoromethyl)ethoxy]-2,4-dioxo-3,4-dihydroquinazolin-1(2H)-yl}piperidine-1-carbaldehyde | 616 |
| 371 | 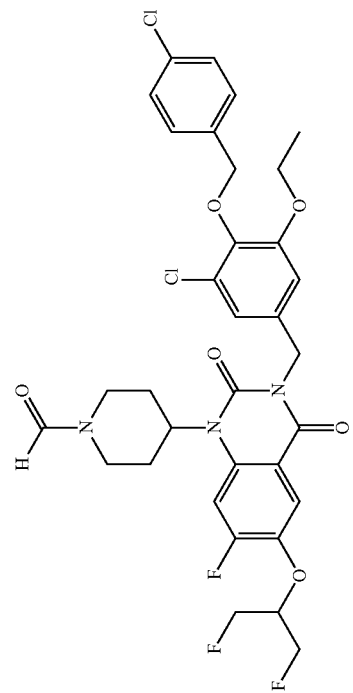 4-[3-{3-chloro-4-[(4-chlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 694 |
| 372 | 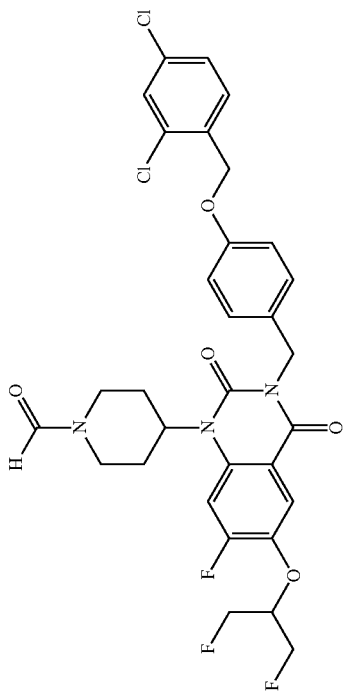 4-[3-{4-[(2,4-dichlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 650 |

| | | |
|---|---|---|
| 373 | 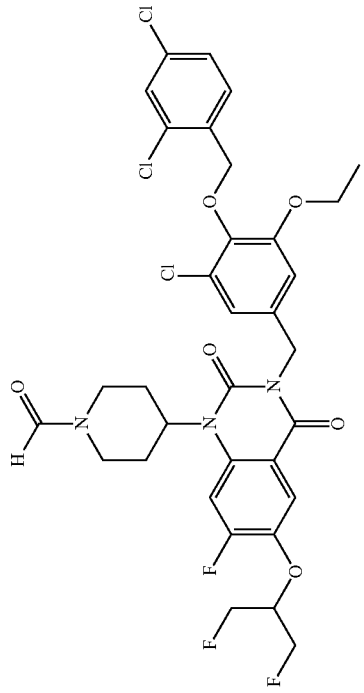 | 4-[3-{3-chloro-4-[(2,4-dichlorobenzyl)oxy]-5-ethoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde 728 |
| 374 | 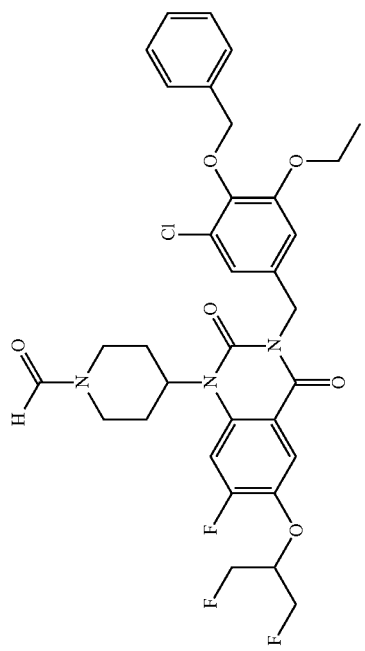 | 4-{3-[4-(benzyloxy)-3-chloro-5-ethoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde 660 |
| 375 | 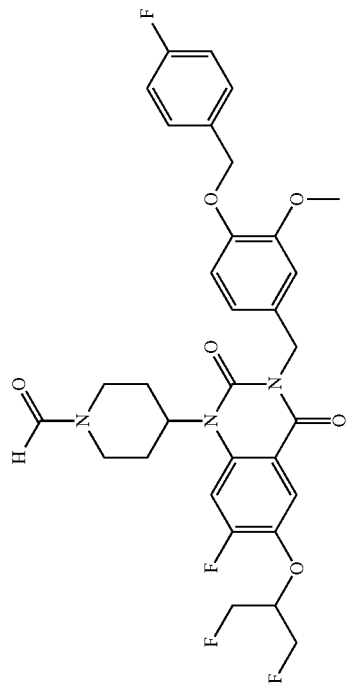 | 4-[7-fluoro-3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde 630 |

| | | |
|---|---|---|
| 376 | 4-[3-{4-[(3,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 377 | 4-[3-(4-{[4-chloro-3-(trifluoromethyl)benzyl]oxy}-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde | 714 |
| 378 | 4-[3-{4-[(3-chlorophenoxy)methyl]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |

-continued

| | | |
|---|---|---|
| 379 | 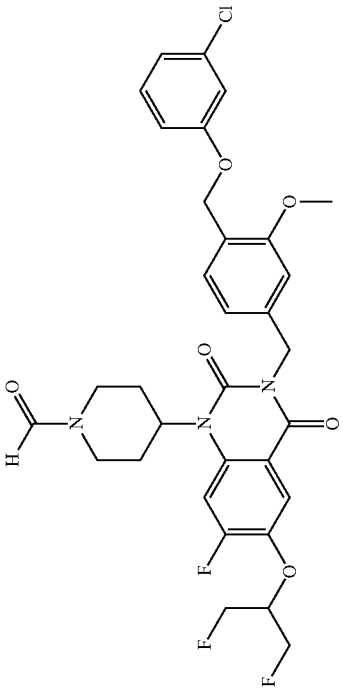 4-[3-[4-[(3-chlorophenoxy)methyl]-3-methoxybenzyl]-7-fluoro-6-[2-fluoro-1-(fluoromethyl)ethoxy]-2,4-dioxo-3,4-dihydroquinazolin-1(2H)-yl]piperidine-1-carbaldehyde | 646 |
| 380 | 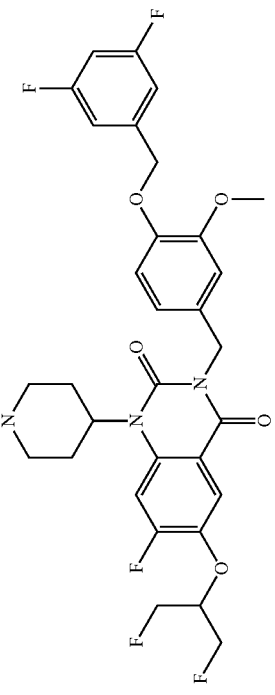 4-[3-{4-[(3,5-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 648 |
| 381 | 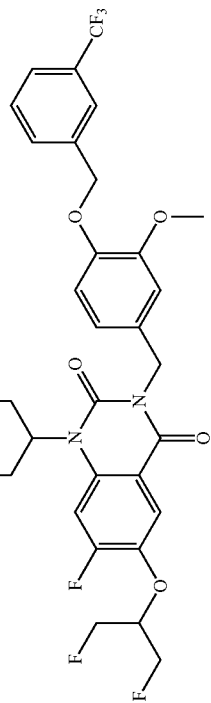 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 680 |

| | | |
|---|---|---|
| 382 | 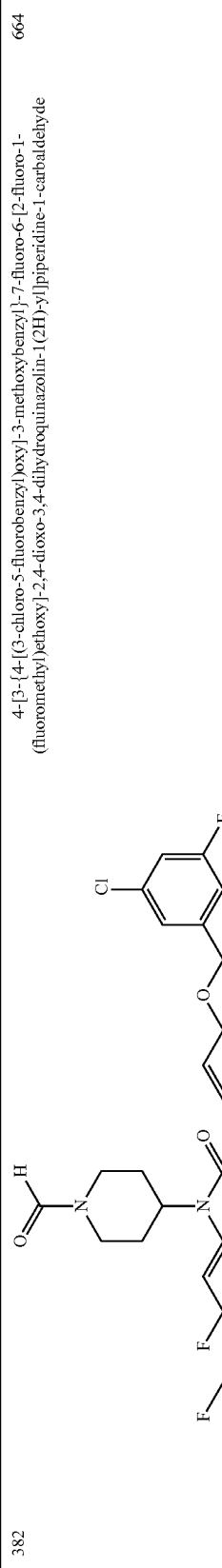 4-[3-{4-[(3-chloro-5-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 664 |
| 383 | 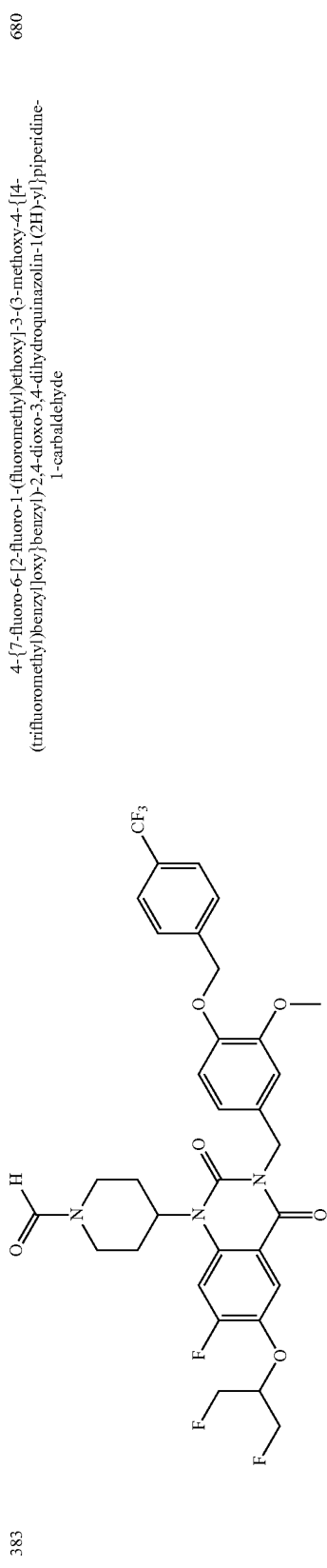 4-{7-fluoro-6-[2-fluoro-1-(fluoromethyl)ethoxy]-3-(3-methoxy-4-{[4-(trifluoromethyl)benzyl]oxy}benzyl)-2,4-dioxo-3,4-dihydroquinazolin-1(2H)-yl}piperidine-1-carbaldehyde | 680 |
| 384 | 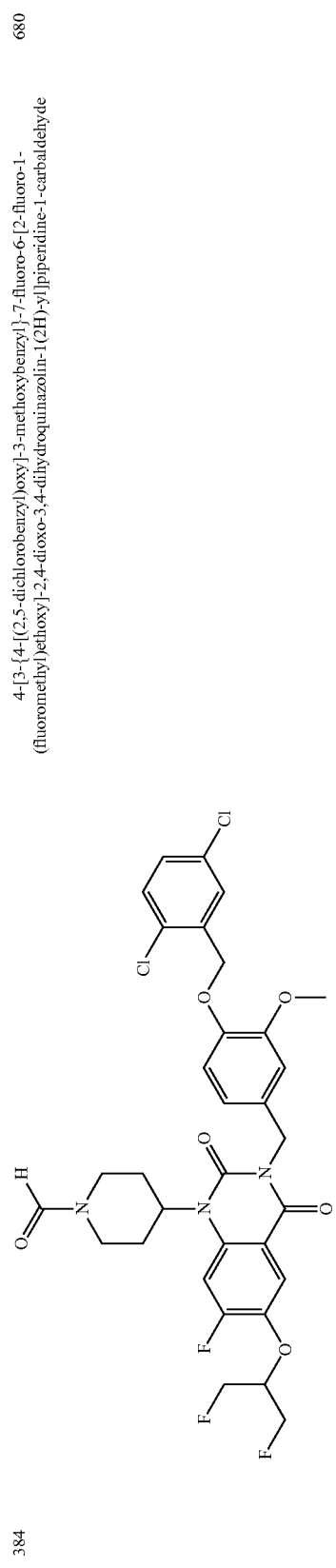 4-[3-{4-[(2,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |

| | | |
|---|---|---|
| 385 | 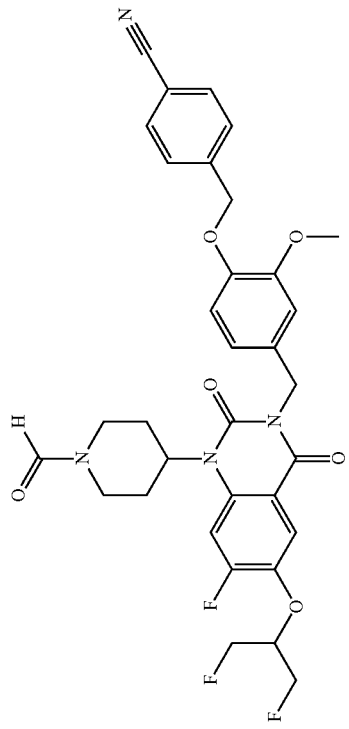 | 4-[[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl]benzonitrile 637 |
| 386 | 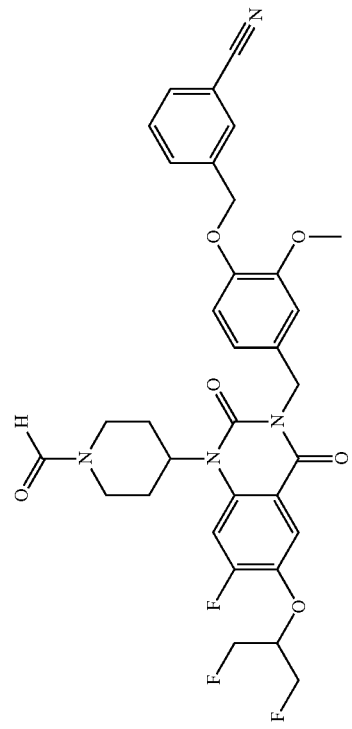 | 3-[[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl]benzonitrile 637 |
| 387 | 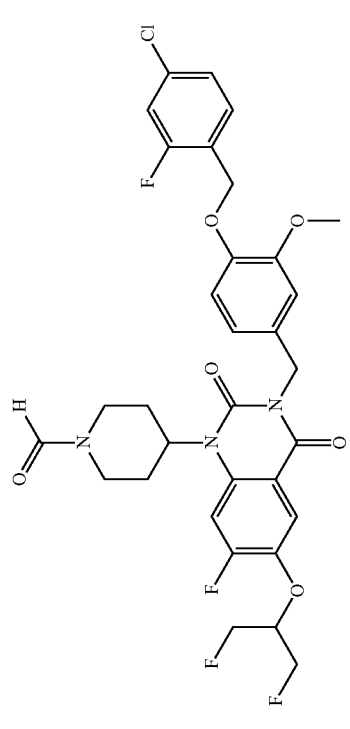 | 4-[3-{4-[(4-chloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde 664 |

| | | |
|---|---|---|
| 388 | [structure with 3,4-dichlorophenyl group] | 4-[3-{4-[1-(3,4-dichlorophenyl)ethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 694 |
| 389 | [structure with OCF₃ group] | 4-{7-fluoro-6-[2-fluoro-1-(fluoromethyl)ethoxy]-3-{4-[(3-hydroxybenzyl)oxy]-3-methoxybenzyl}-2,4-dioxo-3,4-dihydroquinazolin-1(2H)-yl}piperidine-1-carbaldehyde | 696 |
| 390 | [structure with 3-fluorobenzyl group] | 4-[7-fluoro-3-{4-[(3-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 630 |

| | | |
|---|---|---|
| 391 | 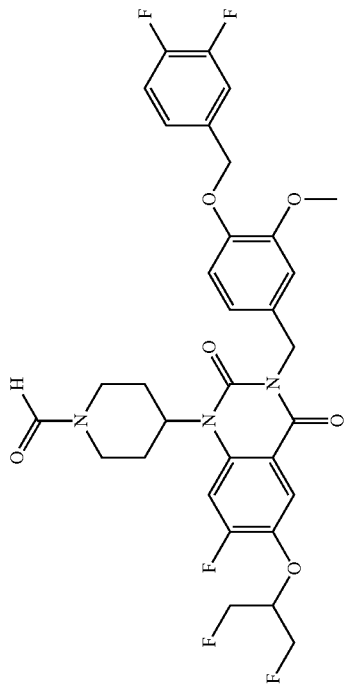 | 648 4-[3-{4-[(3,4-difluorobenzyl)oxy]-3-methoxybenzyl}-7-fluoro-6-[2-fluoro-1-fluoromethyl)ethoxy]-2,4-dioxo-3,4-dihydroquinazolin-1(2H)-yl]piperidine-1-carbaldehyde |
| 392 | 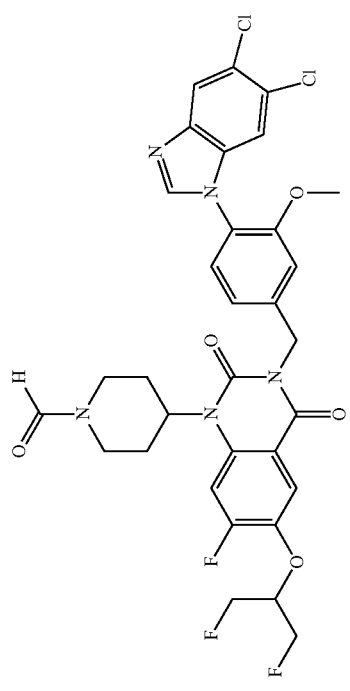 | 660 4-{3-[4-(5,6-dichloro-1H-benzimidazol-1-yl)-3-methoxybenzyl]-7-fluoro-6-[2-fluoro-1-(fluoromethyl)ethoxy]-2,4-dioxo-3,4-dihydroquinazolin-1(2H)-yl]piperidine-1-carbaldehyde |
| 393 | 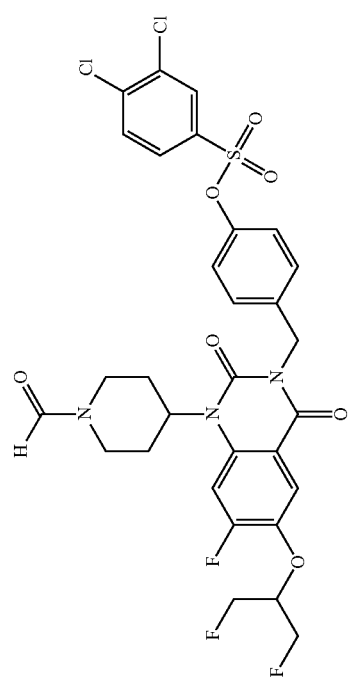 | 700 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)phenyl 3,4-dichlorobenzenesulphonate |

| | | | |
|---|---|---|---|
| 394 | 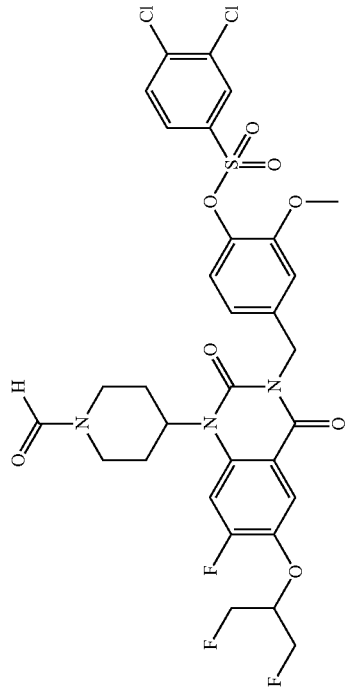 | 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 3,4-dichlorobenzenesulphonate | 730 |
| 395 | 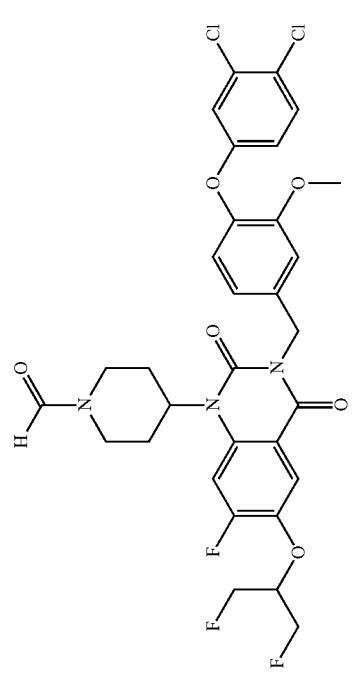 | 4-{3-[4-(3,4-dichlorophenoxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 666 |
| 396 | 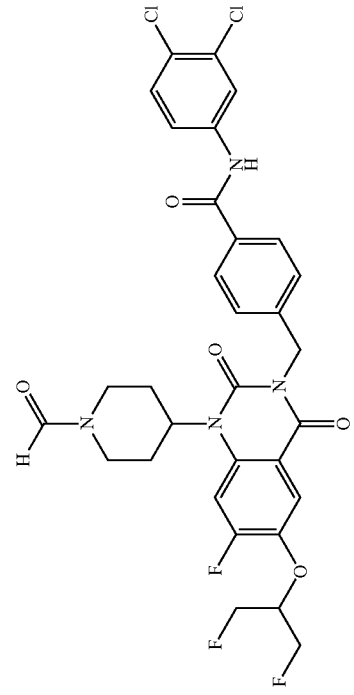 | N-(3,4-dichlorophenyl)-4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzamide | 645 |

-continued

| | | |
|---|---|---|
| 397 | 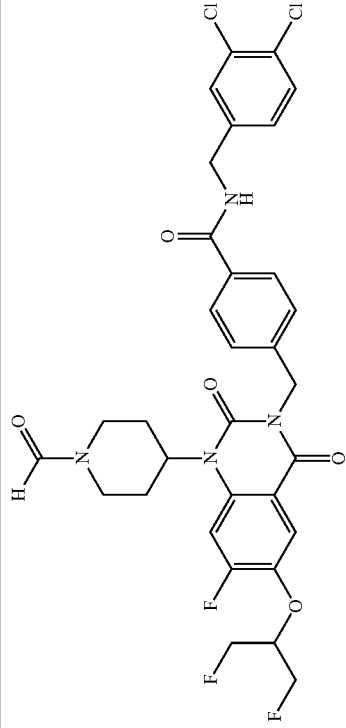 N-(3,4-dichlorobenzyl)-4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzamide | 659 |
| 398 | 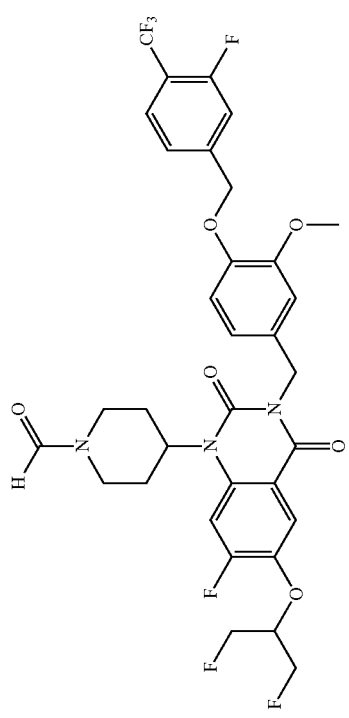 4-{7-fluoro-6-[2-fluoro-1-(fluoromethyl)ethoxy]-3-(4-{[3-fluoro-4-(trifluoromethyl)benzyl]oxy}-3-methoxybenzyl)-2,4-dioxo-3,4-dihydroquinazolin-1(2H)-yl}piperidine-1-carbaldehyde | 698 |
| 399 | 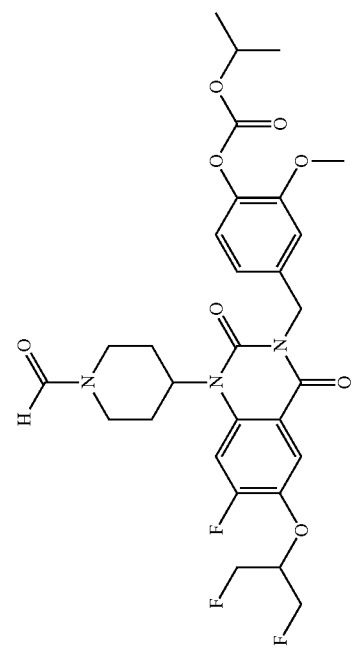 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 1-methylethyl carbonate | 608 |

| | | | |
|---|---|---|---|
| 400 | 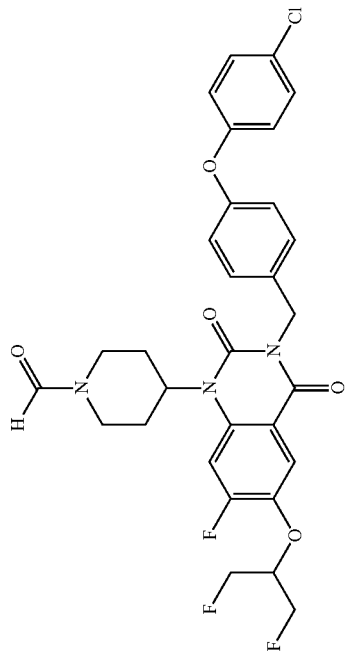 | 4-{3-[4-(4-chlorophenoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 602 |
| 401 | 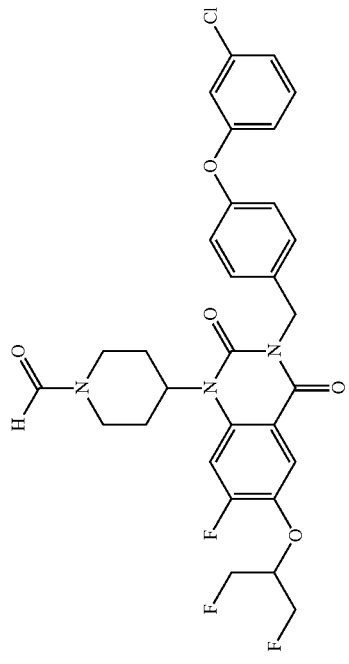 | 4-{3-[4-(3-chlorophenoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 602 |
| 402 | 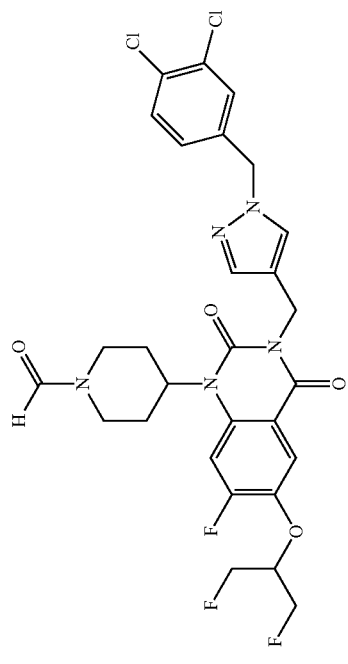 | 4-[3-{[1-(3,4-dichlorobenzyl)-1H-pyrazol-4-yl]methyl}-7-fluoro-6-[2-fluoro-1-(fluoromethyl)ethoxy]-2,4-dioxo-3,4-dihydroquinazolin-1(2H)-yl]piperidine-1-carbaldehyde | 624 |

| | | |
|---|---|---|
| 403 | 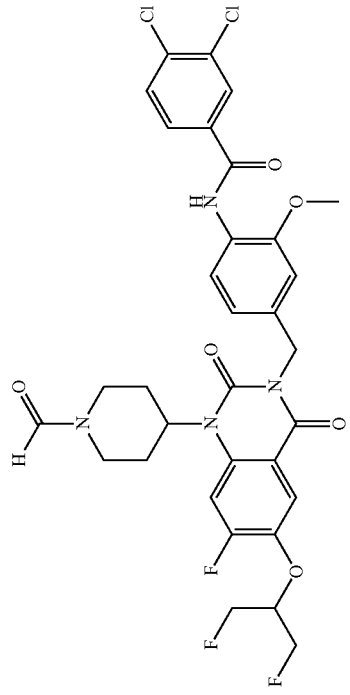 3,4-dichloro-N-[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl]benzamide | 693 |
| 404 | 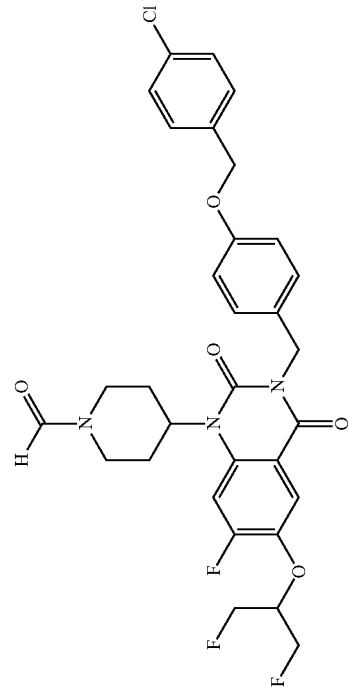 4-[3-{4-[(4-chlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |
| 405 | 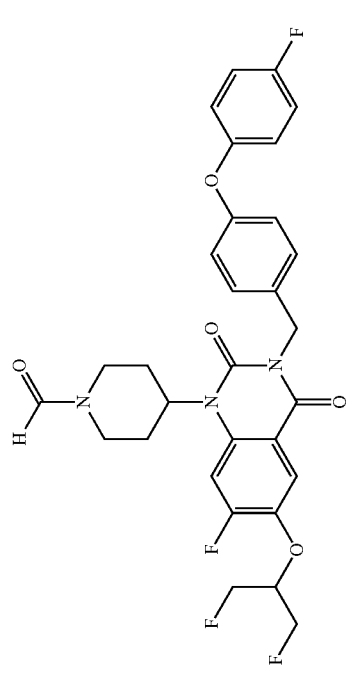 4-{7-fluoro-6-[2-fluoro-1-(fluoromethyl)ethoxy]-3-[4-(4-fluorophenoxy)benzyl]-2,4-dioxo-3,4-dihydroquinazolin-1(2H)-yl}piperidine-1-carbaldehyde | 586 |

| | | |
|---|---|---|
| 406 | 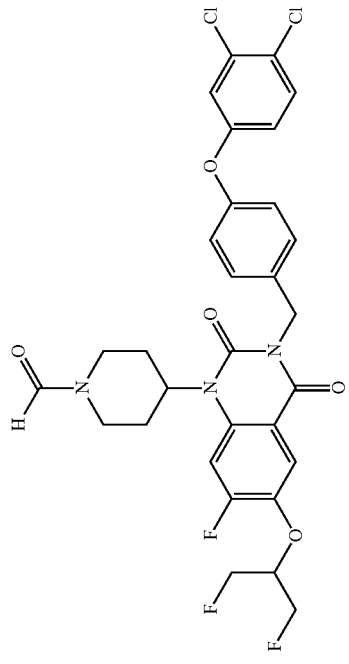 4-[3-[4-(3,4-dichlorophenoxy)benzyl]-7-fluoro-6-[2-fluoro-1-(fluoromethyl)ethoxy]-2,4-dioxo-3,4-dihydroquinazolin-1(2H)-yl]piperidine-1-carbaldehyde | 636 |
| 407 | 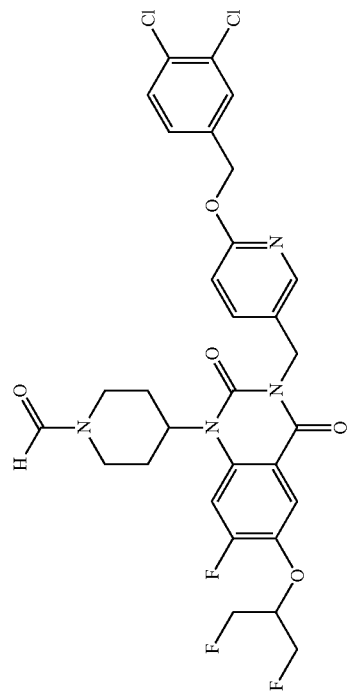 4-[3-({6-[(3,4-dichlorobenzyl)oxy]pyridin-3-yl}methyl)-7-fluoro-6-[2-fluoro-1-(fluoromethyl)ethoxy]-2,4-dioxo-3,4-dihydroquinazolin-1(2H)-yl]piperidine-1-carbaldehyde | 651 |
| 408 | 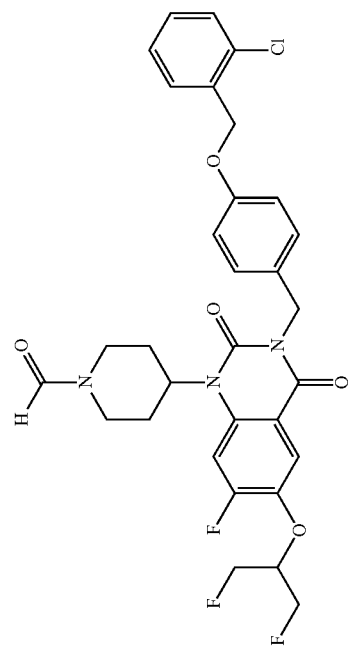 4-[3-{4-[(2-chlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |

-continued

| | | |
|---|---|---|
| 409 | 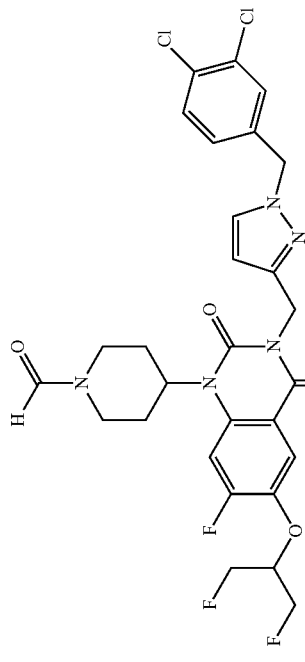 | 4-[3-{(1-(3,4-dichlorobenzyl)-1H-pyrazol-3-yl]methyl}-7-fluoro-6-[2-fluoro-1-(fluoromethyl)ethoxy]-2,4-dioxo-3,4-dihydroquinazolin-1(2H)-yl]piperidine-1-carbaldehyde | 624 |
| 410 | 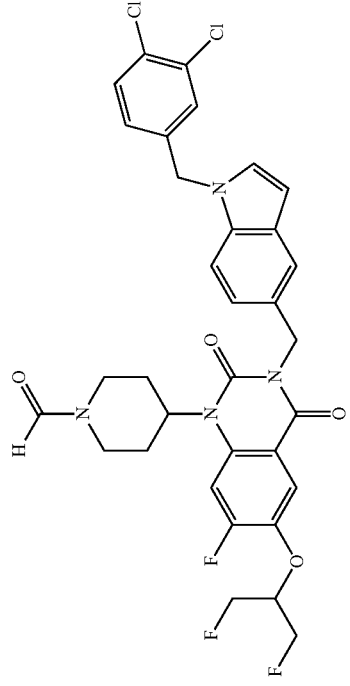 | 4-[3-{[1-(3,4-dichlorobenzyl)-1H-indol-5-yl]methyl}-7-fluoro-6-[2-fluoro-1-(fluoromethyl)ethoxy]-2,4-dioxo-3,4-dihydroquinazolin-1(2H)-yl]piperidine-1-carbaldehyde | 673 |
| 411 | 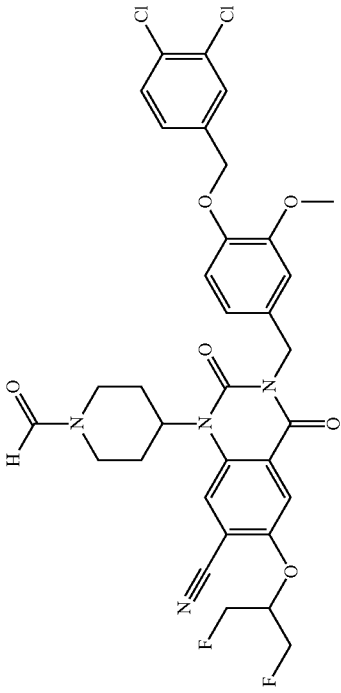 | 3-{4-[(3,4-dichlorobenzyl)oxy]-3-methoxybenzyl}-6-[2-fluoro-1-(fluoromethyl)ethoxy]-1-(1-formylpiperidin-4-yl)-2,4-dioxo-1,2,3,4-tetrahydroquinazoline-7-carbonitrile | 687 |

| | | |
|---|---|---|
| 412 | 4-{3-[4-(5-chloro-6-fluoro-1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde 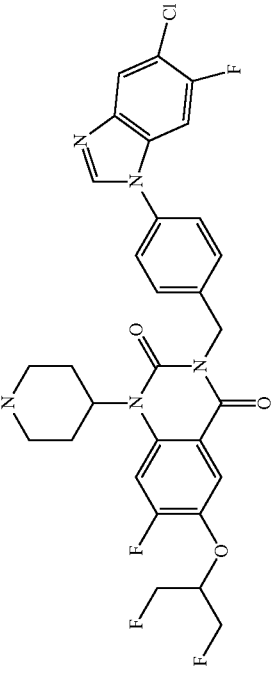 | 644 |
| 413 | 4-{3-[4-(5-chloro-1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde 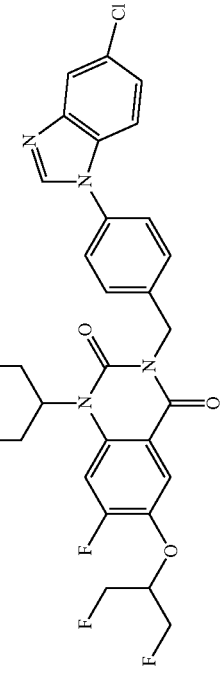 | 626 |
| 414 | 4-[3-{4-[(4-chloro-2-methoxybenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde 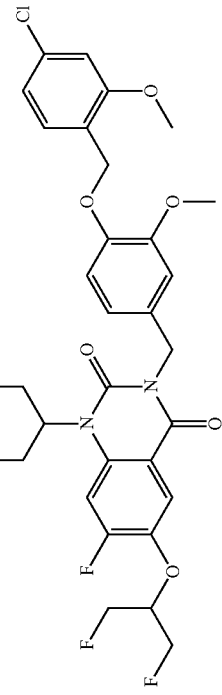 | 676 |

| | | |
|---|---|---|
| 415 | 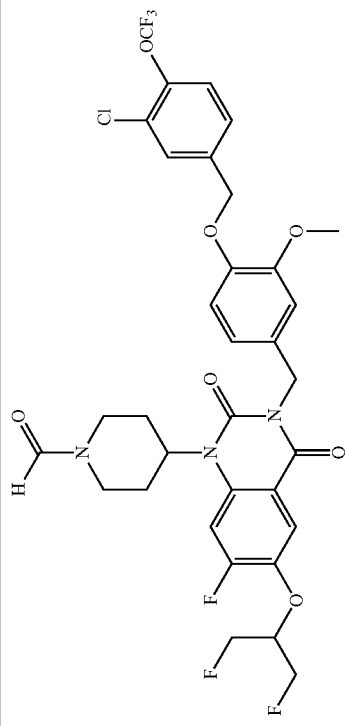 4-[3-{4-[(3-chloro-4-hydroxybenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 730 |

The compounds of the invention form the subject of pharmacological trials which have shown their advantage as therapeutically active substances.

1) Measurement of the Inhibitory Activity of the Compounds According to the Invention with Regard to PDE7

The ability of the compounds of formula (I) to inhibit PDE7 is measured using an enzymatic assay based on the separation of radioactive cAMP (substrate of PDE7) from the radioactive 5'-AMP (product of the enzymatic reaction) by thin layer chromatography on polyethyleneimine (PEI) cellulose, after halting the enzymatic reaction. The 5'-AMP is extracted quantitatively from the PEI cellulose and its radioactivity is measured using a liquid scintillation counter.

The inhibitory activity of the compounds of formula (I) with regard to PDE7 is represented by the inhibition constant $IC_{50}$, defined as the concentration of the compound (inhibitor) tested in the assay which makes it possible to reduce the enzymatic activity of PDE7 by 50%. The lower the $IC_{50}$ values, the greater the inhibitory power of the compounds.

Materials

The [$^3$H]-cAMP (NET 275; 25 to 40 Ci/mmol) was purchased from Perkin-Elmer (NEN Life Sciences, Boston, United States), the rolipram was purchased from Sigma (St Louis, Mo., United States) and the sheets of polyethyleneimine cellulose F made of plastic for thin layer chromatography were purchased from Merck (Darmstadt, Germany). All the other products used are of commercial origin.

Enzyme

Human PDE7 was partially purified from the HUT-78 cell line by following a method analogous to that described by Bloom and Beavo (Proc. Natl. Acad. Sci. USA, (1996) 93, 14188-14192). The enzyme preparation obtained is stored at −80° C. in a buffer comprising 20 mM of Tris-HCl (pH 7.0), 5 mM of $MgCl_2$, 4 mM of EDTA, 1 mM of dithiothreitol and 20% of glycerol. As the partially purified PDE7 is contaminated by PDE4, it is necessary to add 10 μM of rolipram (selective inhibitor of PDE4) in the enzymatic assay in order to completely inhibit the PDE4 activity. The Michaelis constant (Km) of PDE7 for cAMP, measured using the radiochemical assay described below, is 21 nM.

Solutions of Compounds According to the Invention

The compounds of formula (I) to be tested as PDE7 inhibitors are dissolved in DMSO at a concentration of 10 mM. These solutions are subsequently diluted in cascade in DMSO in order to obtain solutions with the desired concentrations. The latter are subsequently diluted to one-twentieth in the assay buffer to give 5% DMSO solutions. The latter are finally diluted to one-fifth in the enzymatic assay.

The solution of rolipram (added in the assay in order to completely inhibit the contaminating PDE4 activity) is prepared in an identical way and contributes 1% of DMSO to the enzymatic assay.

PDE7 Enzymatic Assay

The assay is carried out in 1.5 ml Eppendorf tubes comprising 40 mM of Tris-HCl (pH 7.5), 15 mM of $MgCl_2$, 1 mM of EGTA, 0.5 mg/ml of bovine serum albumin, 0.063 pCi of [$^3$H]-cAMP (corresponding to a cAMP concentration of between 15 and 25 nM), 10 μM of rolipram and PDE7 in a final volume of 100 μl. The assay is carried out in the absence (control sample) or in the presence (treated sample) of the compounds tested as PDE7 inhibitors. The final concentration of DMSO in the assay is 2%. The reaction is initiated by addition of enzyme and the samples are maintained at ambient temperature for 30 minutes. The enzymatic dilution is adjusted so as to obtain a degree of conversion of 10 to 15%. The enzymatic reaction is halted by immersion of the stoppered Eppendorf tubes in a water bath at 100° C. for 3 minutes. Blanks (reaction halted immediately after addition of the enzyme) are included in each experiment. The samples are subsequently centrifuged at 10 000×g for 1 minute and an aliquot portion of 10 μl of supernatant is deposited 2 cm from the bottom edge of a sheet of PEI cellulose on which 10 μg of cAMP and 10 μg of 5'-AMP have been deposited beforehand. In order to facilitate the migration and to make it easier to cut out the strips of PEI cellulose comprising the 5'-AMP, which take place subsequently, 18 migration lanes with a width of 1 cm are delimited per plate by scraping the cellulose with a spatula over a width of 1 mm. The plates are developed over their entire length with a 0.30 M solution of LiCl in water by ascending chromatography. The 5'-AMP (Rf=0.20) and the cAMP (Rf=0.47) are visualized under UV light at 254 nm. The strips of PEI cellulose comprising the 5'-AMP are cut out and the nucleotide is quantitatively extracted in counting flasks with 2 ml of a solution which is 16M in formic acid and 2M in ammonium formate in water (rotary stirrer for 15 min). After addition of 10 ml of scintillation liquid (OptiPhase HiSafe 3 from Perkin-Elmer/Wallac), the radioactivity is counted using a liquid scintillation counter (model 1414, Perkin-Elmer/Wallac). Each assay is carried out in duplicate. The radioactivity specifically associated with the 5'-AMP formed in the enzymatic reaction is obtained by subtracting the mean value of blanks from the mean value of the controls (or treated samples).

The percentage of inhibition of PDE7 at a given concentration of the compound tested (inhibitor) is calculated using the equation: I %=[mean value of the controls−mean value of the treated samples]×100/[mean value of the controls−mean value of the blanks].

The $IC_{50}$ is the concentration of the compound (inhibitor) tested in the assay which makes it possible to reduce the enzymatic activity of PDE7 by 50%.

Results

As illustrative and nonlimiting examples, the following quinazolinediones inhibit PDE7 with the $IC_{50}$ values indicated below:

| Compound | $IC_{50}$ (μM) |
|---|---|
| No. 16: 4-[6-(2,2-difluoroethoxy)-3-(3,4-dimethoxybenzyl)-2,4-dioxo-3,4-dihydroquinazolin-1(2H)-yl]piperidine-1-carbaldehyde | 0.015 |
| No. 11: 4-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde | 0.039 |
| No. 72: 4-[3-(3,4-dimethoxybenzyl)-6-(2-hydroxyethoxy)-2,4-dioxo-3,4-dihydroquinazolin-1(2H)-yl]piperidine-1-carbaldehyde | 0.089 |
| No. 77: N-{[3-(3,4-dimethoxybenzyl)-1-(1-formylpyrrolidin-3-yl)-2,4-dioxo-1,2,3,4-tetrahydroquinazolin-6-yl]methyl}acetamide | 0.82 |
| No. 97: 4-[5,7-dichloro-3-(3,4-dimethoxybenzyl)-2,4-dioxo-3,4-dihydroquinazolin-1(2H)-yl]piperidine-1-carbaldehyde | 0.061 |
| No. 111: 4-[6-(difluoromethoxy)-3-(3,4-dimethoxybenzyl)-2,4-dioxo-3,4-dihydroquinazolin-1(2H)-yl]piperidine-1-carbaldehyde | 0.0067 |

2) Measurement of the Inhibitory Activity of the Compounds According to the Invention with Regard to PDE8

By using for PDE8 an enzymatic assay equivalent to that described for PDE7, the following $IC_{50}$ values are obtained:

| Compound | IC$_{50}$ PDE7 (µM) | IC$_{50}$ PDE8 (µM) |
|---|---|---|
| No. 11 | 0.039 | 0.14 |
| No. 251 | 0.046 | 0.39 |
| No. 294 | 0.037 | 0.015 |

3) Inhibition of T Cell Proliferation
Isolation of Peripheral Blood Mononuclear Cells (=PB-MNCs)

Human peripheral blood mononuclear cells (PBMNCs) were separated from the blood of healthy donors using a centrifuging gradient on a Ficoll-Paque™ Plus (GE Healthcare Bio-Sciences AB code 17-1440-03, Uppsala). A mixture of 5.0 ml of blood and 5.0 ml of phosphate buffered saline (PBS Gibco 14190) was deposited on 10.0 ml of Ficoll-Paque in a 50 ml Blue max tube (Becton Dickinson 352070) and centrifuged with 900 g for 30 min. The band of PBMNCs was withdrawn, washed in PBS and then centrifuged with 900 g for 10 minutes. Finally, the PBMNCs were suspended (2.5× 10$^5$ cells/ml) in an RPMI 1640 complete medium+Glutamax (Gibco 61870) additivated with 10% of FCS, the complement of which has been heat inactivated, and with penicillin-streptomycin (Gibco 15140).

Measurement of the Proliferation by Incorporation of [$^3$H]-thymidine.

The PBMNCs were cultured in flat-bottomed 96-well plates, in a proportion of 0.5×10$^5$ cells/well in 200 µl of RPMI 1640 complete medium. The cells were activated by two monoclonal antibodies, one of anti-CD3 specificity, 20 ng/ml (Pharmingen 555329), and the other of anti-CD28 specificity, 200 ng/ml (Pharmingen 555725), in the presence of PDE7 inhibitors at five different concentrations, 10 µM, 3.3 µM, 1.1 µM, 0.36 µM and 0.12 µM, or of cyclosporin A, which acts as positive control of the halting of proliferation. The two monoclonal antibodies employed simultaneously bring about an increased intensity of the transcriptional response of the T cells activated via CD3 alone (Diehn M. et al., 2002. Genomic expression programs and the integration of the CD28 costimulatory signal in T cell activation. Proc. Natl. Acad. Sci. USA, 99, 11796-11801). Furthermore, the two antibodies employed mimic the optimum condition of the in vivo activation, which employs the TCR and the CD28 coreceptor. After 72 hours at 37° C. in 5% of CO$_2$ and 90% of humidified air, the cultures were labelled with 1 µCi [methyl-$^3$H]-thymidine (Amersham TRK120). After incubating for an additional 8 hours, the PBMNCs were collected on a Tomtec cell collector (Wallac) using a glass fibre filter (Wallac 1450-421), and incorporation of the [$^3$H]-thymidine in the nucleus of the cells was measured using a Microbeta 1450-Trilux (Wallac). The inhibition of the proliferation, expressed as percentage, was calculated using the following equation: 100−(cpm mean value of the cells in the presence of the compound/cpm mean value of the cells in the absence of the compound)×100.

Results

The inhibitory activities of the compounds of formula (I) according to the invention for the proliferation correspond to IC$_{50}$ values (concentration of the inhibitor which brings about 50% reduction in the incorporation of [$^3$H]-thymidine in the nuclei of the cells). The lower the IC$_{50}$ values, the more the compounds are powerful inhibitors of the proliferation of T lymphocytes.

The following quinazolinediones inhibit the proliferation of PBMNCs with IC$_{50}$ values indicated below (mean of the three experiments):

| Compound | IC$_{50}$ (µM) |
|---|---|
| No. 1: 2-{[3-(3,4-dimethoxybenzyl)-1-(1-formylpiperidin-4-yl)-2,4-dioxo-1,2,3,4-tetrahydroquinazolin-6-yl]oxy}propanenitrile | 0.4 µM |
| No. 11: 4-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde | 0.9 µM |
| No. 16: 4-[6-(2,2-difluoroethoxy)-3-(3,4-dimethoxybenzyl)-2,4-dioxo-3,4-dihydroquinazolin-1(2H)-yl]piperidine-1-carbaldehyde | 1.3 µM |

The compounds according to the invention exhibit good pharmacological properties and are particularly capable of being used in the preparation of medicaments, in particular of medicaments which are inhibitors of PDE7 or, for some of the compounds of the invention, of medicaments which are inhibitors of PDE7 and of PDE8.

According to another of its aspects, the subject matter of the invention is thus medicaments which comprise at least one compound of formula (I).

The compounds according to the invention can be of use in particular in the treatment and/or prevention of inflammatory or immunoinflammatory diseases including, for example, asthma, chronic obstructive pulmonary disease (COPD), allergic rhinitis, allergies, Crohn's disease, ulcerative colitis, myasthenia gravis, atopic dermatitis, psoriasis, lupus erythematosus disseminatus, rheumatoid arthritis, diabetes or multiple sclerosis, in the treatment of organ transplants, in the treatment and/or prevention of certain types of cancers, such as osteosarcoma or adenocarcinoma, in the treatment and/or prevention of bone diseases, such as osteopenia or osteoporosis, in the treatment and/or prevention of acute insufficiency, or in the treatment and/or prevention of pain, in particular neuropathic pain and visceral pain.

The use of the compounds of general formula (I) in the preparation of a medicament intended to treat the abovementioned pathologies forms an integral part of the invention, and in particular compounds of formula (I) chosen from compounds Nos. 1 to 6, 11 to 14, 16, 20, 22 to 25, 32 to 43, 47 to 52, 55 to 59, 72, 74, 76, 78, 79, 89 to 91, 97, 102, 108, 111, 112, 114, 116 to 118, 124, 130, 131, 133 to 135, 143, 145, 155, 158, 160, 165 to 167, 170, 175, 178, 183 to 186, 188, 189, 190, 193, 194, 200, 201, 203, 206, 207, 212, 213, 215, 216, 218, 223, 224, 226, 228, 230, 232 to 234, 239, 240, 242, 243, 245, 246, 250, 251, 254, 258, 263, 264, 270, 275, 276, 278 to 280, 282, 283, 285 to 287, 289, 292, 294, 295, 287 to 302, 305 to 312, 315 to 345, 349 to 355, 357, 358, 360, 362, 369, 371, 373, 375 to 377, 379 to 394 and 403.

According to another of its aspects, the present invention relates to pharmaceutical compositions comprising, as active principle, at least one compound according to the invention. These pharmaceutical compositions comprise an effective dose of at least one compound of formula (I) according to the invention and also at least one pharmaceutically acceptable excipient.

The said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its optional salt, solvate or hydrate can be administered in unit administration form, as a mixture with conventional pharmaceutical excipients, to animals and human beings for the prophylaxis or treatment of the above disorders or diseases.

The appropriate unit administration forms comprise forms by the oral route, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. Use may be made, for topical application, of the compounds according to the invention in creams, gels, ointments or lotions.

By way of example, a unit administration form of a compound according to the invention in the form of a tablet can comprise the following components :

| | |
|---|---:|
| Compound No. 1 (2-{[3-(3,4-dimethoxybenzyl)-1-(1-formylpiperidin-4-yl)-2,4-dioxo-1,2,3,4-tetrahydroquinazolin-6-yl]oxy}propanenitrile) | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said unit forms comprise doses in order to make possible daily administration of 0.5 mg to 800 mg of active principle per individual, more particularly of 0.5 mg to 200 mg, according to the pharmaceutical dosage form.

There may be cases where higher or lower dosages are appropriate; such dosages do not depart from the scope of the invention. According to the usual practice, the dosage appropriate to each patient is determined by the physician according to the method of administration and the weight and response of the said patient.

The present invention, according to another of its aspects, also relates to a method for the treatment and/or prevention of the pathologies indicated above which comprises the administration, to a patient, of an effective dose of a compound according to the invention or of one of its hydrates or solvates.

The invention claimed is:

1. A compound corresponding to the general formula (I)

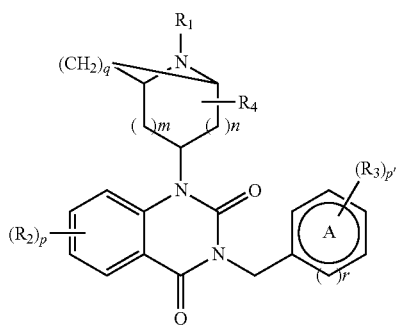

(I)

in which
A represents an aryl group or a heteroaryl group;
$R_1$ represents:
a hydrogen atom,
—C(O)R in which R is a hydrogen atom, a ($C_1$-$C_6$) alkoxy group, an aryl group, a ($C_3$-$C_6$) cycloalkyl group or a ($C_1$-$C_6$) alkyl group, the said alkyl optionally being substituted by:
one to five hydroxyl group(s),
a benzyloxy group,
a ($C_1$-$C_6$) alkoxy group, optionally substituted by an aryl, or
a ($C_3$-$C_6$) cycloalkyl group,
—($C_1$-$C_6$) alkyl group;
$R_2$ represents:
a hydrogen atom,
a halogen atom,
a cyano group,
a nitro group,
a ($C_1$-$C_6$) alkyl group optionally substituted by an —$NH_2$ or else by an —NHC(O)Rb group,
an —ORa group in which Ra represents:
a hydrogen atom,
a ($C_1$-$C_6$) alkyl group optionally substituted by one to 13 halogen atom(s), by one to five hydroxyl group(s), by an aryl group and/or by one to five cyano group(s),
a ($C_2$-$C_6$) alkynyl group,
an aryl group;
$R_3$ represents:
a hydrogen atom,
a halogen atom,
a hydroxyl group,
a cyano group,
an —$SCF_3$ group,
a nitro group,
an oxo group,
an —$S(O)_{0-2}$-alkyl group, an —$S(O)_{0-2}$-heterocycloalkyl group, an —O—$SO_2$-aryl group optionally substituted by one to five halogen atom(s),
an -alkylaminoalkyl or -cycloalkylaminoalkyl group
-sulphonamide group,
an aryl group or a heteroaryl group, the said group being monocyclic or polycyclic and in addition optionally being substituted by a ($C_1$-$C_6$) alkyl group, by one to five halogen atom(s) or by a ($C_1$-$C_6$) alkoxy group,
a heterocycloalkyl group optionally substituted by a ($C_1$-$C_6$) alkyl group,
a ($C_1$-$C_6$) alkyl group optionally substituted by:
one to five halogen atom(s),
an aryl group which can be substituted by one to five halogen atom(s) or by one to five hydroxyl group(s),
a heteroaryl group,
one to five hydroxyl group(s) which can be substituted by an aryl group itself optionally substituted by one to five halogen atom(s), or
a heterocycloalkyl group optionally substituted by a CO(O)Ra group or by a ($C_1$-$C_6$) alkyl group,
a —C(O)NRbRc group,
a —C(O)ORc group or an —O—C(O)ORc group,
a ($C_1$-$C_6$) alkoxy group, optionally substituted by
an aminoalkyl group,
an aminocycloalkyl group,
a cycloalkyl group,
a heterocycloalkyl group,
a monocyclic or polycyclic heteroaryl group,
one to five hydroxyl group(s),
one to five halogen atom(s),
a ($C_1$-$C_6$) alkoxy group,
a —C(O)ORc group,
a —C(O)NRbRc group,
an oxo group, and/or an aryl group, itself optionally substituted by one to five halogen atom(s), a cyano group, a ($C_1$-$C_6$) alkoxy group, an —O-haloalkyl group and/or a haloalkyl group, an —O-cycloalkyl group, an —O-aryl group or an —O-heterocycloalkyl group, each optionally substituted by an aryl group, itself optionally substituted by one to five halogen atom(s) or by a ($C_1$-$C_6$) alkyl group, an oxo group, one to five halogen atom(s), and/or a ($C_1$-$C_6$) alkyl group, which can itself be substituted by an aryl group and/or an oxo group, an —NH—CO—NH-aryl group, an —NH—CO—NH-heteroaryl group or an —NH—CO—NH—($C_1$-$C_6$) alkyl group, each optionally being substituted by one to five halogen atom(s), by a cyano group, by a nitro group, by one to five hydroxyl group(s) or by a ($C_1$-$C_6$) alkoxy group, an —NH—CO-aryl group or an —NH—CO-heteroaryl group, each optionally being substituted by one to five halogen atom(s);

or else $R_3$ forms, with A, a polycyclic heteroaryl group optionally substituted by a ($C_1$-$C_6$) alkoxy group or a ($C_1$-$C_6$) alkyl group optionally substituted by an aryl group which can itself be substituted by one to five halogen atom(s);

$R_4$ represents a hydrogen atom, an oxo group or a ($C_1$-$C_6$) alkyl group;

Rb represents:

a hydrogen atom, a ($C_1$-$C_6$) alkyl group optionally substituted by one to five halogen atom(s), by one to five hydroxyl, cyano, amino, heterocycloalkyl or ($C_1$-$C_6$) alkoxy group(s) or by an aryl group optionally substituted by one to five halogen atom(s), a ($C_3$-$C_6$) cycloalkyl group, a ($C_2$-$C_6$) alkynyl group, a ($C_1$-$C_6$) alkoxy group, an aryl group optionally substituted by one to five halogen atom(s);

Rc represents a hydrogen atom or a ($C_1$-$C_6$) alkyl group optionally substituted by one to five halogen atom(s);

or then Rb and Rc form, together with the nitrogen atom to which they are attached, a polycyclic heteroaryl group or a heterocycloalkyl group;

m and n represent, independently of one another, the value 0, 1 or 2, it being understood that m+n=2;

p and p' represent, independently of one another, the value 1, 2 or 3, it being understood that, when p is greater than or equal to 2, then the $R_2$ groups are on separate carbon atoms and can be different from one another and, when p' is greater than or equal to 2, then the $R_3$ groups are on separate carbon atoms and can be different from one another;

q represents the value 0, it being understood that, when q=0, then the nitrogenous heterocyclic group attached to the nitrogen situated in the 1 position of the 2,4-dioxo-1,2,3,4-tetrahydroquinazoline ring system is no longer bridged and is of the type:

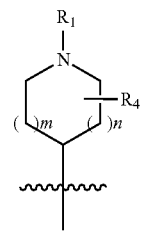

r represents the value 0 or 1.

2. The compound of general formula (I) according to claim 1, characterized in that A represents a phenyl group or a pyridyl group.

3. The compound of general formula (I) according to claim 1 or 2, characterized in that q=0, and m and n=1.

4. The compound of general formula (I) according to claim 3, characterized in that $R_2$ represents a methyl substituted by an —NH—CO—Rb group.

5. The compound of general formula (I) according to claim 3, characterized in that $R_2$ represents an —ORa group.

6. The compound of general formula (I) according to claim 3, characterized in that $R_2$ is a halogen atom or a cyano or a hydrogen or a hydroxyl or a ($C_1$-$C_6$) alkyl optionally substituted by an —$NH_2$ or else by an —NHC(O)Rb group.

7. The compound of general formula (I) according to claim 1, characterized in that A is a phenyl, $R_1$ is a —C(O)R group in which R represents a hydrogen atom, q is equal to 0, n and m have the value 1 and $R_2$ is —ORa.

8. The compound of general formula (I) according to claim 1, characterized in that A is a phenyl, $R_1$ is a —C(O)R group in which R represents a hydrogen atom, q is equal to 0, n and m have the value 1 and $R_2$ is a methyl substituted by the —NH—CO—Rb group.

9. The compound of general formula (I) according to claim 1, characterized in that A is a phenyl, $R_1$ is a —C(O)R group in which R represents a hydrogen atom, q is equal to 0, n and m have the value 1, p is equal to 2, one of the $R_2$ groups is —ORa, and the other of the $R_2$ groups is a halogen atom.

10. The compound of general formula (I) according to claim 3, characterized in that the $R_2$ group is in the 6 position of the 2,4-dioxo-1,2,3,4-tetrahydroquinazoline ring system and in that there may additionally be an identical or different $R_2$ group in the 7 position of the 2,4-dioxo-1,2,3,4-tetrahydroquinazoline ring system.

11. A compound selected from the following:

No. 1: 2-{[3-(3,4-dimethoxybenzyl)-1-(1-formylpiperidin-4-yl)-2,4-dioxo-1,2,3,4-tetrahydroquinazolin-6-yl]oxy}propanenitrile;

No. 2: 1-(1-acetylpiperidin-4-yl)-3-3,4-dimethoxybenzyl)-6-hydroxyquinazoline-2,4(1H,3H)-dione;

No. 3: {[1-(1-acetylbenzyl)-4-yl)-3-(3,4-dimethoxybenzyl)2,4-dioxo-1,2,3,4-tetrahydroquinazolin-6-yl]oxy}acetonitrile;

No. 4: 2-{[1-(1-acetylpiperidin-4-yl)-3-(3,4-dimethoxybenzyl)-2,4-dioxo-1,2,3,4-tetrahydroquinazolin-6-yl]oxy}propanenitrile;

No. 5: {[3-(3,4-dimethoxybenzyl)-1-(1-formylpiperidin-4-yl)-2,4-dioxo-1,2,3,4-tetrahydroquinazolin-6-yl]oxy}acetonitrile;

No. 11: 4-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde;

No. 12: 1-(1-acetylpiperidin-4-yl)-3-(3,4-dimethoxybenzyl)-6-[2-fluoro-1-(fluoromethyl)ethoxy]quinazoline-2,4(1H,3H)-dione;

No. 13: 4-[3-(3,4-dimethoxybenzyl)-2,4-dioxo-6-(2,2,2-trifluoroethoxy)-3,4-dihydroquinazolin-1(2H)-yl]piperidine-1-carbaldehyde;

No. 14: 1-(1-acetylpiperidin-4-yl)-6-(2,2-difluoroethoxy)-3-(3,4-dimethoxybenzyl)quinazoline-2,4(1H,3H)-dione;

No. 16: 4-[6-(2,2-difluoroethoxy)-3-(3,4-dimethoxybenzyl)-2,4-dioxo-3,4-dihydroquinazolin-1(2H)-yl]piperidine-1-carbaldehyde;

No. 20: N-{[3-(3,4-dimethoxybenzyl)-1-(1-formylpiperidin-4-yl)-2,4-dioxo-1,2,3,4-tetrahydroquinazolin-6-yl]methyl}acetamide;

No. 22: 1-(1-acetylpiperidin-4-yl)-6-(aminomethyl)-3-(3,4-dimethoxybenzyl)quinazoline-2,4(1H,3H)-dione hydrochloride;

No. 23: N-{[3-(3,4-dimethoxybenzyl)-1-(1-formylpiperidin-4-yl)-2,4-dioxo-1,2,3,4-tetrahydroquinazolin-6-yl]methyl}formamide;

No. 24: N-{[1-(1-acetylbenzyl-4-yl)-3-(3,4-dimethoxybenzyl)-2,4-dioxo-1,2,3,4-tetrahydroquinazolin-6-yl]methyl}formamide;

No. 25: N-{[1-(1-acetylpiperidin-4-yl)-3-(3,4-dimethoxybenzyl)-2,4-dioxo-1,2,3,4-tetrahydroquinazolin-6-yl]methyl}acetamide;

No. 33: 4-[3-(3,4-dichlorobenzyl)-6-(2,2-difluoroethoxy)-2,4-dioxo-3,4-dihydroquinazolin-1(2H)-yl]piperidine-1-carbaldehyde;

No. 34: 4-[3-(4-chlorobenzyl)-6-(2,2-difluoroethoxy)-2,4-dioxo-3,4-dihydroquinazolin-1(2H)-yl]piperidine-1-carbaldehyde;

No. 35: methyl 4-{[6-(2,2-difluoroethoxy)-1-(1-formylpiperidin-4-yl)-2,4-dioxo-1,4-dihydroquinazolin-3(2H)-yl]methyl}benzoate;

No. 36: 4-{[6-(2,2-difluoroethoxy)-1-(1-formylpiperidin-4-yl)-2,4-dioxo-1,4-dihydroquinazolin-3(2H)-yl]methyl}benzoic acid;

No. 37: 4-{[6-(2,2-difluoroethoxy)-1-(1-formylpiperidin-4-yl)-2,4-dioxo-1,4-dihydroquinazolin-3(2H)-yl]methyl}-N-(2-methoxyethyl)benzamide;

No. 38: 4-[3-(3,4-dimethoxybenzyl)-6-methyl-2,4-dioxo-3,4-dihydroquinazolin-1(2H)-yl]piperidine-1-carbaldehyde;

No. 39: 4-[6-(2,2-difluoroethoxy)-3-(3-hydroxy-4-methoxybenzyl)-2,4-dioxo-3,4-dihydroquinazolin-1(2H)-yl]piperidine-1-carbaldehyde;

No. 40: 4-[6-(2,2-difluoroethoxy)-3-[3-(2-hydroxyethoxy)-4-methoxybenzyl]-2,4-dioxo-3,4-dihydroquinazolin-1(2H)-yl]piperidine-1-carbaldehyde;

No. 41: 4-[6-(2,2-difluoroethoxy)-3-(3-ethoxy-4-methoxybenzyl)-2,4-dioxo-3,4-dihydroquinazolin-1(2H)-yl]piperidine-1-carbaldehyde;

No. 42: 4-[6-(2,2-difluoroethoxy)-3-[4-methoxy-3-(2-methoxyethoxy)benzyl]-2,4-dioxo-3,4-dihydroquinazolin-1(2H)-yl]piperidine-1-carbaldehyde;

No. 47: 4-[6-(2,2-difluoroethoxy)-3-[3-(3-hydroxypropoxy)-4-methoxybenzyl]-2,4-dioxo-3,4-dihydroquinazolin-1(2H)-yl]piperidine-1-carbaldehyde;

No. 48: 4-[5-chloro-3-(3,4-dimethoxybenzyl)-2,4-dioxo-3,4-dihydroquinazolin-1(2H)-yl]piperidine-1-carbaldehyde;

No. 49: 4-{3-[3-(cyclopentyloxy)-4-methoxybenzyl]-6-(2,2-difluoroethoxy)-2,4-dioxo-3,4-dihydroquinazolin-1(2H)-yl}piperidine-1-carbaldehyde;

No. 50: 2-(5-{[6-(2,2-difluoroethoxy)-1-(1-formylpiperidin-4-yl)-2,4-dioxo-1,4-dihydroquinazolin-3 (2H)-yl]methyl}-2-methoxyphenoxy)acetamide;

No. 51: 4-[6-(2,2-difluoroethoxy)-3-(3,4-dimethoxybenzyl)-2,4-dioxo-3,4-dihydroquinazolin-1(2H)-yl]-3-methylpiperidine-1-carbaldehyde;

No. 56: 4-{3-[4-(cyclopentyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde;

No. 57: 4-[3-(3-chlorobenzyl)-6-[2-fluoro-1-(fluoromethyl)ethoxy]-2,4-dioxo-3,4-dihydroquinazolin-1(2H)-yl]piperidine-1-carbaldehyde;

No. 58: 4-[3-(4-chlorobenzyl)-6-[2-fluoro-1-(fluoromethyl)ethoxy]-2,4-dioxo-3,4-dihydroquinazolin-1(2H)-yl]piperidine-1-carbaldehyde;

No. 59: 4-{3-[3-(cyclopentyloxy)-4-methoxybenzyl]-6-[2-fluoro-1-(fluoromethyl)ethoxy]-2,4-dioxo-3,4-dihydroquinazolin-1(2H)-yl}piperidine-1-carbaldehyde;

No. 72: 4-[3-(3,4-dimethoxybenzyl)-6-(2-hydroxyethoxy)-2,4-dioxo-3,4-dihydroquinazolin-1(2H)-yl]piperidine-1-carbaldehyde;

No. 74: 4-[3-(3,4-dichlorobenzyl)-6-[2-fluoro-1-(fluoromethyl)ethoxy]-2,4-dioxo-3,4-dihydroquinazolin-1(2H)-yl]piperidine-1-carbaldehyde;

No. 76: 4-{3-[(6-chloropyridin-3-yl)methyl]-6-[2-fluoro-1-(fluoromethyl)ethoxy]-2,4-dioxo-3,4-dihydroquinazolin-1(2H)-yl}piperidine-1-carbaldehyde;

No. 78: 4-[3-(3-chloro-4-methoxybenzyl)-6-[2-fluoro-1-(fluoromethyl)ethoxy]-2,4-dioxo-3,4-dihydroquinazolin-1(2H)-yl]piperidine-1-carbaldehyde;

No. 79: 4-[3-(3,4-dimethoxybenzyl)-6-(2-fluoroethoxy)-2,4-dioxo-3,4-dihydroquinazolin-1(2H)-yl]piperidine-1-carbaldehyde;

No. 89: 2-[5-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]acetamide;

No. 90: 4-{6-[2-fluoro-1-(fluoromethyl)ethoxy]-3-(3-hydroxy-4-methoxybenzyl)-2,4-dioxo-3,4-dihydroquinazolin-1(2H)-yl}piperidine-1-carbaldehyde;

No. 91: 4-[3-(3,4-dimethoxybenzyl)-6-ethoxy-2,4-dioxo-3,4-dihydroquinazolin-1(2H)-yl]piperidine-1-carbaldehyde;

No. 97: 4-[5,7-dichloro-3-(3,4-dimethoxybenzyl)-2,4-dioxo-3,4-dihydroquinazolin-1(2H)-yl]piperidine-1-carbaldehyde;

No. 102: 4-[7-chloro-3-(3,4-dimethoxybenzyl)-2,4-dioxo-3,4-dihydroquinazolin-1(2H)-yl]piperidine-1-carbaldehyde;

No. 108: 4-{6-[2-fluoro-1-(fluoromethyl)ethoxy]-3-(3-fluoro-4-methoxybenzyl)-2,4-dioxo-3,4-dihydroquinazolin-1(2H)-yl}piperidine-1-carbaldehyde;

No. 111: 4-[6-(difluoromethoxy)-3-(3,4-dimethoxybenzyl)-2,4-dioxo-3,4-dihydroquinazolin-1(2H)-yl]piperidine-1-carbaldehyde;

No. 112: 4-[3-(3,4-dimethoxybenzyl)-6-(1-methylethoxy)-2,4-dioxo-3,4-dihydroquinazolin-1(2H)-yl]piperidine-1-carbaldehyde;

No. 114: 4-{6-[2-fluoro-1-(fluoromethyl)ethoxy]-3-[4-methoxy-3-(1-methylethoxy)benzyl]-2,4-dioxo-3,4-dihydroquinazolin-1(2H)-yl}piperidine-1-carbaldehyde;

No. 116: 4-{6-[2-fluoro-1-(fluoromethyl)ethoxy]-3-(3-methoxybenzyl)-2,4-dioxo-3,4-dihydroquinazolin-1(2H)-yl}piperidine-1-carbaldehyde;

No. 117: 4-{3-[3,5-bis(trifluoromethyl)benzyl]-6-[2-fluoro-1-(fluoromethyl)ethoxy]-2,4-dioxo-3,4-dihydroquinazolin-1(2H)-yl}piperidine-1-carbaldehyde;

No. 118: 4-[3-(3-ethoxybenzyl)-6-[2-fluoro-1-(fluoromethyl)ethoxy]-2,4-dioxo-3,4-dihydroquinazolin-1(2H)-yl]piperidine-1-carbaldehyde;

No. 124: 4-{3-[3-chloro-4-(2-methoxyethoxy)benzyl]-6-[2-fluoro-1-(fluoromethyl)ethoxy]-2,4-dioxo-3,4-dihydroquinazolin-1(2H)-yl}piperidine-1-carbaldehyde;

No. 130: 4-[3-(3,4-diethoxybenzyl)-6-[2-fluoro-1-(fluoromethyl)ethoxy]-2,4-dioxo-3,4-dihydroquinazolin-1(2H)-yl]piperidine-1-carbaldehyde;

No. 131: 4-[3-(4-ethoxy-3-methoxybenzyl)-6-[2-fluoro-1-(fluoromethyl)ethoxy]-2,4-dioxo-3,4-dihydroquinazolin-1(2H)-yl]piperidine-1-carbaldehyde;

No. 133: 4-{6-[2-fluoro-1-(fluoromethyl)ethoxy]-3-(4-methoxy-3-methylbenzyl)-2,4-dioxo-3,4-dihydroquinazolin-1(2H)-yl}piperidine-1-carbaldehyde;

No. 134: 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde;

No. 135: 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde;

No. 143: 4-{3-[4-(benzyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde;

No. 145: 4-{6-[2-fluoro-1-(fluoromethyl)ethoxy]-3-(3-methoxy-4-nitrobenzyl)-2,4-dioxo-3,4-dihydroquinazolin-1(2H)-yl}piperidine-1-carbaldehyde;

No. 155: 4-[3-(4-ethoxybenzyl)-6-[2-fluoro-1-(fluoromethyl)ethoxy]-2,4-dioxo-3,4-dihydroquinazolin-1(2H)-yl]piperidine-1-carbaldehyde;

No. 158: 4-{6-[2-fluoro-1-(fluoromethyl)ethoxy]-3-[4-(morpholin-4-ylmethyl)benzyl]-2,4-dioxo-3,4-dihydroquinazolin-1(2H)-yl}piperidine-1-carbaldehyde;

No. 160: 4-{6-[2-fluoro-1-(fluoromethyl)ethoxy]-3-(4-morpholin-4-ylbenzyl)-2,4-dioxo-3,4-dihydroquinazolin-1(2H)-yl}piperidine-1-carbaldehyde;

No. 165: 4-[3-(biphenyl-4-ylmethyl)-6-[2-fluoro-1-(fluoromethyl)ethoxy]-2,4-dioxo-3,4-dihydroquinazolin-1(2H)-yl]piperidine-1-carbaldehyde;

No. 166: 4-{6-[2-fluoro-1-(fluoromethyl)ethoxy]-3-[4-(methylsulphanyl)benzyl]-2,4-dioxo-3,4-dihydroquinazolin-1(2H)-yl}piperidine-1-carbaldehyde;

No. 167: 4-{6-[2-fluoro-1-(fluoromethyl)ethoxy]-2,4-dioxo-3-(4-(pyridin-3-yl)benzyl)-3,4-dihydroquinazolin-1(2H)-yl}piperidine-1-carbaldehyde;

No. 170: 4-{6-[2-fluoro-1-(fluoromethyl)ethoxy]-3-(3-methoxy-4-methylbenzyl)-2,4-dioxo-3,4-dihydroquinazolin-1(2H)-yl}piperidine-1-carbaldehyde;

No. 175: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]acetamide;

No. 178: 4-{6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde;

No. 183: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylacetamide;

No. 184: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N,N-dimethylacetamide;

No. 185: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methoxy-N-methylacetamide;

No. 186: 4-{3-[4-(cyclopentyloxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde;

No. 188: 4-{3-[4-(cyclopentyloxy)-3-(1-methylethoxy)benzyl]-6-[2-fluoro-1-(fluoromethyl)ethoxy]-2,4-dioxo-3,4-dihydroquinazolin-1(2H)-yl}piperidine-1-carbaldehyde;

No. 189: 4-{3-[4-(cyclopentyloxy)-3-propoxybenzyl]-6-[2-fluoro-1-(fluoromethyl)ethoxy]-2,4-dioxo-3,4-dihydroquinazolin-1(2H)-yl}piperidine-1-carbaldehyde;

No. 190: 4-{3-[4-(cyclopentyloxy)-3-hydroxybenzyl]-6-[2-fluoro-1-(fluoromethyl)ethoxy]-2,4-dioxo-3,4-dihydroquinazolin-1(2H)-yl}piperidine-1-carbaldehyde;

No. 193: 4-{3-[4-(difluoromethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde;

No. 194: 4-{3-[4-(difluoromethoxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde;

No. 200: 4-{6-[2-fluoro-1-(fluoromethyl)ethoxy]-2,4-dioxo-3-(4-(thiophen-3-yl)-benzyl)-3,4-dihydroquinazolin-1(2H)-yl}piperidine-1-carbaldehyde;

No. 201: 4-{6-[2-fluoro-1-(fluoromethyl)ethoxy]-2,4-dioxo-3-(4-(pyridin-4-yl)benzyl)-3,4-dihydroquinazolin-1(2H)-yl}piperidine-1-carbaldehyde;

No. 203: 4-{6-[2-fluoro-1-(fluoromethyl)ethoxy]-3-[(1-methyl-1H-indol-6-yl)methyl]-2,4-dioxo-3,4-dihydroquinazolin-1(2H)-yl}piperidine-1-carbaldehyde;

No. 206: 4-{3-[4-(cyclopropylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde;

No. 207: 2-[4-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]-N-methylacetamide;

No. 212: 4-{6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde;

No. 213: 4-{6-[2-fluoro-1-(fluoromethyl)ethoxy]-2,4-dioxo-3-(4-(pyridin-2-yl)benzyl)-3,4-dihydroquinazolin-1(2H)-yl}piperidine-1-carbaldehyde;

No. 215: 4-{6-[2-fluoro-1-(fluoromethyl)ethoxy]-2,4-dioxo-3-(4-(thiophen-2-yl)-benzyl)-3,4-dihydroquinazolin-1(2H)-yl}piperidine-1-carbaldehyde;

No. 216: 4-{6-[2-fluoro-1-(fluoromethyl)ethoxy]-2,4-dioxo-3-(quinolin-7-ylmethyl)-3,4-dihydroquinazolin-1(2H)-yl}piperidine-1-carbaldehyde;

No. 218: 4-{6-[2-fluoro-1-(fluoromethyl)ethoxy]-3-[(6-methoxynaphthalen-2-yl)methyl]-2,4-dioxo-3,4-dihydroquinazolin-1(2H)-yl}piperidine-1-carbaldehyde;

No. 223: 4-{3-[4-(1H-benzimidazol-1-yl)benzyl]-6-[2-fluoro-1-(fluoromethyl)ethoxy]-2,4-dioxo-3,4-dihydroquinazolin-1(2H)-yl}piperidine-1-carbaldehyde;

No. 224: 4-{6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde;

No. 226: 4-{6-[2-fluoro-1-(fluoromethyl)ethoxy]-3-[3-methoxy-4-(tetrahydrofuran-3-yloxy)benzyl]-2,4-dioxo-3,4-dihydroquinazolin-1(2H)-yl}piperidine-1-carbaldehyde;

No. 228: 4-[3-{4-[(1-benzylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 230: 4-[3-(1-benzothiophen-5-ylmethyl)-6-[2-fluoro-1-(fluoromethyl)ethoxy]-2,4-dioxo-3,4-dihydroquinazolin-1(2H)-yl]piperidine-1-carbaldehyde;

No. 232: 4-{6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde;

No. 233: 4-[3-(3,4-dimethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde;

No. 234: 4-[3-{4-[(1-acetylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 239: 4-[3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 240: 4-[3-{4-[(4-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 242: 4-[3-{-4-[(3-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 243: 4-{6-[2-fluoro-1-(fluoromethyl)ethoxy]-2,4-dioxo-3-(3-(thiophen-3-yl)benzyl)-3,4-dihydroquinazolin-1(2H)-yl}piperidine-1-carbaldehyde;

No. 245: 4-[3-(4-ethoxy-3-methoxybenzyl)-6-(2-hydroxyethoxy)-2,4-dioxo-3,4-dihydroquinazolin-1(2H)-yl]piperidine-1-carbaldehyde;

No. 246: 4-[3-{4-[2-(2,3-dihydro-1H-indol-1-yl)-2-oxoethoxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 250: 4-[3-{-4-[(3,4-dichlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 251: 4-{6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde;

No. 254: 4-[3-[3-ethoxy-4-(thiophen-2-ylmethoxy)benzyl]-6-[2-fluoro-1-(fluoromethyl)ethoxy]-2,4-dioxo-3,4-dihydroquinazolin-1(2H)-yl]piperidine-1-carbaldehyde;

No. 258: 4-[3-(3,4-dimethoxybenzyl)-6-[2-fluoro-1-(hydroxymethyl)ethoxy]-2,4-dioxo-3,4-dihydroquinazolin-1(2H)-yl]piperidine-1-carbaldehyde;

No. 263: (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid;

No. 264: 4-{6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde;

No. 270: 4-{6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde;

No. 275: 4-{6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde;

No. 276: 4-{6-[2-fluoro-1-(fluoromethyl)ethoxy]-3-[(1-methyl-3-phenyl-1H-pyrazol-5-yl)methyl]-2,4-dioxo-3,4-dihydroquinazolin-1(2H)-yl}piperidine-1-carbaldehyde;

No. 278: 4-{6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde;

No. 279: 4-{6-[2-fluoro-1-(fluoromethyl)ethoxy]-2,4-dioxo-3-[(2-(thiophen-2-yl)pyrimidin-5-yl)methyl]-3,4-dihydroquinazolin-1(2H)-yl}piperidine-1-carbaldehyde;

No. 280: 4-{6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde;

No. 282: 4-{6-[2-fluoro-1-(fluoromethyl)ethoxy]-3-[4-(3-methyl-1,2,4-oxadiazol-5-yl)benzyl]-2,4-dioxo-3,4-dihydroquinazolin-1(2H)-yl}piperidine-1-carbaldehyde;

No. 283: [2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy] acetic acid;

No. 285: 4-{6-[2-fluoro-1-(fluoromethyl)ethoxy]-2,4-dioxo-3-(thieno[2,3-b]pyridin-2-ylmethyl)-3,4-dihydroquinazolin-1(2H)-yl}piperidine-1-carbaldehyde;

No. 286: 4-{6-[2-fluoro-1-(fluoromethyl)ethoxy]-2,4-dioxo-3-[(6-phenylpyridin-3-yl)methyl]-3,4-dihydroquinazolin-1(2H)-yl}piperidine-1-carbaldehyde;

No. 287: 4-{6-[2-fluoro-1-(fluoromethyl)ethoxy]-3-[(6-(morpholin-4-yl)pyridin-3-yl)methyl]-2,4-dioxo-3,4-dihydroquinazolin-1(2H)-yl}piperidine-1-carbaldehyde;

No. 289: 4-{6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde;

No. 292: 4-{6-[2-fluoro-1-(fluoromethyl)ethoxy]-3-[(1-methyl-5-phenyl-1H-pyrazol-3-yl)methyl]-2,4-dioxo-3,4-dihydroquinazolin-1(2H)-yl}piperidine-1-carbaldehyde;

No. 294: 4-({6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile;

No. 295: (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylpropanamide;

No. 297: 4-{7-fluoro-6-[2-fluoro-1-(fluoromethyl)ethoxy]-2,4-dioxo-3-(4-(thiophen-2-yl)benzyl)-3,4-dihydroquinazolin-1(2H)-yl}piperidine-1-carbaldehyde;

No. 298: 4-{6-[2-fluoro-1-(fluoromethyl)ethoxy]-3-[3-methoxy-4-(morpholin-4-ylmethyl)benzyl]-2,4-dioxo-3,4-dihydroquinazolin-1(2H)-yl}piperidine-1-carbaldehyde;

No. 299: 4-{6-[2-fluoro-1-(fluoromethyl)ethoxy]-3-[3-methoxy-4-(piperidin-1-ylmethyl)benzyl]-2,4-dioxo-3,4-dihydroquinazolin-1(2H)-yl}piperidine-1-carbaldehyde;

No. 300: 4-[3-{4-[(3,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 301: 2-[2-(cyclopentyloxy)-5-({6-[2-fluoromethyl)ethoxy]-1-(1-formylpiperidin-4-yl)-2,4-dioxo-1,4-dihydroquinazolin-3(2H)-yl}methyl)phenoxy]-N-ethylacetamide;

No. 302: (2S)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid;

No. 305: 4-{6-[2-fluoro-1-(fluoromethyl)ethoxy]-3-(3-methoxy-4-{[(3R)-2-oxo-1-phenylpyrrolidin-3-yl]

oxy}benzyl)-2,4-dioxo-3,4-dihydroquinazolin-1(2H)-yl}piperidine-1-carbaldehyde;

No. 306: 4-{3-[4-(cyclobutylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde;

No. 307: 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 308: 4-{7-fluoro-6-[2-fluoro-1-(fluoromethyl)ethoxy]-3-(4-hydroxy-3-methoxybenzyl)-2,4-dioxo-3,4-dihydroquinazolin-1(2H)-yl}piperidine-1-carbaldehyde;

No. 309: 4-{3-[4-(cyclopropylmethoxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 310: 4-{7-fluoro-6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde;

No. 311: 4-{7-fluoro-6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde;

No. 312: 4-[3-(4-ethoxy-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde;

No. 315: 4-{7-fluoro-6-[2-fluoro-1-(fluoromethyl)ethoxy]-3-{[6-(3-methoxyphenyl)pyridin-3-yl]methyl}-2,4-dioxo-3,4-dihydroquinazolin-1(2H)-yl}piperidine-1-carbaldehyde;

No. 316: 4-{7-fluoro-6-[2-fluoro-1-(fluoromethyl)ethoxy]-3-{[6-(2-fluorophenyl)pyridin-3-yl]methyl}-2,4-dioxo-3,4-dihydroquinazolin-1(2H)-yl}piperidine-1-carbaldehyde;

No. 317: 4-{7-fluoro-6-[2-fluoro-1-(fluoromethyl)ethoxy]-3-{[6-(4-fluorophenyl)pyridin-3-yl]methyl}-2,4-dioxo-3,4-dihydroquinazolin-1(2H)-yl}piperidine-1-carbaldehyde;

No. 318: 4-{7-fluoro-6-[2-fluoro-1-(fluoromethyl)ethoxy]-3-{[6-(4-methoxyphenyl)pyridin-3-yl]methyl}-2,4-dioxo-3,4-dihydroquinazolin-1(2H)-yl}piperidine-1-carbaldehyde;

No. 319: 4-{7-fluoro-6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde;

No. 320: 4-{3-[3-ethoxy-4-(thiophen-2-ylmethoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 321: 4-{7-fluoro-6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde;

No. 322: 4-{7-fluoro-6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde;

No. 323: 4-{7-fluoro-6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde;

No. 324: 4-{7-fluoro-6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde;

No. 325: 4-[3-{4-[2-(2,3-dihydro-1H-indol-1-yl)-2-oxoethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 326: 4-{7-fluoro-6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde;

No. 327: 4-[3-{4-[(3-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 328: 4-[3-{[6-(3,5-dichlorophenyl)pyridin-3-yl]methyl}-6-[2-fluoro-1-(fluoromethyl)ethoxy]-2,4-dioxo-3,4-dihydroquinazolin-1(2H)-yl]piperidine-1-carbaldehyde;

No. 329: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile;

No. 330: 4-{7-fluoro-6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde;

No. 331: 4-{7-fluoro-6-[2-fluoro-1-(fluoromethyl)ethoxy]-3-{[6-(3-fluorophenyl)pyridin-3-yl]methyl}-2,4-dioxo-3,4-dihydroquinazolin-1(2H)-yl}piperidine-1-carbaldehyde;

No. 332: 3-[5-({7-fluoro-6-[2-fluoro-1-(fluoromethyl)ethoxy]-1-(1-formylpiperidin-4-yl)-2,4-dioxo-1,4-dihydroquinazolin-3(2H)-yl]methyl)pyridin-2-yl}benzonitrile;

No. 333: 4-[3-(3,4-diethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde;

No. 334: 4-[3-{4-[(4-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 335: 4-{7-fluoro-6-[2-fluoro-1-(fluoromethyl)ethoxy]-3-[4-(morpholin-4-ylmethyl)benzyl]-2,4-dioxo-3,4-dihydroquinazolin-1(2H)-yl}piperidine-1-carbaldehyde;

No. 336: 4-{7-fluoro-6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde;

No. 337: 4-{7-fluoro-6-[2-fluoro-1-(fluoromethyl)ethoxy]-3-(4-(morpholin-4-yl)-benzyl)-2,4-dioxo-3,4-dihydroquinazolin-1(2H)-yl}piperidine-1-carbaldehyde;

No. 338: 4-{7-fluoro-6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde;

No. 339: 4-{3-[4-(1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 340: 5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxybenzonitrile;

No. 341: 3-(3,4-dimethoxybenzyl)-6-[2-fluoro-1-(fluoromethyl)ethoxy]-1-(1-formylpiperidin-4-yl)-2,4-dioxo-1,2,3,4-tetrahydroquinazoline-7-carbonitrile;

No. 342: 4-[3-(4-bromobenzyl)-7-fluoro-6-[2-fluoro-1-(fluoromethyl)ethoxy]-2,4-dioxo-3,4-dihydroquinazolin-1(2H)-yl]piperidine-1-carbaldehyde;

No. 343: 4-[3-{4-[(3,4-dichlorobenzyl)oxy]-3-(2-methoxyethoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 344: 4-{3-[4-(benzyloxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 345: 4-[3-{4-[(3,4-dichlorobenzyl)oxy]-3-ethoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 349: 4-[3-{4-[(3,4-dichlorobenzyl)oxy]-3-(2-fluoroethoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 350: 4-[3-{4-[(2-chloro-4-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 351: 4-[3-{4-[(2,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 352: 4-[3-{4-[(2-chloro-6-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 353: 4-[3-{4-[(2,6-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 354: 4-[3-{4-[(2-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 355: 4-[7-fluoro-3-{4-[(2-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 357: 2-[(3,4-dichlorobenzyl)oxy]-5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzonitrile;

No. 358: 4-[3-{-4-[(3,4-dichlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 360: 4-{7-fluoro-6-[2-fluoro-1-(fluoromethyl)ethoxy]-2,4-dioxo-3-[4-(2-phenylethyl)benzyl]-3,4-dihydroquinazolin-1(2H)-yl}piperidine-1-carbaldehyde;

No. 362: 4-[3-{-4-[(4,5-dichloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 369: 4-[3-{4-[(4-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 371: 4-[3-{3-chloro-4-[(4-chlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 373: 4-[3-{3-chloro-4-[(2,4-dichlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl}piperidine-1-carbaldehyde;

No. 375: 4-[7-fluoro-3-{-4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 376: 4-[3-{-4-[(3,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 377: 4-[3-(4-{[4-chloro-3-(trifluoromethyl)benzyl]oxy}-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde;

No. 379: 4-[3-{-4-[(3-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 380: 4-[3-{4-[(3,5-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 381: 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 382: 4-[3-{4-[(3-chloro-5-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 383: 4-{7-fluoro-6-[2-fluoro-1-(fluoromethyl)ethoxy]-3-(3-methoxy-4-{[4-(trifluoromethyl)benzyl]oxy}benzyl)-2,4-dioxo-3,4-dihydroquinazolin-1(2H)-yl}piperidine-1-carbaldehyde;

No. 384: 4-[3-{4-[(2,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 385: 4-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile;

No. 386: 3-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile;

No. 387: 4-[3-{-4-[(4-chloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 388: 4-[3-{4-[1-(3,4-dichlorophenyl)ethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 389: 4-{7-fluoro-6-[2-fluoro-1-(fluoromethyl)ethoxy]-3-{4-[(3-hydroxybenzyl)oxy]-3-methoxybenzyl}-2,4-dioxo-3,4-dihydroquinazolin-1(2H)-yl}piperidine-1-carbaldehyde;

No. 390: 4-[7-fluoro-3-{4-[(3-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde;

No. 391: 4-[3-{-4-[(3,4-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde;

No. 392: 4-{3-[4-(5,6-dichloro-1H-benzimidazol-1-yl)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde;

No. 393: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)phenyl 3,4-dichlorobenzenesulphonate;

No. 394: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 3,4-dichlorobenzene-sulphonate;

No. 403: 3,4-dichloro-N-[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl]benzamide.

12. A pharmaceutical composition, characterized in that it comprises at least one compound of formula (I) according to claim 1 and also at least one pharmaceutically acceptable excipient.

* * * * *

UNITED STATES PATENT AND TRADEMARK OFFICE
CERTIFICATE OF CORRECTION

PATENT NO. : 8,242,126 B2
APPLICATION NO. : 12/754163
DATED : August 14, 2012
INVENTOR(S) : Clauss et al.

Page 1 of 2

It is certified that error appears in the above-identified patent and that said Letters Patent is hereby corrected as shown below:

In column 8, line 30, "or a hydrogen or a hydroxyl optionally substituted by an" should read as -- or a hydrogen or a hydroxyl a ($C_1$-$C_6$)alkyl group optionally substituted by an --.

In column 9, line 14, "No. 5" should read as -- No. 6 --.

In column 32, line 66, "obtained in stage 1.7" should read as -- obtained in stage 1.6 --.

In column 73 compound 40 reads as

"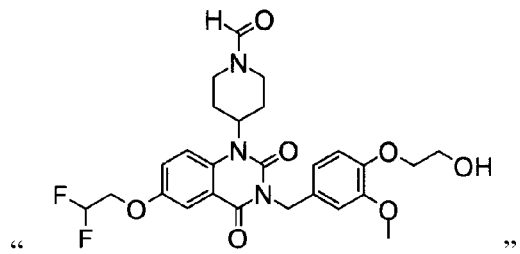"

should read as

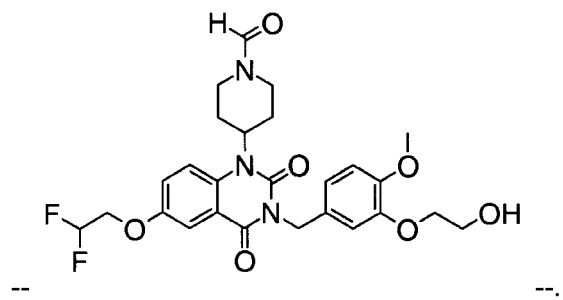

--      --.

Signed and Sealed this
Nineteenth Day of February, 2013

Teresa Stanek Rea
*Acting Director of the United States Patent and Trademark Office*

CERTIFICATE OF CORRECTION (continued)
U.S. Pat. No. 8,242,126 B2

In column 75 compound 42 reads as

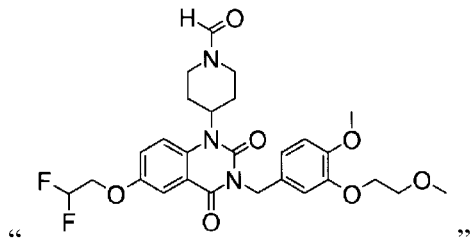

" "

should read as

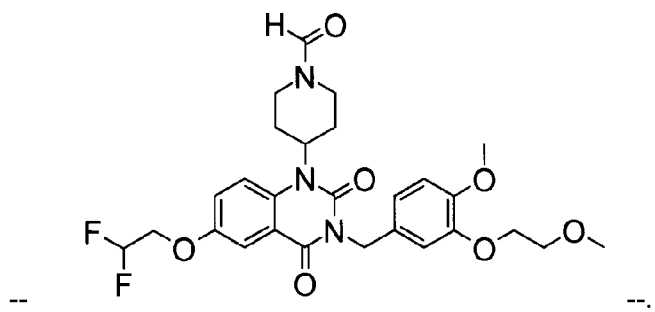

-- --.

In column 165, the chemical name of compound 174 "3-[3,4-bis(cyclopentyloxy)benzyl]-1-(1-ethenylpiperidin-4-yl)-6-[2-fluoro-1-(fluorométhyl)éthoxy]quinazoline-2,4(1H,3H)-dione" should read as -- 3-[3,4-bis(cyclopentyloxy)benzyl]-1-(1-formylpiperidin-4-yl)-6-[2-fluoro-1-(fluorométhyl)éthoxy]quinazoline-2,4(1H,3H)-dione --.

In column 333, the chemical name of compound 415 "4-[3-{4-[(3-chloro-4-hydroxybenzyl)oxy]-3-méthoxybenzyl}-7-fluoro-6-[2-fluoro-1-(fluorométhyl)éthoxy]-2,4-dioxo-3,4-dihydroquinazolin-1(2H)-yl]pipéridine-1-carbaldéhyde" should read as -- 4-[3-{4-[(3-chloro-4-trifluoromethoxybenzyl)oxy]-3-méthoxybenzyl}-7-fluoro-6-[2-fluoro-1-(fluorométhyl)éthoxy]-2,4-dioxo-3,4-dihydroquinazolin-1(2H)-yl]pipéridine-1-carbaldéhyde --.

In column 342, line 59, "No. 5" should read as -- No. 6 --.